United States Patent
Li et al.

(10) Patent No.: US 9,920,041 B2
(45) Date of Patent: *Mar. 20, 2018

(54) COMPOSITIONS AND METHODS FOR INHIBITION OF THE JAK PATHWAY

(71) Applicant: Rigel Pharmaceuticals, Inc., South San Francisco, CA (US)

(72) Inventors: Hui Li, Santa Clara, CA (US); Thilo J. Heckrodt, San Francisco, CA (US); Yan Chen, Foster City, CA (US); Darren John McMurtrie, Daly City, CA (US); Vanessa Taylor, San Francisco, CA (US); Rajinder Singh, Belmont, CA (US); Pingyu Ding, Foster City, CA (US); Rose Yen, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/439,705

(22) Filed: Feb. 22, 2017

(65) Prior Publication Data

US 2017/0158683 A1 Jun. 8, 2017

Related U.S. Application Data

(63) Continuation of application No. 14/725,932, filed on May 29, 2015, now Pat. No. 9,611,260, which is a continuation of application No. 13/685,433, filed on Nov. 26, 2012, now Pat. No. 9,067,925, which is a continuation of application No. 13/192,344, filed on Jul. 27, 2011, now Pat. No. 8,343,954.

(60) Provisional application No. 61/368,570, filed on Jul. 28, 2010.

(51) Int. Cl.
C07D 413/12 (2006.01)
C07B 59/00 (2006.01)
C07F 9/6558 (2006.01)

(52) U.S. Cl.
CPC .......... *C07D 413/12* (2013.01); *C07B 59/002* (2013.01); *C07F 9/65583* (2013.01); *C07B 2200/05* (2013.01)

(58) Field of Classification Search
CPC .................. C07D 413/02; C07F 9/6558
See application file for complete search history.

(56) References Cited

U.S. PATENT DOCUMENTS

| | | | | |
|---|---|---|---|---|
| 8,324,200 | B2 * | 12/2012 | Li | C07D 401/14 514/210.21 |
| 8,343,954 | B2 * | 1/2013 | Li | C07B 59/002 514/210.21 |
| 8,393,954 | B2 | 1/2013 | Li et al. | |
| 9,067,925 | B2 * | 6/2015 | Li | C07B 59/002 |
| 2007/0203161 | A1 | 8/2007 | Argade et al. | |
| 2010/0190770 | A1 | 7/2010 | Li et al. | |
| 2012/0028923 | A1 | 2/2012 | Li et al. | |

FOREIGN PATENT DOCUMENTS

| | | |
|---|---|---|
| EP | 2 565 193 | 6/2013 |
| JP | 2005-516046 | 6/2005 |
| JP | 2011-548150 | 9/2015 |
| RU | 2299201 C2 | 5/2007 |
| WO | WO 02/04429 A1 | 1/2002 |
| WO | WO 03/063794 A2 | 8/2003 |
| WO | WO 2008/118822 | 10/2008 |
| WO | WO 2009/063240 A1 | 5/2009 |
| WO | WO 2010/085684 | 7/2010 |
| WO | WO 2010/085684 A1 | 7/2010 |

OTHER PUBLICATIONS

International Search Report dated Sep. 26, 2011, from International Application No. PCT/US2011/045609.

* cited by examiner

*Primary Examiner* — Alexander R Pagano
*Assistant Examiner* — Ebenezer Sackey
(74) *Attorney, Agent, or Firm* — Travis Young; Klarquist Sparkman, LLP

(57) ABSTRACT

Disclosed are compounds of formula I, compositions containing them, and methods of use for the compounds and compositions in the treatment of conditions in which modulation of the JAK pathway or inhibition of JAK kinases, particularly JAK 2 and JAK3, are therapeutically useful. Also disclosed are methods of making the compounds.

12 Claims, No Drawings

COMPOSITIONS AND METHODS FOR INHIBITION OF THE JAK PATHWAY

CROSS REFERENCE TO RELATED APPLICATION

This application is a continuation of U.S. patent application Ser. No. 14/725,932, filed on May 29, 2015, which is a continuation of U.S. patent application Ser. No. 13/685,433, filed on Nov. 26, 2012, issued as U.S. Pat. No. 9,067,925, which is a continuation of U.S. patent application Ser. No. 13/192,344, filed on Jul. 27, 2011, issued as U.S. Pat. No. 8,343,954, which claims the benefit of the earlier filing date of U.S. Provisional Application No. 61/368,570, filed Jul. 28, 2010. The entire disclosures of these prior applications are incorporated herein by reference.

INTRODUCTION

Field

The present disclosure concerns compounds and methods for their use in modulation of the JAK pathway, inhibition of one or more JAK kinases and in the treatment of conditions in which modulation of the JAK pathway or inhibition of JAK kinases, particularly JAK3, is therapeutically useful.

BACKGROUND

JAnus Kinases (or JAK) are a family of cytoplasmic protein tyrosine kinases including JAK1, JAK2, JAK3 and TYK2. Each of the JAK kinases is selective for the receptors of certain cytokines, though multiple JAK kinases can be affected by particular cytokine or signaling pathways. Studies suggest that JAK3 associates with the common gamma chain (γv) of the various cytokine receptors. In particular, JAK3 selectively binds to receptors and is part of the cytokine signaling pathway for IL-2, IL-4, IL-7, IL-9, IL-15 and IL-21. The kinase JAK1 interacts with, among others, the receptors for cytokines IL-2, IL-4, IL-7, IL-9 and IL-21, while JAK2 interacts with, among others, the receptors for IL-9 and TNF-α. Upon the binding of certain cytokines to their receptors (for example, IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Phosphorylated JAK kinases bind various Signal Transducer and Activator of Transcription (STAT) proteins. These STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), *J. Allergy Clin. Immunol.* 105:877-888). Signaling of JAK/STAT has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), *Mol. Med.* 5:432:456 and Seidel et al., (2000), *Oncogene* 19:2645-2656.

In particular, JAK3 has been implicated in a variety of biological processes. For example, the proliferation and survival of murine mast cells induced by IL-4 and IL-9 have been shown to be dependent on JAK3- and gamma chain-signaling (Suzuki et al., (2000), *Blood* 96:2172-2180). Having a crucial role in IgE receptor-mediated mast cell degranulation responses (Malaviya et al., (1999), *Biochem. Biophys. Res. Commun.* 257:807-813), inhibition of JAK3 kinase has been shown to prevent type I hypersensitivity reactions, including anaphylaxis (Malaviya et al., (1999), *J. Biol. Chem.* 274:27028-27038). JAK3 inhibition has also been shown to result in immune suppression for allograft rejection (Kirken, (2001), *Transpl. Proc.* 33:3268-3270). Kinases, particularly JAK3 kinases, have also been implicated in the mechanism involved in early and late stages of rheumatoid arthritis (Muller-Ladner et al., (2000), *J. Immunol.* 164:3894-3901); familial amyotrophic lateral sclerosis (Trieu et al., (2000), *Biochem Biophys. Res. Commun.* 267:22-25); leukemia (Sudbeck et al., (1999), *Clin. Cancer Res.* 5:1569-1582); mycosis fungoides, a form of T-cell lymphoma (Nielsen et al., (1997), *Prac. Natl. Acad. Sci. USA* 94:6764-6769); and abnormal cell growth (Yu et al., (1997), *J. Immunol.* 159:5206-5210; Catlett-Falcone et al., (1999), *Immunity* 10:105-115).

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), *Mol. Cell. Biol.* 16:4710-6; Jurlander et al., (1997), *Blood.* 89:4146-52; Kaneko et al., (1997), *Clin. Exp. Immun.* 109:185-193; and Nakamura et al., (1996), *J. Biol. Chem.* 271:19483-8). They are also known to be important to lymphocyte differentiation, function and survival. In particular, JAK3 plays an essential role in the function of lymphocytes, macrophages, and mast cells. Given the importance of JAK kinases, particularly JAK3, compounds which modulate the JAK pathway, including those selective for JAK3, can be useful for treating diseases or conditions where the function of lymphocytes, macrophages, or mast cells is involved (Kudlacz et al., (2004) *Am. J. Transplant* 4:51-57; Changelian (2003) *Science* 302:875-878). Conditions in which targeting of the JAK pathway or modulation of the JAK kinases, particularly JAK3, are contemplated to be therapeutically useful include, leukemia, lymphoma, transplant rejection (for example, pancreas islet transplant rejection, bone marrow transplant applications (for example, graft-versus-host disease), autoimmune diseases (for example, diabetes), and inflammation (for example, asthma, allergic reactions). Conditions which can benefit for inhibition of JAK3 are discussed in greater detail below.

In view of the numerous conditions that are contemplated to benefit by treatment involving modulation of the JAK pathway it is immediately apparent that new compounds that modulate JAK pathways and methods of using these compounds should provide substantial therapeutic benefits to a wide variety of patients. Provided herein are novel 2,4-pyrimidinediamine compounds for use in the treatment of conditions in which targeting of the JAK pathway or inhibition of JAK kinases, particularly JAK3, are therapeutically useful.

SUMMARY

In one embodiment, the present disclosure is directed to compounds, prodrugs, and methods of using these compounds and prodrugs thereof in the treatment of conditions in which modulation of the JAK pathway or inhibition of JAK kinases, particularly JAK2, JAK3, or both, will be therapeutically useful.

One embodiment, is a compound of formula I, a salt thereof, or a pharmaceutical composition including the compound:

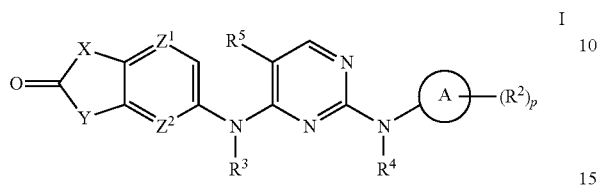

where:
X and Y are each independently O, S, S(O), $SO_2$ or $NR^1$;
each $R^1$ is independently for each occurrence H, optionally substituted $C_{1-6}$alkyl, C(O)—$C_{1-6}$alkyl, $CO_2$—$C_{1-6}$alkyl or $R^{50}$;
each $R^{50}$ is —$C(R^9)_2$-A-$R^{10}$, where A is O or S; each $R^9$ is independently for each occurrence H, optionally substituted $C_{1-6}$alkyl, optionally substituted $C_{6-10}$aryl or optionally substituted $C_{7-16}$arylalkyl; or alternatively, two $R^9$, together with the carbon to which they are attached, form an optionally substituted $C_{3-8}$cycloalkyl group or an optionally substituted 3-8 membered heteroalicyclyl; $R^{10}$ is $R^a$, —$P(O)(OR^{11})_2$, —$P(O)(OR^{11})N(R^{12})_2$ or —$P(O)(N(R^{12})_2)_2$; each $R^{11}$ is independently for each occurrence $R^a$ or a monovalent cationic group; or two $R^{11}$, together with the atoms to which they are attached, form a 4-8 membered cyclic phosphate group, or two $R^{11}$ together represent a divalent cationic group; each $R^{12}$ is independently for each occurrence $R^c$ or —$C_{1-3}$alkyl-$N(R^c)_2$; or two $R^{12}$, each on separate nitrogens of —$P(O)(N(R^{12})_2)_2$, together with the atoms to which they are attached, form a 4-8 membered cyclic phosphonic acid bisamide group; or one $R^{12}$ along with $R^{11}$, of the group —$P(O)(OR^{11})N(R^{12})_2$, together with the atoms to which they are attached, form a 4-8 membered cyclic phosphonamidate group;
ring A is a $C_{6-10}$aryl or a 5-10 membered heteroaryl;
each $R^2$ is independently for each occurrence H, $R^e$, $R^b$, $R^e$ substituted with one or more of the same or different $R^a$, $R^b$, or both, —$OR^e$ substituted with one or more of the same or different $R^a$ and/or $R^b$, —$SR^e$ substituted with one or more of the same or different $R^a$ and/or $R^b$, —$C(O)R^e$ substituted with one or more of the same or different $R^a$ and/or $R^b$, —$N(R^a)R^e$ where $R^e$ is substituted with one or more of the same or different $R^a$ and/or $R^b$, —$S(O)_2R^e$ substituted with one or more of the same or different $R^a$ and/or $R^b$, —$N(R^a)$—$S(O)_2R^e$ where $R^e$ is substituted with one or more of the same or different $R^a$ and/or $R^b$, —$B(OR^a)_2$, —$B(N(R^c)_2)_2$, —$(C(R^a)_2)_m$—$R^b$, —O—$(C(R^a)_2)_m$—$R^b$, —S—$(C(R^a)_2)_m$—$R^b$, —O—$(C(R^b)_2)_m$—$R^a$, —$N(R^a)$—$(C(R^a)_2)_m$—$R^b$, —O—$(CH_2)_m$—$CH((CH_2)_mR^b)R^b$, —$C(O)N(R^a)$—$(C(R^a))_m$—$R^b$, —O—$(C(R^a)_2)_m$—$C(O)N(R^a)$—$(C(R^a)_2)_m$—$R^b$, —$N((C(R^a)_2)_mR^b)_2$, —S—$(C(R^a)_2)_m$—$C(O)N(R^a)$—$(C(R^a)_2)_m$—$R^b$, —$N(R^a)$—$C(O)$—$N(R^a)$—$(C(R^a)_2)_m$—$R^b$, —$N(R^a)$—$C(O)$—$(C(R^a)_2)_m$—$C(R^a)(R^b)_2$ or —$N(R^a)$—$(C(R^a)_2)_m$—$C(O)$—$N(R^a)$—$(C(R^a)_2)_m$—$R^b$;
each $R^a$ is independently for each occurrence H, deuterium, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;
each $R^b$ is independently for each occurrence =O, —$OR^a$, —O—$(C(R^a)_2)_m$—$OR^a$, halo$C_{1-3}$alkyloxy, =S, —$SR^a$, =$NR^a$, =$NOR^a$, —$N(R^c)_2$, halo, —$CF_3$, —CN, —NC, —OCN, —SCN, —NO, —$NO_2$, =$N_2$, —$N_3$, —$S(O)R^a$, —$S(O)_2R^a$, —$SO_3R^a$, —$S(O)N(R^c)_2$, —$S(O)_2N(R^c)_2$, —$OS(O)R^a$, —$OS(O)_2R^a$, —$OSO_3R^a$, —$OS(O)_2N(R^c)_2$, —$C(O)R^a$, —$CO_2R^a$, —$C(O)N(R^c)_2$, —$C(NR^a)$—$N(R^c)_2$, —$C(NOH)$—$R^a$, —$C(NOH)$—$N(R^c)_2$, —$OC(O)R^a$, —$OC(O)OR^a$, —$OC(O)N(R^c)_2$, —$OC(NH)$—$N(R^c)_2$, —$OC(NR^a)$—$N(R^c)_2$, —$N(R^a)$—$S(O)_2H$, —$[N(R^a)C(O)]_nR^a$, —$[N(R^a)C(O)]_nOR^a$, —$[N(R^a)C(O)]_nN(R^c)_2$ or —$[N(R^a)C(NR^a)]_n$—$N(R^c)_2$;
each $R^c$ is independently for each occurrence $R^a$, or, alternatively, two $R^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;
each $R^d$ is =O, —$OR^a$, halo$C_{1-3}$alkyloxy, $C_{1-6}$alkyl, =S, —$SR^a$, =$NR^a$, =$NOR^a$, —$N(R^a)_2$, halo, —$CF_3$, —CN, —NC, —OCN, —SCN, —NO, —$NO_2$, =$N_2$, —$N_3$, —$S(O)R^a$, —$S(O)_2R^a$, —$SO_3R^a$, —$S(O)N(R^a)_2$, —$S(O)_2N(R^a)_2$, —$OS(O)R^a$, —$OS(O)_2R^a$, —$OSO_3R^a$, —$OS(O)_2N(R^a)_2$, —$C(O)R^a$, —$CO_2R^a$, —$C(O)N(R^a)_2$, —$C(NR^a)N(R^a)_2$, —$C(NOH)R^a$, —$C(NOH)N(R^a)_2$, —$OCO_2R^a$, —$OC(O)N(R^a)_2$, —$OC(NR^a)N(R^a)_2$, —$[N(R^a)C(O)]_nR^a$, —$(C(R^a)_2)_n$—$OR^a$, —$N(R^a)$—$S(O)_2R^a$, —$C(O)$—$C_{1-6}$haloalkyl, —$S(O)_2C_{1-6}$haloalkyl, —$OC(O)R^a$, —$O(C(R^a)_2)_m$—$OR^a$, —$S(C(R^a)_2)_m$—$OR^a$, —$N(R^a)C_{1-6}$haloalkyl, —$P(O)(OR^a)_2$, —$N(R^a)$—$(C(R^a)_2)_m$—$OR^a$, —$[N(R^a)C(O)]_nOR^a$, —$[N(R^a)C(O)]_nN(R^a)_2$, —$[N(R^a)C(NR^a)]_nN(R^a)_2$ or —$N(R^a)C(O)C_{1-6}$haloalkyl; two $R^d$, taken together with the atom or atoms to which they are attached, combine to form a 3-10 membered partially or fully saturated mono or bicyclic ring, optionally containing one or more heteroatoms and optionally substituted with one or more $R^a$;
each $R^e$ is independently for each occurrence $C_{1-6}$alkyl, $C_{3-8}$cycloalkyl, $C_{4-11}$ cycloalkylalkyl, $C_{6-10}$aryl, $C_{7-16}$arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;
p is 0, 1, 2, 3 or 4;
each m is 1, 2 or 3;
each n is 0, 1, 2 or 3;
two $R^2$ groups, taken together with the atom or atoms to which they are attached, combine to form a 4-10 membered partially or fully saturated mono or bicyclic ring, optionally containing one or more heteroatoms and optionally substituted with one or more $R^a$ and/or $R^b$;
$Z^1$ and $Z^2$ are each independently CH, $CR^2$ or N;
$R^3$ is H, optionally substituted $C_{1-6}$alkyl or $R^{50}$;
$R^4$ is H, optionally substituted $C_{1-6}$alkyl or $R^{50}$; and
$R^5$ is H, halo, —CN, optionally substituted $C_{1-6}$alkyl, alkynyl, hydroxy, optionally substituted $C_{1-6}$alkoxy, nitro, —$N(R^a)_2$, —$C(O)N(R^a)_2$, —$CO_2R^a$ or —$C(O)R^a$.

Another embodiment is a method of inhibiting an activity of a JAK kinase, including contacting the JAK kinase with an amount of a compound effective to inhibit an activity of the JAK kinase where the compound is according to formula I as described herein. In one embodiment the contact is made in vitro, in another embodiment the contact is made in vivo.

Another embodiment is a method of treating a T-cell mediated autoimmune disease, including administering to a patient suffering from such an autoimmune disease an amount of a compound effective to treat the autoimmune disease where the compound is according to formula I as described herein. In particular disclosed embodiments, the compound is administered in combination with, or adjunctively to, a compound or pharmaceutical composition that inhibits Syk kinase with an $IC_{50}$ of less than 10 μM.

Another embodiment is a method of treating allograft transplant rejection in a transplant recipient, including administering to the transplant recipient an amount of a compound effective to treat or prevent the rejection where the compound is according to formula I as described herein. Administration in this context may include contacting a transplant organ with a compound or pharmaceutical composition described herein prior to transplant and/or concurrent with administration to the transplant recipient.

Yet another embodiment is a method of treating a Type IV hypersensitivity reaction, including administering to a subject an amount of a compound of effective to treat or prevent the hypersensitivity reaction where the compound is according to formula I as described herein.

Another embodiment is a method of treating an ocular disease or disorder, including administering to a subject an amount of a compound of effective to treat or prevent the ocular disease or disorder where the compound is according to formula I as described herein.

Another embodiment is a method of inhibiting a signal transduction cascade in which JAK3 kinase plays a role, including contacting a cell expressing a receptor involved in such a signaling cascade with a compound where the compound is according to formula I as described herein.

One embodiment is a method of treating a JAK kinase-mediated disease, including administering to a subject an amount of compound effective to treat or prevent the JAK kinase-mediated disease where the compound is according to formula I as described herein.

Another embodiment is a pharmaceutical formulation including a compound of formula I as described herein. Therapy using the 2,4-pyrimidinediamine compounds and pharmaceutical formulations described herein can be applied alone, or it can be applied in combination with or adjunctive to other immunosuppressive therapies Another embodiment is a kit including a compound of formula I as described herein, a prodrug thereof or pharmaceutical composition including a compound thereof, packaging and instructions for use.

Another embodiment is a unit dosage formulation including a compound of formula I as described herein, a prodrug thereof or pharmaceutical composition including a compound of formula I.

Other embodiments include methods of using the compounds for screening for other agents used to treat or prevent a JAK kinase mediated disease.

Other embodiments include methods of making the compounds described herein.

Another embodiment is a method of making a compound of formula A-6, comprising:

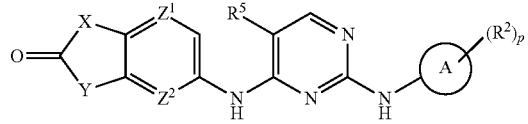

(i) reacting a guanidine of formula A-11 with a 1,3-dielectrophile to make a 4-hydroxy-pyrimidin-2yl-amine of formula A-13;

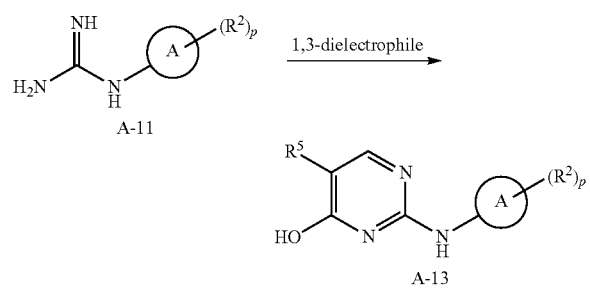

(ii) converting A-13 to a 4-leaving group-pyrimidin-2yl-amine of formula A-14; and

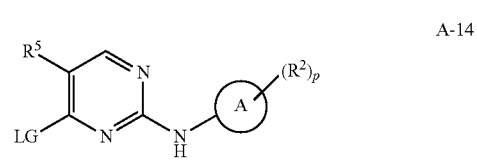

(iii) reacting the 4-leaving group-pyrimidin-2yl-amine A-14 with an aryl or heteroaryl amine, A-3;

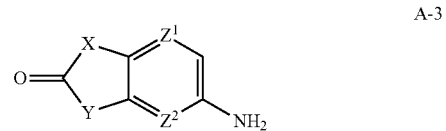

wherein the substituents are as are as recited for Formula I, above. In particular disclosed embodiments, LG is chloride.

In disclosed embodiments, the 1,3-dielectrophile is a β-aldehyde ester of formula A-12:

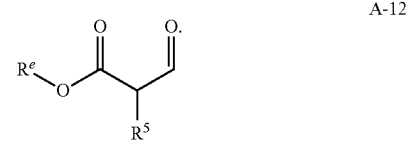

In disclosed embodiments, reacting a guanidine of formula A-11 with the 3-aldehyde ester of formula A-12 to make the 4-hydroxy-pyrimidin-2yl-amine of formula A-13 comprises heating in an alcoholic solvent in the presence of a base. In particular disclosed embodiments, the alcoholic solvent is ethanol, the base is sodium ethoxide, and the reaction is heated to between about 40° C. and about 80° C. for between about 24 h and about 48 h.

In particular disclosed embodiments, converting A-13 to a 4-leaving group-pyrimidin-2yl-amine of formula A-14 comprises heating A-13 in the presence of POCl$_3$. In particular disclosed embodiments, X is O; Y is NR$^1$; and Z$^1$ and Z$^2$ are each CH and reacting the 4-leaving group-pyrimidin-2yl-amine A-14 with the aryl or heteroaryl amine, A-3, comprises heating a mixture of A-14 and A-3 in a solvent at between about 60° C. and about 80° C. in the presence of an acid. In certain embodiments, the solvent is isopropanol and the acid is trifluoroacetic acid. In particular disclosed embodiments ring A is phenyl.

More detailed description for these and other embodiments is provided below.

DETAILED DESCRIPTION

Overview

The invention includes compounds of formula I and the compositions and methods using these compounds in the treatment of conditions in which modulation of the JAK pathway or inhibition of JAK kinases, particularly JAK3, are therapeutically useful. Formulations, uses as screening agents and other utilities are also described.

Terms

As used herein, the following words and phrases are intended to have the meanings as set forth below, except to the extent that the context in which they are used indicates otherwise or they are expressly defined to mean something different.

The symbol "—" means a single bond, "=" means a double bond, "≡" means a triple bond. The symbol "⁓" refers to a group on a double-bond as occupying either position on the terminus of the double bond to which the symbol is attached; that is, the geometry, E- or Z-, of the double bond is ambiguous and both isomers are meant to be included. When a group is depicted removed from its parent formula, the "⁓" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It would be understood by one of ordinary skill in the art that the aforementioned descriptive techniques are common in the chemical arts to provide brevity and simplicity to description of otherwise complex structures.

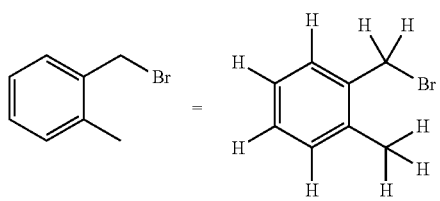

In this application, some ring structures are depicted generically and will be described textually. For example, in the schematic below if ring A is used to describe a phenyl, there are at most four hydrogens on ring A (when R is not H).

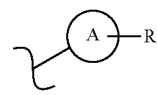

If a group R is depicted as "floating" on a ring system, as for example in the group:

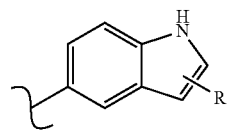

then, unless otherwise defined, a substituent R can reside on any atom of the fused bicyclic ring system, excluding the atom carrying the bond with the "⁓" symbol, so long as a stable structure is formed. In the example depicted, the R group can reside on an atom in either the 5-membered or the 6-membered ring of the indolyl ring system.

When there are more than one such depicted "floating" groups, as for example in the formulae:

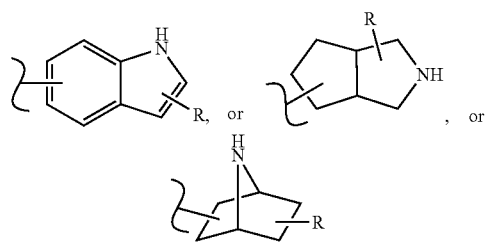

where there are two groups, namely, the R and the bond indicating attachment to a parent structure; then, unless otherwise defined, the "floating" groups can reside on any atoms of the ring system, again assuming each replaces a depicted, implied, or expressly defined hydrogen on the ring system and a chemically stable compound would be formed by such an arrangement.

When a group R is depicted as existing on a ring system containing saturated carbons, as for example in the formula:

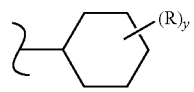

where, in this example, y can be more than one, assuming each replaces a currently depicted, implied, or expressly defined hydrogen on the ring; then, unless otherwise defined, two R's can reside on the same carbon. A simple example is when R is a methyl group; there can exist a geminal dimethyl on a carbon of the depicted ring (an "annular" carbon). In another example, two R's on the same carbon, including that same carbon, can form a ring, thus creating a spirocyclic ring (a "spirocyclyl" group) structure. Using the previous example, where two R's form, for example a piperidine ring in a spirocyclic arrangement with the cyclohexane, as for example in the formula:

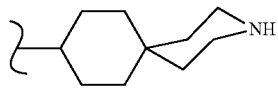

"Alkyl" in its broadest sense is intended to include linear, branched, or cyclic hydrocarbon structures, and combinations thereof. Alkyl groups can be fully saturated or with one or more units of unsaturation, but not aromatic. Generally alkyl groups are defined by a subscript, either a fixed integer or a range of integers. For example, "$C_8$alkyl" includes n-octyl, iso-octyl, 3-octynyl, cyclohexenylethyl, cyclohexylethyl, and the like; where the subscript "8" designates that all groups defined by this term have a fixed carbon number of eight. In another example, the term "$C_{1-6}$alkyl" refers to alkyl groups having from one to six carbon atoms and, depending on any unsaturation, branches and/or rings, the requisite number of hydrogens. Examples of $C_{1-6}$alkyl groups include methyl, ethyl, vinyl, propyl, isopropyl, butyl, s-butyl, t-butyl, isobutyl, isobutenyl, pentyl, pentynyl, hexyl, cyclohexyl, hexenyl, and the like. When an alkyl residue having a specific number of carbons is named generically, all geometric isomers having that number of carbons are intended to be encompassed. For example, either "propyl" or "$C_3$alkyl" each include n-propyl, c-propyl, propenyl, propynyl, and isopropyl. Cycloalkyl is a subset of alkyl and includes cyclic hydrocarbon groups of from three to thirteen carbon atoms. Examples of cycloalkyl groups include c-propyl, c-butyl, c-pentyl, norbornyl, norbornenyl, c-hexenyl, adamantyl and the like. As mentioned, alkyl refers to alkanyl, alkenyl, and alkynyl residues (and combinations thereof)—it is intended to include, for example, cyclohexylmethyl, vinyl, allyl, isoprenyl, and the like. An alkyl with a particular number of carbons can be named using a more specific but still generic geometrical constraint, for example "$C_{3-6}$cycloalkyl" which means only cycloalkyls having between 3 and 6 carbons are meant to be included in that particular definition. Unless specified otherwise, alkyl groups, whether alone or part of another group, for example —C(O)alkyl, have from one to twenty carbons, that is $C_{1-20}$alkyl. In the example "—C(O)alkyl," where there were no carbon count limitations defined, the carbonyl of the —C(O)alkyl group is not included in the carbon count, since "alkyl" is designated generically. But where a specific carbon limitation is given, for example in the term "optionally substituted $C_{1-20}$alkyl," where the optional substitution includes "oxo" the carbon of any carbonyls formed by such "oxo" substitution are included in the carbon count since they were part of the original carbon count limitation. However, again referring to "optionally substituted $C_{1-20}$alkyl," if optional substitution includes carbon-containing groups, for example —CH$_2$CO$_2$H, the two carbons in this group are not included in the $C_{1-20}$alkyl carbon limitation.

When a carbon number limit is given at the beginning of a term which itself comprises two terms, the carbon number limitation is understood as inclusive for both terms. For example, for the term "$C_{7-14}$arylalkyl," both the "aryl" and the "alkyl" portions of the term are included the carbon count, a maximum of 14 in this example, but additional substituent groups thereon are not included in the atom count unless they incorporate a carbon from the group's designated carbon count, as in the "oxo" example above. Likewise when an atom number limit is given, for example "6-14 membered heteroarylalkyl," both the "heteroaryl" and the "alkyl" portion are included the atom count limitation, but additional substituent groups thereon are not included in the atom count unless they incorporate a carbon from the group's designated carbon count. In another example, "$C_{4-10}$cycloalkylalkyl" means a cycloalkyl bonded to the parent structure via an alkylene, alkylidene or alkylidyne; in this example the group is limited to 10 carbons inclusive of the alkylene, alkylidene or alkylidyne subunit. As another example, the "alkyl" portion of, for example "$C_{7-14}$arylalkyl" is meant to include alkylene, alkylidene or alkylidyne, unless stated otherwise, for example as in the terms "$C_{7-14}$arylalkylene" or "$C_{6-10}$aryl-CH$_2$CH$_2$—."

"Alkylene" refers to straight, branched and cyclic (and combinations thereof) divalent radical consisting solely of carbon and hydrogen atoms, containing no unsaturation and having from one to ten carbon atoms, for example, methylene, ethylene, propylene, n-butylene and the like. Alkylene is like alkyl, referring to the same residues as alkyl, but having two points of attachment and, specifically, fully saturated. Examples of alkylene include ethylene (—CH$_2$CH$_2$—), propylene (—CH$_2$CH$_2$CH$_2$—), dimethylpropylene (—CH$_2$C(CH$_3$)$_2$CH$_2$—), cyclohexan-1,4-diyl and the like.

"Alkylidene" refers to straight, branched and cyclic (and combinations thereof) unsaturated divalent radical consisting solely of carbon and hydrogen atoms, having from two to ten carbon atoms, for example, ethylidene, propylidene, n-butylidene, and the like. Alkylidene is like alkyl, referring to the same residues as alkyl, but having two points of attachment and, specifically, at least one unit of double bond unsaturation. Examples of alkylidene include vinylidene (—CH=CH—), cyclohexylvinylidene (—CH=C(C$_6$H$_{13}$)—), cyclohexen-1,4-diyl and the like.

"Alkylidyne" refers to straight, branched and cyclic (and combinations thereof) unsaturated divalent radical consisting solely of carbon and hydrogen atoms having from two to ten carbon atoms, for example, propylid-2-ynyl, n-butylid-1-ynyl, and the like. Alkylidyne is like alkyl, referring to the same residues as alkyl, but having two points of attachment and, specifically, at least one unit of triple bond unsaturation.

Any of the above radicals" "alkylene," "alkylidene" and "alkylidyne," when optionally substituted, can contain alkyl substitution which itself can contain unsaturation. For example, 2-(2-phenylethynyl-but-3-enyl)-naphthalene (IUPAC name) contains an n-butylid-3-ynyl radical with a vinyl substituent at the 2-position of the radical. Combinations of alkyls and carbon-containing substitutions thereon are limited to thirty carbon atoms.

"Alkoxy" refers to the group —O-alkyl, where alkyl is as defined herein. Alkoxy includes, by way of example, methoxy, ethoxy, n-propoxy, isopropoxy, n-butoxy, t-butoxy, sec-butoxy, n-pentoxy, cyclohexyloxy, cyclohexenyloxy, cyclopropylmethyloxy, and the like.

"Haloalkyloxy" refers to the group —O-alkyl, where alkyl is as defined herein, and further, alkyl is substituted with one or more halogens. By way of example, a haloC$_{1-3}$alkyloxy" group includes —OCF$_3$, —OCF$_2$H, —OCHF$_2$, —OCH$_2$CH$_2$Br, —OCH$_2$CH$_2$CH$_2$I, —OC(CH$_3$)$_2$Br, —OCH$_2$Cl and the like.

"Acyl" refers to the group —C(O)H, —C(O)alkyl, —C(O)aryl, —C(O)heterocyclyl, —C(O)arylalkyl or —C(O)heterocyclylalkyl.

"α-Amino Acids" refer to naturally occurring and commercially available α-amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), etc.

"Amino" refers to the group —NH$_2$.

"Amide" refers to the group —C(O)NH$_2$ or —N(H)acyl.

"Aryl" (sometimes referred to as "Ar") refers to a monovalent aromatic carbocyclic group of, unless specified otherwise, from 6 to 15 carbon atoms having a single ring (for example, phenyl) or multiple condensed rings (for example, naphthyl or anthryl) which condensed rings may or may not be aromatic (for example, 2-benzoxazolinone, 2H-1,4-benzoxazin-3(4H)-one-7-yl, 9,10-dihydrophenanthrenyl, indanyl, tetralinyl, and fluorenyl and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic.

"Arylene" refers to an aryl that has at least two groups attached thereto. For a more specific example, "phenylene" refers to a divalent phenyl ring radical. A phenylene, thus can have more than two groups attached, but is defined by a minimum of two non-hydrogen groups attached thereto.

"Arylalkyl," sometimes "aralkyl," refers to a residue in which an aryl moiety is attached to a parent structure via one of an alkylene, alkylidene, or alkylidyne radical. Examples include benzyl, phenethyl, phenylvinyl, phenylallyl and the like. When specified as "optionally substituted," both the aryl, and the corresponding alkylene, alkylidene, or alkylidyne portion of an arylalkyl group can be optionally substituted. By way of example, "C$_{7-11}$arylalkyl" refers to an arylalkyl limited to a total of eleven carbons, for example, a phenylethyl, a phenylvinyl, a phenylpentyl and a naphthyl-methyl are all examples of a "C$_{7-11}$arylalkyl" group.

"Aryloxy" refers to the group —O-aryl, where aryl is as defined herein, including, by way of example, phenoxy, naphthoxy, and the like.

"Carboxyl," "carboxy" or "carboxylate" refers to —CO$_2$H or salts thereof.

"Carboxyl ester" or "carboxy ester" or "ester" refers to the group —CO$_2$alkyl, —CO$_2$aryl, —CO$_2$heterocyclyl, —CO$_2$arylalkyl or —CO$_2$heterocyclylalkyl.

"Carbonate" refers to the group —OCO$_2$alkyl, —OCO$_2$aryl, —OCO$_2$heterocyclyl, —OCO$_2$arylalkyl or —OCO$_2$heterocyclylalkyl.

"Carbamate" refers to the group —OC(O)NH$_2$, —N(H)carboxyl or —N(H)carboxyl ester.

"Cyano" or "nitrile" refers to the group —CN.

"Formyl" refers to the specific acyl group —C(O)H.

"Halo" or "halogen" refers to fluoro, chloro, bromo and iodo.

"Haloalkyl" and "haloaryl" refer generically to alkyl and aryl radicals that are substituted with one or more halogens, respectively. By way of example "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is a dihaloaryl group.

"Heteroalkyl" refers to an alkyl where one or more, but not all, carbons are replaced with a heteroatom. A heteroalkyl group has either linear or branched geometry. By way of example, a "2-6 membered heteroalkyl" is a group that can contain no more than 5 carbon atoms, because at least one of the maximum 6 atoms must be a heteroatom, and the group is linear or branched. Also, for the purposes of this invention, a heteroalkyl group always starts with a carbon atom, that is, although a heteroalkyl may contain one or more heteroatoms, the point of attachment to the parent molecule is not a heteroatom. A 2-6 membered heteroalkyl group includes, for example, —CH$_2$XCH$_3$, —CH$_2$CH$_2$XCH$_3$, —CH$_2$CH$_2$XCH$_2$CH$_3$, —C(CH$_2$)$_2$ XCH$_2$CH$_3$ and the like, where X is O, NH, NC$_{1-6}$alkyl and S(O)$_{0-2}$, for example.

"Perhalo" as a modifier means that the group so modified has all its available hydrogens replaced with halogens. An example would be "perhaloalkyl." Perhaloalkyls include —CF$_3$, —CF$_2$CF$_3$, perchloroethyl and the like.

"Hydroxy" or "hydroxyl" refers to the group —OH.

"Heteroatom" refers to O, S, N, or P.

"Heterocyclyl" in the broadest sense includes aromatic and non-aromatic ring systems and more specifically refers to a stable three- to fifteen-membered ring radical that consists of carbon atoms and from one to five heteroatoms. For purposes of this invention, the heterocyclyl radical can be a monocyclic, bicyclic or tricyclic ring system, which can include fused or bridged ring systems as well as spirocyclic systems; and the nitrogen, phosphorus, carbon or sulfur atoms in the heterocyclyl radical can be optionally oxidized to various oxidation states. In a specific example, the group —S(O)$_{0-2}$—, refers to —S— (sulfide), —S(O)— (sulfoxide), and —SO$_2$— (sulfone) linkages. For convenience, nitrogens, particularly but not exclusively, those defined as annular aromatic nitrogens, are meant to include their corresponding N-oxide form, although not explicitly defined as such in a particular example. Thus, for a compound having, for example, a pyridyl ring; the corresponding pyridyl-N-oxide is meant to be included in the presently disclosed compounds. In addition, annular nitrogen atoms can be optionally quaternized. "Heterocycle" includes heteroaryl and heteroalicyclyl, that is a heterocyclic ring can be partially or fully saturated or aromatic. Thus a term such as "heterocyclylalkyl" includes heteroalicyclylalkyls and heteroarylalkyls. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroaryl" refers to an aromatic group having from 1 to 10 annular carbon atoms and 1 to 4 annular heteroatoms. Heteroaryl groups have at least one aromatic ring component, but heteroaryls can be fully unsaturated or partially unsaturated. If any aromatic ring in the group has a heteroatom, then the group is a heteroaryl, even, for example, if other aromatic rings in the group have no heteroatoms. For example, 2H-pyrido[3,2-b][1,4]oxazin-3(4H)-one-7-yl, indolyl and benzimidazolyl are "heteroaryls." Heteroaryl groups can have a single ring (for example, pyridinyl, imidazolyl or furyl) or multiple condensed rings (for example, indolizinyl, quinolinyl, benzimidazolyl or benzothienyl), where the condensed rings may or may not be aromatic and/or contain a heteroatom, provided that the point of attachment to the parent molecule is through an atom of the aromatic portion of the heteroaryl group. In one embodiment, the nitrogen and/or sulfur ring atom(s) of the heteroaryl group are optionally oxidized to provide for the N-oxide (N—O), sulfinyl, or sulfonyl moieties. Compounds described herein containing phosphorous, in a heterocyclic ring or not, include the oxidized forms of phosphorous. Heteroaryl groups are monocyclic, bicyclic, tricyclic or tetracyclic.

"Heteroaryloxy" refers to —O-heteroaryl.

"Heteroarylene" generically refers to any heteroaryl that has at least two groups attached thereto. For a more specific example, "pyridylene" refers to a divalent pyridyl ring radical. A pyridylene, thus can have more than two groups attached, but is defined by a minimum of two non-hydrogen groups attached thereto.

"Heteroalicyclic" refers specifically to a non-aromatic heterocyclyl radical. A heteroalicyclic may contain unsaturation, but is not aromatic. As mentioned, aryls and heteroaryls are attached to the parent structure via an aromatic ring. So, for example, 2H-1,4-benzoxazin-3(4H)-one-4-yl is a heteroalicyclic, while 2H-1,4-benzoxazin-3(4H)-one-7-yl is an aryl. In another example, 2H-pyrido[3,2-b][1,4]oxazin-3(4H)-one-4-yl is a heteroalicyclic, while 2H-pyrido[3,2-b][1,4]oxazin-3(4H)-one-7-yl is a heteroaryl.

"Heterocyclylalkyl" refers to a heterocyclyl group linked to the parent structure via e.g. an alkylene linker. By way of example, the term "$C_{5-14}$heterocyclylalkyl" includes groups such as (tetrahydrofuran-3-yl)methyl-, (pyridin-4-yl)methyl and 4-(morpholin-4-yl)butan-2-yl, depicted below.

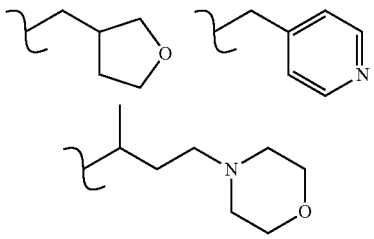

"Heterocyclyloxy" refers to the group —O-heterocyclyl.
"Heterocyclylalkyloxy" refers to the group —O-heterocyclylalkyl.
"Nitro" refers to the group —$NO_2$.
"Oxo" refers to a double bond oxygen radical, =O.
"Oxy" refers to —O. radical (also designated as →O), that is, a single bond oxygen radical. By way of example, N-oxides are nitrogens bearing an oxy radical.

When a group with its bonding structure is denoted as being bonded to two partners; that is, a divalent radical, for example, —$OCH_2$—, then it is understood that either of the two partners can be bound to the particular group at one end, and the other partner is necessarily bound to the other end of the divalent group, unless stated explicitly otherwise. Stated another way, divalent radicals are not to be construed as limited to the depicted orientation, for example "—$OCH_2$—" is meant to mean not only "—$OCH_2$—" as drawn, but also "—$CH_2O$—."

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only synthetically feasible compounds are meant to be included. "Optionally substituted" refers to all subsequent modifiers in a term, for example in the term "optionally substituted aryl$C_{1-8}$alkyl," optional substitution may occur on both the "$C_{1-8}$alkyl" portion and the "aryl" portion of the aryl$C_{1-8}$alkyl group. Also by way of example, optionally substituted alkyl includes optionally substituted cycloalkyl groups. The term "substituted," when used to modify a specified group or radical, means that one or more hydrogen atoms of the specified group or radical are each, independently of one another, replaced with the same or different substituent groups as defined below. Thus, when a group is defined as "optionally substituted" the definition is meant to encompass when the groups is substituted with one or more of the radicals defined below, and when it is not so substituted.

Substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$N(R^{80})_2$, perhaloalkyl, —CN, —OCN, —SCN, —NO, —$NO_2$, =$N_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$P(O)(O^-)_2(M^+)_2$, —$P(O)(O^-)_2M^{2+}$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)N(R^{80})_2$, —$C(NR^{70})(R^{80})_2$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$ is $C_{1-6}$alkyl, 3 to 10-membered heterocyclyl, 3 to 10-membered heterocyclyl$C_{1-6}$alkyl, $C_{6-10}$aryl or $C_{6-10}$aryl$C_{1-6}$alkyl; each $R^{70}$ is independently for each occurrence hydrogen or $R^{60}$; each $R^{80}$ is independently for each occurrence $R^{70}$ or alternatively, two $R^{80}$'s, taken together with the nitrogen atom to which they are bonded, form a 3 to 7-membered heteroalicyclyl which optionally includes from 1 to 4 of the same or different additional heteroatoms selected from O, N and S, of which N optionally has H or $C_1$-$C_3$alkyl substitution; and each $M^+$ is a counter ion with a net single positive charge. Each $M^+$ is independently for each occurrence, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ (a "subscript 0.5 means for example that one of the counter ions for such divalent alkali earth ions can be an ionized form of a compound as described herein and the other a typical counter ion such as chloride, or two ionized compounds can serve as counter ions for such divalent alkali earth ions, or a doubly ionized compound can serve as the counter ion for such divalent alkali earth ions). As specific examples, —N($R^{80}$)$_2$ is meant to include —NH$_2$, —NH-alkyl, —NH-pyrrolidin-3-yl, N-pyrrolidinyl, N-piperazinyl, 4N-methyl-piperazin-1-yl, N-morpholinyl and the like.

Substituent groups for replacing hydrogens on unsaturated carbon atoms in groups containing unsaturated carbons are, unless otherwise specified, —$R^{60}$, halo, —O$^-$M$^+$, —OR$^{70}$, —SR$^{70}$, —S$^-$M$^+$, —N($R^{80}$)$_2$, perhaloalkyl, —CN, —OCN, —SCN, —NO, —NO$_2$, —N$_3$, —SO$_2$R$^{70}$, —SO$_3^-$M$^+$, —SO$_3$R$^{70}$, —OSO$_2$R$^{70}$, —OSO$_3^-$M$^+$, —OSO$_3$R$^{70}$, —PO$_3^{-2}$(M$^+$)$_2$, —PO$_3^{-2}$M$^{2+}$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)N(R$^{70}$)$_2$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR)N(R$^{80}$)$_2$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

Substituent groups for replacing hydrogens on nitrogen atoms in groups containing such nitrogen atoms are, unless otherwise specified, —$R^{60}$, —O$^-$M$^+$, —OR$^{70}$, —SR$^{70}$, —S$^-$M$^+$, —N(R$^{80}$)$_2$, perhaloalkyl, —CN, —NO, —NO$_2$, —S(O)$_2$R$^{70}$, —SO$_3$M$^+$, —SO$_3$R$^{70}$, —OS(O)$_2$R$^{70}$, —OSO$_3^-$M$^+$, —OSO$_3$R$^{70}$, —PO$_3^{2-}$(M$^+$)$_2$, —PO$_3^{2-}$M$^{2+}$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$, R$^{70}$, R$^{80}$ and M$^+$ are as previously defined.

In one embodiment, a group that is substituted has 1, 2, 3, or 4 substituents, 1, 2, or 3 substituents, 1 or 2 substituents, or 1 substituent.

It is understood that in all substituted groups, polymers arrived at by defining substituents with further substituents to themselves (for example, substituted aryl having a substituted aryl group as a substituent which is itself substituted with a substituted aryl group, which is further substituted by a substituted aryl group, etc.) are not intended for inclusion herein. In such case that the language permits such multiple substitutions, the maximum number of such iterations of substitution is three.

"Sulfonamide" refers to the group —SO$_2$NH$_2$, —N(H)SO$_2$H, —N(H)SO$_2$alkyl, —N(H)SO$_2$aryl, or —N(H)SO$_2$heterocyclyl.

"Sulfonyl" refers to the group —SO$_2$H, —SO$_2$alkyl, —SO$_2$aryl, —SO$_2$heterocyclyl, —SO$_2$arylalkyl or —SO$_2$heterocyclylalkyl.

"Sulfanyl" refers to the group: —SH, —S-alkyl, —S-aryl, —S-heterocyclyl, —S-arylalkyl or —S-heterocyclylalkyl.

"Sulfinyl" refers to the group: —S(O)H, —S(O)alkyl, —S(O)aryl, —S(O)heterocyclyl, —S(O)-arylalkyl or —S(O)-heterocyclylalkyl.

"Suitable leaving group" is defined as the term would be understood by one of ordinary skill in the art; that is, a group on a carbon, where upon reaction a new bond is to be formed, the carbon loses the group upon formation of the new bond. A typical example employing a suitable leaving group is a nucleophilic substitution reaction, for example, on a sp$^3$ hybridized carbon (SN$_2$ or SN$_1$), for example where the leaving group is a halide, such as a bromide, chloride, fluoride or iodide, the reactant might be the corresponding benzyl halide. Another typical example of such a reaction is a nucleophilic aromatic substitution reaction (SNAr). Another example is an insertion reaction (for example by a transition metal) into the bond between an aromatic reaction partner bearing a leaving group followed by reductive coupling. "Suitable leaving group" is not limited to such mechanistic restrictions. Examples of suitable leaving groups include halogens, optionally substituted aryl or alkyl sulfonates, phosphonates, azides and —S(O)$_{0-2}$R where R is, for example optionally substituted alkyl, optionally substituted aryl, or optionally substituted heteroaryl. Those of skill in the art of organic synthesis will readily identify suitable leaving groups to perform a desired reaction under different reaction.

"Stereoisomer" and "stereoisomers" refer to compounds that have the same atomic connectivity but different atomic arrangement in space. Stereoisomers include cis-trans isomers, E and Z isomers, enantiomers and diastereomers. Compounds as described herein, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)-for amino acids. The present invention is meant to include all such possible isomers, as well as their racemic and optically pure forms. Optically active (+) and (−), (R)- and (S)-, or (D)- and (L)-isomers can be prepared using chiral synthons, chiral reagents, or resolved using conventional techniques, such as by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer can be synthesized by asymmetric synthesis using optically active reagents, substrates, catalysts or solvents, or by converting one enantiomer to the other by asymmetric transformation. For a mixture of enantiomers, enriched in a particular enantiomer, the major component enantiomer can be further enriched (with concomitant loss in yield) by recrystallization.

When the compounds described herein contain olefinic double bonds or other centers of geometric asymmetry, and unless specified otherwise, it is intended that the compounds include both E and Z geometric isomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible and contemplated herein.

"Meta" for the purposes of this invention refers to the position of a substituent on a phenyl or a six-membered heteroaryl ring relative to another substituent on the ring; the relative position being 1,3-substitution. That is, starting from one substituent as being attached to a first atom of the six-membered ring and, counting atoms inclusive of the first atom, another substituent is on atom 3 of the six-membered ring, the substituents' relative orientation about the six-membered ring is "meta." For example compound J, depicted below, has a methyl group "meta" to N2 of the pyrimidinediamine; compounds K1 and K2 also have a methyl group "meta" to N2 of the pyrimidinediamine. Thus, in some instances, rather than using specific ring atom numbering, the term "meta" is used. In such instances both meta isomers are meant to be included.

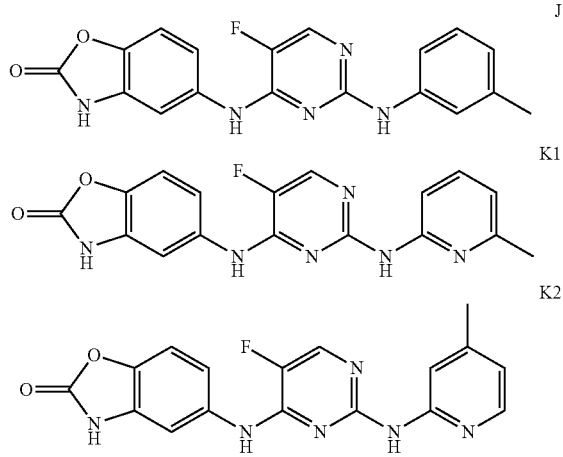

"Para" for the purposes of this invention refers to the position of a substituent on a phenyl or a six-membered heteroaryl ring relative to another substituent on the ring; the relative position being 1,4-substitution. That is, starting from one substituent as being attached to a first atom of the six-membered ring and, counting atoms inclusive of the first atom, another substituent is on atom 4 of the six-membered ring, the substituents' relative orientation about the six-membered ring is "para." For example compound L, depicted below, has a methyl group "para" to N2 of the pyrimidinediamine; compound M also has a methyl group "para" to N2 of the pyrimidinediamine. Thus, in some instances, rather than using specific ring atom numbering, the term "para" is used.

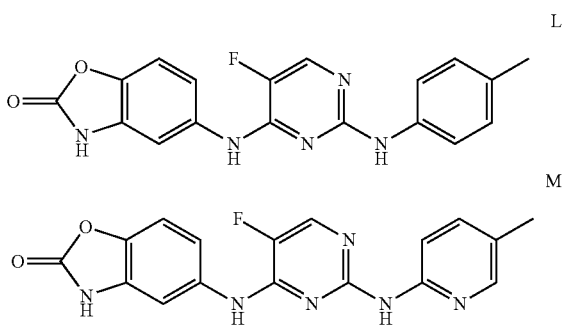

"Patient" or "Subject" refers to mammals and other animals, particularly humans. Thus the methods are applicable to both human therapy and veterinary applications. In one embodiment the patient or subject is a mammal. In another embodiment the patient or subject is a human.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, for example, inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, benzene sulfonic acid, salicylic acid, xinafoic acid (1-hydroxy-2-naphthoic acid), pamoic acid (also called embonic acid or 4,4'-methylenebis (3-hydroxy-2-naphthoic acid) and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts of the presently disclosed compounds can be derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, 2-amino-2-hydroxymethyl-propane-1,3-diol ("Tris" salt), dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like (See, for example, S. M. Berge, et al., "Pharmaceutical Salts," J. Pharm. Sci., 1977; 66:1-19 which is incorporated herein by reference.)

"Pharmaceutically effective amount" and "therapeutically effective amount" refer to an amount of a compound sufficient to treat a specified disorder or disease or one or more of its symptoms and/or to prevent the occurrence of the disease or disorder. The amount of a compound which constitutes a "therapeutically effective amount" will vary depending on the compound, the disease state and its severity, the age of the patient to be treated, and the like. The therapeutically effective amount can be determined routinely by one of ordinary skill in the art.

"Prodrug" refers to compounds that are transformed in vivo to yield the parent compound, for example, by hydrolysis in the gut or enzymatic conversion in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) where the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention can be prepared according to conventional methods. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8th Ed., Pergamon Press, Gilman et al. (eds), 1990 which is herein incorporated by reference). The metabolite of a compound described herein or its salt can itself be a biologically active compound in the body. While a prodrug described herein would meet this criteria, that is, form a described biologically active parent compound in vivo, "metabolite" is meant to encompass those compounds not contemplated to have lost a progroup, but rather all other compounds that are formed in vivo upon administration of a compound as described herein which retain the biological activities described herein. Thus one aspect disclosed 2,4-pyrimidine diamine compounds specifically contemplated herein is a metabolite of a compound described herein. For example, a biologically active metabolite is discovered serendipitously, that is, no prodrug design per se was undertaken. Stated another way, biologically active compounds inherently formed as a result of practicing methods as described herein, are contemplated and disclosed herein. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. The compounds described herein can exist in unsolvated as well as solvated forms with solvents, pharmaceutically acceptable or not, such as water, ethanol, and the like. Solvated forms of the presently disclosed compounds are contemplated herein and are encompassed by the invention, at least in generic terms.

"Treating" or "treatment" as used herein covers the treatment of the disease or condition of interest in a mammal, preferably a human, having the disease or condition of interest, and includes:
(i) preventing the disease or condition from occurring in a mammal, in particular, when such mammal is predisposed to the condition but has not yet been diagnosed as having it;
(ii) inhibiting the disease or condition, for example, arresting or slowing its development;
(iii) relieving the disease or condition, for example, causing regression of the disease or condition or a symptom thereof; or
(iv) stabilizing the disease or condition.

As used herein, the terms "disease" and "condition" can be used interchangeably or can be different in that the particular malady or condition may not have a known causative agent (so that etiology has not yet been worked out) and it is therefore not yet recognized as a disease but only as an undesirable condition or syndrome, where a more or less specific set of symptoms have been identified by clinicians.

Similarly, it is understood that the above definitions are not intended to include impermissible substitution patterns (for example, methyl substituted with 5 fluoro groups). Such impermissible substitution patterns are easily recognized by a person having ordinary skill in the art.

Compounds and Compositions

Disclosed herein are novel 2,4-pyrimidinediamine compounds, prodrugs of the compounds, methods of making the compounds, and methods of using these compounds in the treatment of conditions in which targeting of the JAK pathway or modulation, including inhibition, of JAK kinases, particularly JAK3, are therapeutically useful. These conditions include, but are not limited to, leukemia, lymphoma, transplant rejection (for example, pancreas islet transplant rejection, heart transplant rejection, kidney transplant rejection, liver transplant rejection, lung transplant rejection), bone marrow transplant applications (for example, graft-versus-host disease), autoimmune diseases (for example, diabetes), and inflammation (for example, asthma, allergic reactions, ocular disorders). Given the severity and prevalence of these diseases and conditions, new therapies are needed.

Compounds

The compounds, and salts thereof, described herein are generally pyrimidine 2,4-diamines, substituted at the 5-position with various groups; substituted at the 2-amine with various optionally substituted aromatic groups; and substituted at the 4-amine with one of a benzo[d]oxazol-2(3H)-one, a 1H-benzo[d]imidazol-2(3H)-one, a benzo[d]thiazol-2(3H)-one, a benzo[d][1,3]dithiol-2-one, a benzo[d][1,3]oxathiol-2-one, a benzo[d][1,3]dioxol-2-one, a [1,3]oxathiolo[4,5-b]pyridin-2-one, a thiazolo[5,4-b]pyridin-2(1H)-one, a oxazolo[5,4-b]pyridin-2(1H)-one, a [1,3]oxathiolo[5,4-b]pyridin-2-one, a thiazolo[4,5-b]pyridin-2(3H)-one, a oxazolo[4,5-b]pyridin-2(3H)-one, a [1,3]dioxolo[4,5-b]pyridin-2-one, a [1,3]dithiolo[4,5-b]pyridin-2-one, a 1H-imidazo[4,5-b]pyridin-2(3H)-one, a [1,3]oxathiolo[4,5-b]pyrazin-2-one, a thiazolo[5,4-b]pyrazin-2(3H)-one, a oxazolo[5,4-b]pyrazin-2(3H)-one, a [1,3]dioxolo[4,5-b]pyrazin-2-one, a [1,3]dithiolo[4,5-b]pyrazin-2-one and a 1H-imidazo[4,5-b]pyrazin-2(3H)-one; each optionally substituted with one or more groups including prodrug moieties as described herein. Besides the groups described above, the N2- and N4-amines of the pyrimidinediamine system may also have optionally substituted alkyl groups and/or prodrug groups.

More specifically, the compounds are described in terms of formula I:

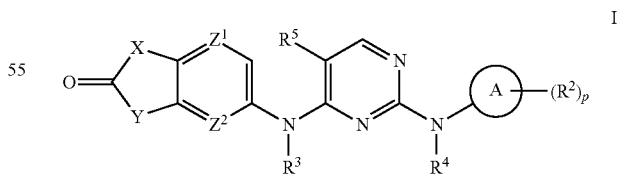

where:
X and Y are each independently O, S, S(O), SO$_2$ or NR$^1$;
each R$^1$ is independently for each occurrence H, optionally substituted C$_{1-6}$alkyl, C(O)—C$_{1-6}$alkyl, CO$_2$—C$_{1-6}$alkyl or R$^{50}$;
each R$^{50}$ is —C(R$^9$)$_2$-A-R$^{10}$, where A is O or S; each R$^9$ is independently for each occurrence H, optionally substituted $C_{1-6}$alkyl, optionally substituted $C_{6-10}$aryl or optionally substituted $C_{7-16}$arylalkyl; or alternatively, two $R^9$, together with the carbon to which they are attached, form an optionally substituted $C_{3-8}$cycloalkyl group or an optionally substituted 3-8 membered heteroalicyclyl; $R^{10}$ is $R^a$, —P(O)(OR$^{11}$)$_2$, —P(O)(OR$^{11}$)N(R$^{12}$)$_2$ or —P(O)(N(R$^{12}$)$_2$)$_2$; each $R^{11}$ is independently for each occurrence $R^a$ or a monovalent cationic group; or two $R^{11}$, together with the atoms to which they are attached, form a 4-8 membered cyclic phosphate group, or two $R^{11}$ together represent a divalent cationic group; each $R^{12}$ is independently for each occurrence $R^c$ or —C$_{1-3}$alkyl-N(R$^c$)$_2$; or two $R^{12}$, each on separate nitrogens of —P(O)(N(R$^{12}$)$_2$)$_2$, together with the atoms to which they are attached, form a 4-8 membered cyclic phosphonic acid bisamide group; or one $R^{12}$ along with $R^{11}$, of the group —P(O)(OR$^{11}$)N(R$^{12}$)$_2$, together with the atoms to which they are attached, form a 4-8 membered cyclic phosphonamidate group;

ring A is a $C_{6-10}$aryl or a 5-10 membered heteroaryl;

each $R^2$ is independently for each occurrence H, $R^e$, $R^b$, $R^e$ substituted with one or more of the same or different $R^a$ and/or $R^b$, —OR$^e$ substituted with one or more of the same or different $R^a$ and/or $R^b$, —SR$^e$ substituted with one or more of the same or different $R^a$ and/or $R^b$, —C(O)R$^e$ substituted with one or more of the same or different $R^a$ and/or $R^b$, —N(R$^a$)R$^e$ where R$^e$ is substituted with one or more of the same or different $R^a$ and/or $R^b$, —S(O)$_2$R$^e$ substituted with one or more of the same or different $R^a$ and/or $R^b$, —N(R$^a$)—S(O)$_2$R$^e$ where R$^e$ is substituted with one or more of the same or different $R^a$ and/or $R^b$, —B(OR$^a$)$_2$, —B(N(R$^c$)$_2$)$_2$, —(C(R$^a$)$_2$)$_m$—R$^b$, —O—(C(R$^a$)$_2$)$_m$—R$^b$, —S—(C(R$^a$)$_2$)$_m$—R$^b$, —O—(C(R$^b$)$_2$)$_m$—R$^a$, —N(R$^a$)—(C(R$^a$)$_2$)$_m$—R$^b$, —O—(CH$_2$)$_m$—CH((CH$_2$)$_m$R$^b$)R$^b$, —C(O)N(R$^a$)—(C(R$^a$)$_2$)$_m$R$^b$, —(C(R$^a$)$_2$)$_m$—C(O)N(R$^a$)—(C(R$^a$)$_2$)$_m$—R$^b$, —N((C(R$^a$)$_2$)$_m$R$^b$)$_2$, —S—(C(R$^a$)$_2$)$_m$—C(O)N(R$^a$)—(C(R$^a$)$_2$)$_m$—R$^b$, —N(R$^a$)—C(O)—N(R$^a$)—(C(R$^a$)$_2$)$_m$—R$^b$, —N(R$^a$)—C(O)—(C(R$^a$)$_2$)$_m$—C(R$^a$)(R$^b$)$_2$ or —N(R$^a$)—(C(R$^a$)$_2$)—C(O)—N(R$^a$)—(C(R$^a$)$_2$)—R$^b$;

each $R^a$ is independently for each occurrence H, deuterium, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;

each $R^b$ is independently for each occurrence =O, —OR$^a$, —O—(C(R$^a$)$_2$)$_m$—OR$^a$, haloC$_{1-3}$alkyloxy, =S, —SR$^a$, =NR$^a$, =NOR$^a$, —N(R$^c$)$_2$, halo, —CF$_3$, —CN, —NC, —OCN, —SCN, —NO, —NO$_2$, =N$_2$, —N$_3$, —S(O)R$^a$, —S(O)$_2$R$^a$, —SO$_3$R$^a$, —S(O)N(R$^c$)$_2$, —S(O)$_2$N(R$^c$)$_2$, —OS(O)R$^a$, —OS(O)$_2$R$^a$, —OSO$_3$R$^a$, —OS(O)$_2$N(R$^c$)$_2$, —C(O)R$^a$, —CO$_2$R$^a$, —C(O)N(R$^c$)$_2$, —C(NR$^a$)—N(R$^c$)$_2$, —C(NOH)—R$^a$, —C(NOH)—N(R$^c$)$_2$, —OC(O)R$^a$, —OC(O)OR$^a$, —OC(O)N(R$^c$)$_2$, —OC(NH)—N(R$^c$)$_2$, —OC(NR$^a$)—N(R$^c$)$_2$, —N(R$^a$)—S(O)$_2$H, —[N(R$^a$)C(O)]$_n$R$^a$, —[N(R$^a$)C(O)]$_n$OR$^a$, —[N(R$^a$)C(O)]$_n$N(R$^c$)$_2$ or —[N(R$^a$)C(NR$^a$)]$_n$—N(R$^c$)$_2$;

each $R^c$ is independently for each occurrence R$^a$, or, alternatively, two R$^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;

each $R^d$ is =O, —OR$^a$, haloC$_{1-3}$alkyloxy, C$_{1-6}$alkyl, =S, —SR$^a$, =NR$^a$, =NOR$^a$, —N(R$^a$)$_2$, halo, —CF$_3$, —CN, —NC, —OCN, —SCN, —NO, —NO$_2$, =N$_2$, —N$_3$, —S(O)R$^a$, —S(O$_2$)R$^a$, —SO$_3$R$^a$, —S(O)N(R$^a$)$_2$, —S(O)$_2$N(R$^a$)$_2$, —OS(O)R$^a$, —OS(O)$_2$R$^a$, —OSO$_3$R$^a$, —OS(O)$_2$N(R$^a$)$_2$, —C(O)R$^a$, —CO$_2$R$^a$, —C(O)N(R$^a$)$_2$, —C(NR$^a$)N(R$^a$)$_2$, —C(NOH)R$^a$, —C(NOH)N(R$^a$)$_2$, —OCO$_2$R$^a$, —OC(O)N(R$^a$)$_2$, —OC(NR$^a$)N(R$^a$)$_2$, —[N(R$^a$)C(O)]$_n$R$^a$, —(C(R$^a$)$_2$)$_n$—OR$^a$, —N(R$^a$)—S(O)$_2$R$^a$, —C(O)—C$_{1-6}$haloalkyl, —S(O)$_2$C$_{1-6}$haloalkyl, —OC(O)R$^a$, —O(C(R$^a$)$_2$)$_m$—OR$^a$, —S(C(R$^a$)$_2$)$_m$—OR$^a$, —N(R$^a$)C$_{1-6}$haloalkyl, —P(O)(OR$^a$)$_2$, —N(R$^a$)—(C(R$^a$)$_2$)$_m$—OR$^a$, —[N(R$^a$)C(O)]$_n$OR$^a$, —[N(R$^a$)C(O)]$_n$N(R$^a$)$_2$, —[N(R$^a$)C(NR$^a$)]$_n$N(R$^a$)$_2$ or —N(R$^a$)C(O)C$_{1-6}$haloalkyl; two R$^d$, taken together with the atom or atoms to which they are attached, combine to form a 3-10 membered partially or fully saturated mono or bicyclic ring, optionally containing one or more heteroatoms and optionally substituted with one or more R$^a$;

each $R^e$ is independently for each occurrence C$_{1-6}$alkyl, C$_{3-8}$cycloalkyl, C$_{4-11}$ cycloalkylalkyl, C$_{6-10}$aryl, C$_{7-16}$arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;

p is 0, 1, 2, 3 or 4;

each m is 1, 2 or 3;

each n is 0, 1, 2 or 3;

two $R^2$ groups, taken together with the atom or atoms to which they are attached, combine to form a 4-10 membered partially or fully saturated mono or bicyclic ring, optionally containing one or more heteroatoms and optionally substituted with one or more R$^a$ and/or R$^b$;

$Z^1$ and $Z^2$ are each independently CH, CR$^2$ or N;

$R^3$ is H, optionally substituted $C_{1-6}$alkyl or R$^{50}$;

$R^4$ is H, optionally substituted $C_{1-6}$alkyl or R$^{50}$; and $R^5$ is H, halo, —CN, optionally substituted $C_{1-6}$alkyl, alkynyl, hydroxy, optionally substituted $C_{1-6}$alkoxy, nitro, —N(R$^a$)$_2$, —C(O)N(R$^a$)$_2$, —CO$_2$R$^a$ or —C(O)R$^a$.

In one embodiment, structural formula I includes compounds where ring A is a phenyl or a pyridyl substituted with one or more groups. In one embodiment, ring A is a phenyl with at least one group para to N2 of the pyrimidinediamine. In another embodiment, ring A is a pyridyl with at least one group para to N2 of the pyrimidinediamine. In a more specific embodiment, ring A is a pyridin-3-yl (where N2 of the pyrimidinediamine is at the 3-yl position) with at least one group para to N2 of the pyrimidinediamine. In another more specific embodiment, ring A is a pyridin-2-yl (where N2 of the pyrimidinediamine is at the 2-yl position) with at least one group para to N2 of the pyrimidinediamine. In other embodiments, one or two meta groups can replace or augment the para group of the above described embodiments. In all of the above embodiments, the groups at the para and/or meta positions can include nitrogen, for example an optionally substituted amine, either directly attached to ring A or in some embodiments tethered to ring A via an alkylene. Such optionally substituted amines include those defined by —N(R$^c$)$_2$ as in relation to formula I. In a specific embodiment, an optionally substituted amine is tethered to ring A via a C$_{1-6}$alkylene. In an even more specific embodiment, the optionally substituted amine is tethered to ring A via a C$_{1-3}$alkylene and the amine, —N(R$^c$)$_2$ as in relation to formula I, is itself substituted with a —N(R$^c$)$_2$ group.

As mentioned, certain presently disclosed compounds have structural formula I where ring A is a phenyl substituted with one or more R$^2$ groups. Thus, in one embodiment, disclosed compounds have formula IA:

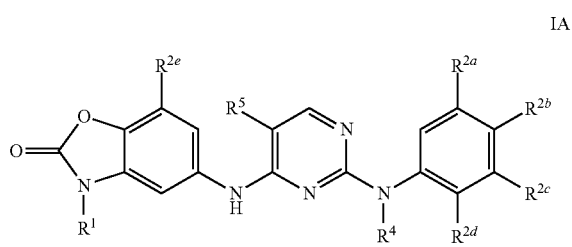

IA where the variables are as described with respect to formula I, and further: R$^1$ is H, optionally substituted C$_{1-6}$alkyl or R$^{50}$; each of R$^{2a}$, R$^{2b}$, R$^{2c}$, R$^{2d}$ and R$^{2e}$ is independently for each occurrence as defined for R$^2$; and R$^5$ is H, halo, —CN, optionally substituted C$_{1-6}$alkyl, nitro, —N(R$^a$)$_2$, —C(O)N(R$^a$)$_2$, —CO$_2$R$^a$ or —C(O)R$^a$. In one embodiment, R$^{2e}$ is halo or optionally substituted C$_{1-6}$alkyl. In another embodiment, R$^{2e}$ is halo or methyl. In another embodiment, R$^{2e}$ is F or methyl.

In one embodiment, R$^{2e}$ and R$^4$ are both H. One such embodiment is a compound of formula IB:

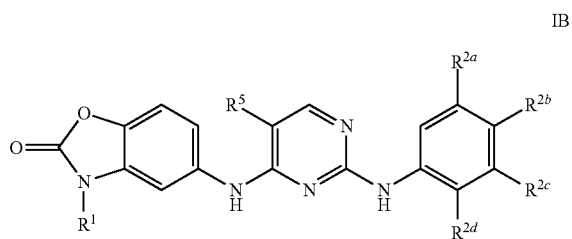

IB where R$^1$ is H or R$^{50}$; each of R$^{2a}$, R$^{2b}$, R$^{2c}$ and R$^{2d}$ is independently for each occurrence as defined for R$^2$ in formula I; and R$^5$ is H, halo, —CN, C$_{1-6}$alkyl, nitro, —N(R$^a$)$_2$, —C(O)N(R$^a$)$_2$, —CO$_2$R$^a$ or —C(O)R$^a$. In one embodiment, R$^5$ is H, halo, —CN, C$_{1-6}$alkyl, nitro, —C(O)N(R$^a$)$_2$, —CO$_2$R$^a$ or —C(O)R$^a$. In another embodiment, R$^5$ is H, halo or C$_{1-6}$alkyl. In another embodiment, R$^5$ is H, halo or methyl. In another embodiment, R$^5$ is halo or methyl. In yet another embodiment, R$^5$ is F or CH$_3$. In yet another embodiment, R$^5$ is CH$_3$.

In one embodiment of the compounds of formula IB as described above, each of R$^{2a}$, R$^{2b}$ and R$^{2c}$ is independently H, C$_{1-6}$alkyl, —OC$_{1-6}$alkyl, —OCF$_3$, —N(H)C$_{1-6}$alkyl, —N(C$_{1-6}$alkyl)$_2$, halo, —OCF$_2$H, —OCH$_2$F, —CF$_3$, —CN, —C(O)R$^a$, —CO$_2$R$^a$, —C(O)N(R$^c$)$_2$, —O(C(R$^a$)$_2$)$_m$—R$^b$ or —(C(R$^a$)$_2$)$_m$—R$^b$; and R$^{2d}$ is H or F; where at least one of R$^{2a}$, R$^{2b}$ and R$^{2c}$ is not H. In another embodiment, each of R$^{2a}$, R$^{2b}$ and R$^{2c}$ is independently H, C$_{1-4}$alkyl, —OC$_{1-4}$alkyl, —OCF$_3$, —N(H)C$_{1-4}$alkyl, —N(C$_{1-4}$alkyl)$_2$, halo, —OCF$_2$H, —OCH$_2$F, —CF$_3$, —CN, —C(O)H, —C(O)C$_{1-4}$alkyl, —CO$_2$R$^a$, —C(O)N(R$^c$)$_2$, —O(CH$_2$)$_2$—OR$^a$ or —(CH$_2$)$_{1-2}$—R$^b$; and R$^{2d}$ is H or F; where at least one of R$^{2a}$, R$^{2b}$ and R$^{2c}$ is not H. In another embodiment, each of R$^{2a}$, R$^{2b}$ and R$^{2c}$ is independently H, C$_{1-2}$alkyl, —OC$_{1-2}$alkyl, —OCF$_3$, —N(H)C$_{1-2}$alkyl, —N(C$_{1-2}$alkyl)$_2$, halo, —OCF$_2$H, —OCH$_2$F, —CF$_3$, —CN, —CO$_2$R$^a$, —C(O)N(R$^c$)$_2$, —O(CH$_2$)$_2$—OC$_{1-2}$alkyl or —(CH$_2$)$_{1-2}$—OH; and R$^{2d}$ is H or F; where at least one of R$^{2a}$, R$^{2b}$ and R$^{2c}$ is not H. In yet another embodiment, each of R$^{2a}$, R$^{2b}$ and R$^{2c}$ is independently C$_{1-2}$alkyl, —OC$_{1-2}$alkyl, —OCF$_3$, —N(H)C$_{1-2}$alkyl, —N(C$_{1-2}$alkyl)$_2$, halo, —OCF$_2$H, —OCH$_2$F, —CF$_3$, —CN, —CO$_2$R$^a$, —C(O)N(R$^c$)$_2$, —O(CH$_2$)$_2$—OC$_{1-2}$alkyl or —(CH$_2$)$_{1-2}$—OH; and R$^{2d}$ is H or F; where at least one of R$^{2a}$, R$^{2b}$ and R$^{2c}$ is not H. In another embodiment, each of R$^{2a}$, R$^{2b}$ and R$^{2c}$ is independently CH$_3$, —OCH$_3$, —OCF$_3$, —N(H)C$_{1-2}$alkyl, —N(C$_{1-2}$alkyl)$_2$, halo or —CF$_3$; and R$^{2d}$ is H or F; where at least one of R$^{2a}$, R$^{2b}$ and R$^{2c}$ is not H. In another embodiment, each of R$^{2a}$, R$^{2b}$ and R$^{2c}$ is independently CH$_3$, —OCH$_3$, —OCF$_3$, —N(H)C$_{1-2}$alkyl, —N(C$_{1-2}$alkyl)$_2$, halo or —CF$_3$; and R$^{2d}$ is H or F; where at least one of R$^{2a}$, R$^{2b}$ and R$^{2c}$ is not H.

For each of the above-described embodiments for compounds of formula IB, there are embodiments where: 1) R$^{2a}$ is H, and R$^{2b}$ and R$^{2c}$ are each independently one of the described non-H groups, 2) R$^{2b}$ is H, and R$^{2a}$ and R$^{2c}$ are each independently one of the described non-H groups, 3) R$^{2c}$ is H, and R$^{2a}$ and R$^{2b}$ are each independently one of the described non-H groups, 4) R$^{2a}$ and R$^{2b}$ are H, and R$^{2c}$ is one of the described non-H groups, 5) 4) R$^{2a}$ and R$^{2c}$ are H, and R$^{2b}$ is one of the described non-H groups, 6) 4) R$^{2b}$ and R$^{2c}$ are H, and R$^{2b}$ is one of the described non-H groups, 7) R$^{2a}$, R$^{2b}$ and R$^{2c}$ are each independently one of the described non-H groups.

In accord with embodiment 1) above, one embodiment is a compound where R$^{2a}$ is H; R$^{2b}$ is C$_{1-3}$alkyl, F or —OC$_{1-3}$alkyl; R$^{2c}$ is —OC$_{1-3}$alkyl; and R$^{2d}$ is H or F. In accord with embodiment 1) above, one embodiment is a compound where R$^{2a}$ is H; R$^{2b}$ is C$_{1-3}$ alkyl; R$^{2c}$ is —OC$_{1-3}$alkyl; and R$^2$ is H or F. In accord with embodiment 1) above, one embodiment is a compound where R$^{2a}$ is H; R$^{2b}$ is C$_{1-3}$alkyl; R$^2$ is —OC$_{1-3}$alkyl; and R$^2$ is F. In accord with embodiment 1) above, one embodiment is a compound where R$^{2a}$ is H; R$^{2b}$ is CH$_3$; R$^{2c}$ is —OCH$_3$; and R$^{2d}$ is F. In accord with embodiment 1) above, one embodiment is a compound where R$^{2a}$ is H; R$^{2b}$ is —OC$_{1-3}$alkyl; R$^{2c}$ is —OC$_{1-3}$alkyl; and R$^{2d}$ is H or F. In accord with embodiment 1) above, one embodiment is a compound where R$^{2a}$ is H; R$^{2b}$ is —OC$_{1-3}$alkyl; R$^{2c}$ is —OC$_{1-3}$alkyl; and R$^{2d}$ is F. In accord with embodiment 1) above, one embodiment is a compound where R$^{2a}$ is H; R$^{2b}$ is —OCH$_3$; R$^{2c}$ is —OCH$_3$; and R$^{2d}$ is F.

In accord with embodiment 7) above, one embodiment is a compound where R$^{2a}$, R$^{2b}$ and R$^{2c}$ are each independently CH$_3$, —OCH$_3$, or F; and R$^{2d}$ is H or F. In accord with embodiment 7) above, one embodiment is a compound where two of R$^{2a}$, R$^{2b}$ and R$^{2c}$ are CH$_3$; the other of R$^{2a}$, R$^{2b}$ and R$^{2c}$ is F; and R$^{2d}$ is H or F. In accord with embodiment 7) above, one embodiment is a compound where two of R$^{2a}$, $R^{2b}$ and $R^{2c}$ are $CH_3$; the other of $R^{2a}$, $R^{2b}$ and $R^{2c}$ is —$OCH_3$; and $R^{2d}$ is H or F. In accord with embodiment 7) above, one embodiment is a compound where two of $R^{2a}$, $R^{2b}$ and $R^{2c}$ are —$OCH_3$; the other of $R^{2a}$, $R^{2b}$ and $R^{2c}$ is F; and $R^2$ is H or F. In accord with embodiment 7) above, one embodiment is a compound where two of $R^{2a}$, $R^{2b}$ and $R^{2c}$ are —$OCH_3$; the other of $R^{2a}$, $R^{2b}$ and $R^{2c}$ is $CH_3$; and $R^{2d}$ is H or F. In accord with embodiment 7) above, one embodiment is a compound where one of $R^{2a}$, $R^{2b}$ and $R^{2c}$ is $CH_3$; one of $R^{2a}$, $R^{2b}$ and $R^{2c}$ is —$OCH_3$; and one of $R^{2a}$, $R^{2b}$ and $R^{2c}$ is F; and $R^{2d}$ is H or F.

Another embodiment is a compound according to formula IB, where two of $R^{2a}$, $R^{2b}$ and $R^{2c}$ are each independently H, $C_{1-6}$alkyl, —$OC_{1-6}$alkyl, —$OCF_3$, halo, —$OCF_2H$, —$OCH_2F$, —$CF_3$, —CN, —$O(C(R^a)_2)_m$—$R^b$ or —$(C(R^a)_2)_m$—$R^b$; one of $R^{2a}$, $R^{2b}$ and $R^{2c}$ is:

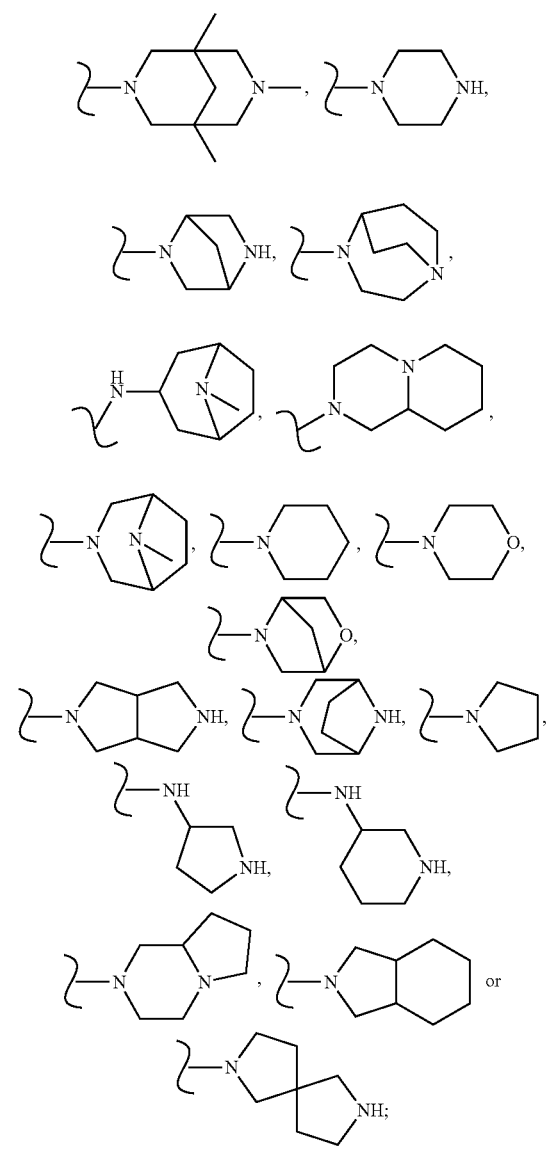

optionally substituted with one or more of the same or different $R^a$ and/or $R^b$ groups; and $R^{2d}$ is H or F. Another embodiment is a compound according to formula IB, where two of $R^{2a}$, $R^{2b}$ and $R^{2c}$ are each independently H, $C_{1-6}$alkyl, —$OC_{1-6}$alkyl, —$OCF_3$, halo, —$OCF_2H$, —$OCH_2F$, —$CF_3$, —CN, —$O(C(R^a)_2)_m$—$R^b$ or —$(C(R^a)_2)_m$—$R^b$; one of $R^{2a}$, $R^{2b}$ and $R^{2c}$ is:

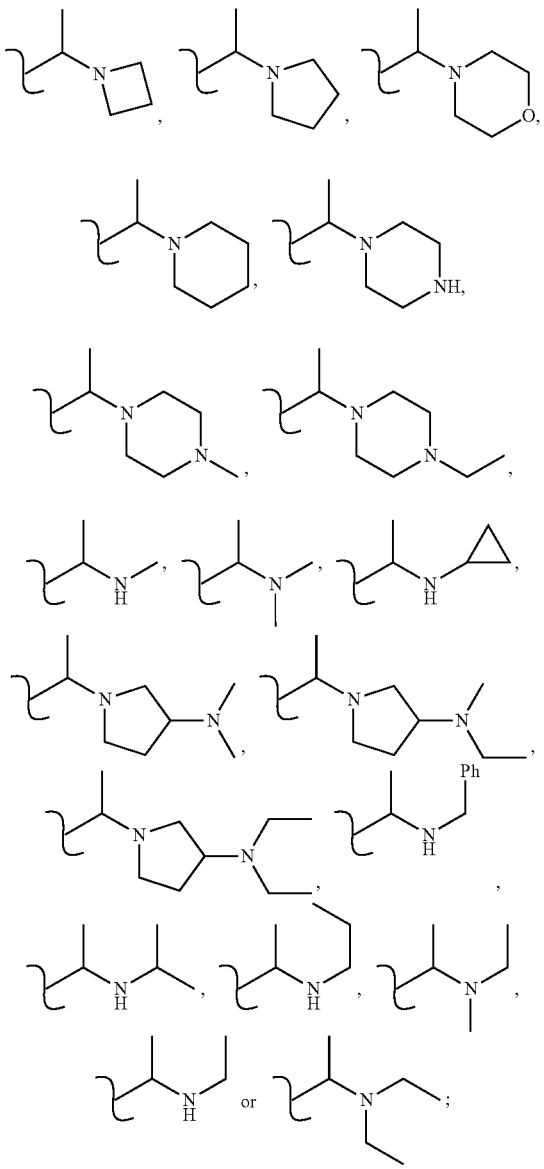

optionally substituted with one or more of the same or different $R^a$ and/or $R^b$ groups, and $R^{2d}$ is H or F.

Another embodiment is a compound according to formula IB, where two of $R^{2a}$, $R^{2b}$ and $R^{2c}$ are each independently H, $C_{1-6}$alkyl, —$OC_{1-6}$alkyl, —$OCF_3$, halo, —$OCF_2H$, —$OCH_2F$, —$CF_3$, —CN, —$O(C(R^a)_2)_m$—$R^b$ or —$(C(R^a)_2)_m$—$R^b$; one of $R^{2a}$, $R^{2b}$ and $R^{2c}$ is a water-solubilizing group; and $R^{2d}$ is H or F. A water-solubilizing group is a group that has hydrophilic character sufficient to improve or increase the water-solubility of the compound in which it is included, as compared to an analog compound that does not include the group. The hydrophilic character can be achieved by, for example, the inclusion of functional groups that ionize under the conditions of use to form charged moieties (for example, carboxylic acids, sulfonic acids and salts, phosphoric acids and salts, amines, etc.); groups that include permanent charges (for example, quaternary ammonium groups); and/or heteroatoms or heteroatomic groups. For example, —O—(C(R$^a$)$_2$)$_m$—R$^b$, —S—(C(R$^a$)$_2$)$_m$—R$^b$, —O—(C(R$^b$)$_2$)$_m$—R$^a$, —N(R$^a$)—(C(R$^a$)$_2$)$_m$—R$^b$, —O—(CH$_2$)$_m$—CH((CH$_2$)$_m$R$^b$)R$^b$, —C(O)N(R$^a$)—(C(R$^a$)$_2$)$_m$—R$^b$ and —N((C(R$^a$)$_2$)$_m$R$^b$)$_2$. More specific examples include —O—C$_{1-6}$alkylene-R$^b$, —S—C$_{1-6}$alkylene-R$^b$, —O—C$_{1-6}$alkylene-R$^a$ where R$^a$ is heterocyclyl, —N(R$^a$)—C$_{1-6}$alkylene-R$^b$, —O—C$_{1-6}$alkylene-CH((CH$_2$)$_{1-2}$R$^b$)R$^b$, —C(O)N(R$^a$)—C$_{1-6}$alkylene-R$^b$ and —N((C(R$^a$)$_2$)$_{1-3}$R$^b$)$_2$. Even more specific examples include —O—C$_{1-4}$-alkylene-R$^b$, —S—C$_{1-4}$alkylene-R$^b$, —O—C$_{1-4}$alkylene-R$^a$ where R$^a$ is heterocyclyl, —N(H)—C$_{1-4}$-alkylene-R$^b$, —O—C$_{1-4}$alkylene-CH((CH$_2$)$_{1-2}$R$^b$)R$^b$, —C(O)N(H)—C$_{1-4}$alkylene-R$^b$ and —N((CH$_2$)$_{1-3}$R$^b$)$_2$. In another specific example, in accord with the formula given above for water-solubilizing groups, the water-solubilizing group is an amino acid tethered from the molecule via a bond to the nitrogen of the amino acid. In a more specific example, a water-solubilizing group is an α-amino acid or derivative thereof attached to the parent ring, e.g. ring A and/or at Z$^1$ or Z$^2$, via the nitrogen of the α-amino acid, for example —N(H)C(R$^a$)$_2$—R$^b$, where R$^b$ is —CO$_2$R$^a$ or —C(O)N(R$^c$)$_2$. In another specific embodiment, the water-solubilizing group is morpholino, piperidinyl, N—C$_{1-6}$alkyl piperidinyl, piperazinyl, N—C$_{1-6}$alkyl piperazinyl, pyrrolidinyl, N—C$_{1-6}$alkyl pyrrolidinyl, diazepinyl, N—C$_{1-6}$alkyl azepinyl, homopiperazinyl, N—C$_{1-6}$alkyl homopiperazinyl, imidazoyl, and the like. In another example the water-solubilizing group is one of the aforementioned rings tethered to the parent molecule via an alkylene, alkylidene, alkylidyne linker. In a more specific embodiment, the water-solubilizing group is one of the aforementioned rings tethered to the parent molecule via a C$_{1-6}$alkylene, where one or two of the alkylene carbons is, independently, replaced with one of O, S or NH, but not where any two of the aforementioned heteroatoms are contiguous in the linker. Other water solubilizing groups are well-known and include, by way of example, hydrophilic groups such as alkyl or heteroalicyclyl groups substituted with one or more of an amine, alcohol, a carboxylic acid, a phosphorous acid, a sulfoxide, a carbohydrate, a sugar alcohol, an amino acid, a thiol, a polyol, an ether, a thioether, and a quaternary amine salt.

Another embodiment is a compound in accord with formula I, of structural formula IC:

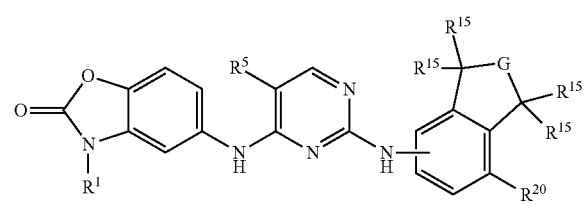

IC where R$^1$ is H or R$^{50}$; R$^5$ is H, halo, —CN, C$_{1-6}$alkyl, nitro, —N(R$^a$)$_2$, —C(O)N(R$^a$)$_2$, —CO$_2$R$^a$ or —C(O)R$^a$; R$^{20}$ is H or C$_{1-6}$alkyl; each R$^{15}$ is independently H or C$_{1-6}$alkyl, or two of R$^{15}$, together on the same carbon, are oxo; and G is O or NH. In another embodiment, R$^5$ is H, halo, —CN, C$_{1-6}$alkyl or nitro. In another embodiment, R$^5$ is H, halo or C$_{1-6}$alkyl. In another embodiment, R$^5$ is H, halo or methyl. In another embodiment, R$^5$ is halo or methyl. In yet another embodiment, R$^5$ is F or CH$_3$. In yet another embodiment, R$^5$ is CH$_3$.

For each of the above embodiments of the compounds of structural formulae I, IA, IB and IC, there is an embodiment where R$^1$ is H or R$^{50}$; R$^{50}$ is —CH$_2$OP(O)(OR$^{11}$)$_2$; and each R$^{11}$ is independently for each occurrence R$^a$ or a monovalent cationic group; or two R$^{11}$, together with the atoms to which they are attached, form a 4-8 membered cyclic phosphate group, or two R$^{11}$ together represent a divalent cationic group. Also, for each of these embodiments, there is a more specific embodiment where each R$^{11}$ is independently for each occurrence H, t-butyl, or a pharmaceutically acceptable cation, such as HOCH$_2$CH$_2$N(CH$_3$)$_3^+$, Na$^+$, Li$^+$ or K$^+$.

As mentioned, the 2,4-pyrimidinediamine compounds and prodrugs, as well as the salts thereof, can also be in the form of hydrates, solvates, and N-oxides, as is well-known in the art. One embodiment is a pharmaceutically acceptable salt form of a compound of formula I. The pharmaceutically acceptable salts of the present invention can be formed by conventional means, such as by reacting the free base form of the product with one or more equivalents of the appropriate acid in a solvent or medium in which the salt is insoluble or in a solvent such as water which is removed in vacuo, by freeze drying, or by exchanging the anions of an existing salt for another anion on a suitable ion exchange resin. The present invention includes within its scope solvates of the 2,4-pyrimidinediamine compounds and salts and hydrates thereof, for example, a hydrated formate salt.

One embodiment is a compound selected from Tables I and II, or a stereoisomer, tautomer, prodrug, solvate, or pharmaceutically acceptable salt thereof.

Many compounds described herein were made as the parent, at least one salt form or both parent and one or more salts. Some specific salts made, referred to by their designation from Tables I-II, include the arginine salt: compound I-130; the calcium salt: compound I-118; the Tris salt: compound I-132; dipotassium salt: compound I-136; the formate salt: compounds I-1, I-8, I-16, I-67, I-84 through I-87, I-157 through I-166, I-196, I-197, II-207 through I-209, II-4, II-5 and II-23 through II-25; the diformate salt: compounds II-2 and II-3; the monotrifluoroacetate salt: compounds I-2 through I-7, I-10, I-11; I-13 through I-15, I-18, I-20 through I-22, I-24, I-29, I-32, I-35 through I-45, I-47 through I-49, I-51, II-54 through I-61, II-64 through I-66, I-68, I-69, I-71 through I-83, I-109 through I-112, I-116, I-117, I-120 through I-127, I-129, I-167, I-168, I-171 through I-185, I-187 through I-195, I-198 through I-202, II-1, II-6, II-7 and II-26 through II-28; the ditrifluoroacetate salt: compounds I-89, I-90, I-95, I-97, I-103, I-104, I-169, I-170, I-186 and II-29 through II-31; the benzene sulfonic acid salt: compounds I-107, II-108, I-131 and I-146; the sulfuric acid salt: compounds I-114 and I-151; the hydrochloride salt: compound I-156; the disodium salt: compound I-115; the mesylate salt: compounds I-106 and I-137; the pamoic acid salt: compound I-135; and the lysine salt: compound I-216. With continued reference to Tables I and II, certain compounds illustrated as parent compounds were prepared as one or more salt forms as indicated in the foregoing paragraph and in the characterization details provided herein.

As is recognized by one of ordinary skill in the art, the present formulae include other salt forms in addition to those specifically described herein. Similarly, one of ordinary skill in the art would understand the presently disclosed formulae to encompass solvates, such as hydrates.

TABLE I

| Cpd | R¹ | R²ᵉ | R⁵ | R²ᵃ | R²ᵇ | R²ᶜ | R²ᵈ | R⁴ |
|---|---|---|---|---|---|---|---|---|
| I-1 | H | H | F | H | $CH_3$ | CN | H | H |
| I-2 | H | H | H | H | $C(O)NH_2$ | H | H | H |
| I-3 | H | H | H | H | H | $C(O)NH_2$ | H | H |
| I-4 | H | H | Cl | H | H | H | H | H |
| I-5 | H | H | Cl | H | $CH_3$ | $CH_3$ | H | H |
| I-6 | H | H | Cl | $CH_3$ | $CH_3$ | $CH_3$ | H | H |
| I-7 | H | H | Cl | H | F | $OCH_3$ | F | H |
| I-8 | H | H | Cl | Cl | H | F | H | H |
| I-9 | H | H | Cl | H | $CH_3$ | $CF_3$ | H | H |
| I-10 | H | H | Cl | $CH_3$ | H | $CH_3$ | H | H |
| I-11 | H | H | Cl | H | $C(O)NH_2$ | H | H | H |
| I-12 | H | H | Cl | $OCH_3$ | H | $CF_3$ | H | H |
| I-13 | H | H | H | F | H | F | H | H |
| I-14 | H | H | Cl | F | H | F | H | H |
| I-15 | H | H | Cl | H | $CF_3$ | H | H | H |
| I-16 | H | H | Br | $CH_3$ | $CH_3$ | $CH_3$ | H | H |
| I-17 | H | H | $CH_3$ | H | $CH_3$ | $N(CH_3)_2$ | H | H |
| I-18 | H | H | HC≡C | $CH_3$ | $CH_3$ | $CH_3$ | H | H |
| I-19 | H | H | $CH_3$ | H | H | $OCH_3$ | F | H |
| I-20 | H | H | F | H | H | $OCH_3$ | F | H |
| I-21 | H | H | Cl | H | H | $OCH_3$ | F | H |
| I-22 | H | H | Br | H | H | $OCH_3$ | F | H |
| I-23 | H | H | H | H | H | $OCH_3$ | F | H |
| I-24 | H | H | $CH_3$ | H | H | $N(CH_3)_2$ | H | H |
| I-25 | H | H | $CH_3$ | H | $N(CH_3)_2$ | H | H | H |
| I-26 | H | H | $CH_3$ | H | H | H | H | $CH_3$ |
| I-27 | H | H | $CH_3$ | H | Br | $OCH_3$ | F | H |
| I-28 | H | H | $CH_3$ | H | Br | H | F | H |
| I-29 | H | H | $CH_3$ | H | $CH_3$ | $OCH_3$ | F | H |
| I-30 | H | H | $CH_3$ | H | $CH_2C(O)H$ | H | H | H |
| I-31 | H | H | $CH_3$ | H | H | C≡CH | H | H |
| I-32 | H | H | Cl | H | $CH_3$ | $OCH_3$ | H | H |
| I-33 | H | H | Cl | H | $CH_3$ | $N(CH_3)_2$ | H | H |
| I-34 | H | H | $CH_3$ | H | $OCH_3$ | $NH_2$ | H | H |
| I-35 | H | H | $CH_3$ | $CH_3$ | $CD_3$ | $CH_3$ | H | H |
| I-36 | H | H | Cl | $CH_3$ | $CD_3$ | $CH_3$ | H | H |
| I-37 | H | H | F | $CH_3$ | $CD_3$ | $CH_3$ | H | H |
| I-38 | H | H | H | $CH_3$ | $CD_3$ | $CH_3$ | H | H |
| I-39 | H | H | $CO_2CH_3$ | H | H | H | H | H |
| I-40 | H | H | $CO_2CH_3$ | $CH_3$ | $CH_3$ | $CH_3$ | H | H |
| I-41 | H | H | $NO_2$ | H | H | H | H | H |
| I-42 | H | H | $NO_2$ | $CH_3$ | $CH_3$ | $CH_3$ | H | H |
| I-43 | H | H | $NO_2$ | H | F | $OCH_3$ | H | H |
| I-44 | H | H | $NO_2$ | H | $CH_3$ | $OCH_3$ | H | H |
| I-45 | H | H | $NO_2$ | H | $CH_3$ | $N(CH_3)_2$ | H | H |
| I-46 | H | H | $CH_3$ | $CH_3$ | $CD_3$ | $CH_3$ | H | H |
| I-47 | H | H | $NO_2$ | $OCH_3$ | H | $CF_3$ | H | H |
| I-48 | H | H | $CO_2CH_3$ | H | F | $OCH_3$ | F | H |
| I-49 | H | H | $CO_2H$ | $CH_3$ | $CH_3$ | $CH_3$ | H | H |
| I-50 | H | H | $CH_3$ | H | $OCH_3$ | $OCH_3$ | F | H |
| I-51 | H | H | Cl | H | $OCH_3$ | $OCH_3$ | F | H |
| I-52 | H | H | Cl | $CH_3$ | $CH_3$ | $OCH_3$ | H | H |
| I-53 | H | H | $CH_3$ | H | $CH_3$ | $O(CH_2)_2OCH_3$ | F | H |
| I-54 | H | H | $CO_2CH_3$ | H | $C(O)NH_2$ | H | H | H |
| I-55 | H | H | $CO_2CH_3$ | $OCH_3$ | H | $CF_3$ | H | H |
| I-56 | H | H | $CO_2CH_3$ | H | $CH_3$ | $OCH_3$ | H | H |
| I-57 | H | H | $CO_2CH_3$ | H | $CH_3$ | $N(CH_3)_2$ | H | H |
| I-58 | H | H | $CO_2CH_3$ | $CH_3$ | F | $OCH_3$ | H | H |
| I-59 | H | H | $CO_2CH_3$ | $CH_3$ | $CH_3$ | $OCH_3$ | H | H |
| I-60 | H | H | $NO_2$ | H | $C(O)NH_2$ | H | H | H |
| I-61 | H | H | F | H | $CH_3$ | $O(CH_2)_2OCH_3$ | F | H |
| I-62 | H | H | H | H | $CH_3$ | $O(CH_2)_2OCH_3$ | F | H |
| I-63 | H | H | $CH_2OH$ | $CH_3$ | $CH_3$ | $CH_3$ | H | H |
| I-64 | H | H | $CH_3$ | $CH_3$ | CN | $CH_3$ | H | H |
| I-65 | H | H | $CH_3$ | H | H | $CH=CH_2$ | H | H |
| I-66 | H | H | Cl | H | $CH_3$ | $O(CH_2)_2OCH_3$ | F | H |
| I-67 | H | H | Cl | H | $CH_3$ | $OCH_3$ | F | H |

TABLE I-continued

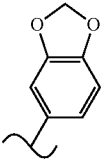

| Cpd | R[1] | R[2e] | R[5] | R[2a] | R[2b] | R[2c] | R[2d] | R[4] |
|---|---|---|---|---|---|---|---|---|
| I-68 | H | H | $CH_3$ | H | $CH_2CH_3$ | $OCH_3$ | F | H |
| I-69 | H | H | Cl | $CH_3$ | CN | $CH_3$ | H | H |
| I-70 | H | H | F | $CH_3$ | CN | $CH_3$ | H | H |
| I-71 | H | H | Cl | H | $CH_2CH_3$ | $OCH_3$ | F | H |
| I-72 | H | H | $CH_3$ | H | H | CN | F | H |
| I-73 | H | H | Cl | H | H | CN | F | H |
| I-74 | H | H | $CO_2CH_3$ | $CH_3$ | F | $CH_3$ | H | H |
| I-75 | H | H | $CH_3$ | H | $OCH_3$ | H | F | H |
| I-76 | H | H | Cl | H | $OCH_3$ | H | F | H |
| I-77 | H | H | $CH_3$ | H | $O(CH_2)_2OCH_3$ | $O(CH_2)_2OCH_3$ | F | H |
| I-78 | H | H | Cl | H | $O(CH_2)_2OCH_3$ | $O(CH_2)_2OCH_3$ | F | H |
| I-79 | H | H | $CH_2OH$ | $CH_3$ | F | $CH_3$ | H | H |
| I-80 | H | H | $CH_2OH$ | $CH_3$ | F | $OCH_3$ | H | H |
| I-81 | H | H | $CH_2OH$ | $CH_3$ | $CH_3$ | $OCH_3$ | H | H |
| I-82 | H | H | $CH_3$ | $CH_3$ | $CH_3$ | $N(CH_3)_2$ | H | H |
| I-83 | H | H | Cl | $CH_3$ | $CH_3$ | $N(CH_3)_2$ | H | H |
| I-84 | H | H | $CH_3$ | $CH_3$ | $CH_3$ | $N(CH_2CH_3)_2$ | H | H |
| I-85 | H | H | $CH_3$ | $CH_3$ | $CH_3$ | $N(H)CH_2CH_3$ | H | H |
| I-86 | H | H | Cl | $CH_3$ | $CH_3$ | $N(CH_2CH_3)_2$ | H | H |
| I-87 | H | H | Cl | $CH_3$ | $CH_3$ | $N(H)CH_2CH_3$ | H | H |
| I-88 | H | 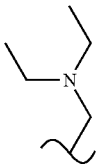 | $CH_3$ | $CH_3$ | $CH_3$ | $CH_3$ | H | H |
| I-89 | H | 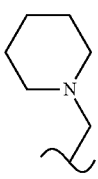 | $CH_3$ | $CH_3$ | $CH_3$ | $CH_3$ | H | H |
| I-90 | H |  | $CH_3$ | $CH_3$ | $CH_3$ | $CH_3$ | H | H |
| I-91 | H |  | $CH_3$ | $CH_3$ | $CH_3$ | $CH_3$ | H | H |
| I-92 | H |  | $CH_3$ | $CH_3$ | $CH_3$ | $CH_3$ | H | H |

TABLE I-continued
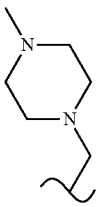
| Cpd | R¹ | R²ᵉ | R⁵ | R²ᵃ | R²ᵇ | R²ᶜ | R²ᵈ | R⁴ |
|---|---|---|---|---|---|---|---|---|
| I-93 | H | 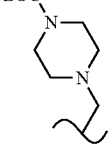 | CH₃ | CH₃ | CH₃ | CH₃ | H | H |
| I-94 | H | 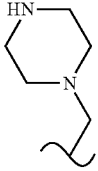 | CH₃ | CH₃ | CH₃ | CH₃ | H | H |
| I-95 | H |  | CH₃ | CH₃ | CH₃ | CH₃ | H | H |
| I-96 | H | 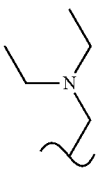 | CH₃ | CH₃ | CH₃ | CH₃ | H | H |
| I-97 | H | H | 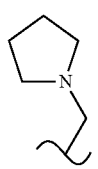 | CH₃ | CH₃ | CH₃ | H | H |
| I-98 | H | H | 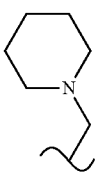 | CH₃ | CH₃ | CH₃ | H | H |
| I-99 | H | H |  | CH₃ | CH₃ | CH₃ | H | H |

TABLE I-continued

[Structure: benzoxazolone-NH-pyrimidine-N(R⁴)-phenyl core with R¹ on oxazolone N, R²ᵉ on benzoxazole, R⁵ on pyrimidine, R²ᵃ, R²ᵇ, R²ᶜ, R²ᵈ on phenyl ring]

| Cpd | R¹ | R²ᵉ | R⁵ | R²ᵃ | R²ᵇ | R²ᶜ | R²ᵈ | R⁴ |
|---|---|---|---|---|---|---|---|---|
| I-100 | H | H | 4-methylpiperazin-1-yl (N-linked via ethyl) | CH₃ | CH₃ | CH₃ | H | H |
| I-101 | H | H | CH₃ | H | OCH₂CH₃ | OCH₂CH₃ | F | H |
| I-102 | H | H | CH₃ | H | OC(CD₃)₃ | OC(CD₃)₃ | F | H |
| I-103 | H | H | CH₃ | CH₃ | CH₃ | OCH₂CH₃ | H | H |
| I-104 | H | H | Cl | CH₃ | CH₃ | OCH₂CH₃ | H | H |
| I-105 | H | H | CH₃ | OCH₃ | F | CH₃ | H | H |
| I-106 | H | H | CH₃ | OCH₃ | F | CH₃ | H | H |
| I-107 | H | H | CH₃ | OCH₃ | F | CH₃ | H | H |
| I-108 | H | H | CH₃ | OCH₃ | CH₃ | CH₃ | H | H |
| I-109 | H | CH₃ | CH₃ | OCH₃ | CH₃ | CH₃ | H | H |
| I-110 | H | CH₃ | F | OCH₃ | CH₃ | CH₃ | H | H |
| I-111 | H | F | CH₃ | OCH₃ | CH₃ | CH₃ | H | H |
| I-112 | H | F | F | OCH₃ | CH₃ | CH₃ | H | H |
| I-113 | H | H | CH₃ | OCH₃ | CH₃ | CH₃ | H | H |
| I-114 | H | H | CH₃ | OCH₃ | F | CH₃ | H | H |
| I-115 | CH₂OP(O)(ONa)₂ | H | CH₃ | OCH₃ | CH₃ | CH₃ | H | H |
| I-116 | H | H | CH₃ | OH | F | CH₃ | H | H |
| I-117 | H | H | CH₃ | OH | CH₃ | CH₃ | H | H |
| I-118 | CH₂OP(O)(OH)₂ | H | CH₃ | OCH₃ | F | CH₃ | H | H |
| I-119 | H | H | F | OCH₃ | H | H | F | H |
| I-120 | H | H | CH₃ | OCH₃ | CH₃ | F | H | H |
| I-121 | H | H | F | OCH₃ | CH₃ | F | H | H |
| I-122 | H | H | CH₃ | OCH₃ | CH₃ | H | F | H |
| I-123 | H | H | F | OCH₃ | CH₃ | H | F | H |
| I-124 | H | H | CH₃ | OCH₃ | Cl | CH₃ | H | H |
| I-125 | NCH₃ | H | CH₃ | OCH₃ | CH₃ | CH₃ | H | H |
| I-126 | NCH₃ | H | CH₃ | CH₃ | CH₃ | CH₃ | H | H |
| I-127 | NCH₃ | H | CH₃ | OCH₃ | F | CH₃ | H | H |
| I-128 | H | H | CH₃ | OCH₃ | CO₂CH₂CH₃ | CH₃ | H | H |
| I-129 | H | H | CH₃ | OCH₃ | CH₂OH | CH₃ | H | H |
| I-130 | CH₂OP(O)(OH)₂ | H | CH₃ | CH₃ | CH3 | CH₃ | H | H |
| I-131 | H | H | CH₃ | CH₃ | CH₃ | CH₃ | H | H |
| I-132 | CH₂OP(O)(OH)₂ | H | CH₃ | CH₃ | CH₃ | CH₃ | H | H |
| I-133 | -CH₂-O-P(O)(OH)-O-CH₂CH₂-N(CH₃)₂ | H | CH₃ | CH₃ | CH₃ | CH₃ | H | H |
| I-134 | -CH₂-O-P(O)(O-CH₂CH₂N(CH₃)₂)-O-CH₂CH₂N(CH₃)₂ | H | CH₃ | CH₃ | CH₃ | CH₃ | H | H |
| I-135 | H | H | CH₃ | CH₃ | CH₃ | CH₃ | H | H |
| I-136 | CH₂OP(O)(OH)₂ | H | CH₃ | CH₃ | CH₃ | CH₃ | H | H |
| I-137 | H | H | CH₃ | CH₃ | CH₃ | CH₃ | H | H |
| I-138 | H | H | CH₃ | CH₃ | CO₂CH₃ | CH₃ | H | H |
| I-139 | H | H | CH₃ | CH₃ | CH₃ | CH₃ | H | CH₂CH₃ |

TABLE I-continued

| Cpd | R$^1$ | R$^{2e}$ | R$^5$ | R$^{2a}$ | R$^{2b}$ | R$^{2c}$ | R$^{2d}$ | R$^4$ |
|---|---|---|---|---|---|---|---|---|
| I-140 | H | H | CH$_3$ | CH$_3$ | CO$_2$H | CH$_3$ | H | H |
| I-141 | H | H | CH$_3$ | CH$_3$ | CO$_2$CH$_2$Ph | CH$_3$ | H | H |
| I-142 | H | H | CH$_3$ | CH$_3$ | CH$_2$OH | CH$_3$ | H | H |
| I-143 | H | H | CH$_3$ | CH$_3$ | CH$_2$OH$_3$ | CH$_3$ | H | H |
| I-144 | H | H | CH$_3$ | CH$_3$ | CH$_3$ | CO$_2$CH$_3$ | H | H |
| I-145 | H | H | CH$_3$ | CH$_3$ | CH$_3$ | CO$_2$H | H | H |
| I-146 | H | H | CH$_3$ | CH$_3$ | F | CH$_3$ | H | H |
| I-147 | H | H | CH$_3$ | CH$_3$ | CH$_3$ | CH$_2$OH | H | H |
| I-148 | H | H | CH$_3$ | CH$_3$ | CH$_2$CH$_2$CH$_2$CH$_3$ | H | H | H |
| I-149 | H | H | CH$_3$ | CH$_3$ | Br | CH$_3$ | H | H |
| I-150 | H | H | CH$_3$ | CH$_3$ | CO$_2$-t-Bu | CH$_3$ | H | H |
| I-151 | H | H | CH$_3$ | CH$_3$ | F | CH$_3$ | H | H |
| I-152 | H | H | CH$_3$ | H | CH$_3$ | CO$_2$H | H | H |
| I-153 | H | H | CH$_3$ | CH$_3$ | F | CO$_2$CH$_3$ | H | H |
| I-154 | H | H | CH$_3$ | CH$_3$ | F | CH$_2$OH | H | H |
| I-155 | H | H | CH$_3$ | CH$_3$ | F | CO$_2$H | H | H |
| I-156 | H | H | CH$_3$ | CH$_3$ | CH$_3$ | CH$_3$ | H | H |
| I-157 | H | H | F | H | C(O)CH$_3$ | H | H | H |
| I-158 | H | H | F | H | -C(O)NH-CH(CH$_3$)-cyclopropyl | H | H | H |
| I-159 | H | H | F | H | -C(O)NH-cyclobutyl | H | H | H |
| I-160 | H | H | F | H | -C(O)NH-propyl | H | H | H |
| I-161 | H | H | F | H | -C(O)NH-cyclopropyl | H | H | H |
| I-162 | H | H | F | H | -C(O)NH-ethyl | H | H | H |
| I-163 | H | H | F | H | -C(O)NH-isopropyl | H | H | H |
| I-164 | H | H | F | H | -C(O)NH-cyclobutyl | OCH$_3$ | H | H |
| I-165 | H | H | F | H | -C(O)NH-cyclopropyl | CF$_3$ | H | H |

TABLE I-continued

| Cpd | R¹ | R²ᵉ | R⁵ | R²ᵃ | R²ᵇ | R²ᶜ | R²ᵈ | R⁴ |
|---|---|---|---|---|---|---|---|---|
| I-166 | H | H | F | H | ![phenylacetamide group] | CF₃ | H | H |
| I-167 | H | H | F | H | CH₃ | SO₂CH₃ | H | H |
| I-168 | H | H | F | H | F | SO₂CH₃ | H | H |
| I-169 | H | H | F | F | H | morpholin-4-yl | H | H |
| I-170 | H | H | F | F | H | 4-methylpiperazin-1-yl | H | H |
| I-171 | H | CH₃ | F | H | H | SO₂NH₂ | H | H |
| I-172 | H | CH₃ | F | H | H | SO₂CH₃ | H | H |
| I-173 | H | CH₃ | F | H | F | SO₂CH₃ | H | H |
| I-174 | H | F | F | H | H | SO₂NH₂ | H | H |
| I-175 | H | H | F | CH₃ | H | OCD₃ | H | H |
| I-176 | H | CH₃ | F | OCH₃ | H | CF₃ | H | H |
| I-177 | H | CH₃ | F | OCH₃ | H | CH₃ | H | H |
| I-178 | H | CH₃ | F | H | OCH₃ | CH₃ | H | H |
| I-179 | H | F | F | OCH₃ | H | CH₃ | H | H |
| I-180 | H | F | F | H | OCH₃ | CH₃ | H | H |
| I-181 | H | H | F | OCH₃ | F | CH₃ | H | H |
| I-182 | H | H | F | CH₃ | OCH₃ | OCH₃ | H | H |
| I-183 | H | CH₃ | F | CH₃ | OCH₃ | OCH₃ | H | H |
| I-184 | H | F | F | CH₃ | OCH₃ | OCH₃ | H | H |
| I-185 | H | H | F | Cl | OCH₃ | OCH₃ | H | H |
| I-186 | H | H | F | CH₃ | 2-morpholinoethoxy | CH₃ | H | H |
| I-187 | H | F | F | CH₃ | H | CH₃ | H | H |
| I-188 | H | F | F | CH₃ | CH₃ | CH₃ | H | H |
| I-189 | H | F | F | CH₃ | F | CH₃ | H | H |
| I-190 | H | CH₃ | F | OCH₃ | F | CH₃ | H | H |
| I-191 | H | F | F | OCH₃ | F | CH₃ | H | H |
| I-192 | H | CH₃ | F | H | F | OCH₃ | F | H |
| I-193 | H | F | F | H | F | OCH₃ | F | H |
| I-194 | H | H | F | OCH₃ | CH₃ | OCH₃ | H | H |
| I-195 | H | H | F | CH₃ | CH₃ | OCH₃ | H | H |
| I-196 | H | H | F | H | OCH₃ | H | H | H |
| I-197 | H | H | F | H | OCH₃ | CF₂H | H | H |
| I-198 | H | H | F | OCH₃ | H | CF₂H | H | H |
| I-199 | H | H | F | OCH₃ | H | CH₂F | H | H |
| I-200 | H | H | F | H | CH(CH₃)₂ | H | H | H |
| I-201 | H | H | F | H | C(CH₃)₃ | H | H | H |
| I-202 | H | H | F | H | CH₃ | H | H | H |
| I-203 | H | H | F | H | CH₃ | pyridin-4-yl | H | H |
| I-204 | H | H | F | H | CH₃ | pyridin-3-yl | H | H |
| I-205 | H | H | F | H | F | pyridin-4-yl | H | H |
| I-206 | H | H | F | H | F | pyridin-3-yl | H | H |
| I-207 | H | H | F | OCH₃ | pyridin-4-yl | H | H | H |
| I-208 | H | H | F | H | OCH₃ | pyridin-4-yl | H | H |
| I-209 | H | H | F | H | OCH₃ | pyridin-3-yl | H | H |

TABLE I-continued

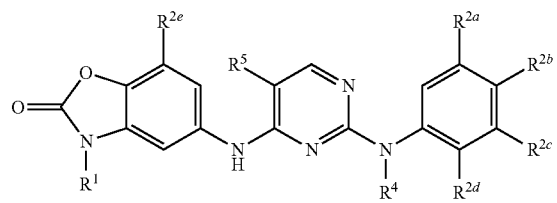

| Cpd | R¹ | R²ᵉ | R⁵ | R²ᵃ | R²ᵇ | R²ᶜ | R²ᵈ | R⁴ |
|---|---|---|---|---|---|---|---|---|
| I-210 | H | H | F | H | H | CH(OH)CF₃ | H | H |
| I-211 | H | H | F | OCH₃ | H | CF₃ | H | H |
| I-212 | H | H | F | H | OCH₃ | CF₃ | H | H |
| I-213 | H | H | F | H | OCH₃ | 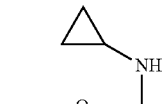 | H | H |
| I-214 | H | H | F | CH₃ | CH₃ | CH₃ | H | H |
| I-215 | H | H | F | CH₃ | F | CH₃ | H | H |
| I-216 | CH₂OP(O)(OH)₂ | H | CH₃ | CH₃ | CH₃ | CH₃ | H | H |
| I-217 | H | H | CH₃ | CH₃ | CH₃ | CH₃ | H | H |
| I-218 | H | H | CH₃ | H | F | OCH₂CH₃ | F | H |
| I-219 | H | H | CH₃ | H | F | OCH(CH₃)₂ | F | H |
| I-220 | H | H | CH₃ | H | CH₂NH₂ | H | H | H |
| I-221 | H | H | CD₃ | CH₃ | F | OCH₃ | H | H |
| I-222 | H | H | CD₃ | CH₃ | F | OCD₃ | H | H |
| I-223 | H | H | CD₃ | CH₃ | CH₃ | OCH₃ | H | H |
| I-224 | H | H | CD₃ | CH₃ | CH₃ | OCD₃ | H | H |
| I-225 | H | H | CD₃ | CH₃ | CH₂OH | OCH₃ | H | H |
| I-226 | CH₂OP(O)[OC(CH₃)₃]₂ | H | CD₃ | CH₃ | F | OCD₃ | H | H |
| I-227 | CH₂OP(O)OH[OC(CH₃)₃] | H | CD₃ | CH₃ | F | OCD₃ | H | H |
| I-228 | CH₂OP(O)(OH)₂ | H | CD₃ | CH₃ | F | OCD₃ | H | H |
| I-229 | CH₂OP(O)(ONa)₂ | H | CD₃ | CH₃ | F | OCD₃ | H | H |
| I-230 | H | H | CH₃ | OCH₃ | CH₂OH | CH₃ | H | H |
| I-231 | H | H | CH₃ | OCH₃ | C(O)OH | CH₃ | H | H |

TABLE II

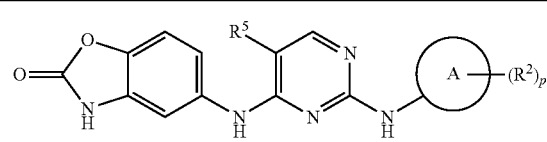

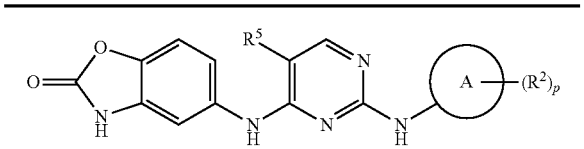

| Cpd | R⁵ | |
|---|---|---|
| II-1 | F | 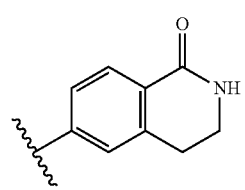 [SMILES: *c1ccc2c(c1)CCNC2=O] |
| II-2 | F | 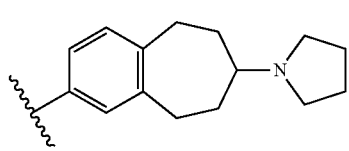 [SMILES: *c1ccc2c(c1)CCC(N1CCCC1)CC2] |
| II-3 | F | 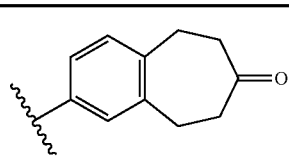 |
| II-4 | F | 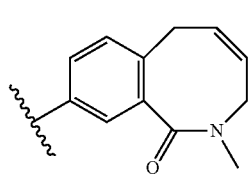 [SMILES: *c1ccc2c(c1)C(=O)N(C)C/C=C\C2] |

TABLE II-continued
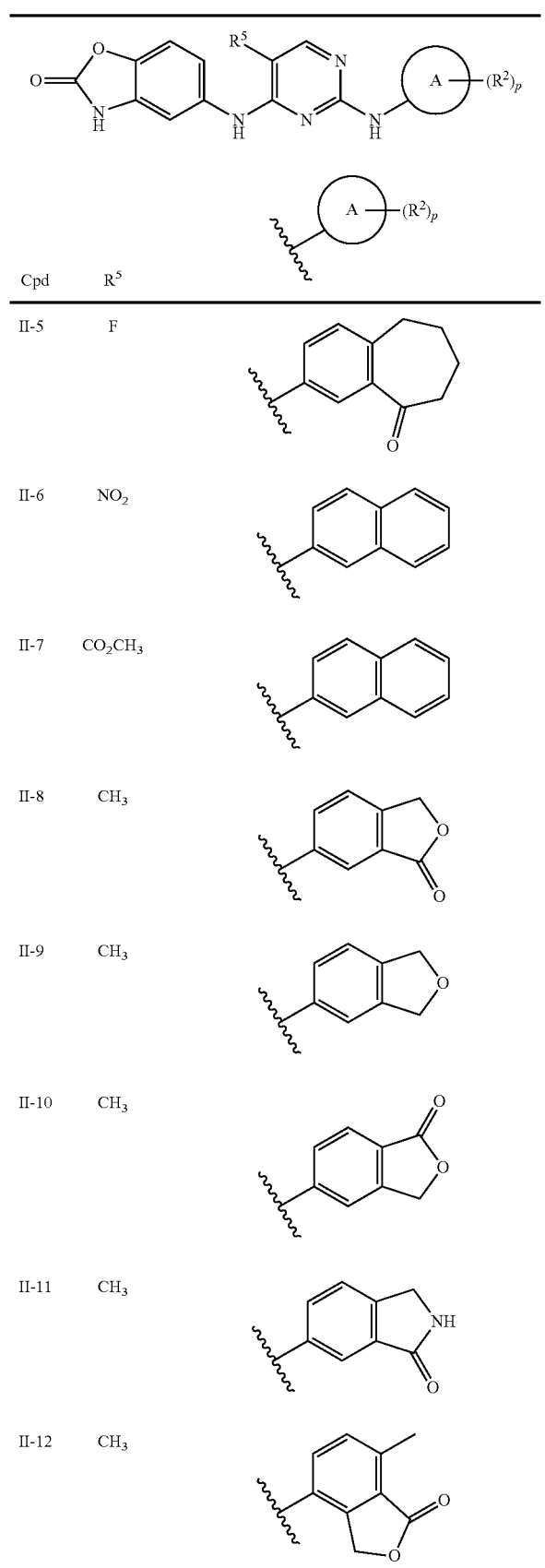
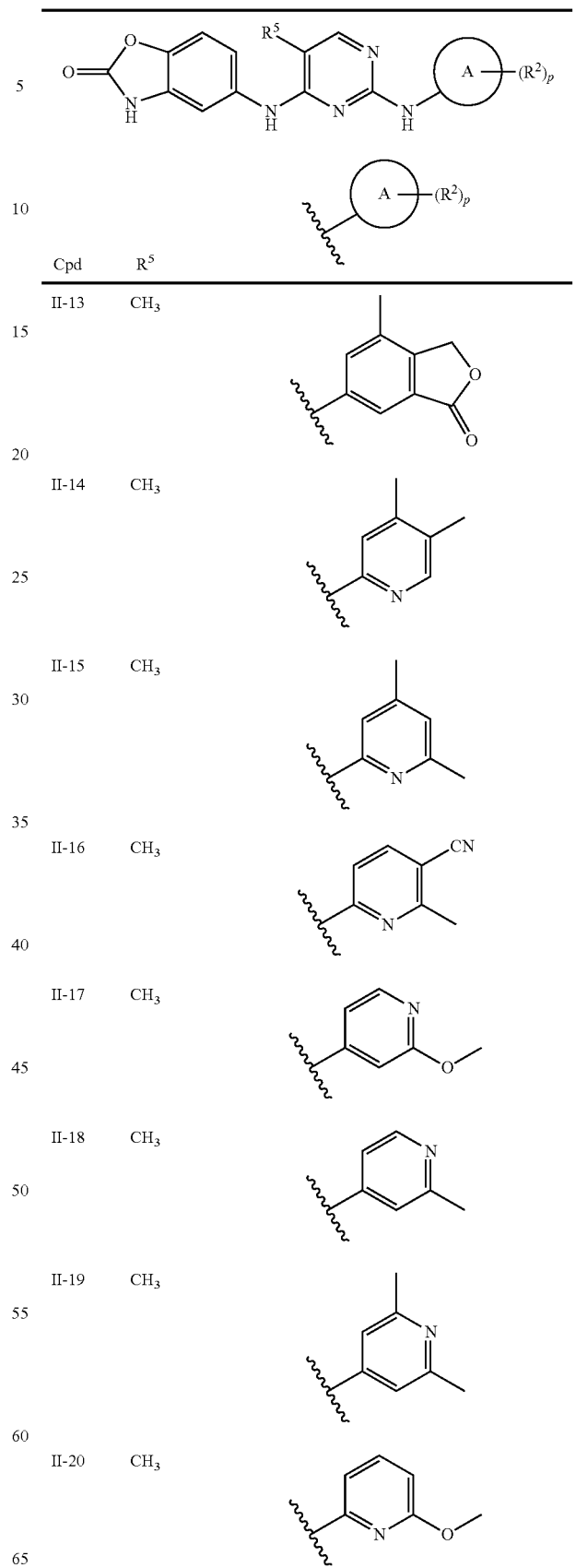

TABLE II-continued

| Cpd | R⁵ | (structure) |
|---|---|---|
| II-21 | CH₃ | 2,3-dimethylpyridin-6-yl |
| II-22 | CH₃ | 5-cyano-4-methylpyridin-2-yl |
| II-23 | F | 1-oxo-2,3-dihydro-1H-benzo[c]azepin-7-yl (NH) |
| II-24 | F | 2-methyl-1-oxo-2,3-dihydro-1H-benzo[c]azepin-7-yl |
| II-25 | F | 3-oxo-3,4-dihydro-2H-benzo[b][1,4]oxazin-7-yl |
| II-26 | F | 2-oxo-1,2,3,4-tetrahydroquinolin-6-yl |
| II-27 | F | 2-oxo-2,3,4,5-tetrahydro-1H-benzo[b]azepin-7-yl |
| II-28 | F | 1-methyl-2-oxo-2,3,4,5-tetrahydro-1H-benzo[b]azepin-7-yl |
| II-29 | CH₃ | 2-morpholinopyridin-4-yl |
| II-30 | F | 2-morpholinopyridin-4-yl |
| II-31 | CH₃ | pyridin-4-yl |

Prodrugs

Those of skill in the art will appreciate that the 2,4-pyrimidinediamine compounds described herein can include functional groups that can be masked with progroups to create prodrugs. Such prodrugs are usually, but need not be, pharmacologically inactive until converted into their active drug form. Indeed, many of the 2,4-pyrimidinediamine compounds described in this invention include promoieties that are hydrolyzable or otherwise cleavable under conditions of use. For example, ester groups commonly undergo acid-catalyzed hydrolysis to yield the parent carboxylic acid when exposed to the acidic conditions of the stomach or base-catalyzed hydrolysis when exposed to the basic conditions of the intestine or blood. Thus, when administered to a subject orally, 2,4-pyrimidinediamine compounds that include ester moieties can be considered prodrugs of their corresponding carboxylic acid, regardless of whether the ester form is pharmacologically active.

The mechanism by which the progroup(s) metabolizes is not critical and can be caused, for example, by hydrolysis under the acidic conditions of the stomach, as described above, and/or by enzymes present in the digestive tract and/or tissues or organs of the body. Indeed, the progroup(s) can be selected to metabolize at a particular site within the body. For example, many esters are cleaved under the acidic conditions found in the stomach. Prodrugs designed to cleave chemically in the stomach to the active 2,4-pyrimidinediamine can employ progroups including such esters. Alternatively, the progroups can be designed to metabolize in the presence of enzymes such as esterases, amidases, lipolases, and phosphatases, including ATPases and kinase, etc. Progroups including linkages capable of metabolizing in vivo are well known and include, by way of example and not limitation, ethers, thioethers, silylethers, silylthioethers, esters, thioesters, carbonates, thiocarbonates, carbamates, thiocarbamates, ureas, thioureas, and carboxamides. In some instances, a "precursor" group that is oxidized by oxidative enzymes such as, for example, cytochrome $P_{450}$ of the liver, to a metabolizable group, can be selected.

In the prodrugs, any available functional moiety can be masked with a progroup to yield a prodrug. Functional groups within the 2,4-pyrimidinediamine compounds that can be masked with progroups for inclusion in a promoiety include, but are not limited to, amines (primary and secondary), hydroxyls, sulfanyls (thiols), and carboxyls. A wide variety of progroups, as well as the resultant promoieties, suitable for masking functional groups in active 2,4-pyrimidinediamine compounds to yield prodrugs are well-known in the art. For example, a hydroxyl functional group can be masked as a sulfonate, ester, or carbonate promoiety, which can be hydrolyzed in vivo to provide the hydroxyl group. An amino functional group can be masked as an amide, carbamate, imine, urea, phosphenyl, phosphoryl, or sulfenyl promoiety, which can be hydrolyzed in vivo to provide the amino group. A carboxyl group can be masked as an ester (including silyl esters and thioesters), amide, or hydrazide promoiety, which can be hydrolyzed in vivo to provide the carboxyl group. Other specific examples of suitable progroups and their respective promoieties will be apparent to those of skill in the art. All of these progroups, alone or in combinations, can be included in the prodrugs.

In some embodiments of the 2,4-pyrimidinediamine compounds and methods of using the compounds, the progroup(s) can be attached to any available primary or secondary amine, including, for example, the N2 nitrogen atom of the 2,4-pyrimidinediamine, the N4 nitrogen atom of the 2,4-pyrimidinediamine, and/or a primary or secondary nitrogen atom included in a substituent on the 2,4-pyrimidinediamine.

As noted above, the identity of the progroup is not critical, provided that it can be metabolized under the desired conditions of use, for example, under the acidic conditions found in the stomach and/or by enzymes found in vivo, to yield a biologically active group, for example, the 2,4-pyrimidinediamines as described herein. Thus, skilled artisans will appreciate that the progroup can include virtually any known or later-discovered hydroxyl, amine or thiol protecting group. Non-limiting examples of suitable protecting groups can be found, for example, in Protective Groups in Organic Synthesis, Greene & Wuts, 2$^{nd}$ Ed., John Wiley & Sons, New York, 1991 (especially pages 10-142 (alcohols, 277-308 (thiols) and 309-405 (amines) the disclosure of which is incorporated herein by reference, herein referred to as "Green & Wuts").

A particularly useful progroup employed in exemplary disclosed compounds is —CH$_2$OP(OH)$_2$ as well as esters, mixed acid esters and salts thereof. In some embodiments, the —CH$_2$OP(OH)$_2$ progroup is attached via a nitrogen atom, annular or not, of the parent molecule. There can be more than one such progroup. Thus, one embodiment is a compound of formula I,

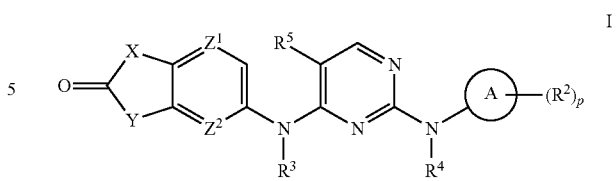

or solvate thereof, where A, X, Y, $Z^1$, $Z^2$, $R^2$, $R^3$, $R^4$, $R^5$ and p are as described herein above, and at least one of $R^1$ (when present), $R^3$ and $R^4$ is $R^{50}$; where $R^{50}$ is —CH$_2$OP(O)(OR$^{11}$)$_2$; each $R^{11}$ is independently for each occurrence H, C$_{1-6}$alkyl or monovalent cationic group, or two $R^{11}$, together with the atoms to which they are attached, form a 4-8 membered cyclic phosphate group

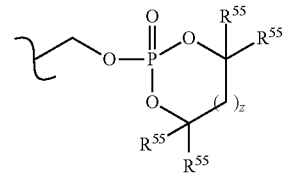

where each $R^{55}$ is independently for each occurrence H, optionally substituted C$_{1-6}$alkyl, optionally substituted 3-8 membered heteroalicyclyl, optionally substituted C$_{6-14}$aryl, optionally substituted C$_{7-20}$arylalkyl, optionally substituted 5-14 membered heteroaryl or optionally substituted 6-15 membered heteroarylalkyl; z is 0, 1, 2 or 3; or two $R^{11}$ together represent a divalent organic or inorganic cationic group, wherein exemplary inorganic divalent cationic groups include those selected from Ba$^{2+}$, Bi$^{2+}$, Ca$^{2+}$, Cu$^{2+}$, Mg$^{2+}$, Ni$^{2+}$, Sr$^{2+}$ and Zn$^{2+}$.

Another embodiment is a compound of formula II

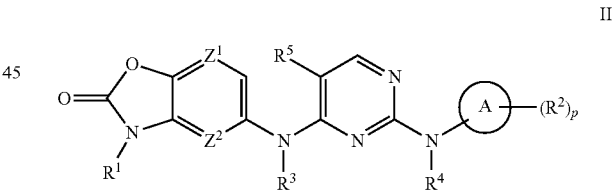

or solvate thereof, where A, $Z^1$, $Z^2$, $R^2$, $R^3$, $R^4$, $R^5$ and p are as described herein above, and at least one of $R^1$, $R^3$ and $R^4$ is $R^{50}$; where $R^{50}$ is —CH$_2$OP(O)(OR$^{11}$)$_2$; each $R^{11}$ is independently for each occurrence H, C$_{1-6}$alkyl or a monovalent cationic group, or two $R^{11}$, together with the atoms to which they are attached, form a 5 or 6-membered cyclic phosphate group, where —CH$_2$OP(O)(OR$^{11}$)$_2$ is

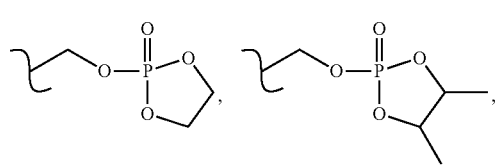

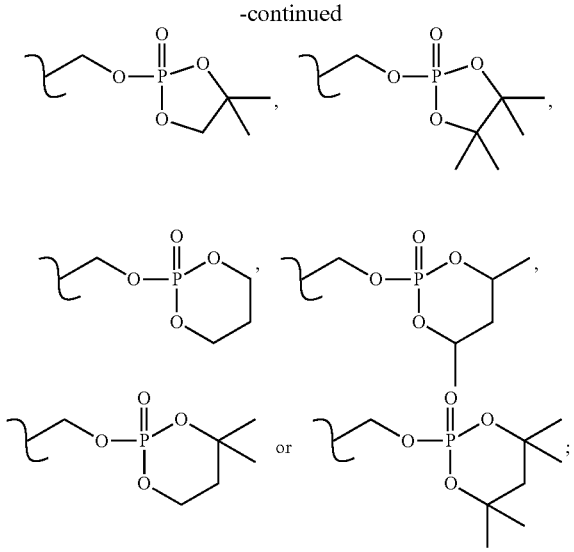

or two $R^{11}$ together represent a pharmaceutically acceptable divalent cationic group, by way of example including those selected from $Ca^{2+}$, $Mg^{2+}$ and $Zn^{2+}$.

Another embodiment is a compound of formula III

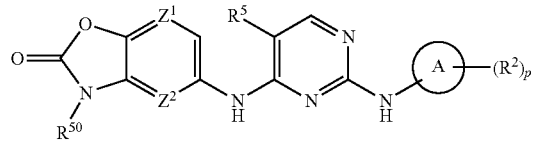

or solvate thereof, where A, $Z^1$, $Z^2$, $R^2$, $R^5$ and p are as described herein above, and $R^{50}$ is —$CH_2OP(O)(OR^{11})_2$; each $R^{11}$ is independently for each occurrence H, $C_{1-6}$alkyl, $Li^+$, $K^+$, $HOCH_2CH_2N(CH_3)_3^+$, $Na^+$ or $NH_4^+$; or two $R^{11}$ together represent a divalent cationic group selected from $Ca^{2+}$, $Mg^{2+}$ and $Zn^{2+}$.

Another embodiment is a compound of formula IV

IV

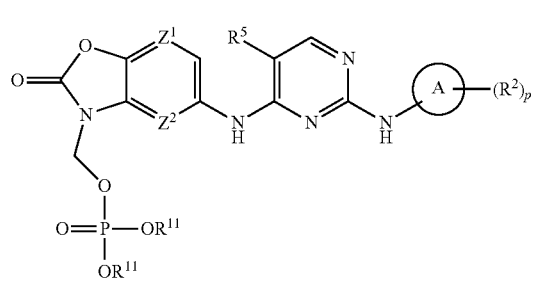

or a solvate thereof, where A, $Z^1$, $Z^2$, $R^2$, $R^5$ and p are as described herein above, and each $R^{11}$ is independently for each occurrence H, t-butyl, $Li^+$, $HOCH_2CH_2N(CH_3)_3^+$, $K^+$, $Na^+$ or $NH_4^+$; or two $R^{11}$ together represent a divalent cationic group selected from $Ca^{2+}$, $Mg^{2+}$ and $Zn^{2+}$.

For each of the prodrug embodiments described in the previous four paragraphs in relation to formula I, II, III and IV, each of the embodiments with respect to formula I, IA, IB and IC above apply. Put another way, for each of the embodiments described with respect to formula I, IA, IB and IC above, there is another embodiment where the specific prodrug embodiments described in the previous four paragraphs applies.

While not intending to be bound by any particular theory of operation, it is believed that progroups —$CH_2OP(O)(OR^{11})_2$, e.g. according to formula IV, metabolize to active compounds via the corresponding hydroxymethylamine intermediate illustrated below:

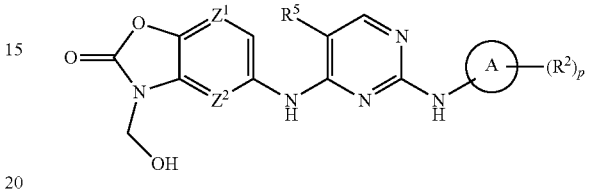

Such hydroxymethylamine compounds, although typically isolable under controlled conditions, are known to be unstable under physiological conditions and various pH ranges where they hydrolyze in vivo to yield formaldehyde and the active drug substance. Based on this observation, compounds as described herein include hydroxymethyl progroups that can be metabolized in vivo, for example by the acidic conditions of the stomach and/or by enzymes present in the digestive tract or other organs and/or tissues or fluids with the body, to yield the active drug substance 2,4-pyrimidinediamine.

Moreover, it is expected that the amino and thio analogs of these hydroxymethylamines, will be similarly unstable at physiological conditions and also hydrolyze in vivo to the active 2,4-pyrimidinediamine drug. Accordingly, compounds as described herein include these corresponding primary amino and thiol compounds. Also, the invention includes compounds in which the primary amine, thiol and hydroxy groups are masked with "protecting" groups that are removed under physiological conditions of use to yield the corresponding hydroxymethyl, thiolmethyl and aminomethyl compounds, that is, with these "protecting groups" these compounds will likewise make suitable prodrugs.

Suitability of any particular progroup for a desired mode of administration can be confirmed in biochemical assays. For example, if a prodrug is to be administered by injection into a particular tissue or organ and the identities of the various enzyme(s) expressed in the tissue or organ are known, the particular prodrug can be tested for metabolism in biochemical assays with the isolated enzyme(s). Alternatively, the particular prodrug can be tested for metabolism to the active 2,4-pyrimidinediamine compound with tissue and/or organ extracts. Using tissue and/or organ extracts can be of particular convenience when the identity(ies) of the enzymes expressed in the target tissues or organs are unknown or in instances when the isolated enzymes are not conveniently available. One of ordinary skill in the art would be able to readily select progroups having metabolic properties (such as kinetics) suitable for particular applications using such in vitro tests. Specific prodrugs could also be tested for suitable metabolism in vitro animal models.

Compounds as described herein bearing the —$CH_2OP(O)(OR^{11})_2$ progroup can be synthesized, for example, as depicted below for compounds of formula IV.

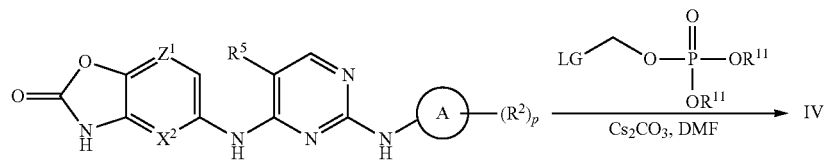

Typically, the proton on the NH of the oxazolidinone ring can be selectively alkylated with the appropriate phosphonate reagent, where LG is a suitable leaving group to form compounds as described herein, in this case of formula IV. Further description of how to make progroups of formula —CH$_2$OP(O)(OR$^{11}$)$_2$ as described herein is specifically taught in U.S. Pat. No. 7,449,458, entitled "Pyrimidinediamine Prodrugs and their Uses," the disclosure of which is hereby incorporated by reference in its entirety.

One of ordinary skill in the art will appreciate that compounds as described herein may exhibit the phenomena of tautomerism, conformational isomerism, geometric isomerism, and/or optical isomerism. For example, the compounds and prodrugs as described herein can include one or more chiral centers and/or double bonds and as a consequence can exist as stereoisomers, such as double-bond isomers (such as, geometric isomers), enantiomers, diastereomers, and mixtures thereof, such as racemic mixtures. As another example, the compounds as described herein can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it would be understood that the invention encompasses any tautomeric, conformational isomeric, optical isomeric, and/or geometric isomeric forms of the compounds described herein, as well as mixtures of these various different isomeric forms. In cases of limited rotation, for example around the 2,4-pyrimidinediamine core structure, atropisomers are also possible and are also specifically included in the compounds as described herein. It is intended that the compounds encompassed herein are, with the exception of forms of isomerism, chemically stable and isolable.

As is understood by one of ordinary skill in the art, certain atoms occur in more than one isotopic form. For example hydrogen occurs as protium ($^1$H), deuterium ($^2$H) and tritium ($^3$H), and carbon occurs naturally as three different isotopes, $^{12}$C, $^{13}$C and $^{14}$C. Thus the presently disclosed formulas include compounds having one or more different isotopic forms of certain elements, including hydrogen and carbon. A person of ordinary skill in the art will recognize that any atom at any position of the disclosed compounds may be isotopically enriched, labeled with at least one isotope, or combinations thereof, with any isotope currently known or discovered in the future. Particular examples of isotopes include isotopes of carbon, hydrogen, nitrogen, oxygen, phosphorous, halogens (e.g. chlorine, fluorine, bromine, and iodine), and combinations thereof. In one embodiment, the presently disclosed compounds are provided in isotopically enriched form. In particular examples, compounds of formula I are enriched in deuterium relative to protium. In one embodiment, one or more groups appended to ring A have deuterium rather than H. In another embodiment, an alkyl group at R$^5$ has deuterium rather than H. Deuterium has a natural abundance of about 0.015%. Accordingly, for approximately every 6,500 hydrogen atoms occurring in nature, there is one deuterium atom. Disclosed herein are compounds enriched in deuterium at one or more positions. Thus, deuterium containing compounds of the disclosure have deuterium at one or more positions (as the case may be) in an abundance of greater than 0.015%.

In one embodiment, a compound of formula (I), at a position designated as having deuterium, has a minimum isotopic enrichment factor of at least 2000 (30% deuterium incorporation) at each atom designated as deuterium in the compound, or at least 3000 (45% deuterium incorporation).

In other embodiments, a compound of formula (I) has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutical Compositions

Another embodiment is a pharmaceutical composition including a compound as described in any of the embodiments herein. Pharmaceutical compositions described herein can be manufactured by means of conventional mixing, dissolving, granulating, dragee-making levigating, emulsifying, encapsulating, entrapping, or lyophilization processes. The compositions can be formulated in conventional manner using one or more physiologically acceptable carriers, diluents, excipients, or auxiliaries which facilitate processing of the active compounds into preparations which can be used pharmaceutically.

The 2,4-pyrimidinediamine compound can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases can also be formed.

One embodiment is a pharmaceutical formulation including a compound of formula I, as described herein, or a prodrug thereof, and at least one pharmaceutically acceptable excipient, diluent, preservative, stabilizer, or mixture thereof.

The compounds can be provided in a variety of formulations and dosages. The compounds can be provided in a pharmaceutically acceptable form, including where the compound can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases can also be formed. It is to be understood that reference to the compound, 2,4-pyrimidinediamine compound, or "active" in discussions of formulations is also intended to include, where appropriate as known to those of skill in the art, formulation of the prodrugs of the 2,4-pyrimidinediamine compounds.

In one embodiment, the compounds are provided as non-toxic pharmaceutically acceptable salts, as noted previously. Suitable pharmaceutically acceptable salts of the compounds described herein include acid addition salts such as those formed with hydrochloric acid, fumaric acid, p-toluenesulphonic acid, maleic acid, succinic acid, acetic acid, citric acid, tartaric acid, carbonic acid, or phosphoric acid. Salts of amine groups can also include quaternary ammonium salts in which the amino nitrogen atom carries a suitable organic group such as an alkyl, alkenyl, alkynyl, or substituted alkyl moiety. Furthermore, where presently disclosed compounds carry an acidic moiety, suitable pharmaceutically acceptable salts thereof can include metal salts such as alkali metal salts, for example, sodium or potassium salts; and alkaline earth metal salts, for example, calcium or magnesium salts.

The pharmaceutical compositions for the administration of the 2,4-pyrimidinediamine compounds can be conveniently presented in dosage unit form and can be prepared by any of the methods well known in the art of pharmacy. The pharmaceutical compositions can be, for example, prepared by uniformly and intimately bringing the active ingredient into association with a liquid carrier, a finely divided solid carrier or both, and then, if necessary, shaping the product into the desired formulation. In the pharmaceutical composition the active object compound is included in an amount sufficient to produce the desired therapeutic effect.

The 2,4-pyrimidinediamine compounds can be administered by oral, parenteral (for example, intramuscular, intraperitoneal, intravenous, ICV, intracisternal injection or infusion, subcutaneous injection, or implant), by inhalation spray nasal, vaginal, rectal, sublingual, urethral (for example, urethral suppository) or topical routes of administration (for example, gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. In addition to the treatment of warm-blooded animals such as mice, rats, horses, cattle, sheep, dogs, cats, and monkeys, the compounds described herein can be effective in humans.

Administration of the compounds described herein, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

For topical administration, the JAK-selective compound(s) or prodrug(s) can be formulated as solutions, gels, ointments, creams, suspensions, etc., as are well-known in the art. Such formulations can be included in a patch or other transdermal delivery system or formulation, for example, a formulation with ingredients specifically designed to aid transport of the compound through the skin and into the body tissues.

Systemic formulations include those designed for administration by injection (for example, subcutaneous, intravenous, intramuscular, intrathecal, or intraperitoneal injection) as well as those designed for transdermal, transmucosal, oral, or pulmonary administration.

Useful injectable preparations include sterile suspensions, solutions, or emulsions of the active compound(s) in aqueous or oily vehicles. The compositions can also contain formulating agents, such as suspending, stabilizing, and/or dispersing agents. The formulations for injection can be presented in unit dosage form, for example, in ampules or in multidose containers, and can contain added preservatives.

Alternatively, the injectable formulation can be provided in powder form for reconstitution with a suitable vehicle, including but not limited to sterile pyrogen free water, buffer, and dextrose solution, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets, or capsules prepared by conventional means with pharmaceutically acceptable excipients such as binding agents (for example, pregelatinised maize starch, polyvinylpyrrolidone, or hydroxypropyl methylcellulose); fillers (for example, lactose, microcrystalline cellulose, or calcium hydrogen phosphate); lubricants (for example, magnesium stearate, talc, or silica); disintegrants (for example, potato starch or sodium starch glycolate); or wetting agents (for example, sodium lauryl sulfate). The tablets can be coated by methods well known in the art with, for example, sugars, films, or enteric coatings.

Additionally, the pharmaceutical compositions containing the 2,4-substituted pyrmidinediamine as active ingredient or prodrug thereof in a form suitable for oral use can also include, for example, troches, lozenges, aqueous, or oily suspensions, dispersible powders or granules, emulsions, hard or soft capsules, or syrups or elixirs. Compositions intended for oral use can be prepared according to any method known to the art for the manufacture of pharmaceutical compositions, and such compositions can contain one or more agents including sweetening agents, flavoring agents, coloring agents, and preserving agents in order to provide pharmaceutically elegant and palatable preparations. Tablets contain the active ingredient (including drug and/or prodrug) in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (for example, corn starch or alginic acid); binding agents (for example starch, gelatin, or acacia); and lubricating agents (for example, magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They can also be coated by the techniques described in the U.S. Pat. Nos. 4,256,108; 4,166,452; and U.S. Pat. No. 4,265,874 to form osmotic therapeutic tablets for control release. The pharmaceutical compositions described herein can also be in the form of oil-in-water emulsions.

Liquid preparations for oral administration can take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives, or hydrogenated edible fats); emulsifying agents (for example, lecithin, or acacia); non-aqueous vehicles (for example, almond oil, oily esters, ethyl alcohol, Cremophore™, or fractionated vegetable oils); and preservatives (for example, methyl or propyl-p-hydroxybenzoates or sorbic acid). The preparations can also contain buffer salts, preservatives, flavoring, coloring, and sweetening agents as appropriate.

Preparations for oral administration can be suitably formulated to give controlled release of the active compound, as is well known.

For buccal administration, the compositions can take the form of tablets or lozenges formulated in the conventional manner.

For nasal administration or administration by inhalation or insufflation, the active compound(s) or prodrug(s) can be conveniently delivered in the form of a dry powder (either alone, as a mixture, for example in a dry blend with lactose, or as a mixed component particle, for example, mixed with phospholipids, such as phosphatidylcholine) form a dry powder inhaler or as an aerosol spray from pressurized packs or a nebulizer with the use of a suitable propellant (for example, dichlorodifluoromethane, trichlorofluoromethane, dichlorotetrafluoroethane, fluorocarbons, carbon dioxide, or other suitable gas). In the case of a pressurized aerosol, the dosage unit can be determined by providing a valve to deliver a metered amount. Capsules and cartridges for use in an inhaler or insufflator (for example, capsules and cartridges including gelatin) can be formulated containing a powder mix of the compound and a suitable powder base such as lactose or starch.

Prior to use in a dry powder or suspension formulation, the drug product typically is micronized to a size suitable for delivery by inhalation (typically less than about 5 microns). This may be achieved as is known to those of skill in the art by an appropriate method, such as spiral jet milling, fluid bed jet milling, supercritical fluid processing, spray drying and the like.

The pharmaceutical compositions can be in the form of a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent. Among the acceptable vehicles and solvents that can be employed are water, Ringer's solution, and isotonic sodium chloride solution. The 2,4-pyrimidinediamine compounds can also be administered in the form of suppositories for rectal or urethral administration of the drug. For rectal and vaginal routes of administration, the active compound(s) can be formulated as solutions (for retention enemas), suppositories, or ointments containing conventional suppository bases such as cocoa butter or other glycerides. In particular embodiments, the compounds can be formulated as urethral suppositories, for example, for use in the treatment of fertility conditions, particularly in males (for example, for the treatment of testicular dysfunction).

The presently disclosed 2,4-pyrimidinediamine compounds can be used for manufacturing a composition or medicament, including medicaments suitable for topical administration. Accordingly, specifically contemplated are methods for manufacturing compositions including 2,4-pyrimidinediamine compounds in a form that is suitable for topical administration. For topical use, creams, ointments, jellies, gels, solutions, suspensions, etc., containing the 2,4-pyrimidinediamine compounds can be employed. In certain embodiments, the 2,4-pyrimidinediamine compounds can be formulated for topical administration with polyethylene glycol (PEG). These formulations can optionally include additional pharmaceutically acceptable ingredients such as diluents, stabilizers, and/or adjuvants. In particular embodiments, the topical formulations are formulated for the treatment of allergic conditions and/or skin conditions including psoriasis, contact dermatitis, and atopic dermatitis, among others described herein.

As those skilled in the art will recognize, the formulation of 2,4-pyrimidinediamine compounds, the quantity of the formulation delivered, and the duration of administration of a single dose depend on the type of inhalation device employed as well as other factors. For some aerosol delivery systems, such as nebulizers, the frequency of administration and length of time for which the system is activated will depend mainly on the concentration of 2,4-pyrimidinediamine compounds in the aerosol. For example, shorter periods of administration can be used at higher concentrations of 2,4-pyrimidinediamine compounds in the nebulizer solution. Devices such as metered dose inhalers can produce higher aerosol concentrations and can be operated for shorter periods to deliver the desired amount of 2,4-pyrimidinediamine compounds in some embodiments. Devices such as dry powder inhalers deliver active agent until a given charge of agent is expelled from the device. In this type of inhaler, the amount of 2,4-pyrimidinediamine compounds in a given quantity of the powder determines the dose delivered in a single administration. The formulation of 2,4-pyrimidinediamine is selected to yield the desired particle size in the chosen inhalation device.

Included among the devices which can be used to administer particular examples of the 2,4-pyrimidinediamine compounds are those well-known in the art, such as metered dose inhalers, liquid nebulizers, dry powder inhalers, sprayers, thermal vaporizers, and the like. Other suitable technology for administration of particular 2,4-pyrimidinediamine compounds includes electrohydrodynamic aerosolizers.

In addition, the inhalation device is preferably practical, in the sense of being easy to use, small enough to carry conveniently, capable of providing multiple doses, and durable. Some specific examples of commercially available inhalation devices are Turbohaler (Astra, Wilmington, Del.), Rotahaler (Glaxo, Research Triangle Park, N.C.), Diskus (Glaxo, Research Triangle Park, N.C.), the Ultravent nebulizer (Mallinckrodt), the Acorn II nebulizer (Marquest Medical Products, Totowa, N.J.) the Ventolin metered dose inhaler (Glaxo, Research Triangle Park, N.C.), and the like. In one embodiment, 2,4-pyrimidinediamine compounds can be delivered by a dry powder inhaler or a sprayer.

Formulations of 2,4-pyrimidinediamine compounds for administration from a dry powder inhaler may typically include a finely divided dry powder containing 2,4-pyrimidinediamine compounds, but the powder can also include a bulking agent, buffer, carrier, excipient, another additive, or the like. In one aspect, hydroxynapthoate salts, such as 1-hydroxy- or 3-hydroxy-2-napthalenecarboxylate salts of the present 2,4-pyrimidinediamines have low hygroscopicity as compared to the corresponding free base form and have excellent compatibility with excipients, stability, micronize well and other pharmaceutical properties. The 1-hydroxy-2-napthalenecarboxylate salts may be referred to as "xinafoate salts." Disclosed herein are xinafoate salts of 2,4-pyrimidinediamine compounds described herein. Xinafoate salts of 2,4-pyrimidinediamines described herein can be administered alone but also can be administered as a formulation in association with one or more pharmaceutically acceptable diluents, excipients or the like. Dry powder formulations of xinafoic acid salt forms of the 2,4-pyrimidinediamine compounds described herein are one embodiment. Such dry powder formulations with or without a carrier or other additive are suitable for administration via inhalation. Additives can be included in a dry powder formulation of 2,4-pyrimidinediamine compounds, for example, to dilute the powder to facilitate for delivery from the particular powder inhaler, to facilitate processing of the formulation, to provide advantageous powder properties to the formulation, to facilitate dispersion of the powder from the inhalation device, to stabilize to the formulation (for example, antioxidants or buffers), to provide taste to the formulation, or the like. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; and the like. For example, a dry powder formulation can be manufactured in several ways, using conventional techniques, such as described in any of the publications mentioned above and incorporated expressly herein by reference, and, for example, Baker, et al., U.S. Pat. No. 5,700,904, the entire disclosure of which is incorporated expressly herein by reference. Particles in the size range appropriate for maximal deposition in the lower respiratory tract can be made by micronizing, milling, or the like. A liquid formulation can be manufactured by dissolving one or more of the presently 2,4-pyrimidinediamine compounds in a suitable solvent, such as water, at an appropriate pH, including buffers or other excipients.

For ocular administration, the 2,4-pyrimidinediamine compound(s) or prodrug(s) can be formulated as a solution, emulsion, suspension, etc., suitable for administration to the eye. Administration to the eye is generally via topical exposure of the eye to the formulation, but also includes injection into the eye if necessary. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

Typically formulations for ocular administration contain a pharmaceutically effective amount of a 2,4-pyrimidinediamine compound disclosed herein, such as from about 0.0001% to about 1.0% by weight (w/w). In certain formulations, the pharmaceutically effective amount of the compound is 0.0003% to about 0.1% (w/w), such as from about 0.003% to about 0.5% (w/w), or from about 0.01% to about 0.03% (w/w).

In certain examples an ophthalmic composition containing a presently disclosed 2,4-pyrimidinediamine compound for ocular administration includes a tonicity agent, a buffer, or both. In certain examples of ophthalmic compositions the tonicity agent is a simple carbohydrate or a sugar alcohol. As is known to those of skill in the art, tonicity agents may be used in the present compositions to adjust the tonicity of the composition, preferably to that of normal tears. Examples of suitable tonicity agents include, without limitation sodium chloride, potassium chloride, magnesium chloride, calcium chloride, carbohydrates, such as dextrose, fructose, galactose, polyols, such as sugar alcohols, including by way of example, mannitol, sorbitol, xylitol, lactitol, isomalt, maltitol and combinations thereof. Compositions containing a buffer contain, in some examples, a phosphate, citrate, or both.

In one aspect, compositions for ocular administration of the presently disclosed 2,4-pyrimidinediamine compounds optionally contain a surfactant, a stabilizing polymer, or both. Surfactants are employed in certain compositions to facilitate the delivery of higher concentrations of the 2,4-pyrimidinediamine compound being administered. Such surfactants can work to solubilize the compound. Exemplary surfactants include polysorbate, poloxamer, polyosyl 40 stearate, polyoxyl castor oil, tyloxapol, triton and sorbitan monolaurate. In certain embodiments the surfactant is selected from Triton X114, tyloxapol and combinations thereof. In still another embodiment of compositions for ocular administration, the stabilizing polymer is carbomer 974p.

For prolonged delivery, the 2,4-pyrimidinediamine compound(s) or prodrug(s) can be formulated as a depot preparation for administration by implantation or intramuscular injection. The active ingredient can be formulated with suitable polymeric or hydrophobic materials (for example, as an emulsion in an acceptable oil) or ion exchange resins, or as sparingly soluble derivatives (for example, as a sparingly soluble salt). Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in, for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) can also be employed, although usually at the cost of greater toxicity.

The pharmaceutical compositions can, if desired, be presented in a pack or dispenser device which can contain one or more unit dosage forms containing the active compound(s). The pack can, for example, include metal or plastic foil, such as a blister pack. The pack or dispenser device can be accompanied by instructions for administration.

Another embodiment is a kit including a compound, prodrug or pharmaceutical composition as described in any of the embodiments above. Kit embodiments are described in more detail below.

Methods of Use

The present invention provides 2,4-pyrimidinediamine compounds, prodrugs and pharmaceutical compositions thereof, as described herein, for use in therapy for the conditions described herein. The present invention further provides use of the compounds of the present invention in the manufacture of a medicament for the treatment of conditions in which targeting of the JAK pathway or inhibition of JAK kinases, particularly JAK3, are therapeutically useful. These include conditions where the function of lymphocytes, macrophages, or mast cells is involved. Conditions in which targeting of the JAK pathway or inhibition of the JAK kinases, particularly JAK3, are therapeutically useful include leukemia, lymphoma, transplant rejection (for example, pancreas islet transplant rejection), bone marrow transplant applications (for example, graft-versus-host disease), autoimmune diseases (for example, rheumatoid arthritis, psoriasis, and the like), inflammation (for example, asthma, etc.) and other conditions as described in greater detail herein.

In another embodiment, the methods can be practiced as a therapeutic approach towards the treatment of the conditions described herein. Thus, in a specific embodiment, the 2,4-pyrimidinediamine compounds (and the various forms described herein, including pharmaceutical formulations including the compounds (in the various forms)) can be used to treat the conditions described herein in animal subjects, including humans. The methods generally include administering to the subject an amount of a compound described herein, or a salt, prodrug, hydrate, or N-oxide thereof, effective to treat the condition. In one embodiment, the subject is a non-human mammal, including, but not limited to, bovine, horse, feline, canine, rodent, or primate. In another embodiment, the subject is a human.

As noted previously, numerous conditions can be treated using the 2,4-substituted pyrimidinediamine compounds, prodrugs thereof, and methods of treatment as described herein. As used herein, "Treating" or "treatment" of a disease in a patient refers to (1) preventing the disease from occurring in a patient that is predisposed or does not yet display symptoms of the disease; (2) inhibiting the disease or arresting its development; or (3) ameliorating or causing regression of the disease. As well understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable. Preferred are compounds that are relatively potent compared to the class as a whole and can be administered at low doses, preferably but not necessarily locally, thus minimizing systemic adverse effects.

The compounds described herein are potent and selective inhibitors of JAK kinases and are particularly selective for cytokine signaling pathways containing JAK3. As a consequence of this activity, the compounds can be used in a variety of in vitro, in vivo, and ex vivo contexts to regulate or inhibit JAK kinase activity, signaling cascades in which JAK kinases play a role, and the biological responses effected by such signaling cascades. For example, in one embodiment, the compounds can be used to inhibit JAK kinase, either in vitro or in vivo, in virtually any cell type expressing the JAK kinase, such as in hematopoietic cells in which, for example, JAK3 is predominantly expressed. They can also be used to regulate signal transduction cascades in which JAK kinases, particularly JAK3, play a role.

Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15, and IL-21 receptor signaling cascades. The compounds can also be used in vitro or in vivo to regulate, and in particular to inhibit, cellular or biological responses affected by such JAK-dependent signal transduction cascades. Such cellular or biological responses include, but are not limited to, IL-4/ramos CD23 upregulation and IL-2 mediated T-cell proliferation. Importantly, the compounds can be used to inhibit JAK kinases in vivo as a therapeutic approach towards the treatment or prevention of diseases mediated, either wholly or in part, by a JAK kinase activity (referred to herein as "JAK kinase mediated diseases"). Non-limiting examples of JAK kinase mediated diseases that can be treated or prevented with the presently disclosed compounds include, but are not limited to, the following: allergies; asthma; autoimmune diseases, including systemic autoimmune disorders, transplant rejection (for example, kidney, heart, lung, liver, pancreas, skin; host versus graft reaction (HVGR), and graft versus host reaction (GVHR)), rheumatoid arthritis, and amyotrophic lateral sclerosis; T-cell mediated autoimmune diseases such as multiple sclerosis, psoriasis, and Sjogren's syndrome; Type II inflammatory diseases such as vascular inflammation (including vasculitis, arteritis, atherosclerosis, and coronary artery disease); diseases of the central nervous system such as stroke; pulmonary diseases such as bronchitis obliterans and primary pulmonary hypertension; solid, delayed Type IV hypersensitivity reactions; and hematologic malignancies such as leukemia and lymphomas.

In addition to the disorders listed above, the disclosed compounds are particularly useful for the treatment of obstructive, restrictive or inflammatory airways diseases of whatever type, etiology, or pathogenesis, in particular an obstructive, restrictive or inflammatory airways disease, including, as mentioned above, asthma, in particular atopic asthma, allergic asthma, non-atopic asthma, bronchial asthma, non-allergic asthma, emphysematous asthma, exercise-induced asthma, emotion-induced asthma, extrinsic asthma caused by environmental factors, infective asthma associated with bacterial, fungal, protozoal and/or viral infection, bronchiolitis, cough variant asthma, drug induced asthma, and the like. The presently disclosed compounds also are particularly useful in treating rhinitis or sinusitis of different etiologies, including without limitation, seasonal allergic rhinitis, perennial allergic rhinitis, vasomotor rhinitis, sinusitis, including acute, chronic, ethmoid, frontal maxillary or sphenoid sinusitis. The disclosed compounds also are useful in treating chronic obstructive pulmonary disease (COPD), chronic obstructive lung disease (COLD), chronic obstructive airways disease (COAD) or small airways obstruction, including, without limitation, chronic bronchitis, pulmonary emphysema, bronchiectasis, cystic fibrosis, bronchiolitis obliterans. Moreover, the disclosed compounds can be used to treat bronchitis, including in particular, acute bronchitis, acute laryngotracheal bronchitis, chronic bronchitis, dry bronchitis, productive bronchitis, infectious asthmatic bronchitis, *staphylococcus* or streptococcal bronchitis and vesicular bronchitis.

One embodiment is a method as described herein employed with a compound according to formula I, or in a more specific embodiment, a compound according to formula IA, IB, IC, II, III or IV in an even more specific embodiment, a species described herein. For brevity, the methods described reference a compound of formula I, but corresponding methods according to the various compound and composition subgenus and species are also meant to be included.

One embodiment is a method of inhibiting an activity of a JAK kinase, including contacting the JAK kinase with an amount of a compound, effective to inhibit an activity of the JAK kinase, of formula I:

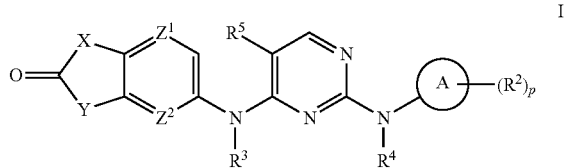

where:
X and Y are each independently O, S, S(O), SO$_2$ or NR$^1$;
each R$^1$ is independently for each occurrence H, optionally substituted C$_{1-6}$alkyl, C(O)—C$_{1-6}$alkyl, CO$_2$—C$_{1-6}$alkyl or R$^{50}$;
each R$^{50}$ is —C(R$^9$)$_2$-A-R$^{10}$, where A is O or S; each R$^9$ is independently for each occurrence H, optionally substituted C$_{1-6}$alkyl, optionally substituted C$_{6-10}$aryl or optionally substituted C$_{7-16}$arylalkyl; or alternatively, two R$^9$, together with the carbon to which they are attached, form an optionally substituted C$_{3-8}$cycloalkyl group or an optionally substituted 3-8 membered heteroalicyclyl; R$^{10}$ is R$^a$, —P(O)(OR$^{11}$)$_2$, —P(O)(OR$^{11}$)N(R$^{12}$)$_2$ or —P(O)(N(R$^{12}$)$_2$)$_2$; each R$^{11}$ is independently for each occurrence R$^a$ or a monovalent cationic group; or two R$^{11}$, together with the atoms to which they are attached, form a 4-8 membered cyclic phosphate group, or two R$^{11}$ together represent a divalent cationic group; each R$^{12}$ is independently for each occurrence R$^c$ or —C$_{1-3}$alkyl-N(R$^c$)$_2$; or two R$^{12}$, each on separate nitrogens of —P(O)(N(R$^{12}$)$_2$)$_2$, together with the atoms to which they are attached, form a 4-8 membered cyclic phosphonic acid bisamide group; or one R$^{12}$ along with R$^{11}$, of the group —P(O)(OR$^{11}$)N(R$^{12}$)$_2$, together with the atoms to which they are attached, form a 4-8 membered cyclic phosphonamidate group;
ring A is a C$_{6-10}$aryl or a 5-10 membered heteroaryl;
each R$^2$ is independently for each occurrence H, R$^e$, R$^b$, R$^e$ substituted with one or more of the same or different R$^a$ and/or R$^b$, —OR$^e$ substituted with one or more of the same or different R$^a$ and/or R$^b$, —SR$^e$ substituted with one or more of the same or different R$^a$ and/or R$^b$, —C(O)R$^e$ substituted with one or more of the same or different R$^a$ and/or R$^b$, —N(R$^a$)R$^e$ where R$^e$ is substituted with one or more of the same or different R$^a$ and/or R$^b$, —S(O)$_2$R$^e$ substituted with one or more of the same or different R$^a$ and/or R$^b$, —N(R$^a$)—S(O)$_2$R$^e$ where R$^e$ is substituted with one or more of the same or different R$^a$ and/or R$^b$, —B(OR$^a$)$_2$, —B(N(R$^c$)$_2$)$_2$, —(C(R$^a$)$_2$)$_m$—R$^b$, —O—(C(R$^a$)$_2$)$_m$—R$^b$, —S—(C(R$^a$)$_2$)$_m$—R$^b$, —O—(C(R$^b$)$_2$)$_m$—R$^a$, —N(R$^a$)—(C(R$^a$)$_2$)$_m$—R$^b$, —O—(CH$_2$)$_m$—CH((CH$_2$)$_m$R$^b$)R$^b$, —C(O)N(R$^a$)—(C(R$^a$)$_2$)$_m$—R$^b$, —O—(C(R$^a$)$_2$)$_m$—C(O)N(R$^a$)—(C(R$^a$)$_2$)$_m$—R$^b$, —N((C(R$^a$)$_2$)$_m$R$^b$)$_2$, —S—(C(R$^a$)$_2$)$_m$—C(O)N(R$^a$)—(C(R$^a$)$_2$)$_m$—R$^b$, —N(R$^a$)—C(O)—(C(R$^a$)$_2$)$_m$—N(R$^a$)—(C(R$^a$)$_2$)$_m$—R$^b$, —N(R$^a$)—C(O)—(C(R$^a$)$_2$)$_m$—C(R$^a$)(R$^b$)$_2$ or —N(R$^a$)—(C(R$^a$)$_2$)$_m$—C(O)—N(R$^a$)—(C(R$^a$)$_2$)$_m$—R$^b$ each R$^a$ is independently for each occurrence H, deuterium, C$_{1-6}$alkyl, C$_{3-8}$-cycloalkyl, C$_{4-11}$cycloalkylalkyl, C$_{6-10}$aryl, C$_{7-6}$arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;
each R$^b$ is independently for each occurrence =O, —OR$^a$, —O—(C(R$^a$)$_2$)$_m$—OR$^a$, haloC$_{1-3}$ alkyloxy, =S, —SR$^a$, =NR$^a$, =NOR$^a$, ~N(R$^c$)$_2$, halo, —CF$_3$, —CN, —NC, —OCN, —SCN, —NO, —NO$_2$, =N$_2$, —N$_3$, —S(O)R$^a$, —S(O)$_2$R$^a$, —SO$_3$R$^a$, —S(O)N(R$^c$)$_2$, —S(O)$_2$N(R$^c$)$_2$, —OS(O)R$^a$, —OS(O)$_2$R$^a$, —OSO$_3$R$^a$, —OS(O)$_2$N(R$^c$)$_2$, —C(O)R$^a$, —CO$_2$R$^a$, —C(O)N(R$^c$)$_2$, —C(NR$^a$)—N(R$^c$)$_2$, —C(NOH)—R$^a$, —C(NOH)—N(R$^c$)$_2$, —OC(O)R$^a$, —OC(O)OR$^a$, —OC(O)N(R$^c$)$_2$, —OC(NH)—N(R$^c$)$_2$, —OC(NR$^a$)—N(R$^c$)$_2$, —N(R$^a$)—S(O)$_2$H, —[N(R$^a$)C(O)]$_n$R$^a$, —[N(R$^a$)C(O)]$_n$OR$^a$, —[N(R$^a$)C(O)]$_n$N(R$^c$)$_2$ or —[N(R$^a$)C(NR$^a$)]$_n$—N(R$^c$)$_2$;
each R$^c$ is independently for each occurrence R$^a$, or, alternatively, two R$^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different R$^a$ and/or R$^d$ groups;
each R$^d$ is =O, —OR$^a$, haloC$_{1-3}$alkyloxy, C$_{1-6}$alkyl, =S, —SR$^a$, =NR$^a$, =NOR$^a$, —N(R$^a$)$_2$, halo, —CF$_3$, —CN, —NC, —OCN, —SCN, —NO, —NO$_2$, =N$_2$, —N$_3$, —S(O)R$^a$, —S(O)$_2$R$^a$, —SO$_3$R$^a$, —S(O)N(R$^a$)$_2$, —S(O)$_2$N(R$^a$)$_2$, —OS(O)R$^a$, —OS(O)$_2$R$^a$, —OSO$_3$R$^a$, —OS(O)$_2$N(R$^a$)$_2$, —C(O)R$^a$, —CO$_2$R$^a$, —C(O)N(R$^a$)$_2$, —C(NR$^a$)N(R$^a$)$_2$, —C(NOH)R$^a$, —C(NOH)N(R$^a$)$_2$, —OCO$_2$R$^a$, —OC(O)N(R$^a$)$_2$, —OC(NR$^a$)N(R$^a$)$_2$, —[N(R$^a$)C(O)]$_n$R$^a$, —(C(R$^a$)$_2$)$_n$—OR$^a$, —N(R$^a$)—S(O)$_2$R$^a$, —C(O)—C$_{1-6}$haloalkyl, —S(O)$_2$C$_{1-6}$haloalkyl, —OC(O)R$^a$, —O(C(R$^a$)$_2$)$_m$—OR$^a$, —S(C(R$^a$)$_2$)$_m$—OR$^a$, —N(R$^a$)C$_{1-6}$haloalkyl, —P(O)(OR$^a$)$_2$, —N(R$^a$)—(C(R$^a$)$_2$)—OR$^a$, —[N(R$^a$)C(O)]$_n$OR$^a$, —[N(R$^a$)C(O)]$_n$N(R$^a$)$_2$, —[N(R$^a$)C(NR$^a$)]$_n$N(R$^a$)$_2$ or —N(R$^a$)C(O)C$_{1-6}$haloalkyl; two R$^d$, taken together with the atom or atoms to which they are attached, combine to form a 3-10 membered partially or fully saturated mono or bicyclic ring, optionally containing one or more heteroatoms and optionally substituted with one or more R$^a$;
each R$^e$ is independently for each occurrence C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;
p is 0, 1, 2, 3 or 4;
each m is 1, 2 or 3;
each n is 0, 1, 2 or 3;
two R$^2$ groups, taken together with the atom or atoms to which they are attached, combine to form a 4-10 membered partially or fully saturated mono or bicyclic ring, optionally containing one or more heteroatoms and optionally substituted with one or more R$^a$ and/or R$^b$;
Z$^1$ and Z$^2$ are each independently CH, CR$^2$ or N;
R$^3$ is H, optionally substituted C$_{1-6}$alkyl or R$^{50}$;
R$^4$ is H, optionally substituted C$_{1-6}$alkyl or R$^{50}$; and R⁵ is H, halo, —CN, optionally substituted $C_{1-6}$alkyl, alkynyl, hydroxy, optionally substituted $C_{1-6}$alkoxy, nitro, —N(R$^a$)$_2$, —C(O)N(R$^a$)$_2$, —CO$_2$R$^a$ or —C(O)R$^a$.

Another embodiment is a method of inhibiting an activity of a JAK kinase, including contacting the JAK kinase with an amount of a compound effective to inhibit an activity of the JAK kinase, where the compound is according to formula I, as described herein. In certain embodiments of the methods described herein, the method is carried out in vivo.

In another embodiment, this invention provides a method of inhibiting an activity of a JAK kinase, including contacting in vitro a JAK3 kinase with an amount of a compound effective to inhibit an activity of the JAK kinase, where the compound is according to formula I, as described herein.

In a specific embodiment, the compounds can be used to treat and/or prevent rejection in organ and/or tissue transplant recipients (i.e., treat and/or prevent allograft rejection). Allografts can be rejected through either a cell-mediated or humoral immune reaction of the recipient against transplant (histocompatibility) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relatively uncommon today.

Acute rejection is thought to be mediated by the accumulation of antigen specific cells in the graft tissue. The T-cell-mediated immune reaction against these antigens (i.e., HVGR or GVHR) is the principle mechanism of acute rejection. Accumulation of these cells leads to damage of the graft tissue. It is believed that both CD4+ helper T-cells and CD8+ cytotoxic T-cells are involved in the process and that the antigen is presented by donor and host dendritic cells. The CD4+ helper T-cells help recruit other effector cells, such as macrophages and eosinophils, to the graft. Accessing T-cell activation signal transduction cascades (for example, CD28, CD40L, and CD2 cascades) are also involved.

The cell-mediated acute rejection can be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial endothelium is primarily involved with extensive proliferation that may gradually occlude the vessel lumen, leading to ischemia, fibrosis, a thickened intima, and atherosclerotic changes. Chronic rejection is mainly due to a progressive obliteration of graft vasculature and resembles a slow, vasculitic process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

Since JAK kinases play a critical role in the activation of T-cells, the 2,4-pyrimidinediamine compounds described herein can be used to treat and/or prevent many aspects of transplant rejection, and are particularly useful in the treatment and/or prevention of rejection reactions that are mediated, at least in part, by T-cells, such as HVGR or GVHR. The 2,4-pyrimidinediamine compounds can also be used to treat and/or prevent chronic rejection in transplant recipients and, in particular, in renal transplant recipients. The compound can also be administered to a tissue or an organ prior to transplanting the tissue or organ in the transplant recipient.

In another embodiment, this invention provides a method of treating a T-cell mediated autoimmune disease, including administering to a patient suffering from such an autoimmune disease an amount of a compound effective to treat the autoimmune disease where the compound is according to formula I, as described herein. In certain embodiments of the methods the autoimmune disease is multiple sclerosis (MS), psoriasis, or Sjogran's syndrome.

Therapy using the 2,4-pyrimidinediamine compounds described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of The Physician's Desk Reference), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand name SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, the 2,4-pyrimidinediamine compounds could be administered either in combination or adjunctively with an inhibitor of a Syk kinase. Syk kinase is a tyrosine kinase known to play a critical role in Fcγ receptor signaling, as well as in other signaling cascades, such as those involving B-Cell receptor signaling (Tumer et al., (2000), Immunology Today 21:148-154) and integrins beta (1), beta (2), and beta (3) in neutrophils (Mocsavi et al., (2002), Immunity 16:547-558). For example, Syk kinase plays a pivotal role in high affinity IgE receptor signaling in mast cells that leads to activation and subsequent release of multiple chemical mediators that trigger allergic attacks. However, unlike the JAK kinases, which help regulate the pathways involved in delayed or cell-mediated Type IV hypersensitivity reactions, Syk kinase helps regulate the pathways involved in immediate IgE-mediated, Type I hypersensitivity reactions. Certain compounds that affect the Syk pathway may or may not also affect the JAK pathways.

Suitable Syk inhibitory compounds are described, for example, in Ser. No. 10/355,543 filed Jan. 31, 2003 (publication no. 2004/0029902); WO 03/063794; Ser. No. 10/631,029 filed Jul. 29, 2003 (publication no. 2007/0060603); WO 2004/014382; Ser. No. 10/903,263 filed Jul. 30, 2004 (publication no. 2005/0234049); PCT/US2004/24716 filed Jul. 30, 2004 (WO005/016893); Ser. No. 10/903,870 filed Jul. 30, 2004 (publication no. 2005/0209224); PCT/US2004/24920 filed Jul. 30, 2004; Ser. No. 60/630,808 filed Nov. 24, 2004; Ser. No. 60/645,424 filed Jan. 19, 2005; and Ser. No. 60/654,620, filed Feb. 18, 2005, the disclosures of which are incorporated herein by reference. The 2,4-pyrimidinediamine described herein and Syk inhibitory compounds could be used alone or in combination with one or more conventional transplant rejection treatments, as described above.

In a specific embodiment, the 2,4-pyrimidinediamine compounds can be used to treat or prevent these diseases in patients that are either initially non-responsive (resistant) to or that become non-responsive to treatment with a Syk inhibitory compound or one of the other current treatments for the particular disease. The 2,4-pyrimidinediamine compounds could also be used in combination with Syk inhibitory compounds in patients that are Syk-compound resistant or non-responsive. Suitable Syk-inhibitory compounds with which the 2,4-pyrimidinediamine compounds can be administered are provided supra.

In another embodiment, this invention provides a method of treating a T-cell mediated autoimmune disease, including administering to a patient suffering from such an autoimmune disease an amount of a compound according to formula I, in combination with or adjunctively to a compound that inhibits Syk kinase with an $IC_{50}$ of at least 10 μM, effective to treat the autoimmune disease.

In another embodiment, this invention provides a method of treating allograft transplant rejection, either acute or chronic, in a transplant recipient, including administering to the transplant recipient an amount of a compound according to formula I effective to treat or prevent the rejection. In a further embodiment, the compound is administered to a tissue or an organ prior to or concurrent with, transplanting the tissue or organ in the transplant recipient. In another embodiment, the compound is administered to the tissue or organ and the patient. In a specific embodiment the allograft transplant rejection is mediated by HVGR or GVHR. In another embodiment, the allograft transplant organ is a kidney, a heart, a liver, or a lung. In another embodiment, in which the allograft transplant organ is a kidney, a heart, a liver, or a lung, the compound is administered in combination with or adjunctively to another immunosuppressant. In a more specific embodiment, the immunosuppressant is cyclosporine, tacrolimus, sirolimus, an inhibitor of IMPDH, mycophenolate, mycophanolate mofetil, an anti-T-Cell antibody or OKT3.

The 2,4-pyrimidinediamine compounds described herein are cytokine moderators of IL-4 signaling. As a consequence, the 2,4-pyrimidinediamine compounds could slow the response of Type I hypersensitivity reactions. Thus, in a specific embodiment, the 2,4-pyrimidinediamine compounds could be used to treat such reactions and, therefore, the diseases associated with, mediated by, or caused by such hypersensitivity reactions (for example, allergies), prophylactically. For example, an allergy sufferer could take one or more of the JAK selective compounds described herein prior to expected exposure to allergens to delay the onset or progress of, or eliminate altogether, an allergic response.

When used to treat or prevent such diseases, the 2,4-pyrimidinediamine compounds can be administered singly, as mixtures of one or more 2,4-pyrimidinediamine compounds, or in mixture or combination with other agents useful for treating such diseases and/or the symptoms associated with such diseases. The 2,4-pyrimidinediamine compounds can also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, β-agonists, tryptase inhibitors, aspirin, cyclooxygenase (COX) inhibitors, methotrexate, anti-TNF drugs, rituximab, PD4 inhibitors, p38 inhibitors, PDE4 inhibitors, and antihistamines, to name a few. The 2,4-pyrimidinediamine compounds can be administered per se in the form of prodrugs or as pharmaceutical compositions, including an active compound.

In another embodiment, this invention provides a method of treating a Type IV hypersensitivity reaction, including administering to a subject an amount of a compound effective to treat or prevent the hypersensitivity reaction, where the compound is according to formula I, as described herein. In one embodiment, the method is practiced prophylactically. In some embodiments, the compound is administered prior to exposure to an allergen.

In another embodiment, this invention provides a method of inhibiting a signal transduction cascade in which JAK3 kinase plays a role, including contacting a cell expressing a receptor involved in such a signaling cascade with a compound, where the compound is according to formula I, as described herein.

In another embodiment, this invention provides a method of treating a JAK kinase-mediated disease, including administering to a subject an amount of compound effective to treat or prevent the JAK kinase-mediated disease, where the compound is according to formula I, as described herein.

In another embodiment, this invention provides a method of treating a JAK kinase-mediated disease, in which the JAK-mediated disease is HVGR or GVHR, including administering to a subject an amount of compound effective to treat or prevent the JAK kinase-mediated disease, where the compound is according to formula I, as described herein.

In another embodiment, ocular disorders are treated using an effective amount of a compound of formula I, as described herein. In one aspect of the disclosed method for treating ocular disorders, administration of one or more of the presently disclosed 2,4-pyrimidinediamine compounds is effective to increase tear production volume as compared to untreated tear production volume, thereby ameliorating a symptom of dry eye syndrome. In one aspect, tear production volume is increased within five days, such as in less than four days, and in some examples in less than two days. In one embodiment, tear production volume is increased by at least about 25% over initial tear production within two days of initial treatment with a presently disclosed 2,4-pyrimidinediamine compound. In other embodiments, tear production is increased at least about 30%, such as at least about 50% over initial tear production within less than two days. Increases in tear production upon administration of the present compounds results, in some instances, in tear production volume comparable to normal tear production. Typically the disclosed compounds, when used for treating ocular disorders topically, are administered at least once daily and typically at most twice a day.

As mentioned, another embodiment provides a method of treating a disease and/or disorder of the eye, which includes administering to a subject an amount of a compound effective to treat the disease and/or disorder of the eye wherein the compound is according to formula I, as described herein. Diseases and disorders of the eye include, but are not limited to, dry eye syndrome, uveitis, allergic conjunctivitus, glaucoma and rosacea (of the eye). Dry eye syndrome (DES), otherwise known as keratoconjunctivitis sicca (KCS), keratitis sicca, sicca syndrome, or xerophthalmia, is an eye disease caused by decreased tear production or increased tear film evaporation commonly found in humans and some animals. Uveitis or iridocyclitis refers to inflammation of the middle layer of the eye (the "uvea") and in common usage may refer to any inflammatory process involving the interior of the eye. Allergic conjunctivitis is inflammation of the conjunctiva (the membrane covering the white part of the eye) due to allergy. Glaucoma refers to a group of diseases that affect the optic nerve and involves a loss of retinal ganglion cells in a characteristic pattern, i.e., a type of optic neuropathy. Raised intraocular pressure is a significant risk factor for developing glaucoma (above 22 mmHg or 2.9 kPa), and inflammatory processes, e.g. uveitis, can cause this rise in intraocular pressure. Rosacea is a chronic inflammatory condition characterized by facial erythema but it can affect the eyes. As mentioned, compounds described herein may be used to treat inflammatory responses. While not wishing to be bound by theory, it is believed that compounds described herein are effective treatments of these eye disorders due, at least in part, to their JAK inhibitory activity.

In one embodiment, for treatment of diseases and/or disorders of the eye, the compounds described herein, or the pharmaceutically acceptable salt forms thereof, are administered either in combination or adjunctively with at least one of an antihistamine, an antibiotic, an anti-inflammatory, an antiviral and a glaucoma medication. Examples of common antibiotics used in the eye are sulfacetamide, erythromycin, gentamicin, tobramycin, ciprofloxacin and ofloxacin. Corticosteroids (sometimes referred to as "steroids") are similar to a natural substance produced by the adrenal gland and are very effective anti-inflammatories for a wide variety of eye problems. Corticosteroids can be safely used in the eye, and do not carry most of the risks associated with oral steroids like prednisone. Cortisteroids used to treat the eye include, but are not limited to, prednisolone, fluorometholone and dexamethasone. Non-steroidal anti-inflammatories for the eye include, but are not limited to, ibuprofen, diclofenac, ketorolac and flurbiprofen. Common antihistamines include livostin, patanol, cromolyn, alomide. There are also non-prescription antihistamines for the eye, which are less potent but can be very helpful in milder case, such as pheniramine. Common antiviral eye medications include, but are not limited to, triflurthymidine, adenine, arabinoside and idoxuridine. Glaucoma medications all attempt to reduce the eye's intraocular pressure, the fluid pressure inside the eye, to prevent damage to the optic nerve resulting in loss of vision. These medications may lower pressure by decreasing the amount of fluid produced in the eye, by increasing the amount of fluid exiting through the eye's natural drain, or by providing additional pathways for fluid to leave the eye. Often more than one glaucoma medication will be used simultaneously, as these effects can combine to lower pressure even further than possible with one medicine alone. Common glaucoma medications include, but are not limited to, betablockers such as timolol, metipranolol, carteolol, betaxolol and levobunolol; prostaglandin analogues such as latanoprost; cholinergic agonists such as pilocarpine and carbachol; alpha agonists such as bromonidine and iopidine; carbonic anhydrase inhibitors such as dorzolamide; and adenergic agonists such as epinephrine and dipivefrin.

Active compounds described herein typically inhibit the JAK/Stat pathway. The activity of a specified compound as an inhibitor of a JAK kinase can be assessed in vitro or in vivo. In some embodiments, the activity of a specified compound can be tested in a cellular assay. Suitable assays include assays that determine inhibition of either the phosphorylation activity or ATPase activity of a JAK kinase. Thus, a compound is said to inhibit an activity of a JAK kinase if it inhibits the phosphorylation or ATPase activity of a JAK kinase with an $IC_{50}$ of about 20 μM or less.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

"Hematopoietic neoplasm" refers to a cell proliferative disorder arising from cells of the hematopoietic lineage. Generally, hematopoiesis is the physiological process whereby undifferentiated cells or stem cells develop into various cells found in the peripheral blood. In the initial phase of development, hematopoietic stem cells, typically found in the bone marrow, undergo a series of cell divisions to form multipotent progenitor cells that commit to two main developmental pathways: the lymphoid lineage and the myeloid lineage. The committed progenitor cells of the myeloid lineage differentiate into three major sub-branches including the erythroid, megakaryocyte, and granulocyte/monocyte developmental pathways. An additional pathway leads to formation of dendritic cells, which are involved in antigen presentation. The erythroid lineage gives rise to red blood cells while the megakaryocytic lineage gives rise to blood platelets. Committed cells of the granulocyte/monocyte lineage split into granulocyte or monocyte developmental pathways, the former pathway leading to formation of neutrophils, eosinophils, and basophils and the latter pathway giving rise to blood monocytes and macrophages.

Committed progenitor cells of the lymphoid lineage develop into the B cell pathway, T cell pathway, or the non-T/B cell pathway. Similar to the myeloid lineage, an additional lymphoid pathway appears to give rise to dendritic cells involved in antigen presentation. The B cell progenitor cell develops into a precursor B cell (pre-B), which differentiates into B cells responsible for producing immunoglobulins. Progenitor cells of the T cell lineage differentiate into precursor T cells (pre-T) that, based on the influence of certain cytokines, develop into cytotoxic or helper/suppressor T cells involved in cell mediated immunity. Non-T/B cell pathway leads to generation of natural killer (NK) cells. Neoplasms of hematopoietic cells can involve cells of any phase of hematopoiesis, including hematopoietic stem cells, multipotent progenitor cells, oligopotent committed progenitor cells, precursor cells, and mature differentiated cells. The categories of hematopoietic neoplasms can generally follow the descriptions and diagnostic criteria employed by those of skill in the art (see, for example, International Classification of Disease and Related Health Problems (ICD 10), World Health Organization (2003)). Hematopoietic neoplasms can also be characterized based on the molecular features, such as cell surface markers and gene expression profiles, cell phenotype exhibited by the aberrant cells, and/or chromosomal aberrations (for example, deletions, translocations, insertions, etc.) characteristic of certain hematopoietic neoplasms, such as the Philadelphia chromosome found in chronic myelogenous leukemia. Other classifications include National Cancer Institute Working Formulation (Cancer, 1982, 49:2112-2135) and Revised European-American Lymphoma Classification (REAL).

"Lymphoid neoplasm" refers a proliferative disorder involving cells of the lymphoid lineage of hematopoiesis. Lymphoid neoplasms can arise from hematopoietic stem cells as well as lymphoid committed progenitor cells, precursor cells, and terminally differentiated cells. These neoplasms can be subdivided based on the phenotypic attributes of the aberrant cells or the differentiated state from which the abnormal cells arise. Subdivisions include, among others, B cell neoplasms, T cell neoplasms, NK cell neoplasms, and Hodgkin's lymphoma.

"Myeloid neoplasm" refers to proliferative disorder of cells of the myeloid lineage of hematopoiesis. Neoplasms can arise from hematopoietic stem cells, myeloid committed progenitor cells, precursor cells, and terminally differentiated cells. Myeloid neoplasms can be subdivided based on the phenotypic attributes of the aberrant cells or the differentiated state from which the abnormal cells arise. Subdivisions include, among others, myeloproliferative diseases, myelodysplastic/myeloproliferative diseases, myelodysplastic syndromes, acute myeloid leukemia, and acute biphenotypic leukemia.

Generally cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma. More specifically, related to particular tissues, organs or areas of the body, Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defomians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. The term "cancerous cell" as provided herein, includes a cell afflicted by any one of the above-identified conditions.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. The presently disclosed compounds are particularly useful in the treatment of T-cell and Nk-cell neoplasms, which are further subdivided into precursor T-cell neoplasms and mature (peripheral) T-cell neoplasms. An exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnoses of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant JAK activity can be treated with the JAK inhibitory compounds.

In some embodiments, the hematopoietic neoplasm treated is a myeloid neoplasm. This group includes a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (for example, Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant JAK activity can be treated with the JAK inhibitory compounds.

In some embodiments, the JAK inhibitory compounds can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1(CBF-alpha)/ETO, Acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

One means of assaying for such inhibition is detection of the effect of the 2,4-pyrimidinediamine compounds on the upregulation of downstream gene products. In the Ramos/IL4 assay, B-cells are stimulated with the cytokine Interleukin-4 (IL-4) leading to the activation of the JAK/Stat pathway through phosphorylation of the JAK family kinases, JAK1 and JAK3, which in turn phosphorylate and activate the transcription factor Stat-6. One of the genes upregulated by activated Stat-6 is the low affinity IgE receptor, CD23. To study the effect of inhibitors (for example, the 2,4-substituted pyrimindinediamine compounds described herein) on the JAK1 and JAK3 kinases, human Ramos B cells are stimulated with human IL-4. 20 to 24 hours post stimulation, cells are stained for upregulation of CD23 and analyzed using FACS. A reduction of the amount of CD23 present compared to control conditions indicates the test compound actively inhibits the JAK kinase pathway. An exemplary assay of this type is described in greater detail in Example 2.

The activity of the compounds described herein can further be characterized by assaying the effect of the 2,4-pyrimidinediamine compounds described herein on the proliferative response of primary human T-cells. In this assay, primary human T-cells derived from peripheral blood and pre-activated through stimulation of the T-cell receptor and CD28, proliferate in culture in response to the cytokine Interleukin-2 (IL-2). This proliferative response is dependent on the activation of JAK1 and JAK3 tyrosine kinases, which phosphorylate and activate the transcription factor Stat-5. The primary human T-cells are incubated with the 2,4-pyrimidinediamine compounds in the presence of IL-2 for 72 hours, and at the assay endpoint intracellular ATP concentrations are measured to assess cell viability. A reduction in cell proliferation compared to control conditions is indicative of inhibition of the JAK kinase pathway.

The activity of the compounds described herein can additionally be characterized by assaying the effect of the 2,4-pyrimidinediamine compounds described herein on A549 lung epithelial cells and U937 cells. A549 lung epithelial cells and U937 cells up-regulate ICAM-1 (CD54) surface expression in response to a variety of different stimuli. Therefore, using ICAM-1 expression as readout, test compound effects on different signaling pathways can be assessed in the same cell type. Stimulation with IL-1β through the IL-1β receptor activates the TRAF6/NFκB pathway resulting in up-regulation of ICAM-1. IFNγ induces ICAM-1 up-regulation through activation of the JAK1/JAK2 pathway. The up-regulation of ICAM-1 can be quantified by flow cytometry across a compound dose curve and $EC_{50}$ values are calculated.

Active compounds as described herein generally inhibit the JAK kinase pathway with an $IC_{50}$ in the range of about 1 mM or less, as measured in the assays described herein. Of course, one of ordinary skill in the art would appreciate that compounds which exhibit lower $IC_{50}$s, (on the order, for example, of 100 µM, 75 µM, 50 µM, 40 µM, 30 µM, 20 µM, 15 µM, 10 µM, 5 µM, 1 µM, 500 nM, 100 nM, 10 nM, 1 nM, or even lower) can be particularly useful in therapeutic applications. In instances where activity specific to a particular cell type is desired, the compound can be assayed for activity with the desired cell type and counter-screened for a lack of activity against other cell types. The desired degree of "inactivity" in such counter screens, or the desired ratio of activity vs. inactivity, may vary for different situations and can be selected by the user.

The 2,4-pyrimidinediamine active compounds also typically inhibit IL-4 stimulated expression of CD23 in B-cells with an $IC_{50}$ in the range of about 20 JAM or less, typically in the range of about 10 µM, 1 µM, 500 nM, 100 nM, 10 nM, 1 nM, or even lower. A suitable assay that can be used is the assay described in Example 2, "Assay for Ramos B-Cell Line Stimulated with IL-4." In certain embodiments, the active 2,4-pyrimidinediamine compounds have an $IC_{50}$ of less than or equal to 5 µM, greater than 5 µM but less than 20 µM, greater than 20 µM, or greater than 20 µM but less than 50 µM in the assay described in Example 2.

Additionally, the 2,4-pyrimidinediamine active compounds typically inhibit an activity of human primary T-cells with an $IC_{50}$ in the range of about 20 µM or less, typically in the range of about 10 µM, 1 µM, 500 nM, 100 nM, 10 nM, 1 nM, or even lower. The $IC_{50}$ against human primary T-cells can be determined in a standard in vitro assay with isolated human primary T-cells. A suitable assay that can be used is the assay described above, "Primary Human T-cell Proliferation Assay Stimulated with IL-2." In some embodiments, the active 2,4-pyrimidinediamine compounds have an $IC_{50}$ of less than or equal to 5 µM, greater than 5 µM but less than 20 µM, greater than 20 µM, or greater than 20 µM but less than 50 µM in the assay described above.

The 2,4-pyrimidinediamine active compounds also typically inhibit expression of ICAM1 (CD54) induced by IFNγ ☐exposure in U937 or A549 cells with an $IC_{50}$ in the range of about 20 µM or less, typically in the range of about 10 µM, 1 µM, 500 nM, 100 nM, 10 nM, 1 nM, or even lower. The $IC_{50}$ against expression of ICAM (CD54) in IFNγ stimulated cells can be determined in a functional cellular assay with an isolated A549 or U937 cell line. The active 2,4-pyrimidinediamine compounds typically have an $IC_{50}$ of less than or equal to 20 µM, greater than 20 µM, or greater than 20 µM but less than 50 µM in the assay.

Utility of the Compounds as Research Tools

One of ordinary skill in the art would understand that certain crystallized, protein-ligand complexes, in particular JAK-ligand complexes, and their corresponding X-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds described herein as their ligand component, are an aspect of the invention.

As well, one of ordinary skill in the art would appreciate that such suitable X-ray quality crystals can be used as part of a method of identifying a candidate agent capable of binding to and modulating the activity of kinases. Such methods can be characterized by the following aspects: a) introducing into a suitable computer program, information defining a ligand binding domain of a kinase in a conformation (for example as defined by X-ray structure coordinates obtained from suitable X-ray quality crystals as described above) where the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods can further entail: performing rational drug design with the model of the three-dimensional structure, and selecting a potential candidate agent in conjunction with computer modeling.

Additionally, one skilled in the art would appreciate that such methods can further entail: employing a candidate agent, so-determined to fit spatially into the ligand binding domain, in a biological activity assay for kinase modulation, and determining whether said candidate agent modulates kinase activity in the assay. Such methods can also include administering the candidate agent, determined to modulate kinase activity, to a mammal suffering from a condition treatable by kinase modulation, such as those described above.

Also, one skilled in the art would appreciate that compounds described herein can be used in a method of evaluating the ability of a test agent to associate with a molecule or molecular complex including a ligand binding domain of a kinase. Such a method can be characterized by the following aspects: a) creating a computer model of a kinase binding pocket using structure coordinates obtained from suitable X-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

Utility of the Compounds as Screening Agents

To employ the compounds described herein in a method of screening for candidate agents that bind to, for example a JAK protein, the protein is bound to a support, and a compound described herein is added to the assay. Alternatively, the compound described herein is bound to the support, for example via a linker that does not prohibitively affect biological activity, and the protein is added. Classes of candidate agents among which novel binding agents can be sought include specific antibodies, non-natural binding agents identified in screens of chemical libraries, peptide analogs, etc. Of particular interest are screening assays for candidate agents that have a low toxicity for human cells. A wide variety of assays can be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, a JAK protein can be done in a number of ways. In one example, the candidate agent (the compound described herein) is labeled, for example, with a fluorescent or radioactive moiety and binding determined directly. For example, this can be done by attaching all or a portion of the JAK protein to a solid support, adding a labeled agent (for example a compound described herein in which at least one atom has been replaced by a detectable isotope), washing off excess reagent, and determining whether the amount of the label is that present on the solid support. Various blocking and washing steps can be utilized as is known in the art. "Labeled" means that the compound is either directly or indirectly labeled with something which provides a detectable signal, for example, radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, a JAK protein can be labeled at tyrosine positions using $^{125}$I, or with fluorophores. Alternatively, more than one component can be labeled with different labels; using $^{125}$I for the proteins, for example, and a fluorophore for the candidate agents.

The compounds described herein can also be used as competitors to screen for additional drug candidates. "Candidate bioactive agent" or "drug candidate" or grammatical equivalents as used herein describe any molecule, for example, protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to JAK proteins.

Candidate agents can encompass numerous chemical classes, though typically they are organic molecules having a molecular weight of more than about 100 daltons and less than about 2,500 daltons. Candidate agents include functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often include cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to a JAK protein, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to for example a JAK protein for a time sufficient to allow binding, if present. Incubations can be performed at any temperature that facilitates optimal activity, typically between 4° C. and 40° C. Incubation periods are selected for optimum activity, but can also be optimized to facilitate rapid high throughput screening. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to a JAK protein and thus is capable of binding to, and potentially modulating, the activity of the JAK protein. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to a JAK protein with a higher affinity. Thus, if the candidate agent is labeled, the presence of the label on the support, coupled with a lack of competitor binding, may indicate the candidate agent is capable of binding to the JAK protein.

It may be of value to identify the binding site of a JAK protein. This can be done in a variety of ways. In one embodiment, once the JAK protein has been identified as binding to the candidate agent, the JAK protein is fragmented or modified and the assays repeated to identify the necessary components for binding.

Modulation is tested by screening for candidate agents capable of modulating the activity of a JAK protein including the steps of combining a candidate agent with the JAK protein, as above, and determining an alteration in the biological activity of the JAK protein. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening can be used to identify drug candidates that bind to a native JAK protein, but cannot bind to a modified JAK protein.

A variety of other reagents can be included in the screening assays. These include reagents like salts, neutral proteins, for example, albumin, detergents, etc. which can be used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components can be added in any order that provides for the requisite binding.

Methods of Administration

The 2,4-pyrimidinediamine compound(s) or prodrug(s) described herein, or compositions thereof, will generally be used in an amount effective to achieve the intended result, for example, in an amount effective to treat or prevent the particular condition being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. As another specific example, therapeutic benefit in the context of transplantation rejection includes the ability to alleviate an acute rejection episode, such as, for example, HVGR or GVHR, or the ability to prolong the time period between onset of acute rejection episodes and/or onset of chronic rejection. Therapeutic benefit also includes halting or slowing the progression of the disease, regardless of whether improvement is realized.

The amount of compound administered will depend upon a variety of factors, including, for example, the particular condition being treated, the mode of administration, the severity of the condition being treated, the age and weight of the patient, the bioavailability of the particular active compound. Determination of an effective dosage is well within the capabilities of those skilled in the art.

As known by those of skill in the art, the preferred dosage of 2,4-pyrimidinediamine compounds will also depend on the age, weight, general health, and severity of the condition of the individual being treated. Dosage may also need to be tailored to the sex of the individual and/or the lung capacity of the individual, where administered by inhalation. Dosage may also be tailored to individuals suffering from more than one condition or those individuals who have additional conditions which affect lung capacity and the ability to breathe normally, for example, emphysema, bronchitis, pneumonia, and respiratory infections. Dosage, and frequency of administration of the compounds or prodrugs thereof, will also depend on whether the compounds are formulated for treatment of acute episodes of a condition or for the prophylactic treatment of a disorder. For example, acute episodes of allergic conditions, including allergy-related asthma, transplant rejection, etc. A skilled practitioner will be able to determine the optimal dose for a particular individual.

For prophylactic administration, the compound can be administered to a patient at risk of developing one of the previously described conditions. For example, if it is unknown whether a patient is allergic to a particular drug, the compound can be administered prior to administration of the drug to avoid or ameliorate an allergic response to the drug. Alternatively, prophylactic administration can be applied to avoid the onset of symptoms in a patient diagnosed with the underlying disorder. For example, a compound can be administered to an allergy sufferer prior to expected exposure to the allergen. Compounds can also be administered prophylactically to healthy individuals who are repeatedly exposed to agents known to one of the above-described maladies to prevent the onset of the disorder. For example, a compound can be administered to a healthy individual who is repeatedly exposed to an allergen known to induce allergies, such as latex, in an effort to prevent the individual from developing an allergy. Alternatively, a compound can be administered to a patient suffering from asthma prior to partaking in activities which trigger asthma attacks to lessen the severity of, or avoid altogether, an asthmatic episode.

In the context of transplant rejection, the compound can be administered while the patient is not having an acute rejection reaction to avoid the onset of rejection and/or prior to the appearance of clinical indications of chronic rejection. The compound can be administered systemically to the patient as well as administered to the tissue or organ prior to transplanting the tissue or organ in the patient.

The amount of compound administered will depend upon a variety of factors, including, for example, the particular indication being treated, the mode of administration, whether the desired benefit is prophylactic or therapeutic, the severity of the indication being treated and the age and weight of the patient, and the bioavailability of the particular active compound. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an $IC_{50}$ of the particular compound as measured in an in vitro assay. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pergamagon Press, and the references cited therein.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Suitable animal models of allergic conjunctivitis are described in Carreras et al., (1993), Br. J. Ophthalmol. 77(8):509-514; Saiga et al., (1992), Ophthalmic Res. 24(1):45-50; and Kunert et al., (2001), Invest. Ophthalmol. Vis. Sci. 42(11):2483-2489. Suitable animal models of systemic mastocytosis are described in O'Keefe et al., (1987), J. Vet. Intern. Med. 1(2):75-80 and Bean-Knudsen et al., (1989), Vet. Pathol. 26(1):90-92. Suitable animal models of hyper IgE syndrome are described in Claman et al., (1990), Clin. Immunol. Immunopathol. 56(1):46-53. Suitable animal models of B-cell lymphoma are described in Hough et al., (1998), Proc. Natl. Acad. Sci. USA 95:13853-13858 and Hakim et al., (1996), J. Immunol. 157(12):5503-5511. Suitable animal models of atopic disorders such as atopic dermatitis, atopic eczema, and atopic asthma are described in Chan et al., (2001), J. Invest. Dermatol. 117(4):977-983 and Suto et al., (1999), Int. Arch. Allergy Immunol. 120(Suppl 1):70-75. Suitable animal models of transplant rejection, such as models of HVGR, are described in O'Shea et al., (2004), Nature Reviews Drug Discovery 3:555-564; Cetkovic-Curlje & Tibbles, (2004), Current Pharmaceutical Design 10:1767-1784; and Chengelian et al., (2003), Science 302:

875-878. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. For example, the compounds can be administered once per week, several times per week (for example, every other day), once per day, or multiple times per day, depending upon, among other things, the mode of administration, the specific indication being treated, and the judgment of the prescribing physician. In cases of local administration or selective uptake, such as local topical administration, the effective local concentration of active compound(s) may not be related to plasma concentration. One of ordinary skill in the art would be able to optimize effective local dosages without undue experimentation.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The foregoing disclosure pertaining to the dosage requirements for the 2,4-substituted pyrimidinediamine compounds is pertinent to dosages required for prodrugs, with the realization, apparent to the skilled artisan, that the amount of prodrug(s) administered will also depend upon a variety of factors, including, for example, the bioavailability of the particular prodrug(s) and the conversation rate and efficiency into active drug compound under the selected route of administration. Determination of an effective dosage of prodrug(s) for a particular use and mode of administration is well within the capabilities of those skilled in the art.

Effective dosages can be estimated initially from in vitro activity and metabolism assays. For example, an initial dosage of prodrug for use in animals can be formulated to achieve a circulating blood or serum concentration of the metabolite active compound that is at or above an $IC_{50}$ of the particular compound as measured in an in vitro assay, such as the in vitro CHMC or BMMC and other in vitro assays described in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903, 263 filed Jul. 30, 2004, and international application Serial No. PCT/US2004/24716 (WO005/016893). Calculating dosages to achieve such circulating blood or serum concentrations, taking into account the bioavailability of the particular prodrug via the desired route of administration, is well within the capabilities of one of ordinary skill in the art. For guidance, the reader is referred to Fingl & Woodbury, "General Principles," In: Goodman and Gilman's The Pharmaceutical Basis of Therapeutics, Chapter 1, pp. 1-46, latest edition, Pagamonon Press, and the references cited therein.

Also provided are kits for administration of the 2,4-pyrimidinediamine, prodrug thereof, or pharmaceutical formulations including the compound that may include a dosage amount of at least one 2,4-pyrimidinediamine or a composition including at least one 2,4-pyrimidinediamine, as disclosed herein. Kits can further include suitable packaging and/or instructions for use of the compound. Kits can also include a means for the delivery of the at least one 2,4-pyrimidinediamine or compositions including at least one 2,4-pyrimidinediamine, such as an inhaler, spray dispenser (for example, nasal spray), syringe for injection, or pressure pack for capsules, tables, suppositories, or other device as described herein. A kit can also provide the compound and reagents to prepare a composition for administration. The composition can be in a dry or lyophilized form or in a solution, particularly a sterile solution. When the composition is in a dry form, the reagent can include a pharmaceutically acceptable diluent for preparing a liquid formulation. The kit can contain a device for administration or for dispensing the compositions, including, but not limited to, syringe, pipette, transdermal patch, or inhalant.

The kits can include other therapeutic compounds for use in conjunction with the compounds described herein. In one embodiment, the therapeutic agents are immunosuppressant or anti-allergen compounds. These compounds can be provided in a separate form or mixed with the compounds of the present invention.

The kits will include appropriate instructions for preparation and administration of the composition, side effects of the compositions, and any other relevant information. The instructions can be in any suitable format, including, but not limited to, printed matter, videotape, computer readable disk or optical disc.

One embodiment is a kit including a compound of formula I, or a prodrug thereof, packaging, and instructions for use.

In another embodiment, this invention provides a kit including the pharmaceutical formulation including a compound of formula I or a prodrug thereof and at least one pharmaceutically acceptable excipient, diluent, preservative, stabilizer, or mixture thereof, packaging, and instructions for use.

Another embodiment is a kit for treating an individual who suffers from or is susceptible to the conditions described herein are provided, including a container including a dosage amount of an 2,4-pyrimidinediamine or composition, as disclosed herein, and instructions for use. The container can be any of those known in the art and appropriate for storage and delivery of oral, intravenous, topical, rectal, urethral, or inhaled formulations.

Kits can also be provided that contain sufficient dosages of the 2,4-pyrimidinediamine or composition to provide effective treatment for an individual for an extended period, such as a week, 2 weeks, 3, weeks, 4 weeks, 6 weeks, or 8 weeks or more.

It will be appreciated by one of skill in the art that the embodiments summarized above can be used together in any suitable combination to generate additional embodiments not expressly recited above, and that such embodiments are considered to be part of the present invention.

Methods of Making

The 2,4-pyrimidinediamine compounds described herein can be synthesized via a variety of different synthetic routes using commercially available starting materials and/or starting materials prepared by conventional synthetic methods. Suitable exemplary methods that can be routinely adapted to synthesize the 2,4-pyrimidinediamine compounds and prodrugs described herein are found in U.S. Pat. No. 5,958,935, the disclosure of which is incorporated herein by reference.

Specific examples describing the synthesis of numerous 2,4-pyrimidinediamine compounds and prodrugs, as well as intermediates therefore, are described in U.S. application Ser. No. 10/355,543, filed Jan. 31, 2003 (US2004/0029902A1), the contents of which are incorporated herein by reference. Suitable exemplary methods that can be routinely used and/or adapted to synthesize active 2,4-substituted pyrimidinediamine compounds can also be found in international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004, and international application Serial No. PCT/US2004/24716 (WO005/016893), the disclosures of which are incorporated herein by reference. All of the compounds described herein (including prodrugs) can be prepared by routine adaptation of these methods.

Exemplary synthetic routes that can be used to synthesize the 2,4-pyrimidinediamine compounds described herein are depicted in Schemes (I)-(II), below. These methods can be routinely adapted to synthesize the 2,4-substituted pyrimidinediamine compounds described herein. After each reaction step, the product can be purified or can, depending on the chemistry, be used in the next step without purification. Specific exemplary methods for making the 2,4-substituted pyrimidinediamines described herein are also included in the examples below. Those of skill in the art will also be able to readily adapt these examples for the synthesis of additional 2,4-substituted pyrimidinediamines as described herein.

Compounds disclosed herein can be synthesized, for example, from substituted or unsubstituted uracils as illustrated in Scheme (I), below. In Scheme (I), ring A, $R^5$, $(R^2)_p$, X, Y, $Z^1$, and $Z^2$ are as defined herein. According to Scheme (I), uracil A-1 is dihalogenated at the 2- and 4-positions using a standard halogenating agent such as $POCl_3$ (or other standard halogenating agent) under standard conditions to yield 2,4-dichloropyrimidine A-2. Depending upon the $R^5$ substituent, in pyrimidinediamine A-2, the chloride at the C4 position can be more reactive towards nucleophiles than the chloride at the C2 position. This differential reactivity can be exploited to synthesize 2,4-pyrimidinediamines I, for example when $R^5$ is F, by first reacting 2,4-dichloropyrimidine A-2 with one equivalent of amine A-3, yielding 4N-substituted-2-chloro-4-pyrimidineamine A-4, followed by amine A-5 to yield a 2,4-pyrimidinediamine of formula A-6 (compounds of formula I, where each of $R^3$ and $R^4$ are H). Compounds of formula I, where either or both of $R^3$ and $R^4$ are non-H, can be made, for example, via alkylation of the NH groups at C2 or C4 of the pyrimidine-2,4-diamine.

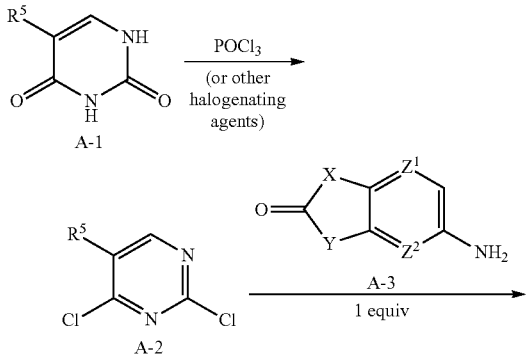

Scheme (I)

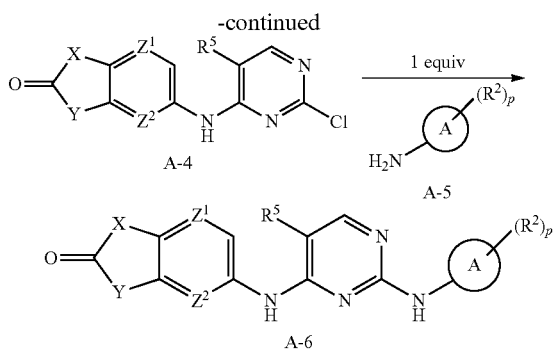

Typically, the C4 halide is more reactive towards nucleophiles. However, as will be recognized by one of ordinary skill in the art, the identity of the $R^5$ substituent may alter this reactivity. For example, when $R^5$ is trifluoromethyl, a 50:50 mixture of 4N-substituted-4-pyrimidineamine A-4 and the corresponding 2N-substituted-2-pyrimidineamine (not depicted) is obtained. The regioselectivity of the reaction can also be controlled by adjusting the solvent and other synthetic conditions (such as temperature), as is well-known in the art. Alternative methods of synthesis allow for complete regioselectivity, for example, when making molecules A-6. One such method is described in relation to Scheme (II) below.

The reactions depicted in Scheme (I) to make A-4 and A-6 (and A-6 in Scheme (II) below) may proceed more quickly when the reaction mixtures are heated via microwave. When heating in this fashion, the following conditions can be used: heat to 175° C. in ethanol for 5-20 min. in a Smith Reactor (Personal Chemistry, Uppsala, Sweden) in a sealed tube (at 20 bar pressure).

The uracil A-1 starting materials can be purchased from commercial sources or prepared using standard techniques of organic chemistry. Commercially available uracils that can be used as starting materials in Scheme (I) include, by way of example and not limitation, uracil (Aldrich #13,078-8; CAS Registry 66-22-8); 5-bromouracil (Aldrich #85,247-3; CAS Registry 51-20-7; 5-fluorouracil (Aldrich #85,847-1; CAS Registry 51-21-8); 5-iodouracil (Aldrich #85,785-8; CAS Registry 696-07-1); 5-nitrouracil (Aldrich #85,276-7; CAS Registry 611-08-5); 5-(trifluoromethyl)-uracil (Aldrich #22,327-1; CAS Registry 54-20-6). Additional 5-substituted uracils are available from General Intermediates of Canada, Inc., Edmonton, Calif. and/or Interchim, Cedex, France, or can be prepared using standard techniques. Myriad textbook references teaching suitable synthetic methods are provided infra.

Amines A-3 and A-5 can be purchased from commercial sources or, alternatively, can be synthesized utilizing standard techniques. For example, suitable amines can be synthesized from nitro precursors using standard chemistry. Specific exemplary reactions used to make anilines are provided in the Examples section. See also Vogel, 1989, *Practical Organic Chemistry*, Addison Wesley Longman, Ltd. and John Wiley & Sons, Inc.

One of ordinary skill in the art would recognize that in some instances, amines A-3 and A-5 and/or substituent X on uracil A-1 can include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Green & Wuts.

Thus, protecting group refers to a group of atoms that, when attached to a reactive functional group in a molecule, mask, reduce or prevent the reactivity of the functional group. Typically, a protecting group can be selectively removed as desired during the course of a synthesis. Examples of protecting groups can also be found in Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated to form acetate and benzoate esters or alkylated to form benzyl and trityl ethers, as well as alkyl ethers, tetrahydropyranyl ethers, trialkylsilyl ethers (for example, TMS or TIPPS groups) and allyl ethers.

Myriad references teaching methods useful for synthesizing pyrimidines generally, as well as starting materials described in the schemes, are known in the art. For specific guidance, the reader is referred to Brown, D. J., "The Pyrimidines", in *The Chemistry of Heterocyclic Compounds*, Volume 16 (Weissberger, A., Ed.), 1962, Interscience Publishers, (A Division of John Wiley & Sons), New York ("Brown I"); Brown, D. J., "The Pyrimidines", in *The Chemistry of Heterocyclic Compounds, Volume 16, Supplement I* (Weissberger, A. and Taylor, E. C., Ed.), 1970, Wiley-Interscience, (A Division of John Wiley & Sons), New York (Brown II"); Brown, D. J., "The Pyrimidines", in *The Chemistry of Heterocyclic Compounds, Volume 16, Supplement II* (Weissberger, A. and Taylor, E. C., Ed.), 1985, An Interscience Publication (John Wiley & Sons), New York ("Brown III"); Brown, D. J., "The Pyrimidines" in *The Chemistry of Heterocyclic Compounds, Volume 52* (Weissberger, A. and Taylor, E. C., Ed.), 1994, John Wiley & Sons, Inc., New York, pp. 1-1509 (Brown IV"); Kenner, G. W. and Todd, A., in *Heterocyclic Compounds*, Volume 6, (Elderfield, R. C., Ed.), 1957, John Wiley, New York, Chapter 7 (pyrimidines); Paquette, L. A., *Principles of Modern Heterocyclic Chemistry*, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., *Heterocyclic Chemistry*, $3^{rd}$ Edition, 1995, Chapman and Hall, London, UK, pp. 1-516; Vorbriiggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclic Chemistry*, $4^{th}$ Edition, 2000, Blackwell Science, Ltd, Oxford, UK, pp. 1-589; and *Comprehensive Organic Synthesis*, Volumes 1-9 (Trost, B. M. and Fleming, I., Ed.), 1991, Pergamon Press, Oxford, UK.

A specific embodiment of Scheme (I) utilizing 5-fluorouracil (Aldrich #32,937-1) as a starting material is illustrated in Scheme (Ia), below. In Scheme (Ia), ring A, $(R^2)_p$, X, Y, $Z^1$, and $Z^2$ are as previously defined for Scheme (I) and formula I. Compound A-10, a 2N,4N-disubstituted-5-fluoro-2,4-pyrimidinediamine, can be obtained by reacting 2,4-dichloro-5-fluoropyrimidine A-8 (commercially available or made from A-7 as depicted for example starting with a uracil and dehydrohalogenating with for example $POCl_3$) with, optimally, one equivalent of amine A-3 to yield 2-chloro-N4-substituted-5-fluoro-4-pyrimidineamine A-9 followed by reaction with one or more equivalents of amine A-5, typically between about 1.1 equivalents of A-5 and about 2 equivalents of A-5. Reaction of A-9 with A-5 can be carried out, for example, via traditional heating, by microwave irradiation and by Buchwald type coupling using metal catalysts, for example, palladium coupling. The latter metal catalyzed coupling reactions are typically used when the nucleophilic partner, A-5, is poorly nucleophilic, and thus reactions where bond insertions and reductive couplings work well are used effect the transformation.

First, amines A-5 are converted to the corresponding guanidine derivatives A-11. For example, amine A-5 is reacted with an appropriately protected guanyl electrophilic partner, for example N,N-bis-Boc-1-guanylpyrazole, for example, in the presence of a base, for example a tertiary amine base. The reaction is typically, but not necessarily, heated to between about 40° C. and about 60° C. for between about 24 h and about 48 h. After this step, any protecting groups are removed.

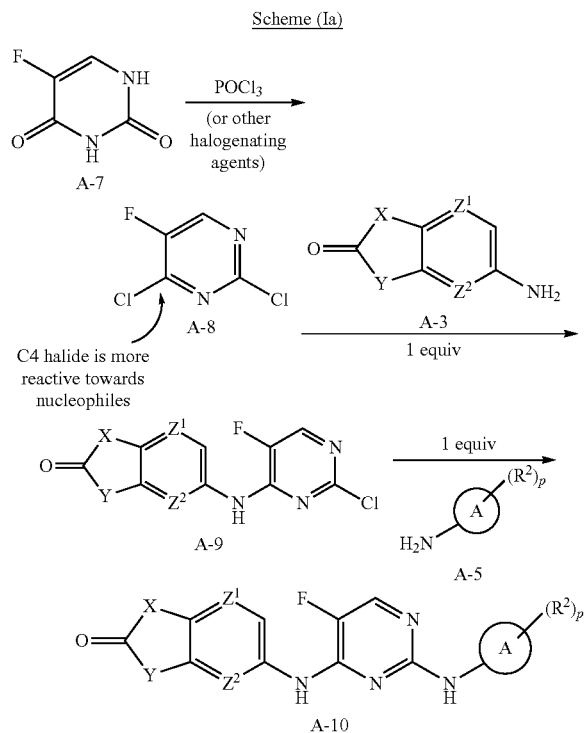

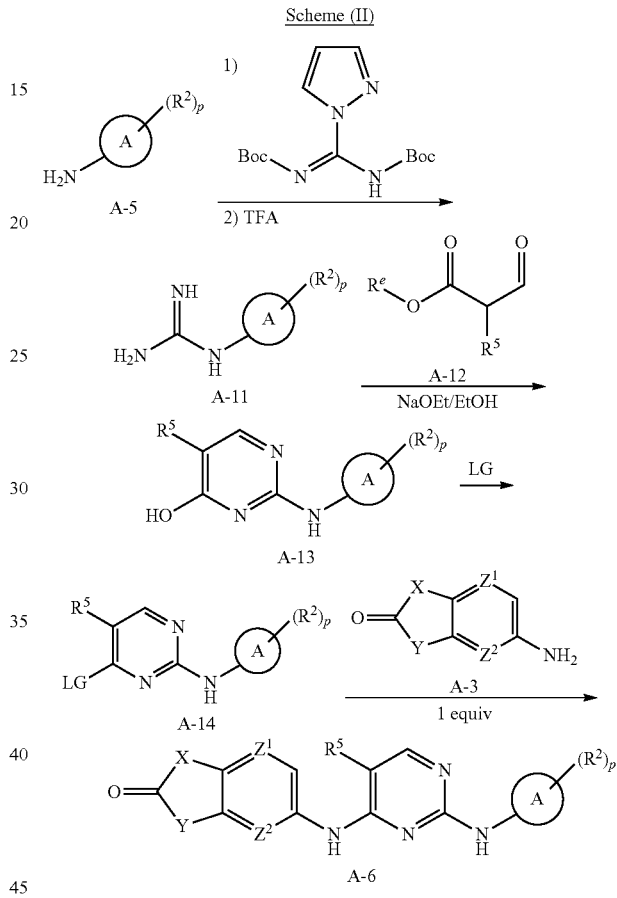

Although many of the synthetic schemes discussed above do not illustrate the use of protecting groups, one of ordinary skill in the art would recognize that in some instances certain substituents, such as, for example, R² and/or other groups, can include functionality requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Green & Wuts.

Schemes I and Ia above describe synthesis of the 2,4-pyrimidinediamines described herein by adding two amine nucleophiles to a pyrimidine dielectrophile, for example a 2,4-dihalopyrimidine. Compounds disclosed herein, including those according to Formula I as described herein and including compounds of Formulas IA, IB, IC, II, III and IV can be synthesized according to Schemes I and Ia. Likewise, such compounds also can be synthesized according to Scheme II below, which describes a novel synthesis of the compounds described herein starting from ring A anilines, building the pyrimidine system onto the aniline via guanyl analogs, and then installing the 4N-heteroaryl ring system.

For example, when N,N-bis-Boc-1-guanylpyrazole is used, an acid is added to the mixture (optionally the volatiles are removed from the reaction first) to remove the Boc protecting groups and provide A-11. Guanidines A-11 are reacted with the appropriate 1,3-dielectrophile, for example β-aldehyde esters, A-12 (where $R^e$ is defined as in formula I), for example by heating the guanidine in an alcoholic solvent in the presence of base. In one example, sodium ethoxide in ethanol is used. The reaction heated to between about 40° C. and about 80° C. for between about 24 h and about 48 h to give the corresponding 4-hydroxy-pyrimidine-2-amine, A-13. One of ordinary skill in the art would appreciate that other 1,3-dielectrophiles can be used to make pyrimidine intermediates A-13, for example, 2-substituted cyanoacetaldehydes and α,β-unsaturated esters such as alkyl 2-(acetoxymethyl)acrylates (Baylis-Hillman acetates, for example as reported in *Bull. Korean Chemical Soc.* 2007, Vol. 28, No. 12, 2505-2507, which is incorporated by reference herein for all purposes), and the like. Intermediates A-13 may be purified in some instances or used "as is" in the next reaction, where they are converted to the corresponding 4-leaving group-pyrimidine-2-amines, A-14. For example, intermediates A-13 can be reacted with, for example, POCl₃ to provide the corresponding 4-chloro-pyrimidine-2-amine, that is, amines A-14 where LG is chlorine. One of ordinary skill in the art would appreciate that other leaving groups would work, for example, the hydroxy group of intermediate A-13 can be converted to a mesylate and then used for the next step, for example, in lieu of a 4-halo intermediate. Compounds A-6 (compounds of formula I where $R^3$ and $R^4$ are H) are formed by reaction of the intermediate A-14 with amines A-3, for example, as described above in Schemes I and Ia in relation to reaction with intermediates A-2 and/or A-8, respectively. Compounds of formula I, where $R^3$ and/or $R^4$ are non-H, are made, for example, by alkylating compounds A-6 with the appropriate alkylating reagents, as would be appreciated by one of ordinary skill in the art. Alternatively, guanidines like A-11, but where the NH bearing ring A is rather $NR^4$ (where $R^4$ is for example alkyl) can be used to make compounds of formula I where $R^4$ is other than H.

Thus, one embodiment is a method of making compounds of formula A-6, where the variables are defined as in relation to formula I, including:
(i) reacting a guanidine of formula A-11 with a 1,3-dielectrophile to make a 4-hydroxy-pyrimidin-2yl-amine of formula A-13;
(ii) converting A-13 to a 4-leaving group-pyrimidin-2yl-amine of formula A-14; and
(iii) reacting the 4-leaving group-pyrimidin-2yl-amine A-14 with an aryl or heteroaryl amine, A-3.

In one embodiment the 1,3-dielectrophile is a β-aldehyde ester, A-12. In one embodiment, the leaving group of A-14 is a halo, in a more specific embodiment a chloro group. In one embodiment, the heteroaryl amine A-3, is a 5-aminobenzo[d]oxazol-2(3H)-one, substituted with groups in accord with formula I. In another embodiment, the heteroaryl amine A-3 is a 6-aminobenzo[d]oxazol-2(3H)-one, substituted with groups in accord with formula I. In another embodiment, the heteroaryl amine A-3 is a 5-amino-1H-benzo[d]imidazol-2(3H)-one, substituted with groups in accord with formula I.

EXAMPLES

The invention is further understood by reference to the following examples, which are not intended to be limiting. Any synthetic methods that are functionally equivalent are within the scope of the invention. Various modifications of the embodiments described herein would be apparent to one of ordinary skill in the art from the foregoing description. Such modifications fall within the scope of the appended claims.

One embodiment is a compound, according to formula I, as described in the examples below.

In the examples below as well as throughout the application, the following abbreviations have the following meanings. If not defined, the terms have their generally accepted meanings.

TFA = trifluoroacetic acid
MeOH = methanol
EtOAc = ethyl acetate
i-PrOH = isopropanol
EtOH = ethanol
s = singlet
d = doublet
mmol = millimole
nM = nanomolar
DMSO = dimethylsulfoxide
mL or ml = milliliter
mg = milligram
psi = pounds per inches²
N = normal
t = triplet
q = quartet
m = multiplet
dd = doublet of doublets
br = broad
MS = mass spectrum
MS (ES) = mass spectrometry (electrospray)
RP-HPLC = reverse phase high pressure liquid chromatography
DMF = dimethylformamide
MeCN = acetonitrile
HPLC = high pressure liquid chromatography
LRMS = low resolution mass spectrometry
BINAP = 2,2'-bis(diphenylphosphino)-1,1'-binaphthyl
MEK = methyl ethyl ketone
μM = micromolar
rpm = revolutions/minute
rt = room temperature
aq. = aqueous
μL = microliter
FBS = fetal bovine serum
LCMS = liquid chromatography mass spectrometry
FACS = Fluorescence Activated Cell Sorting (flow cytometry)
THF = tetrahydrofuran
TLC = thin layer chromatography
DCM = dichloromethane
LC = liquid chromatography
NMP = N-methylpyrrolidinone
M = molar

Example 1: Synthesis of Anilines

Anilines used to make compounds described herein can be purchased commercially and/or synthesized by methods taught herein and known to those of skill in the art. Schemes (III)-(VII) below describe how some anilines were synthesized.

Scheme (III) depicts a general synthetic route to anlines of formula A-16, where the group "OR" is used as an abbreviation for $R^2$, where $R^2$ is —$OR^e$ substituted with one or more of the same or different $R^a$ and/or $R^b$ as defined in relation to formula I. First, 3-fluorocatechol, is alkylated with the appropriate alkylating agent, for example an alkyl halide in the presence of a base, for example, $K_2CO_3$ (typically 2.5 eq of alkyl halide and base). In one example, the mixture is heated in acetone under reflux over night. Half of the solvent is removed under reduced pressure and the salts are filtered off. The remaining solvent is removed in vacuo and the crude product is further purified by flash chromatography eluting with hexanes/ethyl acetate (gradient 0% ethyl acetate to 15% ethyl acetate) to provide intermediate A-16.

The product A-16 is dissolved in dry THF and the flask is sealed with a rubber septum. N,N,N',N',N''-pentamethyldiethylenetriamine (PMDTA, 1.2 eq) is added via syringe and the flask is cooled to −75° C. using an acetone/dry ice bath. n-Butyllithium (1.2 eq) is added via syringe and the reaction mixture is stirred for 90 min. The reaction mixture is subsequently poured into a beaker containing crushed dry ice and allowed to warm to room temperature. A 2M NaOH solution is added to the crude product and the mixture is washed with $Et_2O$ (2×) and EtOAc (1×). The aqueous phase is neutralized using HCl. The precipitated product, A-17, is collected by filtration and dried under vacuum.

Scheme (III)

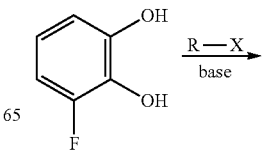

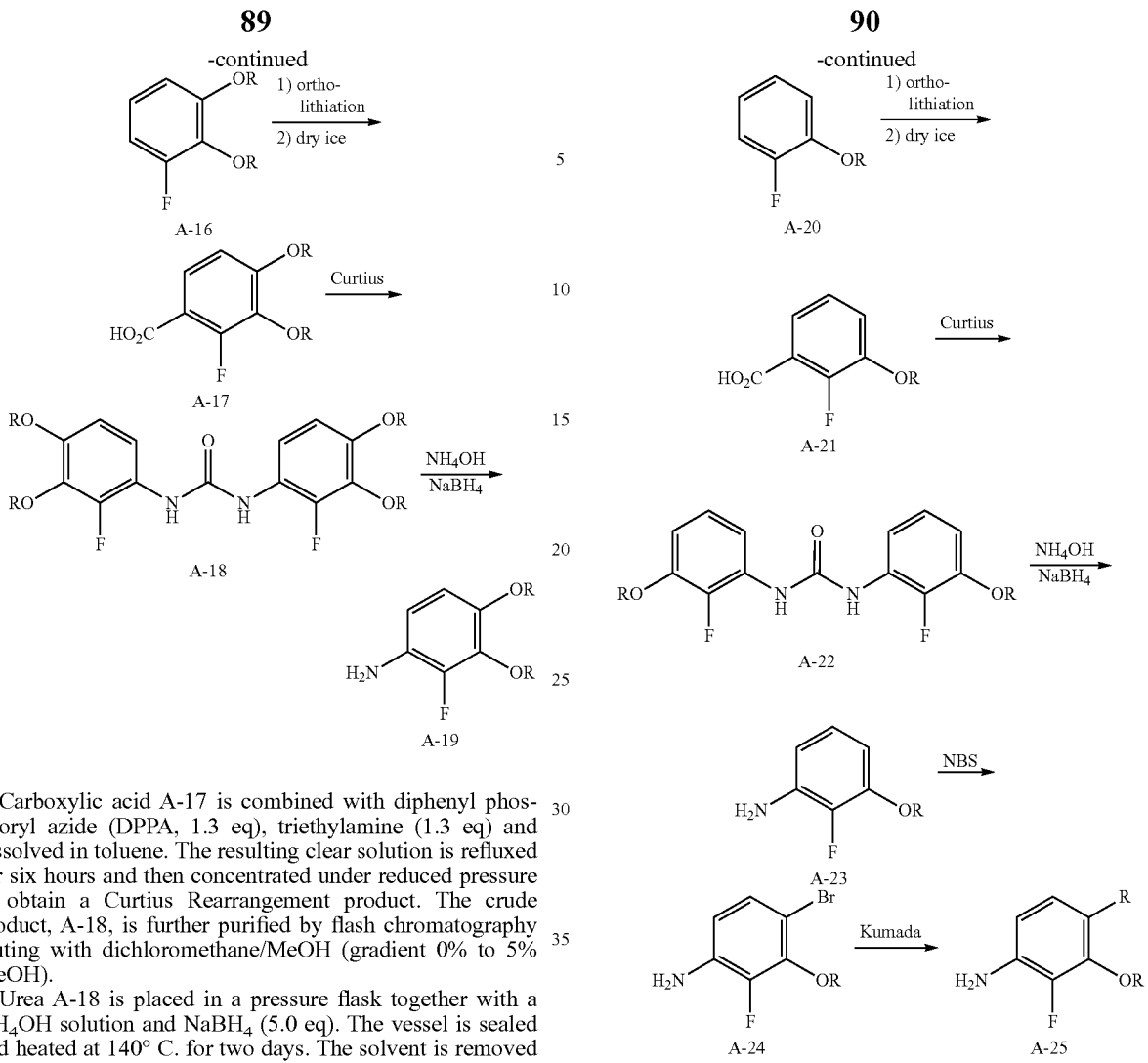

Carboxylic acid A-17 is combined with diphenyl phosphoryl azide (DPPA, 1.3 eq), triethylamine (1.3 eq) and dissolved in toluene. The resulting clear solution is refluxed for six hours and then concentrated under reduced pressure to obtain a Curtius Rearrangement product. The crude product, A-18, is further purified by flash chromatography eluting with dichloromethane/MeOH (gradient 0% to 5% MeOH).

Urea A-18 is placed in a pressure flask together with a NH$_4$OH solution and NaBH$_4$ (5.0 eq). The vessel is sealed and heated at 140° C. for two days. The solvent is removed under reduced pressure and the crude product is purified using flash chromatography eluting with CHCl$_3$/MeOH [with 2M NH$_3$] (gradient 0% to 5%) to provide aniline A-19. This procedure was used to make anilines (ring A) for compounds I-50, I-77, I-101 and I-102.

Scheme (IV) depicts a general synthetic route to anlines of formula A-25, where the group "R" is used as an abbreviation for R$^2$, where R$^2$ is —R$^e$ substituted with one or more of the same or different R$^a$ and/or R$^b$ as defined in relation to formula I. In an analogous fashion as described above in relation to Scheme (III), ortho-fluoro phenol was alkylated to provide intermediates A-20. Ortho-lithiation and carbon dioxide quench gave acids A-21. Curtius rearrangement provided the corresponding anilines, A-22, which were liberated from the urea carbonyl using aminolysis as described above to provide anilines, A-23. Anilines A-23 were used to make, for example, compounds I-19 through I-23.

Anilines A-23 were also brominated using N-bromosuccinimide (NBS), by dissolving them in MeCN, adding NBS (1.0 eq) and stirring the reaction mixture for two hours at room temperature. Bromination occurs regio-selectively para to the NH$_2$ group. The solvent is removed under reduced pressure and the crude product is purified by column chromatography eluting with hexanes/ethyl acetate (9/1) to provide anilines A-24. Anilines A-24 were used, for example, to make compound 1-27.

Anilines A-24 were also subjected to Kumada Coupling by dissolving them in THF and adding the solution to a pressure vessel. The desired alkyl magnesium halide (3M in THF, 3.3 eq) is added dropwise via syringe. Since the first two equivalents of AlkylMgX abstract the aniline protons, gas evolution and heating are observed. After addition of the Grignard reagent, Pd-catalyst ([1,1'-Bis(diphenylphosphino)ferrocene]-dichloropalladium(II), 5 mol %) is added in small portions. The flask is sealed and heated at 80° C. overnight. To quench the reaction, water is added very carefully. The mixture is subsequently extracted with EtOAc (3×) and the combined organic layers are passed through a MgSO$_4$ plug to remove residual water. After evaporation of solvents the crude product is further purified by flash chromatography eluting with CHCl$_3$/MeOH [2M NH$_3$] (gradient 0% to 5%) to provide anilines, A-25. Anilines A-25 were used to make compounds I-29, I-53 and I-68.

Scheme (IV)

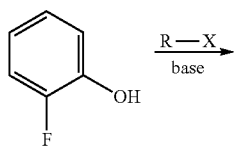

Scheme (V) illustrates a further example of using a Kumada coupling reaction to install alkyl groups on an aniline ring. Specifically, Scheme (V) depicts synthesis of 3,4($d_3$),5-trimethylaniline. First, 3,5-dimethyl aniline (10.0 g, 82.5 mmol) was dissolved in MeCN. NBS (15.4 g, 86.6 mmol) was added and the reaction mixture was stirred for two days at room temperature. Analysis by TLC and HPLC indicated that in addition to the desired product several side products had been formed (regio-isomers and di-brominated side products). Silica gel was added to the reaction mixture and the solvent was evaporated under reduced pressure. The resulting dry crude product was loaded on a chromatography column and purified by eluting with hexanes/ethyl acetate (gradient 0% to 15% ethyl acetate). The product, 4-bromo-3,5-dimethylaniline, was obtained in 50% yield (8.21 g). MS (ES) 200/202

Scheme (V)

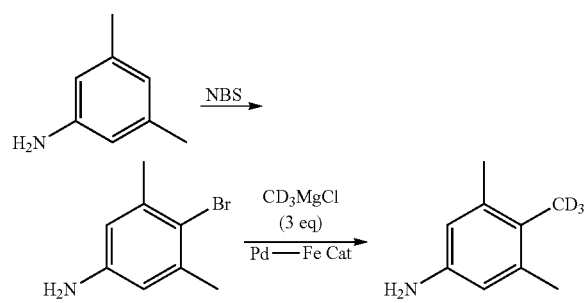

(M+H). The bromide (5.00 g, 24.9 mmol) was dissolved in dry THF (50 ml) and placed in a pressure vessel. Methyl-$d_3$ magnesium chloride (82.2 ml, 82.2 mmol, 1M in $Bu_2O$) was added dropwise via syringe. While adding the first two equivalents a strong reaction, gas evolution and heating was observed as the aniline protons reacted with the Grignard reagent. After completion of the addition, Pd-catalyst ([1,1'-Bis(diphenylphosphino)ferrocene]-dichloropalladium (II), 0.911 g, 5 mol %) was added in small portions. The flask was sealed and heated at 80° C. over night. The reaction was carefully quenched with water. The mixture is subsequently extracted with EtOAc (3×) and the combined organic layers were passed through a $MgSO_4$ plug to remove residual water. After evaporation of solvents the crude product was purified by flash chromatography eluting with DCM/MeOH (gradient 0% to 1% MeOH). The 4-perdeuterated 3,4,5-trimethylaniline was obtained in 43% yield (1.48 g). $^1$H NMR (300 MHz, DMSO) δ 6.19 (s, 2H), 4.57 (s, 2H), 2.05 (s, 6H) ppm; MS (ES) 139 (M+H). Compound 1-35 was made using this aniline.

Scheme (VI) shows synthesis of 4-amino-2,6-dimethyl-benzonitrile. First, 3,5 dimethyl-4-iodo aniline (5.0 g, 20.2 mmol), Cu(I)CN (2.17 g, 24.3 mmol) and DMF (80 ml) were placed in a pressure vessel. The sealed flask was heated in an oil bath at 185° C. After 10 minutes the flask was removed from the oil bath and cooled to room temperature. Analysis of the reaction mixture by LCMS indicated a peak to peak reaction. Most of the DMF was removed under high vacuum using a rotary evaporator. The remaining crude product was loaded onto a flash chromatography column and purified eluting with $CHCl_3$/MeOH [2M $NH_3$] (gradient 0% to 2%). The product was obtained in 62% yield (2.21 g). $^1$H NMR (300 MHz, DMSO) δ 6.29 (s, 2H), 5.92 (s br, 2H), 2.23 (s, 6H) ppm; MS (ES) 147 (M+H). Compound 1-64 was made using this aniline.

Scheme (VI)

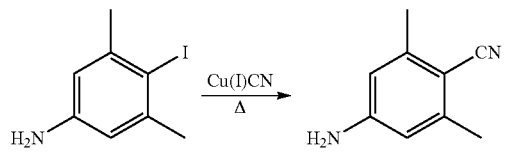

Scheme (VII) depicts the synthesis of 4-fluoro-3-methoxy-5-methylaniline. First, at 0° C., in a $CH_2Cl_2$ (150 mL) solution of 2-fluoro-3-methylphenol (1, 12.6 g, 100 mmol) and HOAc (12 mL, 210 mmol), a $CH_2Cl_2$ (50 mL) solution of bromine (10.5 mL, 205 mmol) was added dropwise over 45 min. After 15 min, the reaction went to completion monitored by LCMS, and was quenched by the addition of $H_2O$ (200 mL). Two layers were mixed well and then separated, aqueous layer was extracted with $CH_2Cl_2$ (50 mL), organic layers were combined, dried ($MgSO_4$), filtered, solvent was removed in vacuo. 4,6-Dibromo-2-fluoro-3-methylphenol was obtained as a solid: 28.4 g (>99% yield); $^1$H NMR (300 MHz, $CDCl_3$) δ 7.48 (d, J=2.1, 1H), 5.49 (d, J=2.8, 1H), 2.30 (d, J=2.8, 3H); LRMS (M−) m/z 282.94.

To a homogeneous $CH_3CN$ (200 mL) solution of 4,6-dibromo-2-fluoro-3-methylphenol (2, 28.4 g, 100 mmol) at rt, $K_2CO_3$ (16.59 g, 120 mmol) was added, followed by MeI (9.3 mL, 150 mmol). The cloudy solution was stirred at 30° C. overnight. The reaction went to completion monitored by LC and TLC. The mixture was cooled to rt, quenched by addition of $H_2O$ (100 mL) and sat. aq. $NH_4Cl$ (100 mL), two layers were mixed well and then separated, aqueous layer was extracted with EtOAc (50 mL), organic layers were combined, dried ($MgSO_4$), filtered, solvent was removed in vacuo. The crude product, an oil, was dissolved in $CH_2Cl_2$ (~80 mL) and the solution was passed through a silica gel pad (~50 g of silica gel), washing with $CH_2Cl_2$ (~100 mL). The filtrate was collected, and the solvent was removed in vacuo. 1,5-Dibromo-3-fluoro-2-methoxy-4-methylbenzene was obtained as a solid: 31.62 g (>99% yield); $^1$H NMR (300 MHz, $CDCl_3$) δ 7.53 (d, J=2.1, 1H), 3.92 (s, 3H), 2.29 (d, J=2.8, 3H).

Scheme (VII)

-continued

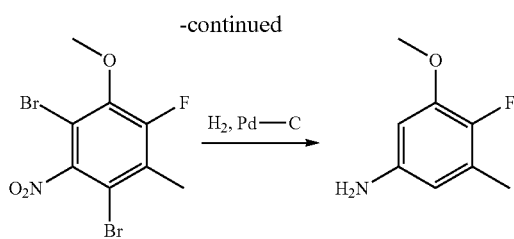

With reference to Scheme VII, at 0° C., into a CH$_2$Cl$_2$ (600 mL) solution of 2-fluoro-3-methylphenol (commercially available from Wonda Science, Montreal, Canada) (100 g, 792.8 mmol) and HOAc (95 mL, 1.66 mol), a CH$_2$Cl$_2$ (200 mL) solution of bromine (83 mL, 1.625 mol) was added dropwise over 2 h. The reaction was >99% complete by LC-MS, and was quenched by the addition of H$_2$O (500 mL). Two layers were mixed well and then separated, aqueous layer was extracted with CH$_2$Cl$_2$ (200 mL), organic layers were combined, dried (MgSO$_4$), filtered, solvent was removed in vacuo. 4,6-dibromo-2-fluoro-3-methylphenol was obtained as an off-white solid: 247.96 g (>99% yield); $^1$H NMR (300 MHz, CDCl$_3$) δ 7.48 (d, J=2.1, 1H), 5.42 (br s, 1H), 2.31 (d, J=2.8, 3H); LRMS (M−) m/z 282.92.

1,5-dibromo-3-fluoro-2-methoxy-4-methylbenzene was prepared from a homogeneous CH$_3$CN (1 L) solution of 4,6-dibromo-2-fluoro-3-methylphenol (~225.1 g, 792.8 mmol) by adding, at room temperature, K$_2$CO$_3$ (131.5 g, 1.18 mol), followed by MeI (74 mL, 951 mmol). The cloudy solution was stirred at 30° C. and, as monitored by LC, the reaction went to completion at 21 h. The reaction mixture was cooled to room temperature, solid was filtered off by filtration, washing with CH$_2$Cl$_2$ (~100 mL×2). Filtrate was collected, solvent was removed in in vacuo. Crude product was suspended in CH$_2$Cl$_2$ (200 mL) and the solution was passed through a silica gel pad (~50 g of silica gel) (note, to remove some darker color baseline impurities and solid initially dissolved in CH$_3$CN), washing with CH$_2$Cl$_2$ (~100 mL×3). Filtrate was collected, solvent was removed in vacuo. 1,5-dibromo-3-fluoro-2-methoxy-4-methylbenzene was obtained as an off-white solid: 249.46 g (>99% yield); $^1$H NMR (300 MHz, CDCl$_3$) δ 7.53 (d, J=2.1, 1H), 3.92 (s, 3H), 2.29 (d, J=2.8, 3H).

To a H$_2$SO$_4$ (100 mL) suspension of 1,5-dibromo-3-fluoro-2-methoxy-4-methylbenzene (3, 30 g, 100 mmol), HNO$_3$ (90% aq, 5.0 mL, 110 mmol) was added over 10 min, with occasional ice bath cooling. Stirring was continued at 30° C. for another 30 min. The reaction went to completion as monitored by LC. The thick pasty mixture was cooled to rt and was poured onto ice (~600 mL solid volume). A precipitate was collected by filtration, washing with water (~100 mL, final aqueous volume: ~600 mL), and was further dried under vacuum. Crude 1,3-dibromo-5-fluoro-4-methoxy-6-methyl-2-nitrobenzene was obtained as a yellow solid (33.7 g), and was stirred in 90 mL of EtOH at 50° C. overnight. The cloudy solution was then cooled to rt, solid was collected by filtration, washing with ice-cold EtOH. A first crop of 1,3-dibromo-5-fluoro-4-methoxy-6-methyl-2-nitrobenzene was obtained as a light yellow solid: 22.6 g; a second crop was obtained from the mother liquor as a yellow solid: 3.90 g (77% combined yield); $^1$H NMR (300 MHz, CDCl$_3$) δ 4.00 (s, 3H), 2.39 (d, J=3.0, 3H).

Into a Parr flask with 1,3-dibromo-5-fluoro-4-methoxy-6-methyl-2-nitrobenzene (4, 102.9 g, 300 mmol) and sodium carbonate (33.4 g, 315 mmol), under N$_2$ atmosphere, MeOH (600 mL) was added, followed by Pd-C (10% on activated carbon, 50% wet, 5.0 g). The Parr flask was placed on a Parr shaker under 30-45 psi of hydrogen. After 21 h, reaction went to completion as monitored by LCMS. Solid was removed by filtration through a celite pad, and was washed with MeOH. Filtrate was collected and solvent was removed in vacuo. A light beige color solid was obtained and was treated with EtOAc (200 mL) and H$_2$O (200 mL), two layers were mixed well and then separated, aqueous layer was extracted with EtOAc (150 mL). Organic layers were combined and were added to a flask with 25 mL of conc. aq. HCl, with stirring. Precipitated solid was collected by filtration, washing with EtOAc, and was further dried under high vac. A white fluffy solid was obtained as 1$^{st}$ crop: 29.99 g as an HCl salt; more white ppt was collected from filtrate as 2$^d$ crop: 17.12 g as an HCl salt; 3$^{rd}$ crop was obtained from filtrate after removal of solvent and solid re-suspended in EtOAc: off-white solid, 8.90 g as HCl salt. Combined 4-fluoro-3-methoxy-5-methylbenzenamine as the HCl salt: 56.01 g (97% yield); $^1$H NMR (300 MHz, CD$_3$OD) δ 6.92 (dd, J=6.9, 2.5, 1H), 6.82 (dd, J=5.3, 2.5, 1H), 3.90 (s, 3H), 2.30 (d, J=2.4, 3H); LRMS (M+) m/z 156.21. Compounds I-58, I-80, II-105 through I-107, II-114, II-118, I-127, I-181, II-190 and I-191 were made using this aniline.

3-Methoxy-4,5-dimethylaniline was prepared in an analogous manner as described in relation to Scheme (VII), starting with 2,3-dimethylphenol (61.08 g, 500 mmol). In the bromination reaction, 4,6-dibromo-2,3-dimethylphenol was obtained as a solid: 140.74 g (>99% yield); $^1$H NMR (300 MHz, CDCl$_3$) δ 7.52 (s, 1H), 5.50 (s, 1H), 2.33 (s, 3H), 2.28 (s, 3H); LRMS (M−) m/z 278.97. In the alkylation reaction, 1,5-dibromo-2-methoxy-3,4-dimethylbenzene was obtained as a light brown oil at rt and was turned into a yellow solid after cooling with dry-ice: 144.97 g (98.6% yield over 2 steps); $^1$H NMR (300 MHz, CDCl$_3$) δ 7.59 (s, 1H), 3.76 (s, 3H), 2.32 (s, 3H), 2.30 (s, 3H). In the nitration, 1,3-dibromo-4-methoxy-5,6-dimethyl-2-nitrobenzene was obtained as an off-white solid: 58.3 g (35% combined yield from two crystallization crops); $^1$H NMR (300 MHz, CDCl$_3$) δ 3.81 (s, 3H), 2.42 (s, 3H), 2.37 (s, 3H). In the reduction reaction, 3-methoxy-4,5-dimethylbenzenamine was obtained as a white solid (HCl salt) in a combined yield from three crystallization crops of 24 g (77%): $^1$H NMR (300 MHz, DMSO) δ 10.04 (s, 3H), 6.81 (s, 1H), 6.77 (s, 1H), 3.81 (s, 3H), 2.27 (s, 3H), 2.09 (s, 3H); LRMS (M+) m/z 152.20. Compounds I-52, I-59, I-81, I-108 through I-113, I-115, I-125 and I-195 were made using this aniline.

Scheme (VIII) depicts synthesis of 4-chloro-3-methoxy-5-methylaniline analogous to that reported in Journal of Medicinal Chemistry, 44(12), 1866-1882; 2001. A suspension of 4-bromo-2-methoxy-6-methylaniline (1 g, 4.63 mmol) in 28% HCl (2 mL) was cooled in an ice bath. To this was added a cooled solution of sodium nitrite (323 mg, 4.68 mmol) in water (1 mL) dropwise with vigorous stirring. In a separate flask was prepared a solution of cuprous chloride (2.29 g, 23.1 mmol) in concentrated HCl (2 mL) that was also cooled in an ice bath. The aniline mixture was quickly poured into this reaction flask. The flask was allowed to warm to room temperature overnight. Another 1 mL of 28% HCl was added and the reaction heated at 60° C. for 3 hours monitoring by LCMS. Upon cooling to room temperature, the reaction was diluted with water and extracted three times with ethyl acetate. The combined organic layers were dried over magnesium sulfate. The crude 5-bromo-2-chloro-1-methoxy-3-methylbenzene was purified by silica gel chromatography (0-20% ethyl acetate/hexanes) to yield 0.9 g (83%) of light yellow solid 3. ¹H NMR (300 MHz, CDCl₃) δ 7.01 (s, 1H), 6.91 (s, 1H), 3.88 (s, 3H), 2.35 (s, 3H).

The catalyst, (CyPF-t-Bu)PdCl₂, was prepared according to Q. Shen and J. F. Hartwig in *J. Am. Chem. Soc.* 2006, 128(31), including 10028-29 supplementary information. In a vial was combined 5-bromo-2-chloro-1-methoxy-3-methylbenzene (235 mg, 1.0 mmol), lithium amide (95%, 230 mg, 10 mmol), and (CyPF-t-Bu)PdCl₂ (7.3 mg, 0.01 mmol) in 1,2-dimethoxyethane (2 mL) purged under argon. The reaction was heated the 80° C. for 24 hours. Upon cooling to room temperature, the reaction was poured over ice water (2 mL), 1M HCl (1 mL) was added, and stirred for 5 minutes. This was then neutralized with saturated NaHCO₃ solution and extracted 3×10 mL with dichloromethane. Organic layers dried over MgSO4 and purified by silica gel chromatography (0-100% ethyl acetate/hexanes). This yielded 30 mg of 4-chloro-3-methoxy-5-methylaniline. ¹H NMR (300 MHz, CDCl₃) δ 6.20 (s, 1H), 6.15 (s, 1H), 3.83 (s, 3H), 2.27 (s, 3H); LCMS (m/z): 172 (MH⁺). Compound I-124 was made using this aniline.

Scheme (VIII)

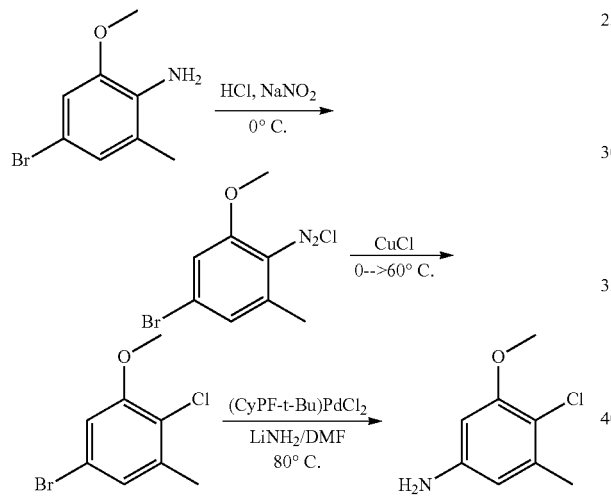

Scheme (IX) depicts synthesis of 3-fluoro-5-methoxy-4-methylaniline. In a round bottom flask was prepared a solution of 1-chloro-4-fluoro-2-methoxybenzene (500 mg, 3.11 mmol) dissolved in anhydrous THF (10 mL). Upon cooling to −78° C., N,N,N',N',N"-pentamethyldiethylenetriamine (PMDTA, 715 L, 3.42 mmol) was added. After 20 minutes, n-butyllithium was added dropwise maintaining the internal temperature at −78° C. After 3 hours, iodomethane was added, cooling bath removed, and the reaction allowed to warm to room temperature overnight. TLC in 1:1 ethyl acetate/hexanes showed no starting material. Solvent volume was reduced via rotary evaporation, then the reaction was diluted with water and ethyl acetate. The organic phase was washed twice with 1N HCl, once with saturated NaHCO₃ solution, once with brine, then dried over Na₂SO₄, and concentrated. This yielded 474 mg (87%) of 1-chloro-4-fluoro-2-methoxy-3-methylbenzene as a colorless oil. ¹H NMR (300 MHz, CDCl₃) δ 7.16 (dd, J=8.9, 5.9 Hz, 1H), 6.77 (t, J=8.7 Hz, 1H), 3.83 (s, 3H), 2.23 (s, 3H).

To a −78° C. cooled solution of 1-chloro-4-fluoro-2-methoxy-3-methylbenzene (470 mg, 2.69 mmol) in THF (5.5 mL) was added sodium amide (95%, 276 mg, 6.72 mmol). After 30 minutes, the solution was warmed to −20 to −30° C. and then benzylamine (441 L, 4.05 mmol) was added dropwise over 1 minute. The reaction was stirred overnight, and LCMS showed no starting material. The reaction was quenched by cooling in an ice bath followed by dropwise addition of saturated NH₄Cl and water. After stirring for 1 hour, the reaction mix was extracted twice with ethyl acetate, and the combined organic phases dried over MgSO₄ and concentrated via rotary evaporation. The crude product was purified by silica gel chromatography (0-30% ethyl acetate/hexanes) to yield a 223 mg (34%) of N-benzyl-3-fluoro-5-methoxy-4-methylaniline as an orange oil. ¹H NMR (300 MHz, CDCl₃) δ 7.40-7.27 (m, 5H), 6.06-6.00 (m, 1H), 6.00 (s, 1H), 4.29 (s, 2H), 3.74 (s, 3H), 2.00 (s, 3H); LCMS (m/z): 246 (MH⁺).

Scheme (IX)

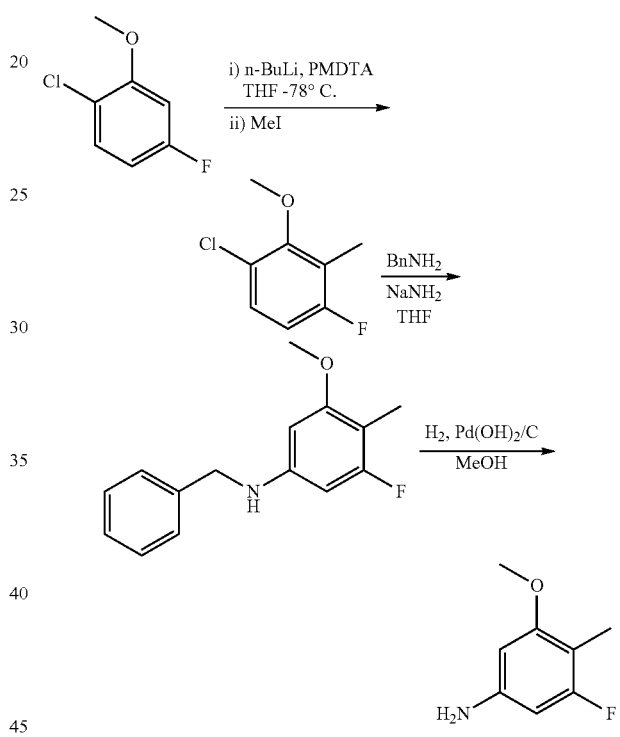

To a solution of N-benzyl-3-fluoro-5-methoxy-4-methylaniline (223 mg, 0.91 mmol) in methanol (25 mL) prepared in a Parr shaker flask was added palladium hydroxide (20% on carbon). This was subjected to 45 psi of hydrogen gas overnight until the LCMS showed complete conversion. The catalyst was filtered and the solution concentrated in vacuo to yield 117 mg (83%) of 3-fluoro-5-methoxy-4-methylaniline as an oil. ¹H NMR (300 MHz, CDCl₃) δ 6.03 (d, J=12.0 Hz, 1H), 6.01 (s, 1H), 3.77 (s, 3H), 2.09 (s, 3H); LCMS (m/z): 156 (MH⁺). Compound I-120 was made using this aniline.

Example 2: Synthesis of 2-halo-pyrimidine-4-amines

Synthesis of 5-(2-chloro-5-methylpyrimidin-4-ylamino)benzo[d]oxazol-2(3H)-one

To a vial with 5-aminobenzo[d]oxazol-2(3H)-one (300.1 mg, 2.0 mmol) and 2,4-dichloro-5-methylpyrimidine (423.8 mg, 2.6 mmol), MeOH (8 mL) and H₂O (2 mL) were added.

The turbid mixture was stirred at room temperature for 64 h. Precipitate from reaction mixture was collected by filtration, washing with EtOAc (3 mL×2), and was further dried in vacuo. 5-(2-Chloro-5-methylpyrimidin-4-ylamino)benzo[d]oxazol-2(3H)-one was obtained as an off-white solid: 394 mg (71% yield); $^1$H NMR (300 MHz, DMSO) δ 11.68 (br s, 1H), 8.62 (s, 1H), 7.94 (d, J=0.8, 1H), 6.97 (d, J=2.0, 1H), 6.82 (d, J=8.1, 1H), 6.74 (dd, J=2.0, 8.1, 1H), 2.15 (s, 3H); LCMS (M+) m/z 277.10.

Synthesis of 5-(2-chloro-5-fluoropyrimidin-4-ylamino)-1H-benzo[d]imidazol-2(3H)-one To a vial with 5-amino-1H-benzo[d]imidazol-2(3H)-one (298.3 mg, 2.0 mmol) and 2,4-dichloro-5-fluoropyrimidine (434.1 mg, 2.6 mmol), MeOH (8 mL) and H$_2$O (2 mL) were added. The turbid solution was stirred at rt for 3 days. Precipitate from reaction mixture was collected by filtration, and washing with EtOAc (3 mL×2), and was further dried in vacuo. 5-(2-Chloro-5-fluoropyrimidin-4-ylamino)-1H-benzo[d]imidazol-2(3H)-one was obtained as an off-white solid: 390.3 mg (70% yield); $^1$H NMR (300 MHz, DMSO) δ 10.69 (s, 1H), 10.63 (s, 1H), 9.87 (s, 1H), 8.27 (d, J=3.6, 1H), 7.35 (d, J=1.9, 1H), 7.18 (dd, J=1.9, 8.3, 1H), 6.93 (d, J=8.3, 1H); LCMS (M+) m/z 279.80.

Synthesis of 6-(2-chloro-5-methylpyrimidin-4-ylamino)benzo[d]oxazol-2(3H)-one

To a vial with 6-aminobenzo[d]oxazol-2(3H)-one (1.0 g, 6.7 mmol) and 2,4-dichloro-5-methylpyrimidine (1.4 g, 8.7 mmol), solvents MeOH (20 mL) and H$_2$O (5 mL) were added. The turbid mixture was stirred at room temperature for 2 days. Precipitate from the reaction mixture was collected by filtration, washing with H$_2$O (3 mL×2) and EtOAc (3 mL×2), and was further drying in vacuo. 6-(2-Chloro-5-methylpyrimidin-4-ylamino)benzo[d]oxazol-2(3H)-one was obtained as a light tan color solid: 1.59 g (86% yield); $^1$H NMR (300 MHz, DMSO) δ 11.59 (s, 1H), 8.87 (s, 1H), 7.99 (s, 1H), 7.56 (s, 1H), 7.28 (d, J=8.3, 1H), 7.06 (d, J=8.3, 1H), 2.14 (s, 3H).

Example 3: Synthesis of 2,4-Pyrimidinediamines Using 2-Halo-Pyrimidine-4-Amines

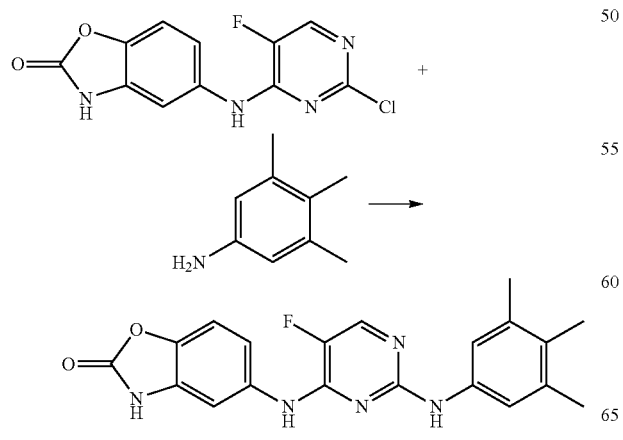

5-Fluoro-N2-(3,4,5-trimethyl)phenyl-N4-(2-oxo-2,3-dihydro-1,3-benzoxazol-5-yl)-2,4-pyrimidinediamine 2-Chloro-5-fluoro-N4-(2-oxo-2,3-dihydro-1,3-benzoxazol-5-yl)-4-pyrimidineamine (50 mg) and 3,4,5-trimethylaniline (50 mg) were suspended in isopropanol (1 mL) and TFA (5 drops). The solution was heated at 100° C. overnight in a sealed tube, then cooled to room temperature. LCMS showed fully conversion to the product. The reaction solution was diluted with 2.0 M NH$_3$ in methanol (5 mL). The solution was sonicated. Precipitation was filtered off and washed with methanol (10 mL), dried to give desired product. $^1$H NMR (300 MHz, DMSO) δ 9.98 (br, 1H), 9.27 (s, 1H), 8.92 (s, 1H), 8.04 (d, J=3.6, 1H), 7.42 (d, J=8.7, 1H), 7.33 (s, 1H), 7.23 (s, 2H), 7.18 (d, J=8.7, 1H), 2.05 (s, 6H), 2.00 (s, 3H); $^{19}$F NMR (282 MHz, DMSO) δ–181.06; LCMS: purity: 100%; MS (m/e): 380.13 (MH$^+$).

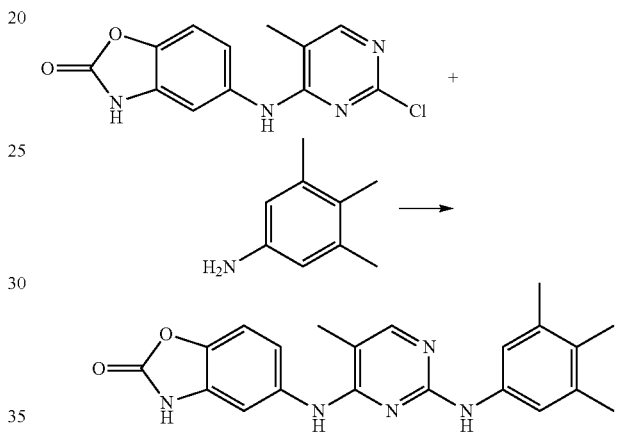

N2-(3,4,5-trimethyl)phenyl-5-methyl-N4-(2-oxo-2,3-dihydro-1,3-benzoxazol-5-yl)-2,4-pyrimidinediamine 2-Chloro-5-methyl-N4-(2-oxo-2,3-dihydro-1,3-benzoxazol-5-yl)-4-pyrimidineamine (300 mg) and 3,4,5-trimethylaniline (300 mg) were suspended in isopropanol (3 mL) and TFA (10 drops). The solution was heated with microwave at 160° C. for 30 minutes in a sealed tube, then cooled to room temperature. LCMS showed fully conversion to the product. The reaction solution was diluted with 2.0 M NH$_3$ in methanol (5 mL). The solution was sonicated. Precipitation was filtered off and washed with methanol (10 mL), dried to give desired product. $^1$H NMR (300 MHz, DMSO) δ 11.39 (br, 1H), 8.70 (s, 1H), 8.29 (s, 1H), 7.83 (s, 1H), 7.30 (d, J=6.3, 2H), 7.21 (m, 3H), 2.06 (s, 3H), 1.99 (s, 6H), 1.98 (s, 3H); LCMS: purity: 96.73%; MS (m/e): 376.27 (MH$^+$).

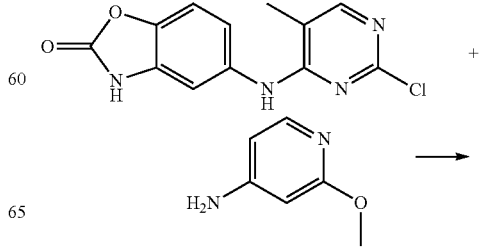

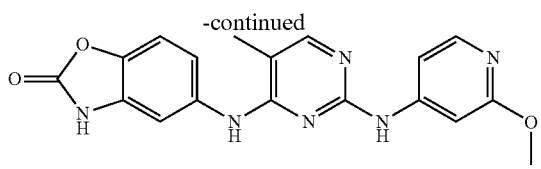

N2-(2-methoxypyridin-4-yl)-5-methyl-N4-(2-oxo-2,3-dihydro-1,3-benzoxazol-5-yl)-2,4-pyrimidinediamine-Chloro-5-methyl-N4-(2-oxo-2,3-dihydro-1,3-benzoxazol-5-yl)-4-pyrimidineamine (50 mg), 2-methoxy-4-aminopyridine (50 mg), palladium acetate (30 mg), BINAP (30 mg) and cesium carbonate (30 mg) were suspended in dioxane (1 mL) and NMP (0.5 mL). The reaction mixture was heated with microwave at 180° C. for 30 minutes in a sealed tube, then cooled to room temperature. The reaction solution was diluted with methanol (5 mL) and sonicated. It was filtered through celite and washed with methanol. The filtrate was evaporated and purified by HPLC to give desired product. $^1$H NMR (300 MHz, DMSO) δ 11.65 (s, 1H), 10.16 (br, 1H), 9.11 (br, 1H), 7.98 (s, 1H), 7.89 (d, J=6.0 Hz, 1H), 7.31-7.10 (m, 5H), 3.72 (s, 3H), 2.14 (s, 3H); LCMS: purity: 97.39%; MS (m/e): 365.35 (MH$^+$).

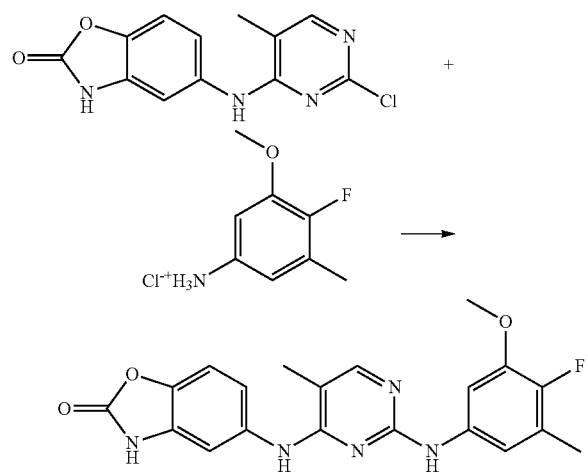

5-(2-(4-fluoro-3-methoxy-5-methylphenylamino)-5-methylpyrimidin-4-ylamino)benzo[d]oxazol-2(3H)-one Into a three-neck round-bottom flask, 5-(2-chloro-5-methylpyrimidin-4-ylamino)benzo[d]oxazol-2(3H)-one (33.2 g, 120 mmol) and 4-fluoro-3-methoxy-5-methylbenzenamine hydrochloride (32.19 g, 168 mmol) were added, followed by i-PrOH (750 mL) and TFA (23.1 mL, 300 mmol). The reaction mixture was stirred under nitrogen atmosphere with gentle refluxing (note: with overhead stirrer at internal temperature of 75-80° C.). After 22 h, by LC-MS, the reaction was >95% complete (note: when ≤3% of the 2-chloropyrimidine starting material remained, the reaction did not progress much further even after another day or two). The reaction mixture was cooled to room temperature, precipitate was collected by filtration, washing with i-PrOH (~50 mL×2). Compound 5-(2-(4-fluoro-3-methoxy-5-methylphenylamino)-5-methylpyrimidin-4-ylamino)benzo[d]oxazol-2(3H)-one trifluoroacetate was obtained as a light tan color solid (still a little bit damp) and was added to a NaHCO$_3$ aqueous solution (15.12 g (180 mmol) of NaHCO$_3$ dissolved in 1 L of H$_2$O). The aqueous suspension was stirred at rt overnight. Solid was collected by filtration, washing with H$_2$O (~150 mL×3), and was further dried under high vacuum. Free base compound 5-(2-(4-fluoro-3-methoxy-5-methylphenylamino)-5-methylpyrimidin-4-ylamino)benzo[d]oxazol-2(3H)-one was obtained as an off-white solid: 44.51 g (93.8% yield).

The benzenesulfonic (besylate) salt of the illustrated product was obtained as follows: Into a MeOH (400 mL) suspension of 5-(2-(4-fluoro-3-methoxy-5-methylphenylamino)-5-methylpyrimidin-4-ylamino)benzo[d]oxazol-2(3H)-one (free base; 39.5 g, 100 mmol), with stirring, benzenesulfonic acid (16.61 g, 105 mmol) was added (note: the reaction mixture turned into an almost homogeneous light brown solution briefly, ppts appeared shortly afterwards). The cloudy solution was stirred at 50° C. for 90 min, cool to rt, solid was collected by filtration, washing with EtOAc (~150 mL×2), and was further dried under high vac. Compound 5-(2-(4-fluoro-3-methoxy-5-methylphenylamino)-5-methylpyrimidin-4-ylamino)benzo[d]oxazol-2(3H)-one besylate was obtained as a very light tan color solid: 52.09 g (94% yield); $^1$H NMR (300 MHz, DMSO) δ 11.99 (br s, 1H), 11.80 (s, 1H), 10.05 (s, 1H), 9.81 (s, 1H), 7.87 (s, 1H), 7.65-7.62 (m, 2H), 7.39-7.33 (m, 4H), 7.29-7.26 (m, 2H), 6.96 (br d, J=7.4 Hz, 1H), 6.91 (br d, J=5.6 Hz, 1H), 3.66 (s, 3H), 2.20 (s, 3H), 2.06 (s, 3H); LRMS (M+) m/z 396.15

Example 4: Synthesis of 2,4-Pyrimidinediamines where the Pyrimidine Core is Installed Via Ring a Guanyl Analogs Scheme (X) depicts the synthesis of N2-(3,5-dimethyl-4-fluoro)phenyl-5-methyl-N4-(2-oxo-2,3-dihydro-1,3-benzoxazol-5-yl)-2,4-pyrimidinediamine starting from 3,5-dimethyl-4-fluoroaniline. First, 3,5-Dimethyl-4-fluoroaniline (500 mg), N,N-bis-Boc-1-guanylpyrazole (1.7 g, 1.5 eq.) and triethylamine (0.75 mL, 1.5 eq.) were dissolved in anhydrous THF (10 mL). The reaction solution was heated at 50° C. for two days, then evaporated to dryness. The residue was dissolved in dichloromethane (1 mL), then trifluoroacetic acid was added to the solution (9 mL). The solution was stirred at room temperature overnight. LCMS confirmed the formation of the guanidine. The solution was evaporated and the residue recrystallized from ethyl acetate and hexanes to give a beige solid as 3,5-dimethyl-4-fluorophenylguanidine TFA salt (740 mg, 70%). $^1$H NMR (300 MHz, DMSO) δ 9.48 (s, 1H), 7.58 (s, 1H), 7.28 (s, 3H), 6.96 (d, J=6.3, 2H), 2.20 (s, 6H); $^{19}$F NMR (282 MHz, DMSO) δ−139.45.

The 3,5-dimethyl-4-fluorophenylguanidine TFA salt (700 mg) and 2-formylpropionic acid ethyl ester (724 mg) were dissolved in anhydrous ethanol (10 mL). To this solution, was added sodium ethoxide (1.18 g). The reaction solution was heated at 70° C. for two days. LCMS showed 10% guanidine starting material remaining. The solution was cooled to room temperature and diluted with water (100 mL). The mixture was extracted with ethyl acetate (3×100 mL) and evaporated. The residue was purified by column chromatography (methanol in dichloromethane=0-30% in 35 min) to give N2-(3,5-dimethyl-4-fluoro)phenyl-4-hydroxy-5-methyl-2-pyrimidineamine (320 mg, 60%). $^1$H NMR (300 MHz, DMSO) δ 10.76 (br, 1H), 8.42 (s, 1H), 7.57 (s, 1H), 7.23 (d, J=6.0, 2H), 2.16 (s, 6H), 1.79 (s, 3H); LCMS: purity: 93.45%; MS (m/e): 248.07 (MH+).

Scheme (X)

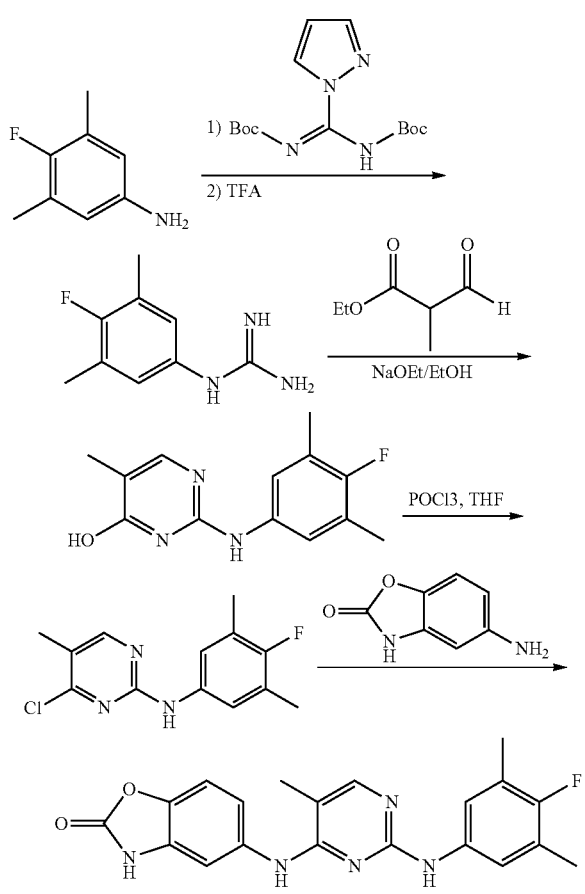

N2-(3,5-dimethyl-4-fluoro)phenyl-4-hydroxy-5-methyl-2-pyrimidineamine (120 mg) was suspended in anhydrous THF (2 mL). Then POCl₃ (0.2 mL) was added to the mixture. The solution was heated at 60° C. for one hour. LCMS showed complete conversion of the 4-hydroxy starting material to the corresponding 4-chloro product. The reaction was quenched with water (40 mL) and extracted with ethyl acetate (40 mL). The organic layer was evaporated and purified by column chromatography (EtOAc in hexanes=0-60% in 35 min) to give 4-chloro-N2-(3,5-dimethyl-4-fluoro)phenyl-5-methyl-2-pyrimidineamine (100 mg, 77%). $^1$H NMR (300 MHz, DMSO) δ 9.69 (s, 1H), 8.63 (s, 1H), 7.34 (d, J=6.6, 2H), 2.16 (s, 6H), 2.14 (s, 3H); $^{19}$F NMR (282 MHz, DMSO) δ−145.51; LCMS: purity: 97.40%; MS (m/e): 266.06 (MH+).

4-Chloro-N2-(3,5-dimethyl-4-fluoro)phenyl-5-methyl-2-pyrimidineamine (80 mg) and 5-amino-2(3H)-benzoxazolone (80 mg) were dissolved in isopropanol (1 mL) and trifluoroacetic acid (5 drops). The solution was heated at 75° C. overnight and then diluted with 2.0 M ammonia in methanol (10 mL). The reaction mixture was sonicated and the precipitation was filtered off, washed with methanol, dried to give N2-(3,5-dimethyl-4-fluoro)phenyl-5-methyl-N4-(2-oxo-2,3-dihydro-1,3-benzoxazol-5-yl)-2,4-pyrimidinediamine. $^1$H NMR (300 MHz, DMSO) δ 11.59 (s, 1H), 8.86 (s, 1H), 8.33 (s, 1H), 7.84 (s, 1H), 7.27 (m, 4H), 7.22 (d, J=9.0, 1H), 2.06 (s, 3H), 1.98 (s, 6H); $^{19}$F NMR (282 MHz, DMSO) δ−147.88; LCMS: purity: 99.86%; MS (m/e): 380.21 (MH+). The free base compound was converted to a besylate salt, compound I-146, and to a sulfate salt, compound I-151.

Example 5: Synthesis of Exemplary Prodrug Compounds

Exemplary prodrug compounds disclosed herein were synthesized as illustrated in Scheme (XI)

Scheme (XI)

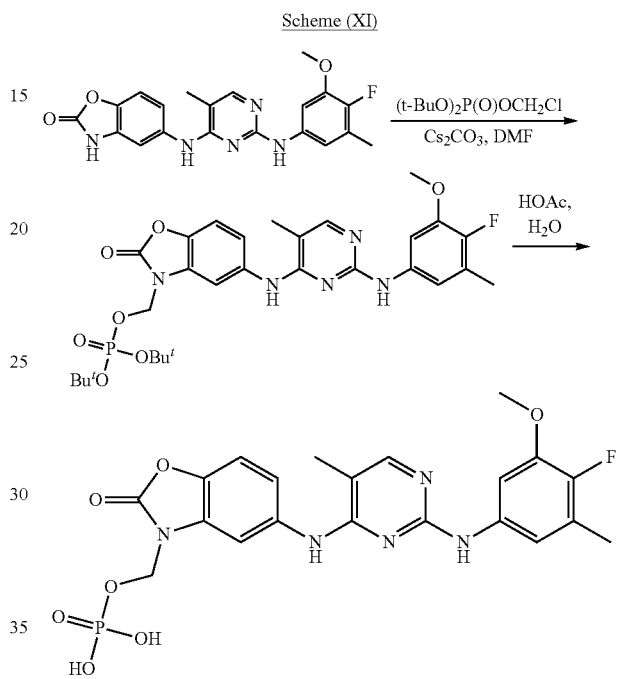

With reference to Scheme (XI), A DMF (300 mL) suspension of 5-(2-(4-fluoro-3-methoxy-5-methylphenylamino)-5-methylpyrimidin-4-ylamino)benzo[d]oxazol-2(3H)-one trifluoroacetate (prepared as described in Example 3)(40.38 g, 79 mmol) and Cs₂CO₃ (78.3 g, 238 mmol) was stirred at rt under Nitrogen atmosphere, after 2.5 h, di-tert-butyl chloromethyl phosphate (26.6 g, 103 mmol) was added and stirring was continued at room temperature. After 49 h, by LC-MS, the reaction was >90% complete (note: due to relatively poor quality of alkylating agent of this batch, additional ~7 g of di-tert-butyl chloromethyl phosphate was added). With stirring, the reaction mixture was poured into 1.2 L of H₂O, ppt formed and was a bit lumpy, additional 500 mL of H₂O was added to ensure the formation of non-sticky solid. Precipitate was collected by filtration, washed with water, and was further dried under high vac. Compound di-tert-butyl (5-(2-(4-fluoro-3-methoxy-5-methylphenylamino)-5-methylpyrimidin-4-ylamino)-2-oxobenzo[d]oxazol-3(2H)-yl)methyl phosphate was obtained as a light brown solid and was used directly in the next reaction.

To the crude di-tert-butyl (5-(2-(4-fluoro-3-methoxy-5-methylphenylamino)-5-methylpyrimidin-4-ylamino)-2-oxobenzo[d]oxazol-3(2H)-yl)methyl phosphate, was added HOAc (280 mL) and H₂O (70 mL), the resultant light brown homogeneous solution was stirred at 65° C. (note: a lighter color ppt was formed between 15-45 min). The reaction was monitored by LC-MS. After 1 h, the mixture was cooled to rt, ppt was collected by filtration, washing with H₂O (~50 mL×2). Product (5-(2-(4-fluoro-3-methoxy-5-methylphenylamino)-5-methylpyrimidin-4-ylamino)-2-oxobenzo[d]oxazol-3(2H)-yl)methyl dihydrogen phosphate was obtained as a light pinkish beige color solid and was used directly in salt formation.

With stirring, to a H$_2$O (500 mL) suspension of crude (5-(2-(4-fluoro-3-methoxy-5-methylphenylamino)-5-methylpyrimidin-4-ylamino)-2-oxobenzo[d]oxazol-3(2H)-yl) methyl dihydrogen phosphate, 1N NaOH (aq., 163 mL, 163 mmol) was added dropwise over 15 min, with ice-bath cooling. Remove ice-bath, add additional H$_2$O until final volume reaching ~1 L. Solid was removed by filtration through a filter paper, washing with H$_2$O Solid (~3 g) appeared as a 1:1 mixture of prodrug and parent compound (I-105) which was formed during previous hydrolysis reaction.). Filtrate was collected, and most H$_2$O was removed by lyophilization (~20 mL of H$_2$O left as solid ice). With stirring, i-PrOH (800 mL) was added to the solid, stirring was continued for 1 h until solid was evenly dispersed in the solution. Solid was collected by filtration, washed with i-PrOH (~100 mL×3), and was further dried under high vac. Compound disodium (5-(2-(4-fluoro-3-methoxy-5-methylphenylamino)-5-methylpyrimidin-4-ylamino)-2-oxobenzo[d]oxazol-3(2H)-yl)methyl phosphate was obtained as a light beige color solid: 38.87 g (89% yield over 3 steps, starting from the TFA salt described above); $^1$H NMR (300 MHz, D$_2$O) δ 7.63 (s, 1H), 7.39-7.33 (m, 2H), 7.13-7.09 (m, 1H), 6.77-6.71 (m, 2H), 5.41 (d, J=6.1 Hz, 2H), 3.62 (s, 3H), 2.01 (br s, 3H), 1.99 (br s, 3H); LRMS (M−) m/z 504.12.

Example 5: Exemplary Synthesized Compounds

The following compounds were made in a similar fashion to the above examples or by methods described herein or known to one of ordinary skill in the art. Analytical data and/or exemplary experimental procedure for making selected compounds follows their name below.

I-1: 5-(5-fluoro-4-(2-oxo-2,3-dihydrobenzo[d]oxazol-5-ylamino)pyrimidin-2-ylamino)-2-methylbenzonitrile formate salt I-2: 4-(4-(2-oxo-2,3-dihydrobenzo[d]oxazol-5-ylamino)pyrimidin-2-ylamino)benzamide trifluoroacetate salt I-3: 3-(4-(2-oxo-2,3-dihydrobenzo[d]oxazol-5-ylamino)pyrimidin-2-ylamino)benzamide trifluoroacetate salt I-4: 5-(5-chloro-2-(phenylamino)pyrimidin-4-ylamino)benzo[d]oxazol-2(3H)-one trifluoroacetate salt I-5: 5-(5-chloro-2-(3,4-dimethylphenylamino)pyrimidin-4-ylamino)benzo[d]oxazol-2(3H)-one trifluoroacetate salt I-6: 5-(5-chloro-2-(3,4,5-trimethylphenylamino)pyrimidin-4-ylamino)benzo[d]oxazol-2(3H)-one trifluoroacetate salt I-7: 5-(5-chloro-2-(2,4-difluoro-3-methoxyphenylamino)pyrimidin-4-ylamino)benzo[d]oxazol-2(3H)-one trifluoroacetate salt I-8: 5-(5-chloro-2-(3-chloro-5-fluorophenylamino)pyrimidin-4-ylamino)benzo[d]oxazol-2(3H)-one formate salt I-9: 5-(5-chloro-2-(4-methyl-3-(trifluoromethyl)phenylamino)pyrimidin-4-ylamino)benzo[d]oxazol-2(3H)-one I-10: 5-(5-chloro-2-(3,5-dimethylphenylamino)pyrimidin-4-ylamino)benzo[d]oxazol-2(3H)-one trifluoroacetate salt I-11: 4-(5-chloro-4-(2-oxo-2,3-dihydrobenzo[d]oxazol-5-ylamino)pyrimidin-2-ylamino)benzamide trifluoroacetate salt I-12: 5-(5-chloro-2-(3-methoxy-5-(trifluoromethyl)phenylamino)pyrimidin-4-ylamino)benzo[d]oxazol-2(3H)-one I-13: 5-(2-(3,5-difluorophenylamino)pyrimidin-4-ylamino)benzo[d]oxazol-2(3H)-one trifluoroacetate salt I-14: 5-(5-chloro-2-(3,5-difluorophenylamino)pyrimidin-4-ylamino)benzo[d]oxazol-2(3H)-one trifluoroacetate salt I-15: 5-(5-chloro-2-(4-(trifluoromethyl)phenylamino)pyrimidin-4-ylamino)benzo[d]oxazol-2(3H)-one trifluoroacetate salt I-16: 5-(5-bromo-2-(3,4,5-trimethylphenylamino)pyrimidin-4-ylamino)benzo[d]oxazol-2(3H)-one formate salt I-17: 5-[2-(3-Dimethylamino-4-methyl-phenylamino)-5-methyl-pyrimidin-4-ylamino]-3H-benzooxazol-2-one $^1$H NMR (300 MHz, DMSO) δ 11.57 (s, 1H), 8.32 (d, J=13.0, 2H), 7.82 (s, 1H), 7.35 (dd, J=8.3, 16.0, 3H), 7.10 (d, J=8.7, 1H), 6.92 (t, J=8.3, 1H), 6.78 (t, J=8.0, 1H), 3.79 (s, 3H), 3.34 (s, 2H), 2.07 (s, 3H) ppm; MS (ES) 391 (M+H).

I-18: 5-[5-Ethynyl-2-(3,4,5-trimethyl-phenylamino)-pyrimidin-4-ylamino]-3H-benzooxazol-2-one trifluoroacetate salt MS (ES) 386 (M+H).

I-19: 5-[2-(2-Fluoro-3-methoxy-phenylamino)-5-methyl-pyrimidin-4-ylamino]-3H-benzooxazol-2-one $^1$H NMR (300 MHz, DMSO) δ 11.75 (s, 1H), 9.91 (s, 1H), 9.65 (s, 1H), 7.87 (s, 1H), 7.26-7.06 (m, 4H), 6.99 (d, J=5.6, 2H), 3.81 (s, 3H), 2.12 (s, 3H) ppm; MS (ES) 382 (M+H).

I-20: 5-(5-fluoro-2-(2-fluoro-3-methoxyphenylamino)pyrimidin-4-ylamino)benzo[d]oxazol-2(3H)-one trifluoroacetate salt I-21: 5-(5-chloro-2-(2-fluoro-3-methoxyphenylamino)pyrimidin-4-ylamino)benzo[d]oxazol-2(3H)-one trifluoroacetate salt I-22: 5-(5-bromo-2-(2-fluoro-3-methoxyphenylamino)pyrimidin-4-ylamino)benzo[d]oxazol-2(3H)-one trifluoroacetate salt I-23: 5-(2-(2-fluoro-3-methoxyphenylamino)pyrimidin-4-ylamino)benzo[d]oxazol-2(3H)-one 1-24: 5-[2-(3-Dimethylamino-phenylamino)-5-methyl-pyrimidin-4-ylamino]-3H-benzooxazol-2-one trifluoroacetate salt $^1$H NMR (300 MHz, DMSO) δ 11.82 (s, 1H), 10.41 (s, 1H), 9.76 (s, 1H), 7.86 (s, 1H), 7.24 (s, 3H), 7.03 (t, J=8.1, 1H), 6.73 (d, J=8.1, 1H), 6.66 (s, 1H), 6.48 (d, J=8.2, 1H), 2.70 (s, 6H), 2.12 (s, 3H); ppm; MS (ES) 377 (M+H).

I-25: 5-[2-(4-Dimethylamino-phenylamino)-5-methyl-pyrimidin-4-ylamino]-3H-benzooxazol-2-one $^1$H NMR (300 MHz, DMSO) δ 11.63 (s br, 1H), 8.59 (s, 1H), 8.24 (s, 1H), 7.78 (s, 1H), 7.40 (d, J=8.9, 2H), 7.34 (d, J=7.9, 2H), 7.18 (d, J=9.0, 1H), 6.57 (d, J=9.0, 2H), 2.77 (s, 6H), 2.05 (s, 3H) ppm; MS (ES) 377 (M+H).

I-26: 5-[5-Methyl-2-(methyl-phenyl-amino)-pyrimidin-4-ylamino]-3H-benzooxazol-2-one $^1$H NMR (300 MHz, DMSO) δ 8.16 (s, 1H), 7.76 (s, 1H), 7.43-7.22 (m, 5H), 7.13 (t, J=7.1, 1H), 6.96 (d, J=8.7, 1H), 3.37 (s, 3H), 2.03 (s, 3H) ppm; MS (ES) 348 (M+H).

I-27: 5-[2-(4-Bromo-2-fluoro-3-methoxy-phenylamino)-5-methyl-pyrimidin-4-ylamino]-3H-benzooxazol-2-one $^1$H NMR (300 MHz, DMSO) δ 8.39 (s, 1H), 8.26 (s, 1H), 7.81 (s, 1H), 7.66 (t, J=8.5, 1H), 7.24-7.08 (m, 2H), 6.99 (d, J=8.3, 1H), 3.77 (s, 2H), 2.06 (s, 2H) ppm; MS (ES) 460/462 (M+H).

I-28: 5-[2-(4-Bromo-2-fluoro-phenylamino)-5-methyl-pyrimidin-4-ylamino]-3H-benzooxazol-2-one $^1$H NMR (300 MHz, DMSO) δ 11.80 (s, 1H), 10.11 (s, 1H), 9.69 (s, 1H), 7.91 (s, 1H), 7.63 (d, J=10.3, 1H), 7.51 (t, J=8.6, 1H), 7.38-7.02 (m, 4H), 2.12 (s, 3H) ppm; MS (ES) 430/432 (M+H).

I-29: 5-[2-(2-Fluoro-3-methoxy-4-methyl-phenylamino)-5-methyl-pyrimidin-4-ylamino]-3H-benzooxazol-2-one trifluoroacetate salt $^1$H NMR (300 MHz, DMSO) δ 11.79 (s, 1H), 10.21 (s, 1H), 9.81 (s, 1H), 7.88 (s, 1H), 7.18 (s, 2H), 7.12 (d, J=7.9, 1H), 6.92 (d, J=8.4, 1H), 3.70 (s, 3H), 2.18 (s, 3H), 2.13 (s, 3H) ppm; MS (ES) 396 (M+H).

I-30: {4-[5-Methyl-4-(2-oxo-2,3-dihydro-benzooxazol-5-ylamino)-pyrimidin-2-ylamino]-phenyl}-acetaldehyde ¹H NMR (300 MHz, DMSO) δ 9.79 (s, 1H), 8.43 (s, 1H), 7.91 (s, 1H), 7.75 (q, J=8.9, 3H), 7.28 (m, 2H), 2.51-2.37 (m, 2H), 2.10 (s, 3H) ppm; MS (ES) 376 (M+H).

I-31: 5-[2-(3-Ethynyl-phenylamino)-5-methyl-pyrimidin-4-ylamino]-3H-benzooxazol-2-one ¹H NMR (300 MHz, DMSO) δ 9.10 (s, 1H), 8.31 (s, 1H), 7.84 (d, J=14.0, 1H), 7.68 (d, J=9.3, 1H), 7.28 (s, 1H), 7.20 (d, J=8.6, 1H), 7.17-7.03 (m, 2H), 6.89 (d, J=7.5, 1H), 3.94 (s, 1H), 2.07 (s, 3H) ppm; MS (ES) 358 (M+H).

I-32: 5-(5-chloro-2-(3-methoxy-4-methylphenylamino)pyrimidin-4-ylamino)benzo[d]oxazol-2(3H)-one trifluoroacetate salt I-33: 5-(5-chloro-2-(3-(dimethylamino)-4-methylphenylamino)pyrimidin-4-ylamino)benzo[d]oxazol-2(3H)-one I-34: 5-[2-(3-Amino-4-methoxy-phenylamino)-5-methyl-pyrimidin-4-ylamino]-3H-benzooxazol-2-one ¹H NMR (300 MHz, DMSO) δ 8.44 (s, 1H), 8.04 (s, 1H), 7.75 (s, 1H), 7.32 (s, 1H), 7.11 (d, J=8.6, 1H), 7.03 (d, J=2.2, 1H), 6.98 (d, J=8.4, 1H), 6.71 (dd, J=2.3, 8.6, 1H), 6.57 (d, J=8.7, 1H), 3.66 (s, 3H), 2.04 (s, 3H) ppm; MS (ES) 379 (M+H).

I-35: 5-[5-Methyl-2-(3,5-dimethyl-4-d₃-methyl-phenylamino)-pyrimidin-4-ylamino]-3H-benzooxazol-2-one trifluoroacetate salt ¹H NMR (300 MHz, DMSO) δ 11.84 (s, 1H), 10.36 (s, 1H), 9.89 (s, 1H), 7.90 (s, 1H), 7.32 (d, J=8.3, 1H), 7.22 (s, 1H), 6.97 (s, 2H), 2.13 (s, 3H), 1.99 (s, 6H) ppm; MS (ES) 379 (M+H).

I-36: 5-(5-chloro-2-(3,5-dimethyl-4-d₃-methyl)phenylamino)pyrimidin-4-ylamino)benzo[d]oxazol-2(3H)-one trifluoroacetate salt I-37: 5-(5-fluoro-2-(3,5-dimethyl-4-d₃-methyl)phenylamino)pyrimidin-4-ylamino)benzo[d]oxazol-2(3H)-one trifluoroacetate salt I-38: 5-(2-(3,5-dimethyl-4-d₃-methyl)phenylamino)pyrimidin-4-ylamino)benzo[d]oxazol-2(3H)-one trifluoroacetate salt I-39: 4-(2-oxo-2,3-dihydro-benzooxazol-5-ylamino)-2-phenylamino-pyrimidine-5-carboxylic acid methyl ester trifluoroacetate salt ¹H NMR (300 MHz, DMSO) δ 11.71 (s, 1H), 9.97 (d, J=30.6, 2H), 8.70 (d, J=3.4, 1H), 7.62 (s, 2H), 7.43-7.08 (m, J=20.8, 5H), 6.96 (s, 1H), 3.83 (s, J=3.4, 3H), 3.40 (s, 2H) ppm; MS (ES) 378 (M+H).

I-40: 4-(2-Oxo-2,3-dihydro-benzooxazol-5-ylamino)-2-(3,4,5-trimethyl-phenylamino)-pyrimidine-5-carboxylic acid methyl ester trifluoroacetate salt ¹H NMR (300 MHz, DMSO) δ 11.75 (s, 1H), 10.13 (s, 1H), 9.82 (s, 1H), 8.22 (d, J=4.8, 1H), 7.49-7.19 (m, 3H), 7.12 (s, 2H), 6.95 (s, 1H), 3.75 (s, 3H), 2.24 (s, 3H), 2.05 (s, 6H) ppm; MS (ES) 420 (M+H).

I-41: 5-(5-nitro-2-(phenylamino)pyrimidin-4-ylamino)benzo[d]oxazol-2(3H)-one trifluoroacetate salt I-42: 5-(5-nitro-2-(3,4,5-trimethylphenylamino)pyrimidin-4-ylamino)benzo[d]oxazol-2(3H)-one trifluoroacetate salt I-43: 5-(2-(2,4-difluoro-3-methoxyphenylamino)-5-nitropyrimidin-4-ylamino)benzo[d]oxazol-2(3H)-one trifluoroacetate salt I-44: 5-(2-(3-methoxy-4-methylphenylamino)-5-nitropyrimidin-4-ylamino)benzo[d]oxazol-2(3H)-one trifluoroacetate salt I-45: 5-(2-(3-(dimethylamino)-4-methylphenylamino)-5-nitropyrimidin-4-ylamino)benzo[d]oxazol-2(3H)-one trifluoroacetate salt I-46: 5-(5-methyl-2-(3,5-dimethyl-4-d₃-methyl)phenylamino)pyrimidin-4-ylamino)benzo[d]oxazol-2(3H)-one I-47: 5-(2-(3-methoxy-5-(trifluoromethyl)phenylamino)-5-nitropyrimidin-4-ylamino)benzo[d]oxazol-2(3H)-one trifluoroacetate salt I-48: 2-(2,4-Difluoro-3-methoxy-phenylamino)-4-(2-oxo-2,3-dihydro-benzooxazol-5-ylamino)-pyrimidine-5-carboxylic acid methyl ester trifluoroacetate salt MS (ES) 444 (M+H).

I-49: 4-(2-Oxo-2,3-dihydro-benzooxazol-5-ylamino)-2-(3,4,5-trimethyl-phenylamino)-pyrimidine-5-carboxylic acid trifluoroacetate salt ¹H NMR (300 MHz, DMSO) δ 11.68 (s, 1H), 10.33 (s, 1H), 9.67 (s, 1H), 8.65 (s, 1H), 7.71-7.49 (m, 1H), 7.36-7.21 (m, 2H), 3.42 (s, 12H), 2.48 (s, 5H), 2.02 (s, 3H) ppm; MS (ES) 406 (M+H).

I-50: 5-[2-(2-Fluoro-3,4-dimethoxy-phenylamino)-5-methyl-pyrimidin-4-ylamino]-3H-benzooxazol-2-one ¹H NMR (300 MHz, DMSO) δ 8.17 (d, J=5.3, 2H), 7.76 (s, 1H), 7.37-7.19 (m, 3H), 7.00 (d, J=8.4, 1H), 6.74 (d, J=9.2, 1H), 3.78 (s, 3H), 3.72 (s, 3H), 2.04 (s, 3H) ppm; MS (ES) 412 (M+H).

I-51: 5-(5-chloro-2-(2-fluoro-3,4-dimethoxyphenylamino)pyrimidin-4-ylamino)benzo[d]oxazol-2(3H)-one trifluoroacetate salt I-52: 5-(5-chloro-2-(3-methoxy-4,5-dimethylphenylamino)pyrimidin-4-ylamino)benzo[d]oxazol-2(3H)-one I-53: 5-{2-[2-Fluoro-3-(2-methoxy-ethoxy)-4-methyl-phenylamino]-5-methyl-pyrimidin-4-ylamino}-3H-benzooxazol-2-one ¹H NMR (300 MHz, DMSO) δ 8.27 (s, 1H), 8.21 (s, 1H), 7.80 (s, 1H), 7.46-7.25 (m, 3H), 7.09 (d, J=8.6, 1H), 6.80 (d, J=8.5, 1H), 4.01-3.93 (m, 2H), 3.57-3.52 (m, 2H), 3.27 (s, 3H), 2.16 (s, 3H), 2.05 (s, 3H) ppm; MS (ES) 440 (M+H).

I-54: 2-(4-Carbamoyl-phenylamino)-4-(2-oxo-2,3-dihydro-benzooxazol-5-ylamino)-pyrimidine-5-carboxylic acid methyl ester trifluoroacetate salt ¹H NMR (300 MHz, DMSO) δ 11.73 (s, 1H), 10.16 (s, 1H), 10.05 (s, 1H), 8.86-8.62 (m, 1H), 7.81 (s, 1H), 7.69 (m, 2H), 7.32 (m, 3H), 3.84 (s, 3H) ppm; MS (ES) 421 (M+H).

I-55: 2-(3-Methoxy-5-trifluoromethyl-phenylamino)-4-(2-oxo-2,3-dihydro-benzooxazol-5-ylamino)-pyrimidine-5-carboxylic acid methyl ester trifluoroacetate salt ¹H NMR (300 MHz, DMSO) δ 11.62 (s, 1H), 10.16 (s, 1H), 9.98 (s, 1H), 8.73 (s, 1H), 7.51 (s, 2H), 7.24 (d, J=8.4, 2H), 7.20-7.03 (m, 1H), 6.77 (s, 1H), 3.84 (s, 3H), 3.66 (s, 3H) ppm; MS (ES) 473 (M+H).

I-56: 2-(3-Methoxy-4-methyl-phenylamino)-4-(2-oxo-2,3-dihydro-benzooxazol-5-ylamino)-pyrimidine-5-carboxylic acid methyl ester trifluoroacetate salt MS (ES) 422 (M+H).

I-57: 2-(3-Dimethylamino-4-methyl-phenylamino)-4-(2-oxo-2,3-dihydro-benzooxazol-5-ylamino)-pyrimidine-5-carboxylic acid methyl ester trifluoroacetate salt ¹H NMR (300 MHz, DMSO) δ 11.78 (s, 1H), 10.25-9.90 (m, 2H), 8.79-8.64 (m, 1H), 7.81-7.44 (m, 2H), 7.44-7.20 (m, 3H), 7.10 (s, 1H), 3.83 (s, 3H), 2.83 (s, 6H), 2.30 (s, 3H) ppm; MS (ES) 435 (M+H).

I-58: 2-(4-Fluoro-3-methoxy-5-methyl-phenylamino)-4-(2-oxo-2,3-dihydro-benzooxazol-5-ylamino)-pyrimidine-5-carboxylic acid methyl ester trifluoroacetate salt ¹H NMR (300 MHz, DMSO) δ 11.69 (s, 1H), 10.03 (s, 1H), 9.98-9.66 (m, 1H), 8.68 (d, J=2.8, 1H), 7.44-7.01 (m, J=37.0, 5H), 3.81 (d, J=2.7, 3H), 3.55 (s, 3H), 1.96 (s, 3H) ppm; MS (ES) 440 (M+H).

I-59: 2-(3-Methoxy-4,5-dimethyl-phenylamino)-4-(2-oxo-2,3-dihydro-benzooxazol-5-ylamino)-pyrimidine-5-carboxylic acid methyl ester trifluoroacetate salt $^1$H NMR (300 MHz, DMSO) δ 11.68 (s, 1H), 10.04 (s, 1H), 9.89-9.68 (m, 1H), 8.68 (s, 1H), 7.44-7.17 (m, 3H), 7.13 (s, 1H), 7.06-6.86 (m, 1H), 3.82 (s, 3H), 3.50 (s, 3H), 2.48 (s, 3H), 1.95 (s, 3H) ppm; MS (ES) 436 (M+H).

I-60: 4-(5-nitro-4-(2-oxo-2,3-dihydrobenzo[d]oxazol-5-ylamino)pyrimidin-2-ylamino)benzamide trifluoroacetate salt I-61: 5-(5-fluoro-2-(2-fluoro-3-(2-methoxyethoxy)-4-methylphenylamino)pyrimidin-4-ylamino)benzo[d]oxazol-2(3H)-one trifluoroacetate salt I-62: 5-(2-(2-fluoro-3-(2-methoxyethoxy)-4-methylphenylamino)pyrimidin-4-ylamino)benzo[d]oxazol-2(3H)-one I-63: 5-[5-Hydroxymethyl-2-(3,4,5-trimethyl-phenylamino)-pyrimidin-4-ylamino]-3H-benzooxazol-2-one $^1$H NMR (300 MHz, DMSO) δ 11.75-11.40 (m, 1H), 8.87 (s, 1H), 8.34 (s, 1H), 7.92 (s, 1H), 7.25 (dd, J=8.3, 15.4, 3H), 5.12 (t, J=5.6, 1H), 4.43 (d, J=5.3, 2H), 2.48 (d, J=1.7, 6H), 2.01 (s, 3H) ppm; MS (ES) 392 (M+H).

I-64: 2,6-Dimethyl-4-[5-methyl-4-(2-oxo-2,3-dihydro-benzooxazol-5-ylamino)-pyrimidin-2-ylamino]-benzonitrile trifluoroacetate salt $^1$H NMR (300 MHz, DMSO) δ 11.75 (s, 1H), 10.47-9.99 (m, 1H), 9.55-9.23 (m, 1H), 7.96 (s, 1H), 7.33 (s, 2H), 7.29-7.07 (m, 1H), 2.15 (s, 6H), 2.13 (s, 3H) ppm; MS (ES) 387 (M+H).

I-65: 5-[5-Methyl-2-(3-vinyl-phenylamino)-pyrimidin-4-ylamino]-3H-benzooxazol-2-one trifluoroacetate salt $^1$H NMR (300 MHz, DMSO) δ 11.76 (s, 1H), 10.45 (s, 1H), 9.74 (s, 1H), 7.92 (s, 1H), 7.50 (s, 1H), 7.40-7.04 (m, 5H), 6.37 (dd, J=10.9, 17.6, 1H), 5.50 (d, J=17.7, 1H), 5.09 (d, J=10.9, 1H), 2.13 (s, 3H) ppm; MS (ES) 360 (M+H).

I-66: 5-(5-chloro-2-(2-fluoro-3-(2-methoxyethoxy)-4-methylphenylamino)pyrimidin-4-ylamino)benzo[d]oxazol-2(3H)-one trifluoroacetate salt I-67: 5-(5-chloro-2-(2-fluoro-3-methoxy-4-methylphenylamino)pyrimidin-4-ylamino)benzo[d]oxazol-2(3H)-one I-68: 5-[2-(4-Ethyl-2-fluoro-3-methoxy-phenylamino)-5-methyl-pyrimidin-4-ylamino]-3H-benzooxazol-2-one trifluoroacetate salt $^1$H NMR (300 MHz, DMSO) δ 11.73 (s, 1H), 10.11-9.84 (m, 1H), 9.70 (s, 1H), 7.94-7.79 (m, 1H), 7.34-7.05 (m, 3H), 6.92 (d, J=8.6, 1H), 3.72 (s, 3H), 2.55 (dd, J=6.6, 14.2, 2H), 2.12 (s, 3H), 1.10 (t, J=7.5, 2H) ppm; MS (ES) 410 (M+H).

I-69: 4-(5-chloro-4-(2-oxo-2,3-dihydrobenzo[d]oxazol-5-ylamino)pyrimidin-2-ylamino)-2,6-dimethylbenzonitrile] trifluoroacetate salt I-70: 4-(5-fluoro-4-(2-oxo-2,3-dihydrobenzo[d]oxazol-5-ylamino)pyrimidin-2-ylamino)-2,6-dimethylbenzonitrile I-71: 5-(5-chloro-2-(4-ethyl-2-fluoro-3-methoxyphenylamino)pyrimidin-4-ylamino)benzo[d]oxazol-2(3H)-one trifluoroacetate salt I-72: 2-fluoro-3-(5-methyl-4-(2-oxo-2,3-dihydrobenzo[d]oxazol-5-ylamino)pyrimidin-2-ylamino)benzonitrile trifluoroacetate salt I-73: 3-(5-chloro-4-(2-oxo-2,3-dihydrobenzo[d]oxazol-5-ylamino)pyrimidin-2-ylamino)-2-fluorobenzonitrile trifluoroacetate salt I-74: methyl 2-(4-fluoro-3,5-dimethylphenylamino)-4-(2-oxo-2,3-dihydrobenzo[d]oxazol-5-ylamino)pyrimidine-5-carboxylate trifluoroacetate salt I-75: 5-(2-(2-fluoro-4-methoxyphenylamino)-5-methylpyrimidin-4-ylamino)benzo[d]oxazol-2(3H)-one trifluoroacetate salt I-76: 5-(5-chloro-2-(2-fluoro-4-methoxyphenylamino)pyrimidin-4-ylamino)benzo[d]oxazol-2(3H)-one trifluoroacetate salt I-77: 5-(2-(2-fluoro-3,4-bis(2-methoxyethoxy)phenylamino)-5-methylpyrimidin-4-ylamino)benzo[d]oxazol-2(3H)-one trifluoroacetate salt I-78: 5-(5-chloro-2-(2-fluoro-3,4-bis(2-methoxyethoxy)phenylamino)pyrimidin-4-ylamino)benzo[d]oxazol-2(3H)-one trifluoroacetate salt I-79: 5-(2-(4-fluoro-3,5-dimethylphenylamino)-5-(hydroxymethyl)pyrimidin-4-ylamino)benzo[d]oxazol-2(3H)-one trifluoroacetate salt I-80: 5-(2-(4-fluoro-3-methoxy-5-methylphenylamino)-5-(hydroxymethyl)pyrimidin-4-ylamino)benzo[d]oxazol-2(3H)-one trifluoroacetate salt I-81: 5-(5-(hydroxymethyl)-2-(3-methoxy-4,5-dimethylphenylamino)pyrimidin-4-ylamino)benzo[d]oxazol-2(3H)-one trifluoroacetate salt I-82: 5-(2-(3-(dimethylamino)-4,5-dimethylphenylamino)-5-methylpyrimidin-4-ylamino)benzo[d]oxazol-2(3H)-one trifluoroacetate salt I-83: 5-(5-chloro-2-(3-(dimethylamino)-4,5-dimethylphenylamino)pyrimidin-4-ylamino)benzo[d]oxazol-2(3H)-one trifluoroacetate salt I-84: 5-(2-(3-(diethylamino)-4,5-dimethylphenylamino)-5-methylpyrimidin-4-ylamino)benzo[d]oxazol-2(3H)-one formate salt I-85: 5-(2-(3-(ethylamino)-4,5-dimethylphenylamino)-5-methylpyrimidin-4-ylamino)benzo[d]oxazol-2(3H)-one formate salt I-86: 5-(5-chloro-2-(3-(diethylamino)-4,5-dimethylphenylamino)pyrimidin-4-ylamino)benzo[d]oxazol-2(3H)-one formate salt I-87: 5-(5-chloro-2-(3-(ethylamino)-4,5-dimethylphenylamino)pyrimidin-4-ylamino)benzo[d]oxazol-2(3H)-one formate salt I-88: 5-(2-(3,4,5-trimethylphenylamino)-5-methylpyrimidin-4-ylamino)-7-(benzo[d][1,3]dioxol-6-yl)benzo[d]oxazol-2(3H)-one $C_{25}H_{25}N_5O_4$. MS (ESI) m/z 496.27 $(M+1)^+$.

I-89: 5-(2-(3,4,5-trimethylphenylamino)-5-methylpyrimidin-4-ylamino)-7-((dimethylamino)methyl)benzo[d]oxazol-2(3H)-one ditrifluoroacetate salt $C_{25}H_{28}N_6O_2$. MS (ESI) m/z 433.19 $(M+1)^+$.

I-90: 7-((diethylamino)methyl)-5-(2-(3,4,5-trimethylphenylamino)-5-methylpyrimidin-4-ylamino)benzo[d]oxazol-2(3H)-one ditrifluoroacetate salt $C_{26}H_{32}N_6O_2$. MS (ESI) m/z 461.24 $(M+1)^+$.

I-91: 5-(2-(3,4,5-trimethylphenylamino)-5-methylpyrimidin-4-ylamino)-7-((pyrrolidin-1-yl)methyl)benzo[d]oxazol-2(3H)-one $C_{26}H_{30}N_6O_2$. MS (ESI) m/z 459.23 $(M+1)^+$.

I-92: 5-(2-(3,4,5-trimethylphenylamino)-5-methylpyrimidin-4-ylamino)-7-((piperidin-1-yl)methyl)benzo[d]oxazol-2(3H)-one $C_{27}H_{32}N_6O_2$. MS (ESI) m/z 473.22 (M+1)+. $^1$H NMR (300 MHz, DMSO) δ 8.70 (s, 1H, NH), 8.41 (s, 1H, NH), 7.84 (s, 1H, ArH), 7.31 (s, 1H, ArH), 7.21 (s, 3H, ArH), 3.32 (s, 2H, CH$_2$), 2.52 (in, 4H, 2CH$_2$), 2.06 (s, 3H, CH$_3$), 1.96 (s, 9H, 3CH$_3$), 1.53 (m, 4H, 3CH$_2$).

I-93: 5-(2-(3,4,5-trimethylphenylamino)-5-methylpyrimidin-4-ylamino)-7-((4-methylpiperazin-1-yl)methyl)benzo[d]oxazol-2(3H)-one $C_{27}H_{33}N_7O_2$. MS (ESI) m/z 488.25 (M+1)+. $^1$H NMR (300 MHz, DMSO) δ 8.67 (s, 1H, NH), 8.34 (s, 1H, NH), 7.81 (s, 1H, ArH), 7.27 (s, 1H, ArH), 7.21 (s, 2H, ArH), 7.10 (s, 1H, ArH), 3.53 (s, 2H, CH$_2$), 2.43 (m, 8H, 4CH$_2$), 2.29 (s, 3H, CH$_3$), 2.05 (s, 3H, CH$_3$), 1.95 (s, 9H, 3CH$_3$).

I-94: tert-butyl 4-((5-(2-(3,4,5-trimethylphenylamino)-5-methylpyrimidin-4-ylamino)-2,3-dihydro-2-oxobenzo[d]oxazol-7-yl)methyl)piperazine-1-carboxylate C$_{31}$H$_{3}$N$_{7}$O$_{4}$. MS (ESI) m/z 574.36 (M+1)$^+$.

I-95: 5-(2-(3,4,5-trimethylphenylamino)-5-methylpyrimidin-4-ylamino)-7-((piperazin-1-yl)methyl)benzo[d]oxazol-2(3H)-one ditrifluoroacetate salt C$_2$H$_{31}$N$_7$O$_2$. MS (ESI) m/z 474.45 (M+1)$^+$.

I-96: 5-(2-(3,4,5-trimethylphenylamino)-5-methylpyrimidin-4-ylamino)-7-((E)-3-chloroprop-1-enyl)benzo[d]oxazol-2(3H)-one C$_{24}$H$_{24}$ClN$_5$O$_2$. MS (ESI) m/z 450.17 (M+1)+.

I-97: 5-(5-((diethylamino)methyl)-2-(3,4,5-trimethylphenylamino)pyrimidin-4-ylamino)benzo[d]oxazol-2(3H)-one ditrifluoroacetate salt C$_{25}$H$_{30}$N$_6$O$_2$. MS (ESI) m/z 447.41 (M+1)$^+$.

I-98: 5-(2-(3,4,5-trimethylphenylamino)-5-((pyrrolidin-1-yl)methyl)pyrimidin-4-ylamino)benzo[d]oxazol-2(3H)-one C$_{25}$H$_{25}$N$_6$O$_2$. MS (ESI) m/z 445.42 (M+1)$^+$. $^1$H NMR (300 MHz, DMSO) δ 9.88 (s, 1H, NH), 8.89 (s, 1H, NH), 7.85 (s, 1H, ArH), 7.30 (m, 3H, ArH), 7.16 (m, 2H, ArH), 3.55 (s, 2H, CH$_2$), 2.52 (m, 4H, 2CH$_2$), 2.07 (s, 6H, 2CH$_3$), 2.01 (s, 3H, CH$_3$), 1.77 (m, 4H, 2CH$_2$).

I-99: 5-(2-(3,4,5-trimethylphenylamino)-5-((piperidin-1-yl)methyl)pyrimidin-4-ylamino)benzo[d]oxazol-2(3H)-one C$_{26}$H$_{30}$N$_6$O$_2$. MS (ESI) m/z 459.44 (M+1)+. $^1$H NMR (300 MHz, DMSO) δ 8.93 (s, 1H, NH), 7.85 (s, 1H, NH), 7.30-7.20 (m, 6H, ArH), 3.32 (s, 2H, CH$_2$), 2.52 (m, 4H, 2CH$_2$), 2.07 (s, 6H, 2CH$_3$), 2.01 (s, 3H, CH$_3$), 1.57 (m, 4H, 2CH$_2$), 1.46 (m, 4H, 2CH$_2$).

I-100: 5-(2-(3,4,5-trimethylphenylamino)-5-((4-methylpiperazin-1-yl)methyl)pyrimidin-4-ylamino)benzo[d]oxazol-2(3H)-one C$_{25}$H$_{31}$N$_7$O$_2$. MS (ESI) m/z 474.48 (M+1)$^+$.

I-101: 5-(2-(3,4-diethoxy-2-fluorophenylamino)-5-methylpyrimidin-4-ylamino)benzo[d]oxazol-2(3H)-one C$_{22}$H$_{22}$FN$_5$O$_4$. MS (ESI) m/z 440.23 (M+1)+. $^1$H NMR (300 MHz, DMSO) δ 11.54 (s, 1H, NH), 7.85 (m, br, 2H, 2NH), 7.77 (s, 1H, ArH), 7.32 (m, 1H, ArH), 7.21 (m, 2H, ArH), 7.09 (d, J=10.0, 1H, ArH), 6.74 (d, J=10.0, 1H, ArH), 4.03 (q, J=6.7, 2H, CH$_2$), 3.94 (q, J=6.7, 2H, CH$_2$), 2.06 (s, 3H, CH$_3$), 1.32 (t, J=6.7, 3H, CH$_3$), 1.19 (t, J=6.7, 3H, CH$_3$).

I-102: 5-(2-(2-fluoro-3,4-d$_6$-dimethoxyphenylamino)-5-methylpyrimidin-4-ylamino)benzo[d]oxazol-2(3H)-one I-103: 5-(2-(3-ethoxy-4,5-dimethylphenylamino)-5-methylpyrimidin-4-ylamino)benzo[d]oxazol-2(3H)-one ditrifluoroacetate salt I-104: 5-(5-chloro-2-(3-ethoxy-4,5-dimethylphenylamino)pyrimidin-4-ylamino)benzo[d]oxazol-2(3H)-one ditrifluoroacetate salt I-105: 5-(2-(4-fluoro-3-methoxy-5-methylphenylamino)-5-methylpyrimidin-4-ylamino)benzo[d]oxazol-2(3H)-one I-106: 5-(2-(4-fluoro-3-methoxy-5-methylphenylamino)-5-methylpyrimidin-4-ylamino)benzo[d]oxazol-2(3H)-one methane sulfonic acid salt $^1$H NMR (300 MHz, DMSO) δ 12.03 (br s, 1H), 11.80 (s, 1H), 10.05 (s, 1H), 9.78 (s, 1H), 7.87 (s, 1H), 7.36-7.25 (m, 3H), 6.97 (br d, J=7.2 Hz, 1H), 6.92 (br d, J=3.9 Hz, 1H), 3.65 (s, 3H), 2.36 (s, 3H), 2.20 (s, 3H), 2.06 (s, 3H); LRMS (M+) m/z 396.14.

I-107: 5-(2-(4-fluoro-3-methoxy-5-methylphenylamino)-5-methylpyrimidin-4-ylamino)benzo[d]oxazol-2(3H)-one benzenesulfonic acid salt $^1$H NMR (300 MHz, DMSO) δ 11.99 (br s, 1H), 11.80 (s, 1H), 10.05 (s, 1H), 9.81 (s, 1H), 7.87 (s, 1H), 7.65-7.62 (m, 2H), 7.39-7.33 (m, 4H), 7.29-7.26 (m, 2H), 6.96 (br d, J=7.4 Hz, 1H), 6.91 (br d, J=5.6 Hz, 1H), 3.66 (s, 3H), 2.20 (s, 3H), 2.06 (s, 3H); LRMS (M+) m/z 396.15.

I-108: 5-(2-(3-methoxy-4,5-dimethylphenylamino)-5-methylpyrimidin-4-ylamino)benzo[d]oxazol-2(3H)-one benzenesulfonic acid salt $^1$H NMR (300 MHz, DMSO) δ 11.91 (s, 1H), 11.80 (s, 1H), 10.04 (s, 1H), 9.83 (s, 1H), 7.85 (s, 1H), 7.66 (br d, J=3.3, 1H), 7.63 (br d, J=1.5, 1H), 7.40-7.33 (m, 4H), 7.29-7.28 (m, 2H), 6.88 (s, 1H), 6.77 (s, 1H), 3.60 (s, 3H), 2.19 (s, 3H), 2.04 (br s, 6H); LRMS (M+) m/z 392.26.

I-109: 5-(2-(3-methoxy-4,5-dimethylphenylamino)-5-methylpyrimidin-4-ylamino)-7-methylbenzo[d]oxazol-2(3H)-one trifluoroacetate trifluoroacetate salt $^1$H NMR (300 MHz, DMSO) δ 12.06 (br s, 1H), 11.73 (s, 1H), 9.99 (s, 1H), 9.58 (s, 1H), 7.85 (s, 1H), 7.16 (s, 1H), 7.11 (s, 1H), 6.90 (s, 1H), 6.83 (s, 1H), 3.58 (s, 3H), 2.28 (s, 3H), 2.18 (s, 3H), 2.04 (br s, 6H); LRMS (M+) m/z 410.09.

I-110: 5-(5-fluoro-2-(3-methoxy-4,5-dimethylphenylamino)pyrimidin-4-ylamino)-7-methylbenzo[d]oxazol-2(3H)-one trifluoroacetate salt I-111: 5-(2-(3-methoxy-4,5-dimethylphenylamino)-5-methylpyrimidin-4-ylamino)-7-fluorobenzo[d]oxazol-2(3H)-one trifluoroacetate trifluoroacetate salt $^1$H NMR (300 MHz, DMSO) δ 12.15 (s, 1H), 10.13 (s, 1H), 9.62 (s, 1H), 7.89 (s, 1H), 7.52 (d, J=12.4 Hz, 1H), 7.19 (s, 1H), 6.92 (s, 1H), 6.83 (s, 1H), 3.66 (s, 3H), 2.19 (s, 3H), 2.12 (s, 3H), 2.06 (s, 3H); LRMS (M+) m/z 414.05.

I-112: 7-fluoro-5-(5-fluoro-2-(3-methoxy-4,5-dimethylphenylamino)pyrimidin-4-ylamino)benzo[d]oxazol-2(3H)-one trifluoroacetate salt $^1$H NMR (300 MHz, DMSO) δ 12.01 (s, 1H), 9.73 (s, 1H), 9.38 (s, 1H), 8.20 (d, J=4.0 Hz, 1H), 7.78 (d, J=13.0 Hz, 1H), 7.26 (s, 1H), 7.16 (s, 1H), 7.06 (s, 1H), 3.68 (s, 3H), 2.14 (s, 3H), 2.04 (s, 3H); LRMS (M+) m/z 414.05.

I-113: 5-(2-(3-methoxy-4,5-dimethylphenylamino)-5-methylpyrimidin-4-ylamino)benzo[d]oxazol-2(3H)-one $^1$H NMR (300 MHz, DMSO) δ 11.62 (s, 1H), 8.81 (s, 1H), 8.36 (s, 1H), 7.91 (s, 1H), 7.39-7.37 (m, 2H), 7.26-7.22 (m, 2H), 7.11 (s, 1H), 3.56 (s, 3H), 2.13 (s, 3H), 2.03 (s, 3H), 1.99 (s, 3H); LRMS (M+) m/z 392.09.

I-114: 5-(2-(4-fluoro-3-methoxy-5-methylphenylamino)-5-methylpyrimidin-4-ylamino)benzo[d]oxazol-2(3H)-one sulfuric acid salt $^1$H NMR (300 MHz, DMSO) δ 11.73 (s, 1H), 9.57 (s, 1H), 9.20 (s, 1H), 7.89 (s, 1H), 7.31 (s, 3H), 7.08 (br d, J=7.5 Hz, 1H), 7.05 (br d, J=6.0 Hz, 1H), 3.64 (s, 3H), 2.17 (s, 3H), 2.05 (s, 3H); LRMS (M+) m/z 396.06.

I-115: Disodium (5-(2-(3-methoxy-4,5-dimethylphenylamino)-5-methylpyrimidin-4-ylamino)-2-oxobenzo[d]oxazol-3(2H)-yl)methyl phosphate $^1$H NMR (300 MHz, D$_2$O) δ 7.61 (s, 1H), 7.45 (dd, J=8.8, 1.8 Hz, 1H), 7.17 (d, J=1.8 Hz, 1H), 6.91 (d, J=8.8 Hz, 1H), 6.71 (s, 1H), 6.57 (s, 1H), 5.34 (d, J=5.8 Hz, 2H), 3.55 (s, 3H), 1.95 (br s, 6H), 1.93 (s, 3H); LRMS (M−) m/z 500.22.

I-116: 5-(2-(4-fluoro-3-hydroxy-5-methylphenylamino)-5-methylpyrimidin-4-ylamino)benzo[d]oxazol-2(3H)-one trifluoroacetate salt $^1$H NMR (300 MHz, DMSO) δ 11.80 (br s, 1H), 10.27 (br s, 1H), 9.85 (br s, 1H), 9.76 (br s, 1H), 7.89 (br s, 1H), 7.35 (d, J=8.8 Hz, 1H), 7.31-7.27 (m, 2H), 6.84 (d, J=2.9 Hz, 1H), 6.75 (d, J=7.4 Hz, 1H), 2.18 (s, 3H), 1.98 (s, 3H); LRMS (M+) m/z 382.27.

I-117: 5-(2-(3-hydroxy-4,5-dimethylphenylamino)-5-methylpyrimidin-4-ylamino)benzo[d]oxazol-2(3H)-one trifluoroacetate salt $^1$H NMR (300 MHz, DMSO) δ 11.81 (s, 1H), 10.21-10.08 (m, 1H), 9.77 (br s, 1H), 9.37 (s, 1H), 7.86 (s, 1H), 7.36-7.28 (m, 3H), 6.85 (s, 1H), 6.56 (s, 1H), 2.18 (s, 3H), 2.01 (s, 3H), 1.96 (s, 3H); LRMS (M+) m/z 378.06.

I-118: (5-(2-(4-fluoro-3-methoxy-5-methylphenylamino)-5-methylpyrimidin-4-ylamino)-2-oxobenzo[d]oxazol-3(2H)-yl)methyl dihydrogen phosphate calcium salt I-119: 5-(5-fluoro-2-(2-fluoro-5-methoxyphenylamino)pyrimidin-4-ylamino)benzo[d]oxazol-2(3H)-one I-120: 5-(2-(3-fluoro-5-methoxy-4-methylphenylamino)-5-methylpyrimidin-4-ylamino)benzo[d]oxazol-2(3H)-one trifluoroacetate salt $^1$H NMR (300 MHz, DMSO) δ 11.72 (s, 1H), 10.15 (s, 1H), 9.62 (s, 1H), 7.88 (s, 1H), 7.28 (d, J=8.3 Hz, 1H), 7.20, (s, 1H), 7.19 (d, J=9.8 Hz, 1H), 7.03 (d, J=12.0 Hz, 1H), 6.71 (s, 1H), 3.60 (s, 3H), 2.13 (s, 3H), 1.93 (s, 3H); LCMS (m/z): 396 (MH+).

I-121: 5-(5-fluoro-2-(3-fluoro-5-methoxy-4-methylphenylamino)pyrimidin-4-ylamino)benzo[d]oxazol-2(3H)-one trifluoroacetate salt I-122: 5-(2-(2-fluoro-5-methoxy-4-methylphenylamino)-5-methylpyrimidin-4-ylamino)benzo[d]oxazol-2(3H)-one trifluoroacetate salt $^1$H NMR (300 MHz, DMSO) δ 11.70 (s, 1H), 9.89 (s, 1H), 9.59 (s, 1H), 7.83 (s, 1H), 7.28-7.12 (m, 4H), 6.98 (d, J=6.7 Hz, 1H), 3.49 (s, 3H), 2.12 (s, 3H), 2.10 (s, 3H); LCMS (m/z): 396 (MH$^+$).

I-123: 5-(5-fluoro-2-(2-fluoro-5-methoxy-4-methylphenylamino)pyrimidin-4-ylamino)benzo[d]oxazol-2(3H)-one trifluoroacetate salt I-124: 5-(2-(4-chloro-3-methoxy-5-methylphenylamino)-5-methylpyrimidin-4-ylamino)benzo[d]oxazol-2(3H)-one trifluoroacetate salt $^1$H NMR (300 MHz, DMSO) δ 11.72 (s, 1H), 9.94 (s, 1H), 9.47 (s, 1H), 7.86 (s, 1H), 7.33-7.17 (m, 3H), 7.09 (s, 1H), 6.97 (s, 1H), 3.58 (s, 3H), 2.12 (s, 3H), 2.04 (s, 3H); LCMS (m/z): 412 (MH$^+$).

I-125: 5-(2-(3-methoxy-4,5-dimethylphenylamino)-5-methylpyrimidin-4-ylamino)-3-methylbenzo[d]oxazol-2(3H)-one trifluoroacetate salt $^1$H NMR (300 MHz, DMSO) δ 10.10 (s, 1H), 9.78 (s, 1H), 7.84 (s, 1H), 7.44 (s, 1H), 7.34 (d, J=8.5 Hz, 1H), 7.24 (d, J=8.4 Hz, 1H), 6.80 (s, 1H), 6.73 (s, 1H), 3.48 (s, 3H), 3.13 (s, 3H), 2.14 (s, 3H), 1.97 (s, 6H); LCMS (m/z): 406 (MH$^+$).

I-126: 5-(2-(3,4,5-trimethylphenylamino)-5-methylpyrimidin-4-ylamino)-3-methylbenzo[d]oxazol-2(3H)-one trifluoroacetate salt $^1$H NMR (300 MHz, DMSO) δ 9.79 (s, 1H), 9.64 (s, 1H), 7.82 (s, 1H), 7.44 (s, 1H), 7.35 (d, J=8.4 Hz, 1H), 7.24 (d, J=8.6 Hz, 1H), 6.98 (s, 2H), 3.16 (s, 3H), 2.13 (s, 3H), 2.01 (s, 3H), 2.00 (s, 6H); LCMS (m/z): 390 (MH$^+$).

I-127: 5-(2-(4-fluoro-3-methoxy-5-methylphenylamino)-5-methylpyrimidin-4-ylamino)-3-methylbenzo[d]oxazol-2(3H)-one trifluoroacetate salt $^1$H NMR (300 MHz, DMSO) δ 10.14 (s, 1H), 9.73 (s, 1H), 7.86 (s, 1H), 7.43 (s, 1H), 7.34 (d, J=8.6 Hz, 1H), 7.24 (d, J=8.6 Hz, 1H), 6.93 (d, J=7.3 Hz, 1H), 6.85 (d, J=5.4 Hz, 1H), 3.55 (s, 3H), 3.18 (s, 3H), 2.14 (s, 3H), 1.99 (s, 3H); LCMS (m/z): 410 (MH$^+$).

I-128: ethyl 4-(4-(2,3-dihydro-2-oxobenzo[d]oxazol-5-ylamino)-5-methylpyrimidin-2-ylamino)-2-methoxy-6-methylbenzoate $^1$H NMR (300 MHz, DMSO) δ 11.58 (s, 1H), 9.07 (s, 1H), 8.38 (s, 1H), 7.90 (s, 1H), 7.32-7.13 (m, 5H), 4.19 (q, J=7.1 Hz, 2H), 3.49 (s, 3H), 2.08 (s, 3H), 1.95 (s, 3H), 1.22 (t, J=7.1 Hz, 3H); LCMS (m/z): 450 (MH$^+$).

I-129: 4-(4-(2,3-dihydro-2-oxobenzo[d]oxazol-5-ylamino)-5-methylpyrimidin-2-ylamino)-2-methoxy-6-methylbenzyl alcohol trifluoroacetate salt $^1$H NMR (300 MHz, DMSO) δ 11.79 (s, 1H), 10.10 (s, 1H), 9.68 (s, 1H), 7.90 (s, 1H), 7.39-7.24 (m, 3H), 6.93 (s, 1H), 6.83 (s, 1H), 4.46 (s, 2H), 3.57 (s, 3H), 2.19 (s, 3H), 2.15 (s, 3H); LCMS (m/z): 408 (MH$^+$).

I-130: 5-methyl-N4-[3-(phosphonooxy)methyl-2-oxo-2,3-dihydro-1,3-benzoxazol-5-yl]-N2-(3,4,5-trimethyl)phenyl-2,4-pyrimidinediamine arginine salt $^1$H NMR (300 MHz, DMSO) δ 10.10 (br, 1H), 8.88 (s, 1H), 8.24 (s, 1H), 7.83 (s, 1H), 7.52 (s, 2H), 7.38 (br, 2H), 7.28-7.19 (m, 4H), 5.41 (d, J=7.2 Hz, 2H), 3.04 (q, 2H), 2.12 (s, 6H), 2.09 (s, 3H), 2.01 (s, 3H), 1.64 (m, 2H), 1.52 (m, 2H); LCMS: purity: 91.62%; MS (m/e): 486.33 (MH$^+$).

I-131: 5-methyl-N4-(2-oxo-2,3-dihydro-1,3-benzoxazol-5-yl)-N2-(3,4,5-trimethyl)phenyl-2,4-pyrimidinediamine benzenesulfonic acid salt $^1$H NMR (300 MHz, DMSO) δ 11.76 (s, 1H), 9.80 (s, 1H), 9.75 (s, 1H), 7.79 (s, 1H), 7.57 (d, J=3.3 Hz, 2H), 7.30 (m, 4H), 7.20 (d, J=6.6 Hz, 2H), 6.96 (s, 2H), 2.13 (s, 3H), 2.03 (s, 9H); LCMS: purity: 95.77%; MS (m/e): 376.39 (MH$^+$).

I-132: 5-methyl-N4-[3-(phosphonooxy)methyl-2-oxo-2,3-dihydro-1,3-benzoxazol-5-yl]-N2-(3,4,5-trimethyl)phenyl-2,4-pyrimidinediamine Tris salt $^1$H NMR (300 MHz, DMSO) δ 10.43 (br, 1H), 9.14 (br, 1H), 8.11 (s, 1H), 7.84 (s, 1H), 7.59 (s, 2H), 7.20 (s, 2H), 5.42 (d, J=7.8 Hz, 2H), 3.44 (s, 6H), 2.14 (s, 6H), 2.09 (s, 3H), 2.02 (s, 3H); LCMS: purity: 97.81%; MS (m/e): 486.30 (MH+).

I-133: N4-{3-[2-(N,N-dimethylamino)ethoxy]phosphinyloxymethyl-2-oxo-2,3-dihydro-1,3-benzoxazol-5-yl}-5-methyl-N2-(3,4,5-trimethyl)phenyl-2,4-pyrimidinediamine $^1$H NMR (300 MHz, DMSO) δ 8.90 (br, 1H), 7.81 (s, 1H), 7.35 (br, 1H), 7.29 (d, J=6.3 Hz, 3H), 7.14 (s, 1H), 6.97 (s, 1H), 5.51 (d, J=9.0 Hz, 2H), 3.93 (m, 2H), 3.15 (m, 2H), 2.69 (s, 6H), 2.14 (s, 6H), 2.11 (s, 3H), 2.04 (s, 3H); LCMS: purity: 97.97%; MS (m/e): 557.40 (MH+).

I-134: N4-{3-bis[2-(N,N-dimethylamino)ethoxy]phosphinyloxymethyl-2-oxo-2,3-dihydro-1,3-benzoxazol-5-yl}-5-methyl-N2-(3,4,5-trimethyl)phenyl-2,4-pyrimidinediamine $^1$H NMR (300 MHz, DMSO) δ 10.20 (br, 1H), 8.86 (br, 1H), 8.50 (br, 1H), 7.82 (s, 1H), 7.38 (s, 2H), 7.28 (s, 2H), 5.51 (d, J=9.3 Hz, 2H), 4.08 (br, 2H), 3.52 (br, 4H), 3.01 (s, 8H), 2.14 (s, 6H), 2.10 (s, 3H), 2.04 (s, 3H); LCMS: purity: 98.27%; MS (m/e): 628.63 (MH+).

I-135: 5-methyl-N4-(2-oxo-2,3-dihydro-1,3-benzoxazol-5-yl)-N2-(3,4,5-trimethyl)phenyl-2,4-pyrimidinediamine pamoic acid salt $^1$H NMR (300 MHz, DMSO) δ 11.64 (s, 1H), 9.11 (br, 1H), 8.77 (br, 1H), 8.39 (s, 2H), 8.12 (d, J=8.4 Hz, 2H), 7.82 (m, 3H), 7.26 (m, 5H), 7.14 (m, 4H), 4.75 (s, 2H), 2.08 (s, 3H), 2.00 (s, 6H), 1.99 (s, 3H); LCMS: purity: 95.55%; MS (m/e): 376.37 (MH+).

I-136: 5-methyl-N4-[3-(phosphonooxy)methyl-2-oxo-2,3-dihydro-1,3-benzoxazol-5-yl]-N2-(3,4,5-trimethyl)phenyl-2,4-pyrimidinediamine dipotassium salt $^1$H NMR (300 MHz, DMSO) δ 7.82 (s, 1H), 7.64 (s, 2H), 7.18 (br, 4H), 5.39 (d, 2H), 2.14 (s, 6H), 2.08 (s, 3H), 2.02 (s, 3H); LCMS: purity: 99.19%; MS (m/e): 486.38 (MH+).

I-137: 5-methyl-N4-(2-oxo-2,3-dihydro-1,3-benzoxazol-5-yl)-N2-(3,4,5-trimethyl)phenyl-2,4-pyrimidinediamine methane sulfonic acid salt $^1$H NMR (300 MHz, DMSO) δ 11.75 (s, 1H), 9.81 (s, 1H), 9.74 (s, 1H), 7.79 (s, 1H), 7.31 (d, J=9.3 Hz, 1H), 7.20 (m, 2H), 6.96 (s, 2H), 2.29 (s, 3H), 2.13 (s, 3H), 2.02 (s, 9H); LCMS: purity: 99.23%; MS (m/e): 376.24 (MH+).

I-138: N2-(3,5-dimethyl-4-methoxycarbonyl)phenyl-5-methyl-N4-(2-oxo-2,3-dihydro-1,3-benzoxazol-5-yl)-2,4-pyrimidinediamine $^1$H NMR (300 MHz, DMSO) δ 11.67 (br, 1H), 7.88 (s, 1H), 7.34 (s, 1H), 7.24 (m, 4H), 3.77 (s, 3H), 2.11 (s, 3H), 2.00 (s, 6H); LCMS: purity: 99.74%; MS (m/e): 420.27 (MH+).

I-139: N2-ethyl-N2-(3,4,5-trimethyl)phenyl-5-methyl-N4-(2-oxo-2,3-dihydro-1,3-benzoxazol-5-yl)-2,4-pyrimidinediamine $^1$H NMR (300 MHz, DMSO) δ 11.80 (s, 1H), 7.53 (s, 1H), 7.42 (s, 1H), 7.28 (s, 2H), 6.99 (s, 2H), 3.71 (q, J=7.2 Hz, 2H), 2.25 (s, 6H), 2.16 (s, 3H), 2.11 (s, 3H), 1.06 (t, J=6.6 Hz, 3H); LCMS: purity: 93.99%; MS (m/e): 404.33 (MH+).

I-140: N2-(4-carboxy-3,5-dimethyl)phenyl-5-methyl-N4-(2-oxo-2,3-dihydro-1,3-benzoxazol-5-yl)-2,4-pyrimidinediamine N2-(4-tert-butoxycarbonyl-3,5-dimethyl)phenyl-5-methyl-N4-(2-oxo-2,3-dihydro-1,3-benzoxazol-5-yl)-2,4-pyrimidinediamine (500 mg) was suspended in methanol (5 mL). 4.0 M HCl in dioxane (1.0 mL) was added. The solution was heated at 40° C. for 2 h and 50° C. for 6 h. The solution was evaporated and diluted with water (10 mL). NaHCO3 was added to the solution to pH 3. The precipitation was filtered off and washed with water, dried to give the desired acid (440 mg). $^1$H NMR (300 MHz, DMSO) δ 11.72 (s, 1H), 7.87 (s, 1H), 7.30 (d, J=8.1 Hz, 1H), 7.22 (s, 2H), 7.15 (s, 2H), 2.12 (s, 3H), 2.05 (s, 6H); LCMS: purity: 99.92%; MS (m/e): 406.32 (MH+).

I-141: N2-(4-benzyloxycarbonyl-3,5-dimethyl)phenyl-5-methyl-N4-(2-oxo-2,3-dihydro-1,3-benzoxazol-5-yl)-2,4-pyrimidinediamine $^1$H NMR (300 MHz, DMSO) δ 11.73 (s, 1H), 9.86 (br, 1H), 9.50 (br, 1H), 7.87 (s, 1H), 7.41-7.29 (m, 6H), 7.20 (s, 1H), 7.14 (s, 3H), 5.28 (s, 2H), 2.13 (s, 3H), 1.98 (s, 6H); LCMS: purity: 100%; MS (m/e): 496.33 (MH+).

I-142: N2-(3,5-dimethyl-4-hydroxymethyl)phenyl-5-methyl-N4-(2-oxo-2,3-dihydro-1,3-benzoxazol-5-yl)-2,4-pyrimidinediamine To N2-(4-carboxy-3,5-dimethyl)phenyl-5-methyl-N4-(2-oxo-2,3-dihydro-1,3-benzoxazol-5-yl)-2,4-pyrimidinediamine (440 mg), was added BH3 (1.0 M in THF, 4 mL). The mixture was stirred at 0° C. to rt overnight, then quenched with methanol (10 mL) and 4.0 M HCl in dioxane was added to pH 7. The reaction solution was evaporated and purified by column chromatography (methanol in dichloromethane=0-30% in 30 min) to give the desired benzyl alcohol. $^1$H NMR (300 MHz, DMSO) δ 8.69 (s, 1H), 8.17 (s, 1H), 7.81 (s, 1H), 7.23 (s, 2H), 7.14 (m, 2H), 7.06 (t, 1H), 4.34 (s, 2H), 2.11 (s, 6H), 2.06 (s, 3H); LCMS: purity: 88.12%; MS (m/e): 392.20 (MH+).

I-143: N2-(3,5-dimethyl-4-methoxymethyl)phenyl-5-methyl-N4-(2-oxo-2,3-dihydro-1,3-benzoxazol-5-yl)-2,4-pyrimidinediamine N2-(3,5-dimethyl-4-hydroxymethyl)phenyl-5-methyl-N4-(2-oxo-2,3-dihydro-1,3-benzoxazol-5-yl)-2,4-pyrimidinediamine was dissolved in methanol and treated with 1.0 M HCl in dioxane (0.1 mL). The solution was evaporated and purified by column chromatography (methanol in dichloromethane=0-30% in 30 min) to give the benzyl methyl ether. $^1$H NMR (300 MHz, DMSO) δ 8.82 (s, 1H), 8.28 (s, 1H), 7.84 (s, 1H), 7.26 (s, 2H), 7.23 (m, 2H), 7.16 (m, 1H), 4.26 (s, 2H), 3.22 (s, 3H), 2.07 (s, 9H); LCMS: purity: 85.20%; MS (m/e): 406.25 (MH+).

I-144: N2-(3,4-dimethyl-5-methoxycarbonyl)phenyl-5-methyl-N4-(2-oxo-2,3-dihydro-1,3-benzoxazol-5-yl)-2,4-pyrimidinediamine 2,3-Dimethylbenzoic acid (1 g) and K$_2$CO$_3$ (1.1 g, 1.2 eq.) were suspended in DMF (10 mL). To the reaction mixture, was added iodomethane (0.5 mL, 1.2 eq.). The reaction was stirred at rt overnight, then diluted with water (80 mL). The solution was extracted with ethyl acetate (80 mL) and evaporated to give the methyl ester. $^1$H NMR (300 MHz, DMSO) δ 7.49 (d, J=7.8 Hz, 1H), 7.33 (d, J=7.5 Hz, 1H), 7.15 (t, J=7.8 Hz, 1H), 3.79 (s, 3H), 2.33 (s, 3H), 2.26 (s, 3H).

Methyl 2,3-dimethylbenzoate was dissolved in concentrated sulfonic acid (10 mL). KNO3 (808 mg, 1.2 eq.) was added to the solution at 0° C., then slowly warmed to rt overnight. The reaction was quenched with water (80 mL), extracted with ethyl acetate (2×80 mL). The organic layers were evaporated to give mixture of nitrated ester and acid (1:1). The mixture was redissolved in DMF (10 mL). K$_2$CO$_3$ (1.1 g) and iodomethane (0.5 mL) were added to the solution. The reaction was stirred at rt for three days, then diluted with water (80 mL). It was extracted with ethyl acetate (3×80 mL) and evaporated. The residue was purified by column chromatography (EtOAc in hexanes=0-30% in 45 min) to give the desired nitrobenzoate ester. $^1$H NMR (300 MHz, DMSO) δ 8.31 (s, 1H), 8.24 (s, 1H), 3.86 (s, 3H), 2.46 (s, 3H), 2.40 (s, 3H).

Methyl 2,3-dimethyl-5-nitrobenzoate was dissolved in methanol and charged with 10% Pd-C. The mixture was reacted under hydrogen in 40 psi for one hour. The catalyst was filtered off over celite, washed with methanol and evaporated to give aniline (500 mg). $^1$H NMR (300 MHz, DMSO) δ 6.74 (d, J=2.1 Hz, 1H), 6.55 (d, J=2.4 Hz, 1H), 4.99 (s, 2H), 3.74 (s, 3H), 2.15 (s, 3H), 2.11 (s, 3H).

2-Chloro-5-methyl-N4-(2-oxo-2,3-dihydro-1,3-benzoxazol-5-yl)-4-pyrimidineamine (500 mg) and methyl 5-amino-2,3-dimethylbenzoate (500 mg) were suspended in isopropanol (5 mL) and TFA (20 drops). The solution was heated at 100° C. overnight in a sealed tube, then cooled to room temperature. LCMS showed fully conversion to the product. The reaction solution was diluted with 2.0 M NH$_3$ in methanol (10 mL). The solution was sonicated. Precipitation was filtered off and washed with methanol (50 mL) until filtrate solution turned to colorless, dried to give desired product (630 mg). $^1$H NMR (300 MHz, DMSO) δ 11.55 (s, 1H), 9.07 (s, 1H), 8.40 (s, 1H), 7.86 (s, 1H), 7.72 (s, 1H), 7.65 (s, 1H), 7.31 (d, J=8.1 Hz, 2H), 7.17 (d, J=8.4 Hz, 1H), 3.67 (s, 3H), 2.20 (s, 3H), 2.08 (s, 3H), 2.04 (s, 3H); LCMS: purity: 97.93%; MS (m/e): 420.38 (MH+).

I-145: N2-(3-carboxy-4,5-dimethyl)phenyl-5-methyl-N4-(2-oxo-2,3-dihydro-1,3-benzoxazol-5-yl)-2,4-pyrimidinediamine N2-(3,4-dimethyl-5-methoxycarbonyl)phenyl-5-methyl-N4-(2-oxo-2,3-dihydro-1,3-benzoxazol-5-yl)-2,4-pyrimidinediamine (500 mg) was suspended in THF (6 mL). To the reaction mixture, was added 1.0 M KOH aqueous solution (6 mL). The reaction was heated at 60° C. for two hours, then diluted with methanol (10 mL) and neutralized with 1N HCl aqueous solution to pH around 6. The reaction mixture was evaporated and then diluted with water (20 mL). The precipitate was collected by filtration, and washed with water, dried to give the desired acid (420 mg). $^1$H NMR (300 MHz, DMSO) δ 11.58 (s, 1H), 9.14 (s, 1H), 8.53 (s, 1H), 7.86 (s, 1H), 7.66 (s, 1H), 7.63 (s, 1H), 7.33 (d, J=8.7 Hz, 1H), 7.28 (s, 1H), 7.19 (d, J=8.7 Hz, 1H), 2.24 (s, 3H), 2.08 (s, 3H), 2.00 (s, 3H); LCMS: purity: 96.84%; MS (m/e): 406.23 (MH+).

I-146: N2-(3,5-dimethyl-4-fluoro)phenyl-5-methyl-N4-(2-oxo-2,3-dihydro-1,3-benzoxazol-5-yl)-2,4-pyrimidinediamine benzenesulfonic acid salt $^1$H NMR (300 MHz, DMSO) δ 11.75 (s, 1H), 9.87 (s, 1H), 9.75 (s, 1H), 7.81 (s, 1H), 7.57 (dd, J=2.4, 7.2 Hz, 2H), 7.33-7.27 (m, 4H), 7.19 (d, J=6.0 Hz, 2H), 7.04 (d, J=6.3 Hz, 2H), 2.13 (s, 3H), 2.02 (s, 6H); LCMS: purity: 97.04%; MS (m/e): 380.24 (MH+).

I-147: N2-(3,4-dimethyl-5-hydroxymethyl)phenyl-5-methyl-N4-(2-oxo-2,3-dihydro-1,3-benzoxazol-5-yl)-2,4-pyrimidinediamine N2-(3-carboxy-4,5-dimethyl)phenyl-5-methyl-N4-(2-oxo-2,3-dihydro-1,3-benzoxazol-5-yl)-2,4-pyrimidinediamine (270 mg) was suspended in anhydrous THF (2 mL), then BH3 (1.0 M in THF, 2 mL) was added to the reaction. The mixture was stirred at rt for 3 days, then quenched with methanol (10 mL) and HCl in dioxane (1.0 M, 3 drops). The reaction solution was evaporated and purified by column chromatography (methanol in dichloromethane=0-30% in 30 min) to give the desired benzyl alcohol (150 mg). $^1$H NMR (300 MHz, DMSO) δ 11.56 (s, 1H), 8.77 (s, 1H), 8.26 (s, 1H), 7.84 (s, 1H), 7.44 (s, 1H), 7.36 (d, J=9.0 Hz, 1H), 7.33 (s, 1H), 7.29 (s, 1H), 7.20 (d, J=9.0 Hz, 1H), 4.90 (t, 1H), 4.32 (d, J=5.4 Hz, 2H), 2.06 (s, 3H), 2.02 (s, 3H), 1.98 (s, 3H); LCMS: purity: 88.60%; MS (m/e): 392.24 (MH+).

I-148: N2-(4-n-butyl-3-methyl)phenyl-5-methyl-N4-(2-oxo-2,3-dihydro-1,3-benzoxazol-5-yl)-2,4-pyrimidinediamine $^1$H NMR (300 MHz, DMSO) δ 11.72 (s, 1H), 9.52 (br, 2H), 7.71 (s, 1H), 7.24-7.04 (m, 6H), 2.27 (s, 2H), 2.11 (s, 3H), 1.28 (m, 4H), 0.80 (m, 3H); LCMS: purity: 81.74%; MS (m/e): 390.19 (MH+).

I-149: N2-(4-bromo-3,5-dimethyl)phenyl-5-methyl-N4-(2-oxo-2,3-dihydro-1,3-benzoxazol-5-yl)-2,4-pyrimidinediamine $^1$H NMR (300 MHz, DMSO) δ 11.59 (s, 1H), 9.02 (s, 1H), 8.39 (s, 1H), 7.87 (s, 1H), 7.43 (s, 2H), 7.27 (s, 1H), 7.24 (s, 2H), 2.09 (s, 6H), 2.07 (s, 3H); LCMS: purity: 97.80%; MS (m/e): 442.13 (MH+).

I-150: N2-(4-tert-butoxycarbonyl-3,5-dimethyl)phenyl-5-methyl-N4-(2-oxo-2,3-dihydro-1,3-benzoxazol-5-yl)-2,4-pyrimidinediamine 3,5-Dimethylaniline (3 g) was dissolved in dichloromethane (50 mL). To the reaction solution, was added trifluoroacetic anhydride (4.8 mL, 1.4 eq.) in water bath. After the reaction was stirred at rt for 15 min., bromine (1.27 mL, 1eq) was added slowly in water bath. The reaction was stirred at rt for three hours, and then quenched with 10% Na2S2O3 (100 mL). The solution was extracted with dichloromethane (3×100 mL). The organic layers were dried over MgSO4. Then it was treated with activated charcoal, filtered and evaporated. The residue was crystallized from dichloromethane and hexanes to give N1-(4-bromo-3,5-dimethylphenyl)-2,2,2-trifluoroacetamide (6.2 g, 84% two steps). $^1$H NMR (300 MHz, DMSO) δ 11.23 (br, 1H), 7.46 (s, 2H), 2.34 (s, 6H).

N1-(4-Bromo-3,5-dimethylphenyl)-2,2,2-trifluoroacetamide (3 g) was dissolved in THF (50 mL). At −78° C., MeLi in ether (1.6 M, 8.9 mL, 1.4 eq.) was added to the solution and stirred for 5 min. Then s-BuLi in cyclohexanes (1.4 M, 10 mL, 1.4 eq.) was added and stirred for 5 min. Boc anhydride (4 g, 1.8 eq.) was then added at −78° C. The reaction solution was allowed to warm to rt and stirred for 3.5 hours. The reaction was quenched with water (100 mL). The solution was extracted with dichloromethane (2×100 mL). The organic layers were evaporated and purified by column chromatography (EtOAc in hexanes=0-50% in 45 min) to give the desired tert-butyl ester. $^1$H NMR (300 MHz, DMSO) δ 11.22 (s, 1H), 7.35 (s, 2H), 2.23 (s, 6H), 1.52 (s, 9H); $^{19}$F NMR (282 MHz, DMSO) 5-89.51.

N1-[4-(tert-butoxy)carbonyl-3,5-dimethylphenyl]-2,2,2-trifluoroacetamide was dissolved in methanol (50 mL) and NaOH aqueous solution (1.0 N, 50 mL). The solution was heated at 60° C. for one hour and rt overnight. It was extracted with ethyl acetate (2×100 mL), evaporated, purified by column chromatography (EtOAc in hexanes=0-50% in 45 min) to give the desired aniline. $^1$H NMR (300 MHz, DMSO) δ 6.17 (s, 2H), 5.22 (br, 2H), 2.10 (s, 6H), 1.47 (s, 9H).

2-Chloro-5-methyl-N4-(2-oxo-2,3-dihydro-1,3-benzoxazol-5-yl)-4-pyrimidineamine (500 mg) and tert-butyl 4-amino-2,6-dimethylbenzoate (500 mg) were suspended in isopropanol (5 mL) and TFA (15 drops). The solution was heated at 100° C. overnight in a sealed tube, then cooled to room temperature. LCMS showed fully conversion to the product. The reaction solution was diluted with 2.0 M NH3 in methanol (20 mL). The solution was sonicated. Precipitation was filtered off and washed with methanol (50 mL) until filtrate solution turned to colorless, dried to give desired product (560 mg). $^1$H NMR (300 MHz, DMSO) δ 11.58 (br, 1H), 9.03 (s, 1H), 8.38 (s, 1H), 7.87 (s, 1H), 7.30 (s, 2H), 7.24 (d, J=5.1 Hz, 3H), 2.08 (s, 3H), 2.01 (s, 6H), 1.49 (s, 9H); LCMS: purity: 91.21%; MS (m/e): 462.28 (MH+).

I-151: N2-(3,5-dimethyl-4-fluoro)phenyl-5-methyl-N4-(2-oxo-2,3-dihydro-1,3-benzoxazol-5-yl)-2,4-pyrimidinediamine sulfuric acid salt $^1$H NMR (300 MHz, DMSO) δ 11.68 (s, 1H), 9.41 (br, 1H), 9.09 (br, 1H), 7.82 (s, 1H), 7.29-7.23 (m, 3H), 7.15 (d, J=6.3 Hz, 2H), 2.10 (s, 3H), 2.00 (s, 6H); LCMS: purity: 98.02%; MS (m/e): 380.26 (MH+).

I-152: N2-(3-carboxy-4-methyl)phenyl-5-methyl-N4-(2-oxo-2,3-dihydro-1,3-benzoxazol-5-yl)-2,4-pyrimidinediamine $^1$H NMR (300 MHz, DMSO) δ 11.66 (s, 1H), 9.92 (br, 1H), 9.50 (br, 1H), 7.83 (s, 1H), 7.78 (s, 1H), 7.54 (d, 1H), 7.23 (s, 2H), 7.19 (s, 1H), 7.12 (d, J=7.8 Hz, 1H), 2.43 (s, 3H), 2.13 (s, 3H); LCMS: purity: 99.90%; MS (m/e): 392.28 (MH+).

I-153: N2-(4-fluoro-3-methoxycarbonyl-5-methyl)phenyl-5-methyl-N4-(2-oxo-2,3-dihydro-1,3-benzoxazol-5-yl)-2,4-pyrimidinediamine $^1$H NMR (300 MHz, DMSO) δ 9.16 (s, 1H), 8.37 (s, 1H), 7.88 (m, 2H), 7.79 (dd, 1H), 7.31 (s, 1H), 7.26 (d, J=6.0 Hz, 1H), 7.19 (d, J=8.4 Hz, 1H), 3.72 (s, 3H), 2.08 (s, 3H), 2.04 (s, 3H); $^{19}$F NMR (282 MHz, DMSO) δ−140.96; LCMS: purity: 97.45%; MS (m/e): 424.28 (MH+).

I-154: N2-(4-fluoro-3-hydroxymethyl-5-methyl)phenyl-5-methyl-N4-(2-oxo-2,3-dihydro-1,3-benzoxazol-5-yl)-2,4-pyrimidinediamine $^1$H NMR (300 MHz, DMSO) δ 11.76 (s, 1H), 10.29 (s, 1H), 9.79 (s, 1H), 7.86 (s, 1H), 7.31 (d, J=9.0 Hz, 1H), 7.19 (m, 3H), 7.13 (d, J=6.3 Hz, 1H), 4.42 (s, 2H), 2.13 (s, 3H), 1.94 (s, 3H); $^{19}$F NMR (282 MHz, DMSO) δ−144.80; LCMS: purity: 90.56%; MS (m/e): 396.31 (MH+).

I-155: N2-(3-carboxy-4-fluoro-5-methyl)phenyl-5-methyl-N4-(2-oxo-2,3-dihydro-1,3-benzoxazol-5-yl)-2,4-pyrimidinediamine $^1$H NMR (300 MHz, DMSO) δ 11.60 (s, 1H), 9.46 (br, 1H), 8.84 (br, 1H), 7.86 (s, 1H), 7.72 (t, 2H), 7.28 (d, J=9.6 Hz, 2H), 7.20 (d, J=8.4 Hz, 1H), 2.09 (s, 3H), 2.00 (s, 3H); LCMS: purity: 94.88%; MS (m/e): 410.21 (MH+).

I-156: 5-methyl-N4-(2-oxo-2,3-dihydro-1,3-benzoxazol-5-yl)-N2-(3,4,5-trimethyl)phenyl-2,4-pyrimidinediamine hydrochloric acid salt $^1$H NMR (300 MHz, DMSO) δ 11.76 (s, 1H), 9.93 (s, 1H), 9.75 (s, 1H), 7.81 (s, 1H), 7.31 (d, J=9.3 Hz, 1H), 7.20 (s, 2H), 6.97 (s, 2H), 2.12 (s, 3H), 2.02 (s, 9H); LCMS: purity: 98.50%; MS (m/e): 376.19 (MH+).

I-157: 5-(2-(4-acetylphenylamino)-5-fluoropyrimidin-4-ylamino)benzo[d]oxazol-2(3H)-one formate salt 1-158: 5-(2-(4-(1-(cyclopropylamino)ethyl)phenylamino)-5-fluoropyrimidin-4-ylamino)benzo[d]oxazol-2(3H)-one formate salt I-159: N-cyclobutyl-4-(5-fluoro-4-(2-oxo-2,3-dihydrobenzo[d]oxazol-5-ylamino)pyrimidin-2-ylamino)benzamide formate salt I-160: 4-(5-fluoro-4-(2-oxo-2,3-dihydrobenzo[d]oxazol-5-ylamino)pyrimidin-2-ylamino)-N-propylbenzamide formate salt I-161: N-cyclopropyl-4-(5-fluoro-4-(2-oxo-2,3-dihydrobenzo[d]oxazol-5-ylamino)pyrimidin-2-ylamino)benzamide formate salt I-162: N-ethyl-4-(5-fluoro-4-(2-oxo-2,3-dihydrobenzo[d]oxazol-5-ylamino)pyrimidin-2-ylamino)benzamide formate salt I-163: 4-(5-fluoro-4-(2-oxo-2,3-dihydrobenzo[d]oxazol-5-ylamino)pyrimidin-2-ylamino)-N-isopropylbenzamide formate salt I-164: N-cyclobutyl-4-(5-fluoro-4-(2-oxo-2,3-dihydrobenzo[d]oxazol-5-ylamino)pyrimidin-2-ylamino)-2-methoxybenzamide formate salt I-165: N-cyclopropyl-4-(5-fluoro-4-(2-oxo-2,3-dihydrobenzo[d]oxazol-5-ylamino)pyrimidin-2-ylamino)-2-(trifluoromethyl)benzamide formate salt I-166: 4-(5-fluoro-4-(2-oxo-2,3-dihydrobenzo[d]oxazol-5-ylamino)pyrimidin-2-ylamino)-N-phenyl-2-(trifluoromethyl)benzamide formate salt I-167: 5-(2-(4-methyl-3-(methylsulfonyl)phenylamino)-5-fluoropyrimidin-4-ylamino)benzo[d]oxazol-2(3H)-one trifluoroacetate salt $^1$H NMR (300 MHz, DMSO) δ 11.64 (s, 1H), 9.62 (s, 1H), 9.54 (s, 1H), 8.19-8.17 (m, 2H), 8.00 (dd, J=8.3, 2.4 Hz, 1H), 7.54 (dd, J=8.7, 1.8 Hz, 1H), 7.42 (s, 1H), 7.32-7.26 (m, 2H), 3.19 (s, 3H), 2.58 (s, 3H);); LRMS (M+) m/z 429.97.

I-168: 5-(2-(4-fluoro-3-(methylsulfonyl)phenylamino)-5-fluoropyrimidin-4-ylamino)benzo[d]oxazol-2(3H)-one trifluoroacetate salt $^1$H NMR (300 MHz, DMSO) δ 11.63 (s, 1H), 9.71 (s, 1H), 9.58 (s, 1H), 8.19-8.15 (m, 2H), 8.11-8.05 (m, 1H), 7.49 (d, J=8.7 Hz, 1H), 7.44-7.38 (m, 2H), 7.28 (d, J=8.7 Hz, 1H), 3.32 (s, 3H);); LRMS (M+) m/z 433.94.

I-169: 5-(2-(3-fluoro-5-morpholinophenylamino)-5-fluoropyrimidin-4-ylamino)benzo[d]oxazol-2(3H)-one ditrifluoroacetate salt $^1$H NMR (300 MHz, DMSO) δ 11.64 (s, 1H), 9.57 (s, 1H), 9.38 (s, 1H), 8.17 (d, J=4.2 Hz, 1H), 7.41 (d, J=8.6 Hz, 1H), 7.38 (s, 1H), 7.26 (d, J=8.6 Hz, 1H), 7.14 (d, J=11.6 Hz, 1H), 6.95 (s, 1H), 6.35 (d, J=12.4 Hz, 1H), 3.69-3.66 (m, 4H), 3.01-2.98 (m, 4H); LRMS (M+) m/z 441.03.

I-170: 5-(2-(3-fluoro-5-(4-methylpiperazin-1-yl)phenylamino)-5-fluoropyrimidin-4-ylamino)benzo[d]oxazol-2(3H)-one ditrifluoroacetate salt $^1$H NMR (300 MHz, DMSO) δ 11.56 (s, 1H), 9.58 (s, 1H), 9.41 (s, 1H), 8.16 (d, J=3.7 Hz, 1H), 8.07 (s, 1H), 8.05-8.01 (m, 1H), 7.42-7.37 (m, 3H), 7.30 (s, 2H), 7.23 (d, J=1.7 Hz, 1H), 2.34 (s, 3H); LRMS (M+) m/z 430.99.

I-171: 3-(5-fluoro-4-(7-methyl-2-oxo-2,3-dihydrobenzo[d]oxazol-5-ylamino)pyrimidin-2-ylamino)benzenesulfonamide trifluoroacetate salt $^1$H NMR (300 MHz, DMSO) δ 11.56 (s, 1H), 9.58 (s, 1H), 9.41 (s, 1H), 8.16 (d, J=3.7 Hz, 1H), 8.07 (s, 1H), 8.05-8.01 (m, 1H), 7.42-7.37 (m, 3H), 7.30 (s, 2H), 7.23 (d, J=1.7 Hz, 1H), 2.34 (s, 3H); LRMS (M+) m/z 430.99.

I-172: 5-(2-(3-(methylsulfonyl)phenylamino)-5-fluoropyrimidin-4-ylamino)-7-methylbenzo[d]oxazol-2(3H)-one trifluoroacetate salt $^1$H NMR (300 MHz, DMSO) δ 11.57 (s, 1H), 9.70 (s, 1H), 9.50 (s, 1H), 8.20-8.18 (m, 1H), 8.15 (s, 1H), 8.10 (br d, J=7.2 Hz, 1H), 7.51-7.43 (m, 2H), 7.33 (s, 1H), 7.22 (s, 1H), 3.16 (s, 3H), 2.34 (s, 3H); LRMS (M+) m/z 429.94.

I-173: 5-(2-(4-fluoro-3-(methylsulfonyl)phenylamino)-5-fluoropyrimidin-4-ylamino)-7-methylbenzo[d]oxazol-2(3H)-one trifluoroacetate salt $^1$H NMR (300 MHz, DMSO) δ 11.56 (s, 1H), 9.68 (s, 1H), 9.49 (s, 1H), 8.17 (d, J=3.8 Hz, 1H), 8.14-8.10 (m, 2H), 7.38 (t, J=9.7 Hz, 1H), 7.30 (s, 1H), 7.24 (s, 1H), 3.32 (s, 3H), 2.34 (s, 3H); LRMS (M+) m/z 447.95.

I-174: 3-(5-fluoro-4-(7-fluoro-2-oxo-2,3-dihydrobenzo[d]oxazol-5-ylamino)pyrimidin-2-ylamino)benzenesulfonamide trifluoroacetate salt $^1$H NMR (300 MHz, DMSO) δ 11.97 (s, 1H), 9.71 (s, 1H), 9.61 (s, 1H), 8.23 (d, J=3.6 Hz, 1H), 8.16 (br s, 1H), 8.02 (ddd, J=7.7, 3.0, 3.0 Hz, 1H), 7.86 (dd, J=13.1, 1.8 Hz, 1H), 7.44 (d, J=7.8 Hz, 1H), 7.40 (ddd, J=7.6, 3.0, 3.0 Hz, 1H), 7.33-7.28 (m, 3H); LRMS (M+) m/z 434.89.

I-175: 5-(5-fluoro-2-(3-d$_3$-methoxy-5-methylphenylamino)pyrimidin-4-ylamino)benzo[d]oxazol-2(3H)-one trifluoroacetate salt $^1$H NMR (300 MHz, DMSO) δ 11.67 (s, 1H), 9.65 (s, 1H), 9.34 (s, 1H), 8.17 (d, J=4.0 Hz, 1H), 7.45 (d, J=8.7 Hz, 1H), 7.40 (s, 1H), 7.28 (d, J=8.7 Hz, 1H), 7.08 (s, 1H), 7.05 (s, 1H), 6.36 (s, 1H), 2.16 (s, 3H); LRMS (M+) m/z 385.07.

I-176: 5-(2-(3-(trifluoromethyl)-5-methoxyphenylamino)-5-fluoropyrimidin-4-ylamino)-7-methylbenzo[d]oxazol-2(3H)-one trifluoroacetate salt $^1$H NMR (300 MHz, DMSO) δ 11.55 (s, 1H), 9.59 (s, 1H), 9.47 (s, 1H), 8.19 (d, J=3.8 Hz, 1H), 7.62 (br s, 2H), 7.24 (s, 1H), 7.20 (s, 1H), 6.75 (s, 1H), 3.73 (s, 3H), 2.32 (s, 3H); LRMS (M+) m/z 450.06.

I-177: 5-(2-(3-methoxy-5-methylphenylamino)-5-fluoropyrimidin-4-ylamino)-7-methylbenzo[d]oxazol-2(3H)-one trifluoroacetate salt $^1$H NMR (300 MHz, DMSO) δ 11.59 (s, 1H), 9.56 (s, 1H), 9.31 (s, 1H), 8.16 (d, J=4.0 Hz, 1H), 7.30 (s, 1H), 7.21 (d, J=1.5 Hz, 1H), 7.09 (s, 1H), 7.03 (s, 1H), 6.36 (s, 1H), 3.64 (s, 3H), 2.31 (s, 3H), 2.15 (s, 3H); LRMS (M+) m/z 396.08.

I-178: 5-(2-(4-methoxy-3-methylphenylamino)-5-fluoropyrimidin-4-ylamino)-7-methylbenzo[d]oxazol-2(3H)-one trifluoroacetate salt $^1$H NMR (300 MHz, DMSO) δ 11.64 (s, 1H), 9.82 (s, 1H), 9.42 (s, 1H), 8.15 (d, J=4.5 Hz, 1H), 7.37-7.31 (m, 3H), 7.20 (s, 1H), 6.87 (d, J=8.8 Hz, 1H), 3.78 (s, 3H), 2.29 (s, 3H), 2.06 (s, 3H); LRMS (M+) m/z 396.08.

I-179: 5-(2-(3-methoxy-5-methylphenylamino)-5-fluoropyrimidin-4-ylamino)-7-fluorobenzo[d]oxazol-2(3H)-one trifluoroacetate salt $^1$H NMR (300 MHz, DMSO) δ 12.00 (s, 1H), 9.73 (s, 1H), 9.42 (s, 1H), 8.21 (d, J=3.9 Hz, 1H), 7.71 (d, J=13.0 Hz, 1H), 7.25 (s, 1H), 7.09-7.08 (m, 2H), 6.40 (s, 1H), 3.68 (s, 3H), 2.21 (s, 3H); LRMS (M+) m/z 400.07.

I-180: 5-(2-(4-methoxy-3-methylphenylamino)-5-fluoropyrimidin-4-ylamino)-7-fluorobenzo[d]oxazol-2(3H)-one trifluoroacetate salt $^1$H NMR (300 MHz, DMSO) δ 11.99 (s, 1H), 9.72 (s, 1H), 9.29 (s, 1H), 8.17 (br d, J=4.1 Hz, 1H), 7.77 (d, J=13.0 Hz, 1H), 7.38-7.36 (m, 2H), 7.24 (br s, 1H), 6.88 (d, J=9.2 Hz, 1H), 3.78 (s, 3H), 2.11 (s, 3H); LRMS (M+) m/z 400.08.

I-181: 5-(2-(4-fluoro-3-methoxy-5-methylphenylamino)-5-fluoropyrimidin-4-ylamino)benzo[d]oxazol-2(3H)-one trifluoroacetate salt $^1$H NMR (300 MHz, DMSO) δ 11.69 (s, 1H), 9.68 (s, 1H), 9.37 (s, 1H), 8.18 (d, J=4.1 Hz, 1H), 7.47 (dd, J=8.6, 1.9 Hz, 1H), 7.40 (s, 1H), 7.28 (d, J=8.6 Hz, 1H), 7.21-7.16 (m, 2H), 3.67 (s, 3H), 2.11 (s, 3H); LRMS (M+) m/z 400.01.

I-182: 5-(2-(3,4-dimethoxy-5-methylphenylamino)-5-fluoropyrimidin-4-ylamino)benzo[d]oxazol-2(3H)-one trifluoroacetate salt $^1$H NMR (300 MHz, DMSO) δ 11.68 (s, 1H), 9.67 (s, 1H), 9.30 (s, 1H), 8.16 (br d, J=4.1 Hz, 1H), 7.49 (dd, J=8.6, 1.9 Hz, 1H), 7.40 (s, 1H), 7.27 (d, J=8.6

Hz, 1H), 7.11 (s, 1H), 7.09 (s, 1H), 3.65 (s, 3H), 3.63 (s, 3H), 2.07 (s, 3H); LRMS (M+) m/z 412.04.

I-183: 5-(2-(3,4-dimethoxy-5-methylphenylamino)-5-fluoropyrimidin-4-ylamino)-7-methylbenzo[d]oxazol-2(3H)-one trifluoroacetate salt $^1$H NMR (300 MHz, DMSO) δ 11.62 (s, 1H), 9.71 (s, 1H), 9.39 (s, 1H), 8.16 (d, J=4.1 Hz, 1H), 7.35 (s, 1H), 7.21 (s, 1H), 7.09 (s, 1H), 7.04 (s, 1H), 3.66 (s, 3H), 3.62 (s, 3H), 2.28 (s, 3H), 2.07 (s, 3H); LRMS (M+) m/z 426.08.

I-184: 5-(2-(3,4-dimethoxy-5-methylphenylamino)-5-fluoropyrimidin-4-ylamino)-7-fluorobenzo[d]oxazol-2(3H)-one trifluoroacetate salt $^1$H NMR (300 MHz, DMSO) δ 11.99 (s, 1H), 9.65 (s, 1H), 9.28 (s, 1H), 8.19 (br d, J=3.8 Hz, 1H), 7.80 (d, J=12.9 Hz, 1H), 7.25 (s, 1H), 7.12 (br s, 2H), 3.70 (s, 3H), 3.67 (s, 3H), 2.13 (s, 3H); LRMS (M+) m/z 430.04.

I-185: 5-(2-(3-chloro-4,5-dimethoxyphenylamino)-5-fluoropyrimidin-4-ylamino)benzo[d]oxazol-2(3H)-one trifluoroacetate salt $^1$H NMR (300 MHz, DMSO) δ 11.66 (s, 1H), 9.54 (s, 1H), 9.36 (s, 1H), 8.18 (br d, J=3.7 Hz, 1H), 7.56 (d, J=1.9 Hz, 1H), 7.44 (dd, J=8.3, 1.2 Hz, 1H), 7.38 (s, 1H), 7.28 (d, J=8.3 Hz, 1H), 7.21 (d, J=1.9 Hz, 1H), 3.70 (s, 3H), 3.69 (s, 3H); LRMS (M+) m/z 432.17.

I-186: 5-(2-(4-(2-morpholinoethoxy)-3,5-dimethylphenylamino)-5-fluoropyrimidin-4-ylamino)benzo[d]oxazol-2(3H)-one ditrifluoroacetate salt $^1$H NMR (300 MHz, DMSO) δ 11.69 (s, 1H), 10.08 (s, 1H), 9.53 (s, 1H), 9.22 (s, 1H), 8.15 (d, J=4.0 Hz, 1H), 7.48 (dd, J=8.6, 1.6 Hz, 1H), 7.37 (d, J=1.6 Hz, 1H), 7.31-7.27 (m, 2H), 4.07-3.57 (m, 10H), 3.32-3.21 (m, 2H), 2.15 (s, 3H); LRMS (M+) m/z 495.11.

I-187: 5-(2-(3,5-dimethylphenylamino)-5-fluoropyrimidin-4-ylamino)-7-fluorobenzo[d]oxazol-2(3H)-one trifluoroacetate salt $^1$H NMR (300 MHz, DMSO) δ 12.00 (s, 1H), 9.64 (s, 1H), 9.31 (s, 1H), 8.20 (d, J=3.9 Hz, 1H), 7.75 (d, J=12.7 Hz, 1H), 7.28 (br s, 2H), 7.24 (br s, 1H), 6.61 (s, 1H), 2.20 (s, 6H); LRMS (M+) m/z 384.03.

I-188: 5-(2-(3,4,5-trimethylphenylamino)-5-fluoropyrimidin-4-ylamino)-7-fluorobenzo[d]oxazol-2(3H)-one trifluoroacetate salt $^1$H NMR (300 MHz, DMSO) δ 11.99 (s, 1H), 9.61 (s, 1H), 9.20 (s, 1H), 8.18 (d, J=3.9 Hz, 1H), 7.76 (d, J=13.2 Hz, 1H), 7.28-7.23 (m, 3H), 2.17 (s, 6H), 2.09 (s, 3H); LRMS (M+) m/z 398.06.

I-189: 5-(2-(4-fluoro-3,5-dimethylphenylamino)-5-fluoropyrimidin-4-ylamino)-7-fluorobenzo[d]oxazol-2(3H)-one trifluoroacetate salt $^1$H NMR (300 MHz, DMSO) δ 12.00 (s, 1H), 9.64 (s, 1H), 9.31 (s, 1H), 8.19 (d, J=3.8 Hz, 1H), 7.73 (d, J=12.7 Hz, 1H), 7.35 (s, 1H), 7.32 (s, 1H), 7.24 (br s, 1H), 2.15 (br s, 6H); LRMS (M+) m/z 402.03.

I-190: 5-(2-(4-fluoro-3-methoxy-5-methylphenylamino)-5-fluoropyrimidin-4-ylamino)-7-methylbenzo[d]oxazol-2(3H)-one trifluoroacetate salt $^1$H NMR (300 MHz, DMSO) δ 11.62 (s, 1H), 9.59 (s, 1H), 9.35 (s, 1H), 8.16 (d, J=4.1 Hz, 1H), 7.31 (s, 1H), 7.26-7.20 (m, 2H), 7.12 (dd, J=5.7, 2.0 Hz, 1H), 3.65 (s, 3H), 2.29 (s, 3H), 2.09 (d, J=1.6 Hz, 3H); LRMS (M+) m/z 414.05.

I-191: 5-(2-(4-fluoro-3-methoxy-5-methylphenylamino)-5-fluoropyrimidin-4-ylamino)-7-fluorobenzo[d]oxazol-2(3H)-one trifluoroacetate salt $^1$H NMR (300 MHz, DMSO) δ 12.01 (s, 1H), 9.73 (s, 1H), 9.42 (s, 1H), 8.21 (d, J=3.9 Hz, 1H), 7.75 (dd, J=13.0, 1.5 Hz, 1H), 7.26 (s, 1H), 7.22 (br d, J=7.6 Hz, 1H), 7.18 (br d, J=5.7 Hz, 1H), 3.73 (s, 3H), 2.16 (d, J=1.7 Hz, 3H); LRMS (M+) m/z 418.02.

I-192: 5-(2-(2,4-difluoro-3-methoxyphenylamino)-5-fluoropyrimidin-4-ylamino)-7-methylbenzo[d]oxazol-2(3H)-one trifluoroacetate salt $^1$H NMR (300 MHz, DMSO) δ 11.57 (s, 1H), 9.57 (s, 1H), 9.02 (s, 1H), 8.13 (d, J=4.1 Hz, 1H), 7.39-7.31 (m, 2H), 7.16-7.09 (m, 2H), 3.90 (br s, 3H), 2.22 (s, 3H); LRMS (M+) m/z 418.08.

I-193: 5-(2-(2,4-difluoro-3-methoxyphenylamino)-5-fluoropyrimidin-4-ylamino)-7-fluorobenzo[d]oxazol-2(3H)-one trifluoroacetate salt $^1$H NMR (300 MHz, DMSO) δ 11.94 (s, 1H), 9.66 (s, 1H), 9.00 (s, 1H), 8.15 (t, J=4.1 Hz, 1H), 7.70 (d, J=13.2 Hz, 1H), 7.33 (br dd, J=14.3, 8.7 Hz, 1H), 7.19-7.09 (m, 2H), 3.92 (s, 3H); 422.04.

I-194: 5-(2-(3,5-dimethoxy-4-methylphenylamino)-5-fluoropyrimidin-4-ylamino)benzo[d]oxazol-2(3H)-one trifluoroacetate salt $^1$H NMR (300 MHz, DMSO) δ 11.68 (s, 1H), 9.65 (s, 1H), 9.36 (s, 1H), 8.17 (d, J=4.0 Hz, 1H), 7.52 (dd, J=8.7, 1.8 Hz, 1H), 7.43 (d, J=1.8 Hz, 1H), 7.25 (d, J=8.7 Hz, 1H), 7.01 (br s, 2H), 3.61 (s, 6H), 1.95 (s, 3H); LRMS (M+) m/z 412.40.

I-195: 5-(2-(3-methoxy-4,5-dimethylphenylamino)-5-fluoropyrimidin-4-ylamino)benzo[d]oxazol-2(3H)-one trifluoroacetate salt $^1$H NMR (300 MHz, DMSO) δ 11.70 (s, 1H), 9.71 (s, 1H), 9.35 (s, 1H), 8.17 (d, J=4.1 Hz, 1H), 7.49 (dd, J=8.6, 1.8 Hz, 1H), 7.41 (d, J=1.8 Hz, 1H), 7.27 (d, J=8.6 Hz, 1H), 7.15 (s, 1H), 7.04 (s, 1H), 3.61 (s, 3H), 2.09 (s, 3H), 2.02 (s, 3H); LRMS (M+) m/z 396.21.

I-196: 5-(2-(4-methoxyphenylamino)-5-fluoropyrimidin-4-ylamino)benzo[d]oxazol-2(3H)-one formate salt $^1$H NMR (300 MHz, DMSO) δ 11.61 (s, 1H), 9.30 (s, 1H), 8.99 (s, 1H), 8.03 (s, 1H), 7.53-7.41 (m, 3H), 7.36 (s, 1H), 7.21 (d, J=8.6 Hz, 1H), 6.77 (d, J=8.9 Hz, 2H), 3.67 (s, 3H); LCMS (m/z): 368 (MH+).

I-197: 5-(2-(3-(difluoromethyl)-4-methoxyphenylamino)-5-fluoropyrimidin-4-ylamino)benzo[d]oxazol-2(3H)-one formate salt $^1$H NMR (300 MHz, DMSO) δ 9.31 (s, 1H), 9.16 (s, 1H), 8.07 (s 1H), 7.74 (d, J=10.5 Hz, 2H), 7.46 (d, J=8.7 Hz, 1H), 7.36 (s, 1H), 7.19 (d, J=8.7 Hz, 1H), 6.98 (t, J=61.4, 49.4 Hz, 1H), 6.97 (s, 1H), 3.77 (s, 3H); LCMS (m/z): 418 (MH+).

I-198: 5-(2-(3-(difluoromethyl)-5-methoxyphenylamino)-5-fluoropyrimidin-4-ylamino)benzo[d]oxazol-2(3H)-one trifluoroacetate salt $^1$H NMR (300 MHz, DMSO) δ 11.58 (s, 1H), 9.44 (s, 2H), 8.13 (s, 1H), 7.44-7.39 (m, 3H), 7.34 (s, 1H), 7.21 (d, J=8.6 Hz, 1H), 6.98 (s, 1H), 6.79 (s, 1H), 6.79 (t, J=57.0 Hz 1H), 6.60 (s, 1H), 3.65 (s, 3H); LCMS (m/z): 418 (MH+).

I-199: 5-(2-(3-(fluoromethyl)-5-methoxyphenylamino)-5-fluoropyrimidin-4-ylamino)benzo[d]oxazol-2(3H)-one trifluoroacetate salt $^1$H NMR (300 MHz, DMSO) δ 11.60 (s, 1H), 9.60 (s, 1H), 9.45 (s, 1H), 8.13 (d, J=3.9 Hz, 1H), 7.40 (d, J=8.7 Hz, 1H), 7.34-7.23 (m, 4H), 6.52 (s, 1H), 5.21 (d, J=47.7 Hz, 2H), 3.63 (s, 3H); LCMS (m/z): 400 (MH+).

I-200: 5-(2-(4-isopropylphenylamino)-5-fluoropyrimidin-4-ylamino)benzo[d]oxazol-2(3H)-one trifluoroacetate salt $^1$H NMR (300 MHz, DMSO) δ 11.69 (s, 1H), 9.88 (s, 1H), 9.57 (s, 1H), 8.14 (s, 1H), 7.44-7.33 (m, 4H), 7.23 (d, J=8.6 Hz, 1H), 7.09 (d, J=8.5 Hz, 2H), 2.79 (dt, J=13.6, 6.7 Hz, 1H), 1.14 (d, J=6.9 Hz, 6H); LCMS (m/z): 380 (MH+).

I-201: 5-(2-(4-tert-butylphenylamino)-5-fluoropyrimidin-4-ylamino)benzo[d]oxaxazol-2(3H)-one trifluoroacetate salt $^1$H NMR (300 MHz, DMSO) δ 11.69 (s, 1H), 9.88 (s, 1H), 9.55 (s, 1H), 8.14 (s, 1H), 7.44-7.33 (m, 4H), 7.23 (d, J=8.6 Hz, 3H), 1.22 (s, 9H); LCMS (m/z): 394 (MH+).

I-202: 5-(2-(p-tolylamino)-5-fluoropyrimidin-4-ylamino)benzo[d]oxazol-2(3H)-one trifluoroacetate salt $^1$H NMR (300 MHz, DMSO) δ 11.68 (s, 1H), 9.78 (s, 1H), 9.47 (s, 1H), 8.12 (d, J=4.3 Hz, 1H), 7.46-7.22 (m, 5H), 7.02 (d, J=8.1 Hz, 2H), 2.21 (s, 3H); LCMS (m/z): 352 (MH+).

I-203: 5-(2-(4-methyl-3-(pyridin-4-yl)phenylamino)-5-fluoropyrimidin-4-ylamino)benzo[d]oxazol-2(3H)-one $^1$H NMR (300 MHz, DMSO) δ 11.51 (s, 1H), 9.36 (s, 1H), 9.29 (s, 1H), 8.58 (s, 2H), 8.08 (s, 1H), 7.64 (s, 1H), 7.56 (d, J=8.2 Hz, 1H), 7.40-7.30 (m, 4H), 7.14 (d, J=8.5 Hz, 1H), 7.01 (d, J=8.6 Hz, 1H), 2.14 (s, 3H); LCMS (m/z): 429 (MH+).

I-204: 5-(2-(4-methyl-3-(pyridin-3-yl)phenylamino)-5-fluoropyrimidin-4-ylamino)benzo[d]oxazol-2(3H)-one $^1$H NMR (300 MHz, DMSO) δ 11.52 (s, 1H), 9.42 (s, 1H), 9.33 (s, 1H), 8.58 (s, 1H), 8.52 (s, 1H), 8.09 (s, 1H), 7.84 (d, J=7.9 Hz, 1H), 7.63 (s, 1H), 7.57-7.47 (m, 2H), 7.38 (d, J=8.7 Hz, 1H), 7.29 (s, 1H), 7.15 (d, J=8.4 Hz, 1H), 6.98 (d, J=8.6 Hz, 1H), 2.13 (s, 3H); LCMS (m/z): 429 (MH+).

I-205: 5-(2-(4-fluoro-3-(pyridin-4-yl)phenylamino)-5-fluoropyrimidin-4-ylamino)benzo[d]oxazol-2(3H)-one $^1$H NMR (300 MHz, DMSO) δ 11.44 (s, 1H), 9.50 (s, 2H), 8.67 (d, J=6.2 Hz, 2H), 8.13 (s, 1H), 8.03 (s, 1H), 7.69-7.61 (m, 3H), 7.34-7.22 (m, 3H), 7.04 (d, J=8.6 Hz, 1H); LCMS (m/z): 433 (MH+).

I-206: 5-(2-(4-fluoro-3-(pyridin-3-yl)phenylamino)-5-fluoropyrimidin-4-ylamino)benzo[d]oxazol-2(3H)-one $^1$H NMR (300 MHz, DMSO) δ 11.47 (s, 1H), 9.49 (d, J=5.7 Hz, 2H), 8.63 (s, 1H), 8.59 (s, 1H), 8.13 (s, 1H), 7.92 (d, J=7.3 Hz, 2H), 7.64-7.58 (m, 1H), 7.55-7.48 (m, 1H), 7.36-7.29 (m, 2H), 7.26-7.19 (m, 1H), 6.99 (d, J=8.7 Hz, 1H); LCMS (m/z): 433 (MH+).

I-207: 5-(2-(3-methoxy-4-(pyridin-4-yl)phenylamino)-5-fluoropyrimidin-4-ylamino)benzo[d]oxazol-2(3H)-one formate salt $^1$H NMR (300 MHz, DMSO) δ 9.25 (d, J=7.4 Hz, 2H), 8.56 (s, 1H), 8.41 (s, 1H), 8.34 (d, J=7.6 Hz, 2H), 7.71 (d, J=8.7 Hz, 1H), 7.36 (s, 1H), 7.16 (s, 2H), 6.73 (s, 2H), 6.38 (d, J=8.6 Hz, 1H), 6.34 (s, 1H), 3.87 (s, 3H); LCMS (m/z): 445 (MH+).

I-208: 5-(2-(4-methoxy-3-(pyridin-4-yl)phenylamino)-5-fluoropyrimidin-4-ylamino)benzo[d]oxazol-2(3H)-one formate salt $^1$H NMR (300 MHz, DMSO) δ 9.32 (s, 1H), 9.17 (s, 1H), 8.48 (d, J=5.9 Hz, 2H), 8.25 (s, 1H), 8.06 (d, J=3.7 Hz, 1H), 7.69 (s, 1H), 7.62 (d, J=8.8 Hz, 1H), 7.41-7.34 (m, 4H), 7.02 (d, J=9.1 Hz, 2H), 3.72 (s, 3H); LCMS (m/z): 445 (MH+).

I-209: 5-(2-(4-methoxy-3-(pyridin-3-yl)phenylamino)-5-fluoropyrimidin-4-ylamino)benzo[d]oxazol-2(3H)-one formate salt $^1$H NMR (300 MHz, DMSO) δ 9.31 (s, 1H), 9.14 (s, 1H), 8.53 (s, 1H), 8.45 (d, J=4.8 Hz, 1H), 8.06 (d, J=3.7 Hz, 1H), 7.75 (d, J=8.3 Hz, 1H), 7.65 (s, 1H), 7.60 (d, J=9.0 Hz, 1H), 7.43-7.31 (m, 4H), 6.99 (dd, J=8.7, 5.4 Hz, 2H), 3.71 (s, 3H); LCMS (m/z): 445 (MH+).

I-210: 5-fluoro-N2-[3-(1-hydroxy-2,2,2-trifluoroethyl)]phenyl-N4-(2-oxo-2,3-dihydro-1,3-benzoxazol-5-yl)-2,4-pyrimidinediamine $^1$H NMR (300 MHz, DMSO) δ 11.61 (s, 1H), 9.56 (s, 1H), 9.46 (s, 1H), 8.11 (d, J=3.9 Hz, 1H), 7.73 (d, J=8.7 Hz, 1H), 7.62 (s, 1H), 7.47 (dd, J=2.1, 8.7 Hz, 1H), 7.34 (d, J=2.4 Hz, 1H), 7.22 (d, J=7.8 Hz, 1H), 7.19 (d, J=7.8 Hz, 1H), 7.01 (d, J=8.1 Hz, 1H), 6.77 (br, 1H), 4.93 (q, J=6.9 Hz, 1H); 19F NMR (282 MHz, DMSO) δ−92.49 (d, J=9); LCMS: purity: 98.08%; MS (m/e): 436.14 (MH+).

I-211: 5-fluoro-N2-(3-methoxy-5-trifluoromethyl)phenyl-N4-(2-oxo-2,3-dihydro-1,3-benzoxazol-5-yl)-2,4-pyrimidinediamine $^1$H NMR (300 MHz, DMSO) δ 11.53 (br, 1H), 9.52 (s, 1H), 9.44 (s, 1H), 8.14 (d, J=3.9 Hz, 1H), 7.61 (s, 1H), 7.54 (s, 1H), 7.35 (d, J=8.7 Hz, 1H), 7.32 (s, 1H), 7.20 (d, J=8.7 Hz, 1H), 6.68 (s, 1H), 3.68 (s, 3H); 19F NMR (282 MHz, DMSO) δ −76.96, −179.03; LCMS: purity: 96.31%; MS (m/e): 436.20 (MH+).

I-212: 5-fluoro-N2-(4-methoxy-3-trifluoromethyl)phenyl-N4-(2-oxo-2,3-dihydro-1,3-benzoxazol-5-yl)-2,4-pyrimidinediamine $^1$H NMR (300 MHz, DMSO) δ 11.57 (s, 1H), 9.37 (s, 1H), 9.27 (s, 1H), 8.08 (d, J=3.6, 1H), 7.89 (s, 1H), 7.80 (d, J=9.3, 1H), 7.40 (d, J=9.0, 1H), 7.33 (s, 1H), 7.19 (d, J=8.7, 1H), 7.10 (d, J=8.7, 1H), 3.79 (s, 3H); 19F NMR (282 MHz, DMSO) δ−76.38, −180.13; LCMS: purity: 98.02%; MS (m/e): 436.19 (MH+).

I-213: N2-[3-(cyclopropylaminocarbonylmethoxy)-4-methoxy]phenyl-5-fluoro-N4-(2-oxo-2,3-dihydro-1,3-benzoxazol-5-yl)-2,4-pyrimidinediamine $^1$H NMR (300 MHz, DMSO) δ 11.56 (s, 1H), 9.29 (s, 1H), 8.99 (s, 1H), 8.02 (d, J=3.6, 1H), 7.88 (d, 1H), 7.47 (d, J=8.4, 1H), 7.36 (s, 1H), 7.23 (d, J=8.1, 2H), 7.18 (d, J=8.7, 1H), 6.83 (d, J=8.4, 1H), 4.23 (s, 2H), 3.71 (s, 3H), 2.64 (m, 1H), 0.60 (q, J=5.7, 2H), 0.45 (m, 2H); 19F NMR (282 MHz, DMSO) δ−180.69; LCMS: purity: 83.84%; MS (m/e): 481.23 (MH+).

I-214: 5-fluoro-N2-(3,4,5-trimethyl)phenyl-N4-(2-oxo-2,3-dihydro-1,3-benzoxazol-5-yl)-2,4-pyrimidinediamine $^1$H NMR (300 MHz, DMSO) δ 9.98 (br, 1H), 9.27 (s, 1H), 8.92 (s, 1H), 8.04 (d, J=3.6, 1H), 7.42 (d, J=8.7, 1H), 7.33 (s, 1H), 7.23 (s, 2H), 7.18 (d, J=8.7, 1H), 2.05 (s, 6H), 2.00 (s, 3H); 19F NMR (282 MHz, DMSO) δ−181.06; LCMS: purity: 100%; MS (m/e): 380.13 (MH+).

I-215: N2-(3,5-dimethyl-4-fluoro)phenyl-5-fluoro-N4-(2-oxo-2,3-dihydro-1,3-benzoxazol-5-yl)-2,4-pyrimidinediamine $^1$H NMR (300 MHz, DMSO) δ 11.27 (br, 1H), 9.32 (s, 1H), 9.06 (s, 1H), 8.06 (d, J=3.9, 1H), 7.39 (d, J=8.4, 1H), 7.33-7.27 (m, 3H), 7.21 (d, J=9.0, 1H), 2.04 (s, 6H); 19F NMR (282 MHz, DMSO) δ−119.33, −180.66; LCMS: purity: 100%; MS (m/e): 384.10 (MH+).

I-216: 5-methyl-N4-[3-(phosphonooxy)methyl-2-oxo-2,3-dihydro-1,3-benzoxazol-5-yl]-N2-(3,4,5-trimethyl)phenyl-2,4-pyrimidinediamine lysine salt $^1$H NMR (300 MHz, DMSO) δ 10.44 (br, 1H), 9.11 (br, 1H), 8.18 (s, 1H), 7.84 (s, 1H), 7.598 (s, 2H), 7.21 (s, 2H), 5.42 (d, J=7.8 Hz, 2H), 3.10 (t, 1H), 2.65 (t, 2H), 2.14 (s, 6H), 2.09 (s, 3H), 2.02 (s, 3H), 1.63-1.56 (m, 2H), 1.41 (m, 4H); LCMS: purity: 92.76%; MS (m/e): 486.33 (MH+).

I-217: N2-(3,4,5-trimethyl)phenyl-5-methyl-N4-(2-oxo-2,3-dihydro-1,3-benzoxazol-5-yl)-2,4-pyrimidinediamine $^1$H NMR (300 MHz, DMSO) δ 11.39 (br, 1H), 8.70 (s, 1H), 8.29 (s, 1H), 7.83 (s, 1H), 7.30 (d, J=6.3, 2H), 7.21 (m, 3H), 2.06 (s, 3H), 1.99 (s, 6H), 1.98 (s, 3H); LCMS: purity: 96.73%; MS (m/e): 376.27 (M+H).

I-220: 5-(2-(4-(aminomethyl)phenylamino)-5-methylpyrimidin-4-ylamino)benzo[d]oxazol-2(3H)-one

MS (ES) 363 (M+H), 361 (M−H).

Deuterated compounds were prepared generally as stated above, and further as follows. d$_4$-Thymine (3.00 g, 23.1 mmol) was placed in a pressure vessel and POCl$_3$ (25 ml)

was added. The white suspension was heated for 3 hours at 130° C. After approximately 1 hour the suspension became a clear yellow solution. The reaction was then quenched by slowly pouring the reaction mixture into a baker containing crushed ice. The aqueous phase was then extracted with DCM (3×50 ml) and dried over MgSO4. After evaporation of solvents the reaction product was obtained as a white solid (3.72 g, 96%). The JAK inhibitors were prepared by the standard sequence of 1$^{st}$ S$_N$Ar reaction with the LHS carbamate aniline and 2$^{nd}$ S$_N$Ar reaction with the RHS aniline or d-aniline (deuterated anilines were prepared the same way as the non-deuterated anilines using CD$_3$I instead of MeI).

I-221: 5-(2-(4-fluoro-3-methoxy-5-methylphenylamino)-6-D-5-trideuteromethylpyrimidin-4-ylamino)benzo[d]oxazol-2(3H)-one

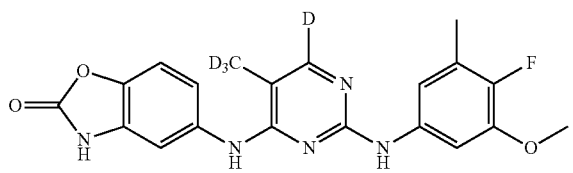

MS (ES) 400 (M+H), 398 (M–H).

I-222: 5-(2-(4-fluoro-3-trideuteromethoxy-5-methylphenylamino)-6-D-5-trideuteromethylpyrimidin-4-ylamino)benzo[d]oxazol-2(3H)-one

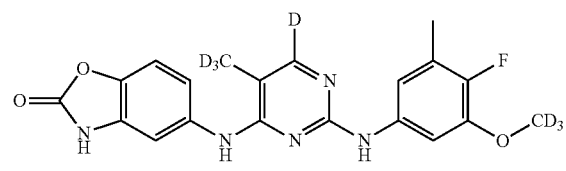 [SMILES: [2H]c1nc(Nc2cc(C)c(F)c(OC([2H])([2H])[2H])c2)nc(Nc2ccc3oc(=O)[nH]c3c2)c1C([2H])([2H])[2H]]

$^1$H NMR (300 MHz, DMSO) δ 11.96 (s, 1H), 10.75 (s, 1H), 10.04 (s, 1H), 7.37-7.13 (m, 3H), 6.88 (ddd, J=7.6, 6.5, 2.0 Hz, 2H), 1.95 (s, 3H); MS (ES) 403 (M+H), 401 (M–H).

I-223: 5-(2-(3-methoxy-4,5-dimethylphenylamino)-6-D-5-trideuteromethylpyrimidin-4-ylamino)benzo[d]oxazol-2(3H)-one

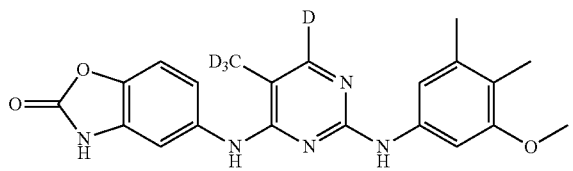 [SMILES: [2H]c1nc(Nc2cc(C)c(C)c(OC)c2)nc(Nc2ccc3oc(=O)[nH]c3c2)c1C([2H])([2H])[2H]]

MS (ES) 396 (M+H), 394 (M–H).

I-224: 5-(2-(3-trideuteromethoxy-4,5-dimethylphenylamino)-6-D-5-trideuteromethylpyrimidin-4-ylamino)benzo[d]oxazol-2(3H)-one

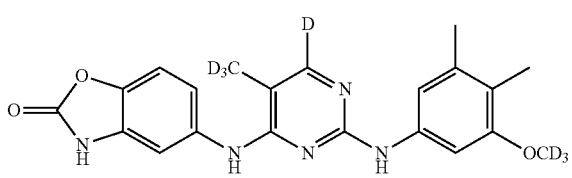

$^1$H NMR (300 MHz, DMSO) δ 11.78 (s, 1H), 10.22 (s, 1H), 9.80 (s, 1H), 7.24 (m, 3H), 6.82 (s, 1H), 6.71 (s, 1H), 1.97 (s, 6H); MS (ES) 399 (M+H), 397 (M–H).

I-225: 5-(2-(4-(hydroxymethyl)-3-methoxy-5-methylphenylamino)-6-D-5-trideuteromethylpyrimidin-4-ylamino)benzo[d]oxazol-2(3H)-one

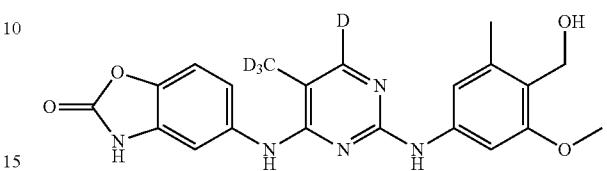

$^1$H NMR (300 MHz, DMSO) δ 8.82 (s, 1H), 8.31 (s, 1H), 7.33 (m, 2H), 7.26-7.02 (m, 3H), 4.37 (s, 2H), 4.31 (s br, 1H), 3.50 (s, 3H), 2.10 (s, 3H); MS (ES) 412 (M+H), 410 (M–H).

I-226: 5-(2-(4-fluoro-3-trideuteromethoxy-5-methylphenylamino)-6-D-5-trideuteromethylpyrimidin-4-ylamino)-2-oxobenzo[d]oxazol-3(2H)-yl)methyl di-tert-butyl phosphate

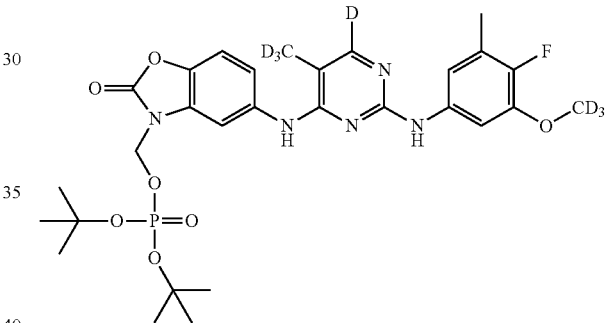

$^1$H NMR (300 MHz, CDCl$_3$) δ 9.11 (s, 1H), 8.82 (s, 1H), 7.58 (d, J=7.4 Hz, 1H), 7.10 (d, J=8.6 Hz, 1H), 7.05 (d, J=5.7 Hz, 1H), 6.75 (d, J=8.6 Hz, 1H), 6.43 (s, 1H), 5.78 (d, J=9.8 Hz, 2H), 2.22 (s, 3H), 1.40 (s, 18H); MS (ES) 625 (M+H), 623 (M–H).

I-227: 5-(2-(4-fluoro-3-trideuteromethoxy-5-methylphenylamino)-6-D-5-trideuteromethylpyrimidin-4-ylamino)-2-oxobenzo[d]oxazol-3(2H)-yl)methyl tert-butyl hydrogen phosphate

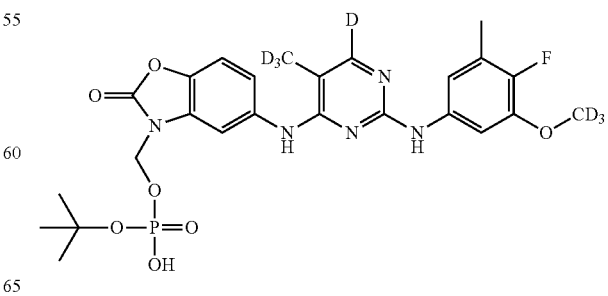

MS (ES) 569 (M+H), 567 (M–H).

I-228: 5-(2-(4-fluoro-3-trideuteromethoxy-5-methylphenylamino)-6-D-5-trideuteromethylpyrimidin-4-ylamino)-2-oxobenzo[d]oxazol-3(2H)-yl)methyl dihydrogen phosphate

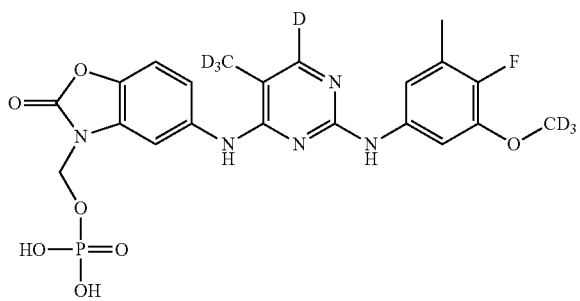 [SMILES: [2H]c1nc(Nc2cc(C)c(F)c(OC([2H])([2H])[2H])c2)nc(Nc2ccc3oc(=O)n(COP(=O)(O)O)c3c2)c1C([2H])([2H])[2H]]

MS (ES) 513 (M+H), 511 (M−H).

I-229: Di-sodium (5-(2-(4-fluoro-3-trideuteromethoxy-5-methylphenylamino)-6-D-5-trideuteromethylpyrimidin-4-ylamino)-2-oxobenzo[d]oxazol-3(2H)-yl)methyl phosphate

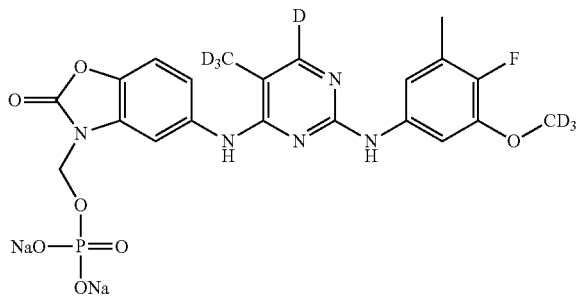

$^1$H NMR (300 MHz, D$_2$O) δ 7.33 (d, J=8.8 Hz, 1H), 7.07 (s, 1H), 6.76 (d, J=8.7 Hz, 1H), 6.59 (d, J=5.9 Hz, 1H), 6.47 (d, J=7.2 Hz, 1H), 5.34 (d, J=5.6 Hz, 2H), 1.82 (s, 3H); MS (ES) 513 (M+H), 511 (M−H).

I-230: 4-(4-(2,3-dihydro-2-oxobenzo[d]oxazol-5-ylamino)-5-methylpyrimidin-2-ylamino)-2-methoxy-6-methylbenzyl alcohol

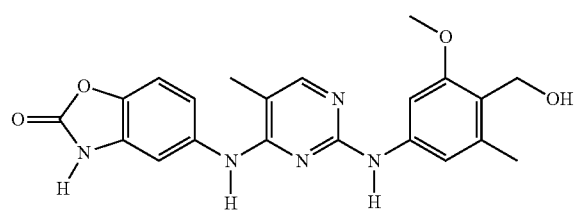 [SMILES: COc1cc(Nc2ncc(C)c(Nc3ccc4oc(=O)[nH]c4c3)n2)cc(C)c1CO]

1H NMR (300 MHz, DMSO) δ 11.60 (s, 1H), 8.88 (s, 1H), 8.35 (s, 1H), 7.89 (s, 1H), 7.35 (d, J=8.2 Hz, 1H), 7.34 (s, 1H), 7.22 (d, J=8.2 Hz, 1H), 7.17 (s, 1H), 7.10 (s, 1H), 4.36 (m, 3H), 3.51 (s, 3H), 2.12 (s, 3H), 2.10 (s, 3H). LCMS (m/z): 408.4 (MH+).

I-231: 4-(4-(2,3-dihydro-2-oxobenzo[d]oxazol-5-ylamino)-5-methylpyrimidin-2-ylamino)-2-methoxy-6-methylbenzoic acid

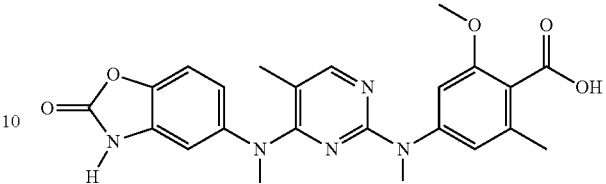

1H NMR (300 MHz, DMSO) δ 12.71 (br s, 1H), 11.71 (s, 1H), 9.74 (br s, 1H), 9.26 (br s, 1H), 7.89 (s, 1H), 7.27 (s, 3H), 7.06 (s, 1H), 6.96 (s, 1H), 3.55 (s, 3H), 2.15 (s, 3H), 2.00 (s, 3H). LCMS (m/z): 422.2 (MH+).

II-1: 5-(5-fluoro-2-(1-oxo-1,2,3,4-tetrahydroisoquinolin-6-ylamino)pyrimidin-4-ylamino)benzo[d]oxazol-2(3H)-one trifluoroacetate salt II-2: 5-(5-fluoro-2-(7-(pyrrolidin-1-yl)-6,7,8,9-tetrahydro-5H-benzo[7]annulen-2-ylamino)pyrimidin-4-ylamino)benzo[d]oxazol-2(3H)-one diformate salt II-3: 5-(5-fluoro-2-(7-oxo-6,7,8,9-tetrahydro-5H-benzo[7]annulen-2-ylamino)pyrimidin-4-ylamino)benzo[d]oxazol-2(3H)-one diformate salt II-4: (Z)-5-(5-fluoro-2-(2-methyl-1-oxo-1,2,3,6-tetrahydrobenzo[c]azocin-9-ylamino)pyrimidin-4-ylamino)benzo[d]oxazol-2(3H)-one formate salt II-5: 5-(5-fluoro-2-(5-oxo-6,7,8,9-tetrahydro-5H-benzo[7]annulen-2-ylamino)pyrimidin-4-ylamino)benzo[d]oxazol-2(3H)-one formate salt II-6: 5-(2-(naphthalen-2-ylamino)-5-nitropyrimidin-4-ylamino)benzo[d]oxazol-2(3H)-one trifluoroacetate salt II-7: 2-(Naphthalen-2-ylamino)-4-(2-oxo-2,3-dihydro-benzooxazol-5-ylamino)-pyrimidine-5-carboxylic acid methyl ester trifluoroacetate salt $^1$H NMR (300 MHz, DMSO) δ 11.67 (s, 1H), 10.29-10.14 (m, 1H), 9.99 (s, 1H), 8.75 (s, 1H), 8.22 (s, 1H), 8.01-7.83 (m, 1H), 7.76 (s, 2H), 7.68-7.56 (m, 1H), 7.41-7.24 (m, 4H), 7.25-6.99 (m, 1H), 3.85 (s, 3H) ppm; MS (ES) 428 (M+H).

II-8: 5-methyl-N4-(2-oxo-2,3-dihydro-1,3-benzoxazol-5-yl)-N2-(1-oxo-1,3-dihydro-isobenzofuran-6-yl)-2,4-pyrimidinediamine $^1$H NMR (300 MHz, DMSO) δ 11.50 (br, 1H), 9.38 (s, 1H), 8.39 (s, 1H), 8.24 (s, 1H), 7.90 (d, J=9.6 Hz, 2H), 7.41 (d, J=8.7 Hz, 1H), 7.30 (t, J=2.4 Hz, 2H), 7.21 (d, J=9.3 Hz, 1H), 5.27 (s, 2H), 2.10 (s, 3H); LCMS: purity: 88.61%; MS (m/e): 390.40 (MH+).

II-9: N2-(1,3-dihydro-isobenzofuran-5-yl)-5-methyl-N4-(2-oxo-2,3-dihydro-1,3-benzoxazol-5-yl)-2,4-pyrimidinediamine $^1$H NMR (300 MHz, DMSO) δ 11.42 (br, 1H), 9.05 (s, 1H), 8.35 (s, 1H), 7.86 (s, 1H), 7.71 (s, 1H), 7.36 (d, J=8.4 Hz, 1H), 7.25 (m, 3H), 7.03 (d, J=8.4 Hz, 1H), 4.87 (s, 2H), 4.76 (s, 2H), 2.07 (s, 3H); LCMS: purity: 97.34%; MS (m/e): 376.30 (MH+).

II-10: 5-methyl-N4-(2-oxo-2,3-dihydro-1,3-benzoxazol-5-yl)-N2-(1-oxo-1,3-dihydro-isobenzofuran-5-yl)-2,4-pyrimidinediamine $^1$H NMR (300 MHz, DMSO) δ 11.69 (s, 1H), 10.04 (br, 1H), 8.98 (br, 1H), 7.95 (s, 2H), 7.59 (m, 2H), 7.36 (d, J=8.4 Hz, 1H), 7.26 (m, 2H), 5.14 (s, 2H), 2.13 (s, 3H); LCMS: purity: 81.74%; MS (m/e): 390.19 (MH+).

II-11: 5-methyl-N4-(2-oxo-2,3-dihydro-1,3-benzoxazol-5-yl)-N2-(1-oxo-1,3-dihydro-2H-isoindol-6-yl)-2,4-pyrimidinediamine $^1$H NMR (300 MHz, DMSO) δ 11.34 (br, 1H), 9.19 (s, 1H), 8.46 (s, 1H), 8.31 (s, 1H), 8.02 (s, 1H), 7.90 (s, 1H), 7.81 (d, J=7.5 Hz, 1H), 7.36 (d, J=6.6 Hz, 2H), 7.30 (d, J=8.7 Hz, 1H), 7.22 (d, J=9.0 Hz, 1H), 4.24 (s, 2H), 2.09 (s, 3H); LCMS: purity: 100%; MS (m/e): 389.21 (MH+).

II-12: 5-methyl-N4-(2-oxo-2,3-dihydro-1,3-benzoxazol-5-yl)-N2-(1-oxo-1,3-dihydro-7-methylisobenzofuran-4-yl)-2,4-pyrimidinediamine $^1$H NMR (300 MHz, DMSO) δ 11.60 (s, 1H), 9.73 (br, 1H), 9.53 (br, 1H), 7.79 (s, 1H), 7.70 (d, J=8.4 Hz, 1H), 7.46 (d, J=8.1 Hz, 1H), 7.14 (m, 3H), 5.32 (s, 2H), 2.40 (s, 3H), 2.12 (s, 3H); LCMS: purity: 90.64%; MS (m/e): 404.26 (MH+).

II-13: 5-methyl-N4-(2-oxo-2,3-dihydro-1,3-benzoxazol-5-yl)-N2-(1-oxo-1,3-dihydro-4-methylisobenzofuran-6-yl)-2,4-pyrimidinediamine $^1$H NMR (300 MHz, DMSO) δ 11.56 (s, 1H), 9.96 (br, 1H), 9.37 (br, 1H), 7.90 (s, 1H), 7.77 (s, 1H), 7.58 (s, 1H), 7.27-7.19 (m, 3H), 5.28 (s, 2H), 2.13 (s, 3H), 2.12 (s, 3H); LCMS: purity: 97.52%; MS (m/e): 404.29 (MH+).

II-14: N2-(4,5-dimethylpyridin-2-yl)-5-methyl-N4-(2-oxo-2,3-dihydro-1,3-benzoxazol-5-yl)-2,4-pyrimidinediamine $^1$H NMR (300 MHz, DMSO) δ 11.71 (s, 1H), 9.27 (s, 1H), 8.84 (s, 2H), 8.31 (s, 1H), 8.20 (s, 1H), 7.32 (s, 1H), 7.28 (s, 1H), 6.86 (s, 1H), 2.30 (s, 3H), 2.28 (s, 3H), 2.11 (s, 3H); LCMS: purity: 96.43%; MS (m/e): 363.38 (MH+).

II-15: N2-(4,6-dimethylpyridin-2-yl)-5-methyl-N4-(2-oxo-2,3-dihydro-1,3-benzoxazol-5-yl)-2,4-pyrimidinediamine $^1$H NMR (300 MHz, DMSO) δ 11.79 (s, 1H), 9.67 (s, 1H), 8.06 (s, 1H), 7.76 (m, 1H), 7.48 (m, 2H), 7.28 (m, 2H), 6.89 (m, 1H), 2.24 (s, 3H), 2.19 (s, 3H); LCMS: purity: 95.84%; MS (m/e): 363.39 (MH+).

II-16: N2-(5-cyano-6-methylpyridin-2-yl)-5-methyl-N4-(2-oxo-2,3-dihydro-1,3-benzoxazol-5-yl)-2,4-pyrimidinediamine $^1$H NMR (300 MHz, DMSO) δ 8.01 (s, 1H), 7.67 (m, 1H), 7.46 (m, 2H), 7.37 (s, 1H), 2.17 (s, 3H); LCMS: purity: 86.13%; MS (m/e): 374.36 (MH+).

II-17: N2-(2-methoxypyridin-4-yl)-5-methyl-N4-(2-oxo-2,3-dihydro-1,3-benzoxazol-5-yl)-2,4-pyrimidinediamine $^1$H NMR (300 MHz, DMSO) δ 11.65 (s, 1H), 10.16 (br, 1H), 9.11 (br, 1H), 7.98 (s, 1H), 7.89 (d, J=6.0 Hz, 1H), 7.31-7.10 (m, 5H), 3.72 (s, 3H), 2.14 (s, 3H); LCMS: purity: 97.39%; MS (m/e): 365.35 (MH+).

II-18: 5-methyl-N2-(2-methylpyridin-4-yl)-N4-(2-oxo-2,3-dihydro-1,3-benzoxazol-5-yl)-2,4-pyrimidinediamine $^1$H NMR (300 MHz, DMSO) δ 11.67 (s, 1H), 10.75 (s, 1H), 8.79 (s, 1H), 8.28 (d, 1H), 8.07 (s, 1H), 7.93 (br, 1H), 7.71 (br, 1H), 7.32 (d, J=8.1 Hz, 1H), 7.27 (s, 1H), 7.25 (d, J=8.4 Hz, 1H), 2.34 (s, 3H), 2.16 (s, 3H); LCMS: purity: 98.95%; MS (m/e): 349.35 (MH+).

II-19: N2-(2,6-dimethylpyridin-4-yl)-5-methyl-N4-(2-oxo-2,3-dihydro-1,3-benzoxazol-5-yl)-2,4-pyrimidinediamine $^1$H NMR (300 MHz, DMSO) δ 11.69 (s, 1H), 10.68 (s, 1H), 8.79 (s, 1H), 8.05 (s, 1H), 7.62 (br, 2H), 7.33 (d, J=8.4 Hz, 1H), 7.24 (d, J=8.1 Hz, 2H), 2.34 (s, 6H), 2.15 (s, 3H); LCMS: purity: 99.04%; MS (m/e): 363.37 (MH+).

II-20: N2-(6-methoxypyridin-2-yl)-5-methyl-N4-(2-oxo-2,3-dihydro-1,3-benzoxazol-5-yl)-2,4-pyrimidinediamine $^1$H NMR (300 MHz, DMSO) δ 11.80 (s, 1H), 8.09 (s, 1H), 7.71 (m, 2H), 7.48 (m, 2H), 7.29 (s, 1H), 6.60 (d, 1H), 3.92 (s, 3H), 2.18 (s, 3H); LCMS: purity: 90.96%; MS (m/e): 365.34 (MH+).

II-21: N2-(5,6-dimethylpyridin-2-yl)-5-methyl-N4-(2-oxo-2,3-dihydro-1,3-benzoxazol-5-yl)-2,4-pyrimidinediamine $^1$H NMR (300 MHz, DMSO) δ 11.80 (s, 1H), 11.14 (br, 1H), 9.71 (s, 1H), 8.07 (s, 1H), 7.63 (d, J=7.8 Hz, 1H), 7.35 (d, J=9.0 Hz, 1H), 7.29 (m, 2H), 7.02 (d, J=8.7 Hz, 1H), 2.52 (s, 3H), 2.20 (s, 3H), 2.19 (s, 3H); LCMS: purity: 98.29%; MS (m/e): 363.35 (MH+).

II-22: N2-(5-cyano-4-methylpyridin-2-yl)-5-methyl-N4-(2-oxo-2,3-dihydro-1,3-benzoxazol-5-yl)-2,4-pyrimidinediamine $^1$H NMR (300 MHz, DMSO) δ 11.73 (s, 1H), 8.63 (s, 1H), 7.99 (s, 1H), 7.30 (s, 2H), 6.53 (br, 4H), 2.29 (s, 3H), 2.17 (s, 3H); LCMS: purity: 78.01%; MS (m/e): 374.32 (MH+).

II-23: 5-(5-fluoro-2-(1-oxo-2,3-dihydro-1H-benzo[c]azepin-7-ylamino)pyrimidin-4-ylamino)benzo[d]oxazol-2(3H)-one formate salt II-24: 5-(5-fluoro-2-(2-methyl-1-oxo-2,3-dihydro-1H-benzo[c]azepin-7-ylamino)pyrimidin-4-ylamino)benzo[d]oxazol-2(3H)-one formate salt II-25: 7-(4-(2,3-dihydro-2-oxobenzo[d]oxazol-5-ylamino)-5-fluoropyrimidin-2-ylamino)-2H-benzo[b][1,4]oxazin-3(4H)-one formate salt $^1$H NMR (300 MHz, DMSO) δ 11.57 (s, 1H), 10.49 (s, 1H), 9.46 (s, 1H), 9.22 (s, 1H), 8.07 (s, 1H), 7.39-7.33 (m, 3H), 7.21 (d, J=8.3 Hz, 1H), 7.08 (d, J=8.4 Hz, 1H), 6.69 (d, J=8.5 Hz, 1H), 4.44 (s, 2H); LCMS (m/z): 409 (MH+).

II-26: 6-(4-(2,3-dihydro-2-oxobenzo[d]oxazol-5-ylamino)-5-fluoropyrimidin-2-ylamino)-3,4-dihydroquinolin-2(1H)-one trifluoroacetate salt $^1$H NMR (300 MHz, DMSO) δ 11.65 (s, 1H), 9.95 (s, 1H), 9.82 (s, 1H), 9.49 (s, 1H), 8.12 (s, 1H), 7.40-7.33 (m, 3H), 7.23 (d, J=8.7 Hz, 2H), 6.71 (d, J=8.5 Hz, 1H), 2.66 (t, J=7.4 Hz, 2H), 2.36 (t, J=7.5 Hz, 2H); LCMS (m/z): 407 (MH+).

II-27: 7-(4-(2,3-dihydro-2-oxobenzo[d]oxazol-5-ylamino)-5-fluoropyrimidin-2-ylamino)-4,5-dihydro-1H-benzo[b]azepin-2(3H)-one trifluoroacetate salt $^1$H NMR (300 MHz, DMSO) δ 11.65 (s, 1H), 9.71 (s, 1H), 9.45 (s, 1H), 9.31 (s, 1H), 8.13 (s, 1H), 7.46 (s, 1H), 7.42-7.30 (m, 3H), 7.24 (d, J=8.6 Hz, 1H), 6.80 (d, J=8.6 Hz, 1H), 2.48-2.44 (m, 2H, overlapped with DMSO peak), 2.08 (t, J=7.1 Hz, 2H), 1.98 (dd, J=13.5, 6.7 Hz, 2H); LCMS (m/z): 421 (MH+).

II-28: 7-(4-(2,3-dihydro-2-oxobenzo[d]oxazol-5-ylamino)-5-fluoropyrimidin-2-ylamino)-4,5-dihydro-1-methyl-1H-benzo[b]azepin-2(3H)-one trifluoroacetate salt $^1$H NMR (300 MHz, DMSO) δ 11.64 (s, 1H), 9.66 (s, 1H), 9.48 (s, 1H), 8.13 (s, 1H), 7.48-7.36 (m, 3H), 7.32 (s, 1H), 7.24 (d, J=8.6 Hz, 1H), 7.13 (d, J=8.5 Hz, 1H), 3.15 (s, 3H), 2.40 (t, J=6.5 Hz, 2H), 2.07 (t, J=6.9 Hz, 2H), 1.93 (dd, J=13.5, 7.1 Hz, 2H); LCMS (m/z): 435 (MH+).

II-29: 5-(5-methyl-2-(2-morpholinopyridin-4-ylamino)pyrimidin-4-ylamino)benzo[d]oxazol-2(3H)-one ditrifluoroacetate salt $^1$H NMR (300 MHz, DMSO) δ 11.70 (s, 1H), 10.41 (s, 1H), 8.80 (s, 1H), 8.10 (s, 1H), 7.85 (d, J=7.0 Hz, 1H), 7.66 (s, 1H), 7.36 (s, 1H), 7.31 (br s, 2H), 7.19 (d, J=7.0 Hz, 1H), 3.66-3.63 (m, 4H), 3.25-3.22 (m, 4H), 2.20 (s, 3H); LRMS (M+) m/z 419.98.

II-30: 5-(5-fluoro-2-(2-morpholinopyridin-4-ylamino)pyrimidin-4-ylamino)benzo[d]oxazol-2(3H)-one ditrifluoroacetate salt $^1$H NMR (300 MHz, DMSO) δ 11.71 (s, 1H), 10.51 (s, 1H), 9.78 (s, 1H), 8.32 (d, J=3.5 Hz, 1H), 7.89 (d, J=7.0 Hz, 1H), 7.65 (s, 1H), 7.43-7.38 (m, 2H), 7.32 (d, J=8.5 Hz, 1H), 7.20 (d, J=7.0 Hz, 1H), 3.69-3.66 (m, 4H), 3.32-3.30 (m, 4H); LRMS (M+) m/z 423.96.

II-31: 5-(5-methyl-2-(pyridin-4-ylamino)pyrimidin-4-ylamino)benzo[d]oxazol-2(3H)-one ditrifluoroacetate salt $^1$H NMR (300 MHz, DMSO) δ 11.75 (br s, 1H), 10.92 (s, 1H), 8.87 (br s, 1H), 8.46 (d, J=5.9 Hz, 2H), 8.16-8.10 (m, 2H), 7.38-7.36 (m, 2H), 7.32 (d, J=8.6 Hz, 1H), 6.82 (d, J=6.3 Hz, 1H), 2.22 (s, 3H); LRMS (M+) m/z 335.03.

Example 6: Xinafoic Acid Salt

Preparative Example

The following example illustrates the preparation of a xinafoate salt of a 2,4-pyrimidinediamine described herein. A suspension of a 2,4-pyrimidinediamine as described herein (1 equiv) in a ketonic solvent (about 20 ml solvent/g of 2,4-pyrimidinediamine, for example MEK), is heated to between about 50° C. and about 60° C. Water (about 1 ml water/g of 2,4-pyrimidinediamine) is added, resulting in a solution. The solution may be passed through a filter for clarification if necessary. The solution is held to between about 50° C. and about 60° C. for between about 30 minutes and about 1.5 h. A homogeneous solution of 1-hydroxy-2-naphthoic acid (1.1 equiv) in a ketone solvent (about 4 ml solvent/g of naphthoic acid, for example MEK) is added which results in precipitation of a solid after between about 5 minutes and 15 minutes. The reaction is cooled to ambient temperature, stirred for between about 15 h and about 20 h, and then cooled to between about 0° C. and about 10° C. for between about 1 h and about 2 h. The precipitated xinafoic acid salt is then filtered and collected. The filtered solid is washed, for example twice with a ketonic solvent (about 2 ml/g, for example MEK) and dried under reduced pressure at between about 40° C. and about 60° C., for between about 10 h and about 20 h. The xinafoic acid salt is the processed accordingly, for example, micronized and formulated as described herein, for example, in a formulation for administration by inhalation. In a particular embodiment, compound I-217 is the 2,4-pyrimidinediamine used in this Example.

Example 7: Assay for CD23 Expression on Ramos B-Cells Stimulated by IL-4

B-cells stimulated with cytokine Interleukin-4 (IL-4) activate the JAK/Stat pathway through phosphorylation of the JAK family kinases, JAK-1 and JAK-3, which in turn phosphorylate and activate the transcription factor Stat-6. One of the genes upregulated by activated Stat-6 is the low affinity IgE receptor, CD23. To study the effect of inhibitors on the JAK family kinases, human Ramos B cells were stimulated with human IL-4 and the surface expression of CD23 was measured.

The Ramos B-cell line was acquired from ATCC (ATCC Catalog No. CRL-1596). The cells were cultured in RPMI 1640 (Cellgro, MediaTech, Inc., Herndon, Va., Cat No. 10-040-CM) with 10% FBS, heat inactivated (JRH Biosciences, Inc., Lenexa, Kans., Cat No. 12106-500M) according to ATCC propagation protocol. Cells were maintained at a density of $3.5 \times 10^5$. The day before the experiment, Ramos B-cells were diluted to $3.5 \times 10^5$ cells/mL to ensure that they were in a logarithmic growth phase.

Cells were spun down and suspended in RPMI with 5% serum. $5 \times 10^4$ cells were used per point in a 96-well tissue culture plate. Cells were pre-incubated with compound or DMSO (Sigma-Aldrich, St. Louis, Mo., Cat No. D2650) vehicle control for 1 hour in a 37° C. incubator. Cells were then stimulated with IL-4 (Peprotech Inc., Rocky Hill, N.J., Cat No. 200-04) for a final concentration of 50 units/mL for 20-24 hours. Cells were then spun down and stained with anti-CD23-PE (BD Pharmingen, San Diego, Calif., Cat No. 555711) and analyzed by FACS. Detection was performed using a BD LSR I System Flow Cytometer, purchased from Becton Dickinson Biosciences of San Jose, Calif. The $IC_{50}$ calculated based on the results of this assay are provided in Table IX.

Example 8: Assay for Human Primary T-Cell Proliferation Stimulated by IL-2

Primary human T-cells derived from peripheral blood and pre-activated through stimulation of the T-cell receptor and CD28, proliferate in vitro in response to the cytokine Interleukin-2 (IL-2). This proliferative response is dependent on the activation of JAK-1 and JAK-3 tyrosine kinases, which phosphorylate and activate the transcription factor Stat-5.

Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 min at 4° C. at 1750 rpm. The lymphocytes at the serum: ficoll interface were recovered and washed twice with 5 volumes of PBS. The cells were resuspended in Yssel's medium (Gemini Bio-products, Woodland, Calif., Catalog #400-103) containing 40 U/mL recombinant IL2 (R and D Systems, Minneapolis, Minn., Catalog #202-IL (20 gig)) and seeded into a flask pre-coated with 1 µg/mL anti-CD3 (BD Pharmingen, San Diego, Calif., Catalog #555336) and 5 µg/mL anti-CD28 (Immunotech, Beckman Coulter of Brea Calif., Catalog #IM1376). The primary T-cells were stimulated for 3-4 days, then transferred to a fresh flask and maintained in RPMI with 10% FBS and 40 U/mL IL-2.

The day prior to the assay set up, primary T-cells were centrifuged and resuspended in fresh RPMI with 10% FBS but without IL-2 and starved overnight. For the assay, the primary T-cells were centrifuged and resuspended Yssel's medium at $2 \times 10^6$ cells/mL. 50 µL of cell suspension containing 80 U/mL IL-2 was added to each well of a flat bottom 96 well black plate. For the unstimulated control, IL-2 was omitted from the last column on the plate. Compounds were serially diluted in dimethyl sulfoxide (DMSO, 99.7% pure, cell culture tested, Sigma-Aldrich, St. Louis, Mo., Catalog No. D2650) from 5 mM in 3-fold dilutions, and then diluted 1:250 in Yssel's medium. 50 µL of 2× compound was added per well in duplicate and the cells were allowed to proliferate for 72 hours at 37° C.

Proliferation was measured using CellTiter-Glo® Luminescent Cell Viability Assay (Promega), which determines the number of viable cells in culture based on quantitation of the ATP present, as an indicator of metabolically active cells. The substrate was thawed and allowed to come to ambient temperature. After mixing the Cell Titer-Glo reagent and diluent together, 100 L was added to each well. The plates were mixed on an orbital shaker for two minutes to induce lysis and incubated at ambient temperature for an additional ten minutes to allow the signal to equilibrate. Detection was performed using a Wallac Victor2 1420 multilabel counter purchased from Perkin Elmer, Shelton, Conn.

Example 9: Assay for ICAM1 Expression on A549 Epithelial Cells Stimulated by IFNγ

Lung epithelial cells, A549, up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The A549 lung epithelial carcinoma cell line originated from the American Type Culture Collection. Routine culturing was with F12K media (Mediatech Inc., Lenexa, Kans., Cat. No. 10-025-CV) with 10% fetal bovine serum, 100 I.U. penicillin and 100 ng/mL streptomycin (complete F12k media). Cells were incubated in a humidified atmosphere of 5% $CO_2$ at 37° C. Prior to use in the assay, A549 cells were washed with PBS and trypsinized (Mediatech Inc., Cat. No. 25-052-CI) to lift the cells. The trypsin cell suspension was neutralized with complete F12K media and centrifuged to pellet the cells. The cell pellet was resuspended in complete F12K media at a concentration of $2.0 \times 10^5$/mL. Cells were seeded at 20,000 per well, 100 µL total volume, in a flat bottom tissue culture plate and allowed to adhere overnight.

On day two, A549 cells were pre-incubated with test compound or DMSO (control) (Sigma-Aldrich, St. Louis, Mo., Catalog No. D2650) for 1 hour. The cells were then stimulated with IFNγ (75 ng/mL) (Peprotech Inc., Rocky Hill, N.J., Cat. No. 300-02) and allowed to incubate for 24 hours. The final test compound dose range was 30 µM to 14 nM in 200 µL F12K media containing 5% FBS, 0.3% DMSO.

On day three, the cell media was removed and the cells were washed with 200 µL PBS (phosphate buffered saline). Each well was trypsinized to dissociate the cells, then neutralized by addition of 200 µL complete F12K media. Cells were pelleted and stained with an APC conjugated mouse anti-human ICAM-1 (CD54) (BD Pharmingen, San Diego, Calif., Catalog #559771) antibody for 20 minutes at 4° C. Cells were washed with ice cold FACS buffer (PBS+ 2% FBS) and surface ICAM-1 expression was analyzed by flow cytometry. Detection was performed using a BD LSR I System Flow Cytometer, purchased from BD Biosciences of San Jose, Calif. Events were gated for live scatter and the geometric mean was calculated (Becton-Dickinson Cell-Quest software version 3.3, Franklin Lakes, N.J.). Geometric means were plotted against the compound concentration to generate a dose response curve.

Example 10: Assay for ICAM1 Expression on U937 Myeloid Cells Stimulated by IFNγ

Human U937 monocytic cells up-regulate ICAM-1 (CD54) surface expression in response to a variety of different stimuli. Therefore, using ICAM-1 expression as readout, compound effects on different signaling pathways can be assessed in the same cell type. IFNγ up-regulates ICAM-1 through activation of the JAK/Stat pathway. In this example, the up-regulation of ICAM-1 by IFNγ was assessed.

The U937 human monocytic cell line was obtained from ATCC of Rockville Md., catalog number CRL-1593.2, and cultured in RPM 1-1640 medium containing 10% (v/v) FCS. U937 cells were grown in 10% RPMI. The cells were then plated at a concentration of 100,000 cells per 160 µL in 96 well flat bottom plates. The test compounds were then diluted as follows: 10 mM test compound was diluted 1:5 in DMSO (3 µL 10 mM test compound in 12 µL DMSO), followed by a 1:3 serial dilution of test compound in DMSO (6 µL test compound serially diluted into 12 µL DMSO to give 3-fold dilutions). Then 4 µL of test compound was transferred to 76 µL of 10% RPMI resulting in a 10× solution (100 µM test compound, 5% DMSO). For control wells, 4 JAL of DMSO was diluted into 76 µL 10% RPMI. The assay was performed in duplicate with 8 points (8 3-fold dilution concentrations from 10 µM) and with 4 wells of DMSO only (control wells) under stimulated conditions and 4 wells of DMSO only under unstimulated conditions.

The diluted compound plate was mixed 2× using a multimek (Beckman Coulter of Brea, Calif.) and then 20 µL of the diluted compounds was transferred to the 96 well plate containing 160 µL of cells, which were then mixed again twice at low speeds. The cells and compounds were then pre-incubated for 30 minutes at 37° C. with 5% $CO_2$.

The 10× stimulation mix was made by preparing a 100 ng/mL solution of human IFNγ in 10% RPMI. The cells and compound were then stimulated with 20 µL of IFNγ stimulation mix to give a final concentration of 10 ng/mL IFNγ, 10 µM test compound, and 0.5% DMSO. The cells were kept under conditions for stimulation for 18-24 hours at 37° C. with 5% $CO_2$.

The cells were transferred to a 96 well round bottom plate for staining and then kept on ice for the duration of the staining procedure. Cells were spun down at 1000 rpm for 5 minutes at 4° C., following which the supernatant was removed. Following removal of the supernatant, 1 µL APC conjugated mouse anti-human ICAM-1 antibody was added per 100 µL FACS buffer. The cells were then incubated on ice in the dark for 30 minutes. Following incubation, 150 µL of FACS buffer was added and the cells were centrifuged at 1000 rpm for 5 minutes at 4° C., following which the supernatant was removed. After removal of the supernatant, 200 µL of FACS buffer was added and the cells were resuspended. After suspension, the cells were centrifuged at 1000 rpm for 5 min at 4° C. Supernatant was then removed prior to resuspension of the cells in 150 µL FACS buffer.

Detection was performed using a BD LSR I System Flow Cytometer, purchased from BD Biosciences of San Jose, Calif. The live cells were gated for live scatter and the geometric mean of ICAM-APC was measured (Becton-Dickinson CellQuest software version 3.3, Franklin Lakes, N.J.). Both % live cells and ICAM-1 expression was analyzed. The assays for the test compounds were carried out in parallel with a control compound of known activity. The $EC_{50}$ for the control compound is typically 40-100 nM.

Example 11: JAK1, JAK2 and JAK3 Fluorescence Polarization Kinase Assays

This assay can be utilized to determine the potency of a compound described herein against certain JAK kinases and the selectivity of a compound described herein in inhibiting certain JAK kinase activity in vitro.

Reagents and Buffers
Tyrosine Kinase Kit Green (Invitrogen, Cat# P2837)
Acetylated Bovine Gamma Globulin (BGG) (Invitrogen, Cat# P2255)
Active JAK1 (Carna Biosciences)
Active JAK2 (Carna Biosciences)
Active JAK3 (Carna Biosciences)
TK2 Peptide (Biotin-EGPWLEEEEEAYGWMDF-CONH2) (SynPep Custom Synthesis)
Methods Test compounds were serially diluted in DMSO starting from 500× the desired final concentration and then diluted to 1% DMSO in kinase buffer (20 mM HEPES, pH 7.4, 5 mM $MgCl_2$, 2 mM $MnCl_2$, 1 mM DTT, 0.1 mg/mL acetylated BGG). Test compound in 1% DMSO (0.2% DMSO final) was mixed 1:5 with ATP and substrate in kinase buffer at ambient temperature.

The kinase reactions were performed in a final volume of 20 µL containing peptide substrate and ATP and started by addition of kinase in kinase buffer. The reactions were allowed to proceed at ambient temperature. Final substrate, ATP and enzyme concentrations and reaction times for the different kinase assays are listed in Table III.

TABLE III

Final Substrate, ATP, Enzyme Concentrations and Reaction Times

| Enzyme | Enzyme Amount per Reaction | Substrate | Substrate Concentration | ATP Concentration | Assay Time |
|---|---|---|---|---|---|
| JAK1 | 20 ng | TK2 | 10 µM | 5 µM | 20 min |
| JAK2 | 0.3 ng | TK2 | 10 µM | 5 µM | 20 min |
| JAK3 | 2 ng | TK2 | 10 µM | 5 µM | 20 min |

The reactions were stopped by adding 20 µL of PTK quench mix containing EDTA/anti-phosphotyrosine antibody (1× final)/fluorescent phosphopeptide tracer (0.5× final) diluted in FP Dilution Buffer according to manufacturer's instructions (Invitrogen). The plates were incubated for 30 minutes in the dark at ambient temperature and then read on a Polarion fluorescence polarization plate reader (Tecan).

Data were converted to amount of phosphopeptide present using a calibration curve generated by competition with the phosphopeptide competitor provided in the Tyrosine Kinase Assay Kit, Green (Invitrogen). For $IC_{50}$ determination, the compounds were tested at eleven concentrations in duplicate and curve-fitting was performed by non-linear regression analysis using Matlab version 6.5 (MathWorks, Inc., Natick, Mass., USA).

Example 12: Constitutively-Active JAK2-Dependent Cell Proliferation Assays

A mutation in the JH2 pseudokinase domain of JAK2 (JAK2 V617F) has been described in chronic myeloproliferative disorders as well as a subset of acute myeloid leukemia (AML) cell lines. Mutation of the negative regulatory JH2 domain dysregulates the kinase enabling it to constitutively associate with the EPO receptor and become activated. UKE-1 cells, derived from an AML patient, express JAK2 V617F which drives their proliferation. The IL-3-dependent BaF3 myeloid cell line was engineered to express JAK2 V617F allowing it to proliferate in an IL-3-independent manner. The effect of JAK inhibitors on the proliferation of these cell lines can be used to assess the cellular activity of the compounds against JAK2.

Reagents and Buffers

Dimethyl Sulfoxide (DMSO) (Sigma-Aldrich, Cat No. D2650) (Control)

Iscove's DMEM, ATCC Catalog #30-2005

1 M HEPES, Cellgro Catalog #25-060-CI (100 mL)

100 mM Sodium Pyruvate, Cellgro Catalog #25-000-CI (100 mL)

Penicillin/Streptomycin, 10000 U/mL each, Cellgro Catalog #30-002-CI (100 mL)

RPMI 1640 (Cellgro, Cat No. 10-040-CM)

Fetal Bovine Serum (JRH, Cat No. 12106-500M)

Donor Equine Serum, Hyclone Catalog #SH30074.02 (100 mL)

50 µM hydrocortisone solution, Sigma Catalog #H6909-10 ml (10 mL)

Culture Conditions

BaF3 V617F cells were maintained and plated in RPMI with 10% FBS. Plating density for these cells was $1 \times 10^5$ cells/mL.

UKE-1 were maintained and plated in Iscove's DMEM containing 10% FBS, 10% equine serum, 1% penicillin/streptomycin and 1 uM hydrocortisone. Plating density for these cells was $0.4 \times 10^6$ cells/mL Methods The cells were resuspended in a corresponding medium at a required cell density (see above). 100µ of cell suspension was added to each well of a flat bottom 96 well white plate. The compound was serially diluted in DMSO from 5 mM in 3-fold dilutions, and then diluted 1:250 in the RPMI 1640 medium containing 5% FBS and pen/strep. 100 µL of resulting 2× compound solution was added per well in duplicate and the cells were allowed to proliferate for 72 hours at 37° C.

Proliferation was measured using Cell Titer-Glo. The substrate was thawed and allowed to come to room temperature. After removal of top 100 µL of medium from each well, 100 µL of the premixed Cell Titer-Glo reagent was added to each well. The plates were mixed on an orbital shaker for three minutes to induce lysis and incubated at ambient temperature for an additional five minutes to allow the signal to equilibrate. The Luminescence was read on the Wallac Plate Reader.

The results of the ability of the compounds described herein to inhibit JAK3 activity, when tested under conditions described in Example 3 above, are shown in Table IV below. The compound designations in Table IV are consistent with those of Tables I-II above. In Table IV the activity is indicated by the following ranges: "A" represents compounds having an $IC_{50} < 0.5$ M; "B" represents compounds having an $IC_{50} \geq 0.5$ µM and $<5$ µM; "C" represents compounds having an $IC_{50} \geq 5$ µM and $<10$ µM; and "D" represents compounds having activity $\geq 10$ µM. A blank in Table IV indicates that the compound was not tested in the assay of Example 3.

TABLE IV

| | |
|---|---|
| I-1 | A |
| I-2 | A |
| I-3 | B |
| I-4 | A |
| I-5 | A |
| I-6 | D |
| I-7 | A |
| I-8 | A |
| I-9 | A |
| I-10 | A |
| I-11 | A |
| I-12 | A |
| I-13 | B |
| I-14 | A |
| I-15 | A |
| I-16 | A |
| I-17 | A |
| I-18 | A |
| I-19 | A |
| I-20 | B |
| I-21 | A |
| I-22 | A |
| I-23 | B |
| I-24 | A |
| I-25 | A |
| I-26 | B |
| I-27 | A |
| I-28 | A |
| I-29 | A |
| I-30 | A |
| I-31 | A |
| I-32 | A |
| I-33 | A |
| I-34 | A |
| I-35 | A |

TABLE IV-continued

| | |
|---|---|
| I-36 | A |
| I-37 | D |
| I-38 | A |
| I-39 | D |
| I-40 | A |
| I-41 | C |
| I-42 | D |
| I-43 | D |
| I-44 | D |
| I-45 | D |
| I-46 | A |
| I-47 | D |
| I-48 | D |
| I-49 | D |
| I-50 | A |
| I-51 | A |
| I-52 | A |
| I-53 | A |
| I-54 | D |
| I-55 | D |
| I-56 | D |
| I-57 | D |
| I-58 | D |
| I-59 | D |
| I-60 | D |
| I-61 | A |
| I-62 | B |
| I-63 | A |
| I-64 | A |
| I-65 | A |
| I-66 | A |
| I-67 | A |
| I-68 | A |
| I-69 | A |
| I-70 | A |
| I-71 | A |
| I-72 | A |
| I-73 | A |
| I-74 | C |
| I-75 | A |
| I-76 | A |
| I-77 | A |
| I-78 | A |
| I-79 | A |
| I-80 | B |
| I-81 | B |
| I-82 | A |
| I-83 | A |
| I-84 | A |
| I-85 | A |
| I-86 | A |
| I-87 | A |
| I-88 | D |
| I-89 | B |
| I-90 | B |
| I-91 | B |
| I-92 | B |
| I-93 | B |
| I-94 | C |
| I-95 | C |
| I-96 | B |
| I-97 | B |
| I-98 | C |
| I-99 | D |
| I-100 | B |
| I-101 | A |
| I-102 | A |
| I-103 | A |
| I-104 | A |
| I-105 | A |
| I-106 | A |
| I-107 | A |
| I-108 | A |
| I-109 | A |
| I-110 | A |
| I-111 | A |
| I-112 | A |
| I-113 | A |
| I-114 | A |
| I-115 | B |

TABLE IV-continued

| | |
|---|---|
| I-116 | |
| I-117 | |
| I-118 | |
| I-119 | C |
| I-120 | A |
| I-121 | A |
| I-122 | B |
| I-123 | C |
| I-124 | A |
| I-125 | A |
| I-126 | A |
| I-127 | A |
| I-128 | A |
| I-129 | A |
| I-130 | A |
| I-131 | A |
| I-132 | A |
| I-133 | C |
| I-134 | D |
| I-135 | A |
| I-136 | B |
| I-137 | A |
| I-138 | A |
| I-139 | D |
| I-140 | B |
| I-141 | A |
| I-142 | A |
| I-143 | A |
| I-144 | A |
| I-145 | B |
| I-146 | A |
| I-147 | A |
| I-148 | C |
| I-149 | A |
| I-150 | A |
| I-151 | A |
| I-152 | C |
| I-153 | A |
| I-154 | A |
| I-155 | B |
| I-156 | A |
| I-157 | A |
| I-158 | A |
| I-159 | A |
| I-160 | A |
| I-161 | A |
| I-162 | A |
| I-163 | A |
| I-164 | A |
| I-165 | A |
| I-166 | A |
| I-167 | A |
| I-168 | A |
| I-169 | A |
| I-170 | A |
| I-171 | A |
| I-172 | A |
| I-173 | A |
| I-174 | A |
| I-175 | A |
| I-176 | D |
| I-177 | D |
| I-178 | A |
| I-179 | D |
| I-180 | A |
| I-181 | A |
| I-182 | A |
| I-183 | A |
| I-184 | A |
| I-185 | A |
| I-186 | A |
| I-187 | A |
| I-188 | A |
| I-189 | A |
| I-190 | B |
| I-191 | A |
| I-192 | B |
| I-193 | B |
| I-194 | B |
| I-195 | A |

TABLE IV-continued

| | |
|---|---|
| I-196 | A |
| I-197 | A |
| I-198 | A |
| I-199 | A |
| I-200 | B |
| I-201 | B |
| I-202 | B |
| I-203 | A |
| I-204 | A |
| I-205 | A |
| I-206 | A |
| I-207 | D |
| I-208 | A |
| I-209 | A |
| I-210 | A |
| I-211 | A |
| I-212 | A |
| I-213 | A |
| I-214 | D |
| I-215 | A |
| I-216 | |
| I-217 | A |
| II-1 | A |
| II-2 | A |
| II-3 | A |
| II-4 | A |
| II-5 | A |
| II-6 | D |
| II-7 | D |
| II-8 | A |
| II-9 | A |
| II-10 | A |
| II-11 | A |
| II-12 | A |
| II-13 | A |
| II-14 | D |
| II-15 | B |
| II-16 | D |
| II-17 | A |
| II-18 | A |
| II-19 | A |
| II-20 | A |
| II-21 | B |
| II-22 | B |
| II-23 | A |
| II-25 | A |
| II-26 | A |
| II-27 | A |
| II-28 | A |

Although the foregoing invention has been described in some detail to facilitate understanding, the described embodiments are to be considered illustrative and not limiting. It will be apparent to one of ordinary skill in the art that certain changes and modifications can be practiced within the scope of the appended claims.

We claim:
1. A compound of formula IA:

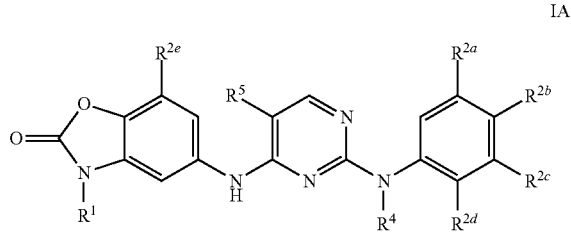

IA or salt thereof, wherein:
$R^1$ is H, optionally substituted $C_{1-6}$alkyl, C(O)—$C_{1-6}$alkyl, $CO_2$—$C_{1-6}$alkyl or $R^{50}$;

each $R^{50}$ is —$C(R^9)_2$-A-$R^{10}$, where A is O or S; each $R^9$ is independently for each occurrence H, optionally substituted $C_{1-6}$alkyl, optionally substituted $C_{6-10}$aryl or optionally substituted $C_{7-16}$arylalkyl; or alternatively, two $R^9$, together with the carbon to which they are attached, form an optionally substituted $C_{3-8}$cycloalkyl group or an optionally substituted 3-8 membered heteroalicyclyl; $R^{10}$ is $R^a$, —$P(O)(OR^{11})_2$, —$P(O)(OR^{11})N(R^{12})_2$ or —$P(O)(N(R^{12})_2)_2$; each $R^{11}$ is independently for each occurrence $R^a$ or a monovalent cationic group; or two $R^{11}$, together with the atoms to which they are attached, form a 4-8 membered cyclic phosphate group; each $R^{12}$ is independently for each occurrence $R^c$ or —$C_{1-3}$alkyl-$N(R^c)_2$; or two $R^{12}$, each on separate nitrogens of —$P(O)(N(R^{12})_2)_2$, together with the atoms to which they are attached, form a 4-8 membered cyclic phosphonic acid bisamide group; or one $R^{12}$ along with $R^{11}$, of the group —$P(O)(OR^{11})N(R^{12})_2$, together with the atoms to which they are attached, form a 4-8 membered cyclic phosphonamidate group;

each of $R^{2a-2c}$ is independently for each occurrence H, $R^e$, $R^b$, $R^e$ substituted with one or more of the same or different $R^a$ and/or $R^b$, —$OR^e$ substituted with one or more of the same or different $R^a$ and/or $R^b$, —$SR^e$ substituted with one or more of the same or different $R^a$ and/or $R^b$, —$C(O)R^e$ substituted with one or more of the same or different $R^a$ and/or $R^b$, —$N(R^a)R^e$ where $R^e$ is substituted with one or more of the same or different $R^a$ and/or $R^b$, —$S(O)_2R^e$ substituted with one or more of the same or different $R^a$ and/or $R^b$, —$N(R^a)$—$S(O)_2R^e$ where $R^e$ is substituted with one or more of the same or different $R^a$ and/or $R^b$, —$B(OR^a)_2$, —$B(N(R^c)_2)_2$, —$(C(R^a)_2)_m$—$R^b$, —O—$(C(R^a)_2)_m$—$R^b$, —S—$(C(R^a)_2)_m$—$R^b$, —O—$(C(R^b)_2)_m$—$R^a$, —$N(R^a)$—$(C(R^a)_2)_m$—$R^b$, —O—$(CH_2)_m$—CH$((CH_2)_mR^b)R^b$, —$C(O)N(R^a)$—$(C(R^a)_2)_m$—$R^b$, —O—$(C(R^a)_2)_m$—$C(O)N(R^a)$—$(C(R^a)_2)_m$—$R^b$, —$N((C(R^a)_2)_mR^b)_2$, —S—$(C(R^a)_2)_m$—$C(O)N(R^a)$—$(C(R^a)_2)_m$—$R^b$, —$N(R^a)$—$C(O)$—$N(R^a)$—$(C(R^a)_2)_m$—$R^b$, —$N(R^a)$—$C(O)$—$(C(R^a)_2)_m$—$C(R^a)(R^b)_2$ or —$N(R^a)$—$(C(R^a)_2)_m$—$C(O)$—$N(R^a)$—$(C(R^a)_2)_m$—$R^b$;

$R^{2d}$ is F;
$R^{2e}$ is halo or optionally substituted $C_{1-6}$alkyl;

each $R^a$ is independently for each occurrence H, deuterium, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;

each $R^b$ is independently for each occurrence =O, —$OR^a$, —O—$(C(R^a)_2)_m$—$OR^a$, halo$C_{1-3}$alkyloxy, =S, —$SR^a$, =$NR^a$, =$NOR^a$, —$N(R^c)_2$, halo, —$CF_3$, —CN, —NC, —OCN, —SCN, —NO, —$NO_2$, =$N_2$, —$N_3$, —$S(O)R^a$, —$S(O)_2R^a$, —$SO_3R^a$, —$S(O)N(R^c)_2$, —$S(O)_2N(R^c)_2$, —$OS(O)R^a$, —$OS(O)_2R^a$, —$OSO_3R^a$, —$OS(O)_2N(R^c)_2$, —$C(O)R^a$, —$CO_2R^a$, —$C(O)N(R^c)_2$, —$C(NR^a)$—$N(R^c)_2$, —$C(NOH)$—$R^a$, —$C(NOH)$—$N(R^c)_2$, —$OC(O)R^a$, —$OC(O)OR^a$, —$OC(O)N(R^c)_2$, —$OC(NH)$—$N(R^c)_2$, —$OC(NR^a)$—$N(R^c)_2$, —$N(R^a)$—$S(O)_2H$, —$[N(R^a)C(O)]_nR^a$, —$[N(R^a)C(O)]_nOR^a$, —$[N(R^a)C(O)]_nN(R^c)_2$ or —$[N(R^a)C(NR^a)]_n$—$N(R^c)_2$;

each $R^c$ is independently for each occurrence $R^a$, or, alternatively, two $R^c$ are taken together with the nitrogen atom to which they are bonded to form a 3 to 10-membered heteroalicyclyl or a 5-10 membered heteroaryl optionally comprising one or more of the same or different additional heteroatoms and which is optionally substituted with one or more of the same or different $R^a$ and/or $R^d$ groups;

each $R^d$ is =O, —$OR^a$, halo$C_{1-3}$alkyloxy, $C_{1-6}$alkyl, =S, —$SR^a$, =$NR^a$, =$NOR^a$, —$N(R^a)_2$, halo, —$CF_3$, —CN, —NC, —OCN, —SCN, —NO, —$NO_2$, =$N_2$, —$N_3$, —$S(O)R^a$, —$S(O_2)R^a$, —$SO_3R^a$, —$S(O)N(R^a)_2$, —$S(O)_2N(R^a)_2$, —$OS(O)R^a$, —$OS(O)_2R^a$, —$OSO_3R^a$, —$OS(O)_2N(R^a)_2$, —$C(O)R^a$, —$CO_2R^a$, —$C(O)N(R^a)_2$, —$C(NR^a)N(R^a)_2$, —$C(NOH)R^a$, —$C(NOH)N(R^a)_2$, —$OCO_2R^a$, —$OC(O)N(R^a)_2$, —$OC(NR^a)N(R^a)_2$, —$[N(R^a)C(O)]_nR^a$, —$(C(R^a)_2)_n$—$OR^a$, —$N(R^a)$—$S(O)_2R^a$, —C(O)—$C_{1-6}$haloalkyl, —$S(O)_2C_{1-6}$haloalkyl, —$OC(O)R^a$, —$O(C(R^a)_2)_m$—$OR^a$, —$S(C(R^a)_2)_m$—$OR^a$, —$N(R^a)C_{1-6}$haloalkyl, —$P(O)(OR^a)_2$, —$N(R^a)$—$(C(R^a)_2)_m$—$OR^a$, —$[N(R^a)C(O)]_nOR^a$, —$[N(R^a)C(O)]_nN(R^a)_2$, —$[N(R^a)C(NR^a)]_nN(R^a)_2$ or —$N(R^a)C(O)C_{1-6}$haloalkyl;

two $R^d$, taken together with the atom or atoms to which they are attached, combine to form a 3-10 membered partially or fully saturated mono or bicyclic ring, optionally containing one or more heteroatoms and optionally substituted with one or more $R^a$;

each $R^e$ is independently for each occurrence $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-10 membered heteroalicyclyl, 4-11 membered heteroalicyclylalkyl, 5-15 membered heteroaryl or 6-16 membered heteroarylalkyl;

each m is 1, 2 or 3;

each n is 0, 1, 2 or 3;

two of $R^{2a-2c}$ groups, taken together with the atom or atoms to which they are attached, combine to form a 4-10 membered partially or fully saturated mono or bicyclic ring, optionally containing one or more heteroatoms and optionally substituted with one or more $R^a$ and/or $R^b$;

$R^4$ is H or optionally substituted $C_{1-6}$alkyl; and $R^5$ is H, halo, —CN, optionally substituted $C_{1-6}$alkyl, nitro, —$N(R^a)_2$, —$C(O)N(R^a)_2$, —$CO_2R^a$ or —$C(O)R^a$.

2. The compound of claim 1, wherein $R^{2a}$ is H; $R^{2b}$ is $C_{1-3}$alkyl; and $R^{2c}$ is —$OC_{1-3}$alkyl.

3. The compound of claim 2, wherein $R^{2a}$ is H; $R^{2b}$ is $CH_3$; and $R^{2c}$ is —$OCH_3$.

4. The compound of claim 1, wherein $R^{2a}$ is H; $R^{2b}$ is —$OC_{1-3}$alkyl; and $R^{2c}$ is —$OC_{1-3}$alkyl.

5. The compound of claim 4, wherein $R^{2a}$ is H; $R^{2b}$ is —$OC_{1-3}$alkyl; and $R^{2c}$ is —$OC_{1-3}$alkyl.

6. The compound of claim 5, wherein $R^{2a}$ is H; $R^{2b}$ is —$OCH_3$; and $R^{2c}$ is —$OCH_3$.

7. The compound of claim 1, wherein $R^{2a}$, $R^{2b}$ and $R^{2c}$ are each independently $CH_3$, —$OCH_3$, or F.

8. The compound of claim 7, wherein two of $R^{2a}$, $R^{2b}$ and $R^{2c}$ are $CH_3$; and the other of $R^{2a}$, $R^{2b}$ and $R^{2c}$ is F.

9. The compound of claim 7, wherein two of $R^{2a}$, $R^{2b}$ and $R^{2c}$ are $CH_3$; and the other of $R^{2a}$, $R^{2b}$ and $R^{2c}$ is —$OCH_3$.

10. The compound of claim 7, wherein two of $R^{2a}$, $R^{2b}$ and $R^{2c}$ are —$OCH_3$; and the other of $R^{2a}$, $R^{2b}$ and $R^{2c}$ is F.

11. The compound of claim 7, wherein two of $R^{2a}$, $R^{2b}$ and $R^{2c}$ are —$OCH_3$; and the other of $R^{2a}$, $R^{2b}$ and $R^{2c}$ is $CH_3$.

12. The compound of claim 7, wherein one of $R^{2a}$, $R^{2b}$ and $R^{2c}$ is $CH_3$; one of $R^{2a}$, $R^{2b}$ and $R^{2c}$ is —$OCH_3$; and one of $R^{2a}$, $R^{2b}$ and $R^{2c}$ is F.

\* \* \* \* \*